(12) United States Patent
Olson et al.

(10) Patent No.: US 12,103,960 B2
(45) Date of Patent: Oct. 1, 2024

(54) VEGF TRAPS AND MINI-TRAPS AND METHODS FOR TREATING OCULAR DISORDERS AND CANCER

(71) Applicant: Regeneron Pharmaceuticals, Inc., Tarrytown, NY (US)

(72) Inventors: William Olson, Yorktown Heights, NY (US); Joel Martin, Putnam Valley, NY (US); Neil Stahl, Carmel, NY (US); Jee Kim, Ardsley, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 17/314,503

(22) Filed: May 7, 2021

(65) Prior Publication Data
US 2021/0347852 A1 Nov. 11, 2021

Related U.S. Application Data

(60) Provisional application No. 63/022,178, filed on May 8, 2020.

(51) Int. Cl.
| | |
|---|---|
| C07K 14/71 | (2006.01) |
| A61K 38/00 | (2006.01) |
| A61P 27/02 | (2006.01) |
| A61P 27/06 | (2006.01) |
| A61P 35/00 | (2006.01) |

(52) U.S. Cl.
CPC ............ C07K 14/71 (2013.01); A61P 27/02 (2018.01); *A61K 38/00* (2013.01); *C07K 2317/53* (2013.01)

(58) Field of Classification Search
CPC .... C07K 14/71; C07K 2317/54; A61K 38/00; A61P 27/02; A61P 27/06; A61P 35/00
See application file for complete search history.

(56) References Cited

U.S. PATENT DOCUMENTS

| | | |
|---|---|---|
| 4,399,216 A | 8/1983 | Axel et al. |
| 4,740,461 A | 4/1988 | Kaufman |
| 4,816,567 A | 3/1989 | Cabilly et al. |
| 4,912,040 A | 3/1990 | Kaufman et al. |
| 4,959,455 A | 9/1990 | Clark et al. |
| 5,122,469 A | 6/1992 | Mather et al. |
| 5,168,062 A | 12/1992 | Stinski |
| 5,385,839 A | 1/1995 | Stinski |
| 5,633,162 A | 5/1997 | Keen et al. |
| 5,705,364 A | 1/1998 | Etcheverry et al. |
| 5,721,121 A | 2/1998 | Etcheverry et al. |
| 5,952,199 A | 9/1999 | Davis-Smyth et al. |
| 6,100,071 A | 8/2000 | Davis-Smyth et al. |
| 6,121,230 A | 9/2000 | Charnock-Jones et al. |
| 6,171,825 B1 | 1/2001 | Chan et al. |
| 6,177,401 B1 | 1/2001 | Ullrich et al. |
| 6,309,862 B1 | 10/2001 | Jarekrans et al. |
| 6,383,486 B1 | 5/2002 | Davis-Smyth et al. |
| 6,833,349 B2 | 12/2004 | Xia et al. |
| 6,872,699 B2 | 3/2005 | Ullrich et al. |
| 6,897,294 B2 | 5/2005 | Davis-Smyth et al. |
| 6,936,441 B2 | 8/2005 | Reiter et al. |
| 7,070,959 B1 | 7/2006 | Papadopoulos et al. |
| 7,087,411 B2 | 8/2006 | Daly et al. |
| 7,279,159 B2 | 10/2007 | Daly et al. |
| 7,303,746 B2 | 12/2007 | Wiegand et al. |
| 7,303,747 B2 | 12/2007 | Wiegand et al. |
| 7,306,799 B2 | 12/2007 | Wiegand et al. |
| 7,374,757 B2 | 5/2008 | Papadopoulos et al. |
| 7,374,758 B2 | 5/2008 | Papadopoulos et al. |
| 7,396,664 B2 | 7/2008 | Daly et al. |
| 7,399,612 B2 | 7/2008 | Daly et al. |
| 7,521,049 B2 | 4/2009 | Wiegand et al. |
| 7,524,499 B2 | 4/2009 | Papadopoulos et al. |
| 7,531,173 B2 | 5/2009 | Wiegand et al. |
| 7,608,261 B2 | 10/2009 | Furfine et al. |
| 7,635,474 B2 | 12/2009 | Daly et al. |
| 7,666,582 B2 | 2/2010 | Pawel-Rammingen et al. |
| 7,704,500 B2 | 4/2010 | Papadopoulos et al. |
| 7,750,138 B2 | 7/2010 | Fang et al. |
| 7,771,721 B2 | 8/2010 | Davis-Smyth et al. |
| 7,807,164 B2 | 10/2010 | Furfine et al. |
| 7,928,072 B2 | 4/2011 | Scaria et al. |

(Continued)

FOREIGN PATENT DOCUMENTS

| | | |
|---|---|---|
| CN | 101279092 A | 10/2008 |
| CN | 101397343 A | 4/2009 |

(Continued)

OTHER PUBLICATIONS

Alt et al.; Determination of critical quality attributes for monoclonal antibodies using quality by design principles; Biologicals; 44; 2016; 291-305.
Altschul et al.; Basic local alignment search tool; J. Mol. Biol; 215; 1990; 403-10.
Altschul et al.; Gapped BLAST and PSI-BLAST: a new generation of protein database search programs; Nucleic Acids Res.; 25; 1997; 3389-402.
Altschul et al.; Protein database searches using compositionally adjusted substitution matrices; FEBS J.; 272(20); 2005; 5101-9.
Altschul; A Protein Alignment Scoring System Sensitive at All Evolutionary Distances; J. Mol. Evol.; 36; 1993; 290-300.
Altschul; Amino acid substitution matrices from an information theoretic perspective; J. Mol. Biol. 219; 1991; 555-65.

(Continued)

*Primary Examiner* — Julie Ha
(74) *Attorney, Agent, or Firm* — Troutman Pepper Hamilton Sanders LLP

(57) ABSTRACT

Vascular endothelial growth factor (VEGF) traps and VEGF mini-traps that include VEGF receptor Ig-like domains, fused to a multimerizing component, are disclosed. The VEGF traps and VEGF mini-traps bind to VEGF and block its interaction with the VEGF receptor. Such molecules are useful for treating angiogenic eye disorders (e.g., age-related macular degeneration), cancer and for other undesired angiogenesis.

10 Claims, 66 Drawing Sheets

Specification includes a Sequence Listing.

(56) References Cited

U.S. PATENT DOCUMENTS

| | | |
|---|---|---|
| 7,951,585 B2 | 5/2011 | Ke |
| 7,964,377 B2 | 6/2011 | Papadopoulos et al. |
| 7,964,399 B2 | 6/2011 | Ullrich et al. |
| 7,972,598 B2 | 7/2011 | Daly et al. |
| 8,029,791 B2 | 10/2011 | Papadopoulos et al. |
| 8,084,234 B2 | 12/2011 | Papadopoulos et al. |
| 8,092,803 B2 | 1/2012 | Furfine et al. |
| 8,110,546 B2 | 2/2012 | Dix et al. |
| 8,216,575 B2 | 7/2012 | Yu |
| 8,268,313 B2 | 9/2012 | Davis-Smyth et al. |
| 8,268,591 B2 | 9/2012 | Davis-Smyth et al. |
| 8,273,353 B2 | 9/2012 | Davis-Smyth et al. |
| 8,343,737 B2 | 1/2013 | Papadopoulos et al. |
| 8,404,638 B2 | 3/2013 | Dix et al. |
| 8,481,046 B2 | 7/2013 | Furfine et al. |
| 8,586,713 B2 | 11/2013 | Davis et al. |
| 8,647,842 B2 | 2/2014 | Papadopoulos et al. |
| 8,658,602 B2 | 2/2014 | Scaria et al. |
| 8,697,396 B2 | 4/2014 | Dall'Acqua et al. |
| 8,710,004 B2 | 4/2014 | Dix et al. |
| 8,777,906 B1 | 7/2014 | Gray |
| 8,802,107 B2 | 8/2014 | Furfine et al. |
| 8,921,316 B2 | 12/2014 | Dix et al. |
| 8,926,972 B2 | 1/2015 | Zhou et al. |
| 8,956,830 B2 | 2/2015 | Prentice et al. |
| 9,139,644 B2 | 9/2015 | Papadopoulos et al. |
| 9,217,168 B2 | 12/2015 | Prentice |
| 9,254,338 B2 | 2/2016 | Yancopoulos |
| 9,273,113 B2 | 3/2016 | Davis-Smyth et al. |
| 9,340,594 B2 | 5/2016 | Furfine et al. |
| 9,416,167 B2 | 8/2016 | Dix et al. |
| 9,441,029 B2 | 9/2016 | Stefano et al. |
| 9,487,810 B2 | 11/2016 | Prentice et al. |
| 9,511,140 B2 | 12/2016 | Dix et al. |
| 9,580,489 B2 | 2/2017 | Furfine et al. |
| 9,605,043 B2 | 3/2017 | Hong et al. |
| 9,636,400 B2 | 5/2017 | Dix et al. |
| 9,657,084 B2 | 5/2017 | Ke et al. |
| 9,657,102 B2 | 5/2017 | Smith et al. |
| 9,663,810 B2 | 5/2017 | Prentice |
| 9,669,069 B2 | 6/2017 | Yancopoulos |
| 9,708,386 B2 | 7/2017 | Papadopoulos et al. |
| 9,815,892 B2 | 11/2017 | Scaria et al. |
| 9,914,763 B2 | 3/2018 | Furfine et al. |
| 9,926,583 B2 | 3/2018 | Prentice et al. |
| 9,931,330 B2 | 4/2018 | Zarnitsyn et al. |
| 9,988,611 B2 | 6/2018 | Her et al. |
| 10,130,681 B2 | 11/2018 | Yancopoulos |
| 10,144,944 B2 | 12/2018 | Prentice |
| 10,308,917 B2 | 6/2019 | Stefano et al. |
| 10,392,430 B2 | 8/2019 | Papadopoulos et al. |
| 10,400,025 B2 | 9/2019 | Furfine et al. |
| 10,406,226 B2 | 9/2019 | Dix et al. |
| 10,464,992 B2 | 11/2019 | Furfine et al. |
| 10,576,128 B2 | 3/2020 | Sigl |
| 10,626,142 B2 | 4/2020 | Tustian et al. |
| 10,646,456 B2 | 5/2020 | Went et al. |
| 10,738,130 B2 | 8/2020 | Haber et al. |
| 10,772,972 B2 | 9/2020 | Rudge et al. |
| 10,828,345 B2 | 11/2020 | Yancopoulos |
| 10,857,205 B2 | 12/2020 | Yancopoulos |
| 10,857,231 B2 | 12/2020 | Dix et al. |
| 10,888,601 B2 | 1/2021 | Yancopoulos |
| 10,973,879 B2 | 4/2021 | Vitti et al. |
| 11,053,280 B2 | 7/2021 | Tustian et al. |
| 11,066,458 B2 | 7/2021 | Furfine et al. |
| 11,084,865 B2 | 8/2021 | Furfine et al. |
| 11,098,112 B2 | 8/2021 | Tustian et al. |
| 11,098,311 B2 | 8/2021 | Franklin |
| 11,104,715 B2 | 8/2021 | Lawrence et al. |
| 11,174,283 B2 | 11/2021 | Tustian et al. |
| 11,180,540 B2 | 11/2021 | Tustian et al. |
| 11,186,625 B2 | 11/2021 | Wang et al. |
| 11,253,572 B2 | 2/2022 | Yancopoulos |
| 11,286,290 B2 | 3/2022 | Tustian et al. |
| 11,299,532 B2 | 4/2022 | Tustian et al. |
| 11,306,135 B2 | 4/2022 | Wang et al. |
| 11,407,813 B2 | 8/2022 | Tustian et al. |
| 11,440,950 B2 | 9/2022 | Franklin |
| 11,459,373 B2 | 10/2022 | Tustian et al. |
| 11,459,374 B2 | 10/2022 | Tustian et al. |
| 11,472,861 B2 | 10/2022 | Lawrence |
| 11,485,770 B2 | 11/2022 | Wang et al. |
| 11,505,593 B2 | 11/2022 | Wang et al. |
| 11,505,594 B2 | 11/2022 | Tustian et al. |
| 11,535,663 B2 | 12/2022 | Lawrence et al. |
| 11,542,317 B1 | 1/2023 | Wang et al. |
| 11,548,932 B2 | 1/2023 | Wang et al. |
| 11,559,564 B2 | 1/2023 | Yancopoulos |
| 11,649,273 B2 | 5/2023 | Tustian et al. |
| 11,707,506 B2 | 7/2023 | Yancopoulos |
| 11,730,794 B2 | 8/2023 | Yancopoulos |
| 11,732,024 B2 | 8/2023 | Furfine et al. |
| 11,732,025 B2 | 8/2023 | Wang et al. |
| 11,753,459 B2 | 9/2023 | Wang et al. |
| 2004/0014667 A1 | 1/2004 | Daly et al. |
| 2004/0213787 A1 | 10/2004 | Sleman et al. |
| 2004/0236072 A1 | 11/2004 | Olmsted et al. |
| 2004/0266686 A1 | 12/2004 | Xia et al. |
| 2004/0266688 A1 | 12/2004 | Nayak et al. |
| 2005/0032699 A1 | 2/2005 | Holash et al. |
| 2005/0163798 A1 | 7/2005 | Papadopoulos et al. |
| 2005/0260203 A1 | 11/2005 | Wiegand et al. |
| 2006/0030000 A1 | 2/2006 | Alitalo et al. |
| 2007/0212770 A1 | 9/2007 | Grillberger et al. |
| 2007/0224178 A1 | 9/2007 | Scaria et al. |
| 2008/0009040 A1 | 1/2008 | Grillberger et al. |
| 2008/0206238 A1 | 8/2008 | Liu |
| 2008/0220004 A1 | 9/2008 | Wiegand et al. |
| 2008/0242587 A1 | 10/2008 | Kim |
| 2009/0264358 A1 | 10/2009 | Yu |
| 2010/0047208 A1 | 2/2010 | Ke |
| 2010/0215655 A1 | 8/2010 | Fang et al. |
| 2010/0272719 A1 | 10/2010 | Yu |
| 2010/0303781 A1 | 12/2010 | Bjoerck et al. |
| 2011/0028698 A1 | 2/2011 | Papadopoulos et al. |
| 2011/0081680 A1 | 4/2011 | Grillberger et al. |
| 2011/0229933 A1 | 9/2011 | Krishnan et al. |
| 2012/0329709 A1 | 12/2012 | Collins et al. |
| 2013/0045492 A1 | 2/2013 | Babb et al. |
| 2013/0084635 A1 | 4/2013 | Papadopoulos et al. |
| 2013/0281355 A1 | 10/2013 | Vijayasankaran et al. |
| 2014/0134162 A1 | 5/2014 | Stavenhagen et al. |
| 2014/0171623 A1 | 6/2014 | Dall'Acqua et al. |
| 2014/0243504 A1 | 8/2014 | Davis et al. |
| 2014/0271622 A1 | 9/2014 | Prentice |
| 2014/0273095 A1 | 9/2014 | Abike et al. |
| 2014/0314779 A1 | 10/2014 | Vijayasankaran et al. |
| 2016/0018409 A1 | 1/2016 | Higel |
| 2017/0002056 A1 | 1/2017 | Ke et al. |
| 2017/0174779 A1 | 6/2017 | Varghese et al. |
| 2017/0174781 A1 | 6/2017 | Brownstein |
| 2018/0023070 A1 | 1/2018 | Kjellman et al. |
| 2018/0072986 A1 | 3/2018 | Park et al. |
| 2018/0265543 A1 | 3/2018 | Sanaie et al. |
| 2018/0134794 A1 | 5/2018 | Babb et al. |
| 2018/0208647 A1 | 7/2018 | Ferrara et al. |
| 2018/0221507 A1 | 8/2018 | Gudas et al. |
| 2018/0223249 A1 | 8/2018 | Johnson et al. |
| 2018/0230210 A1 | 8/2018 | Hickman |
| 2018/0230540 A1 | 8/2018 | Ghosh et al. |
| 2018/0326126 A1 | 11/2018 | Fiedler |
| 2019/0025323 A1 | 1/2019 | Higel et al. |
| 2019/0030123 A1 | 1/2019 | Sigl |
| 2019/0276528 A1 | 9/2019 | Liu et al. |
| 2019/0298801 A1 | 10/2019 | Kerwin et al. |
| 2019/0343918 A1 | 11/2019 | Graham et al. |
| 2019/0388539 A1 | 12/2019 | Dix et al. |
| 2020/0017572 A1 | 1/2020 | Furfine et al. |
| 2020/0131246 A1 | 4/2020 | Furfine et al. |
| 2020/0246423 A1 | 8/2020 | Liu et al. |
| 2020/0390693 A1 | 12/2020 | Kim et al. |
| 2021/0010025 A1* | 1/2021 | Danos .............. A61K 38/179 |
| 2021/0023173 A1 | 1/2021 | Yancopoulos |

(56) References Cited

U.S. PATENT DOCUMENTS

| | | |
|---|---|---|
| 2021/0085753 A1 | 3/2021 | Yancopoulos |
| 2021/0205410 A1 | 7/2021 | Vitti et al. |
| 2021/0393738 A1 | 12/2021 | Ke |

FOREIGN PATENT DOCUMENTS

| | | |
|---|---|---|
| CN | 100502945 C | 6/2009 |
| CN | 101541825 | 9/2009 |
| CN | 101721699 A | 6/2010 |
| CN | 102233132 A | 11/2011 |
| CN | 102311502 A | 1/2012 |
| CN | 102380096 A | 3/2012 |
| CN | 102580085 A | 7/2012 |
| CN | 102757496 | 10/2012 |
| CN | 103212075 A | 7/2013 |
| CN | 105770871 | 7/2016 |
| CN | 106188294 A | 12/2016 |
| CN | 106279412 | 1/2017 |
| CN | 106539808 A | 3/2017 |
| CN | 107428817 | 12/2017 |
| CN | 108883172 | 11/2018 |
| CN | 109929027 | 6/2019 |
| CN | 109929038 | 6/2019 |
| EP | 0283942 | 9/1988 |
| EP | 0832189 | 1/1998 |
| EP | 1458861 A2 | 9/2004 |
| EP | 1639007 A2 * | 3/2006 ............ A61P 27/00 |
| EP | 2000483 A9 | 3/2009 |
| EP | 1767546 B1 | 3/2012 |
| EP | 2527429 | 11/2012 |
| EP | 1767642 B1 | 4/2014 |
| EP | 2968549 | 1/2016 |
| EP | 2971040 | 1/2016 |
| EP | 3098241 B1 | 10/2017 |
| EP | 3256580 | 12/2017 |
| WO | 2000/075319 A1 | 12/2000 |
| WO | WO2000/075319 | 12/2000 |
| WO | WO2001/139793 | 6/2001 |
| WO | WO2001/092337 | 12/2001 |
| WO | 2002/060489 A1 | 8/2002 |
| WO | WO2002/101019 | 12/2002 |
| WO | 2003051914 A2 | 6/2003 |
| WO | WO2003/075841 | 9/2003 |
| WO | 2005/000895 A3 | 1/2005 |
| WO | 2005/121176 A1 | 12/2005 |
| WO | 2005/121343 A1 | 12/2005 |
| WO | 2005123104 A2 | 12/2005 |
| WO | 2006009809 A2 | 1/2006 |
| WO | 2006015297 A2 | 2/2006 |
| WO | 2006/104852 A2 | 10/2006 |
| WO | WO2006/131347 | 12/2006 |
| WO | WO2007/077217 | 7/2007 |
| WO | 2007/112675 A1 | 10/2007 |
| WO | 2007/149334 A2 | 12/2007 |
| WO | WO2008/028686 | 3/2008 |
| WO | WO2008/128227 | 10/2008 |
| WO | WO2008/132568 | 11/2008 |
| WO | WO2008/154014 | 12/2008 |
| WO | WO2009/027041 | 5/2009 |
| WO | WO2010/138502 | 12/2010 |
| WO | 2011/14469 A1 | 2/2011 |
| WO | WO2011/014838 | 2/2011 |
| WO | WO2011/061275 | 5/2011 |
| WO | 2012/97019 A1 | 7/2012 |
| WO | WO2013/028330 | 2/2013 |
| WO | WO2013/054250 | 4/2013 |
| WO | 2013/078767 A1 | 6/2013 |
| WO | 2013/112438 A1 | 8/2013 |
| WO | 2013/112986 A1 | 8/2013 |
| WO | WO2014/020160 | 2/2014 |
| WO | 2014043361 A1 | 3/2014 |
| WO | WO2014/035475 | 3/2014 |
| WO | WO2014/144911 | 9/2014 |
| WO | WO2014/145098 | 9/2014 |
| WO | WO2015/058369 | 4/2015 |
| WO | 2015/109898 A1 | 7/2015 |
| WO | 2015/110067 A1 | 7/2015 |
| WO | WO2015/120056 | 8/2015 |
| WO | WO-2016073894 A1 * | 5/2016 ............ C07K 16/24 |
| WO | 2016/85750 A1 | 6/2016 |
| WO | 2016/115732 A1 | 7/2016 |
| WO | WO2016/128558 | 8/2016 |
| WO | WO2016/128559 | 8/2016 |
| WO | WO2016/156476 | 10/2016 |
| WO | 2017129685 A1 | 8/2017 |
| WO | WO2017/168296 | 10/2017 |
| WO | 2017201204 A1 | 11/2017 |
| WO | WO2018/094316 | 5/2018 |
| WO | WO2018/116198 | 6/2018 |
| WO | WO2019/036626 | 2/2019 |
| WO | 2019/079494 A1 | 4/2019 |
| WO | 2019075270 A1 | 4/2019 |
| WO | WO2019/099965 | 5/2019 |
| WO | 2019108770 A1 | 6/2019 |
| WO | 2019178151 A1 | 9/2019 |
| WO | 2019/217927 A1 | 11/2019 |
| WO | WO2020/016318 | 1/2020 |
| WO | 2020/055123 A1 | 3/2020 |
| WO | 2020/087003 A1 | 4/2020 |
| WO | WO2020/160133 | 8/2020 |
| WO | WO2020/229584 | 11/2020 |
| WO | 2021/046245 A1 | 3/2021 |
| WO | 2021/113591 A1 | 6/2021 |
| WO | 2021226444 A2 | 11/2021 |

OTHER PUBLICATIONS

Altschul; Evaluating the statistical significance of multiple distinct local alignments; Theoretical and Computational Methods in Genome Research; Plenum, New York; 1997; 1-14.

An et al.; A new tool for monoclonal antibody analysis Application of IdeS proteolysis in IgG domain-specific characterization; mAbs 6:4, Jul./Aug. 2014; 879-93.

Australian Government, Department of Health and Aging-Therapeutic Goods Administration, Australian Public Assessment Report for Aflibercept; Jul. 2012.

Carillo et al.; Glycosylation Analysis of Therapeutic Glycoproteins Produced in CHO Cells, Methods Mol Biol. 2017; 1603:227-41.

Cheung et al.; Intravitreal administration, but not systemic administration, of VEGF Mini-Trap effectively inhibits neovascularization in the Oxygen Induced Retinopathy (OIR) in mice; ARVO Annual Meeting Abstract; Jun. 2021; 2 pages.

Chiara et al.; Molecular features of interaction between VEGFA and anti angiogenic drugs used in retinal diseases: a computational approach; Front. Pharmacol; vol. 6; Oct. 29, 2015; pp. 1-13.

CIELAB Insighton Color; Application Notes; 8(11); 2008; 4 pages.

Dayhoff et al.; A model of evolutionary change in proteins; in Atlas of Protein Sequence and Structure; vol. 5, suppl. 3; Natl. Biomed. Res. Found., Washington, D.C.; 1978; 345-52.

Deboer et al.; The tac promoter: a functional hybrid derived from the trp and lac promoters; Proc. Natl. Acad. Sci. USA 80; 1983; 21-5.

Dembo et al.; Limit Distribution of Maximal Non-Aligned Two-Sequence Segmental Score; Ann. Prob.; 1994; 22:2022-39.

European Pharmacopoeia, 8th edition, Jul. 15, 2013.

FD (Fair Disclosure) Wire; Regeneron Pharmaceuticals Inc at BMO Biopharma Day: Spotlight on Rare Disease and Ophthalmology (Virtual)—Final; ASC Services II Media, LLC; Jun. 22, 2021 ; 8 pages.

Gish et al.; Identification of protein coding regions by database similarity search; Nature Genet.; 3; 1993; 266-72.

Global IP News—Medical Patent News; U.S. Patent and Trademark Office Releases Regeneron Pharmaceuticals's Patent Application for VEGF Traps and Mini-Traps and Methods for Treating Ocular Disorders and Cancer; ProQuest Information and Learning; Nov. 12, 2021.

Hach; Objective color assessment and quality control in the chemical, pharmaceutical and cosmetic industries; Application Report No. 3.11 e; 2016; 30 pages.

(56) References Cited

OTHER PUBLICATIONS

Hawkins et al.; Detection, identification, and quantification of oxidative protein modifications; J. Biol. Chem.; 2019; 294(51) 19683-708.
Heier et al.;Intravitreal Aflibercept (VEGF Trap-Eye) in Wet Age-related Macular Degeneration; Ophthalmology; vol. 119, No. 12; Dec. 2012; 2537-48.
Henikoff et al.; Amino acid substitution matrices from protein blocks; Proc. Natl. Acad. Sci. USA 89; Nov. 15, 1992; 10915-19.
Hossler et al.; Optimal and consistent protein glycosylation in mammalian cell culture; Glycobiology 19(9); 2009; 936-49.
International Preliminary Report on Patentability and Written Opinion issued in Application No. PCT/US2020/063238; dated May 17, 2022; 12 pages.
International Search Report and Written Opinion issued in Application No. PCT/US2020/063238; dated Mar. 29, 2021; 24 pages.
International Search Report and Written Opinion issued in Application No. PCT/US2021/031271; dated Jan. 4, 2022; 12 pages.
Karlin et al.; Applications and statistics for multiple high-scoring segments in molecular sequences; Proc. Natl. Acad. Sci. USA; 90; Jun. 15, 1993; 5873-7.
Karlin et al.; Methods for assessing the statistical significance of molecular sequence features by using general scoring schemes; Proc. Natl. Acad. Sci.USA; 87 (6); Mar. 1, 1990; 2264-8.
Leidich et al.; An Aflibercept-derived Mini-VEGF-Trap as a Potential Next-Generation VEGF Inhibitor; ARVO Annual Meeting Abstract; Jun. 2021; 2 pages.
Li et al.; Characterization of the Degradation Products of a Color-Changed Monoclonal Antibody: Tryptophan-Derived Chromophores; Anal Chem; 86; Jun. 17, 2017; 6850-7.
Li et al.; Chemical instability of protein pharmaceuticals: Mechanisms of oxidation and strategies for stabilization. Biotechnology and bioengineering, 1995, vol. 48 (5), 490-500.
Liu et al.; Predictive In Vitro Vitreous and Serum Models and Methods to Assess Thiol-Related Quality Attributes in Protein Therapeutics; Anal. Chem.; 2020, 92; 6869-76.
LUMITIN Brochure; LUMITIN: The New Choice of Anti-VEGF Treatment; 8 pages.
Perdivara et al.; Mass spectrometric identification of oxidative modifications of tryptophan residues in proteins: chemical artifact or posttranslational modification?; J Am Soc Mass Spectrom. Jul. 2010; 21(7): 1114-17.
Schoneich; Mechanisms of metal-catalyzed oxidation of histidine to 2-oxo-histidine in peptides and proteins, Journal of Pharmaceutical and Biomedical Analysis; 21; 2000; 1093-7.
US Fed News; International Patent: Regeneron Pharmaceuticals, Inc. Files Application for "VEGF Mini-Traps and Methods of Use Thereof"; HT Media Ltd.; Jun. 14, 2021; 1 page.
US Fed News; International Patent: Regeneron Pharmaceuticals, Inc. Files Application for "VEGF Traps and Mini-Traps and Methods for Treating Ocular Disorders and Cancer"; HT Media Ltd.; Mar. 10, 2022; 1 page.
Villa-Komaroff et al.; A bacterial clone synthesizing proinsulin; Proc. Natl. Acad. Sci. USA 75; 1978; 3727-31.
Wagner et al.; Nucleotide sequence of the thymidine kinase gene of herpes simplex virus type 1; Proc. Natl. Acad. Sci. USA 78; Mar. 1981; 1441-5.
Wang et al.; Simultaneous monitoring of oxidation, deamidation, isomerization, and glycosylation of monoclonal antibodies by liquid chromatography-mass spectrometry method with ultrafast tryptic digestion; MABS; 2016, vol. 8, No. 8, 1477-86.
Yu et al.; Production, characterization, and pharmacokinetic properties of antibodies with N-linked mannose-5 glycans, mAbs. Jul.-Aug. 2012;4(4):475-87.
Hunter Lab, Applications Note, CIE L*C*h Color Scale, vol. 8, No. 11 (2008).
Eylea Prescribing Information (2011).
Uchida & Kawakishi, 2-Oxo-histidine as a novel biological marker for oxidatively modified proteins, FEBS Lett, 1993 Oct 18;332(3):208-10.
Traore et al., Structural and functional characterization of 2-oxo-histidine in oxidized PerR protein, Nature Chemical Biology vol. 5, No. Jan. 1, 2009.
Liu et al., Discovery and Characterization of a Photo-Oxidative HistidineHistidine Cross-Link in IgG1 Antibody Utilizing 18O Labeling and Mass Spectrometry, Anal. Chem. 2014, 86, 4940-8.
Esther M. Yoo et al., "Human IgG2 Can Form Covalent Dimers", The Journal of Immunology, 2003, 170:3134-3138, doi: 10.4049.
Hanieh Khalili et al., "Comparative Binding of Disulfide-Bridged PEG-Fabs", Bioconjugate Chemistry, 2012, 23:2262-2277, dx.doi.org/10.1021/bc300372r.
Platania et al., Molecular features of interaction between VEGFA and anti-angiogenic drugs used in retinal diseases: a computational approach, Front Pharmacol Oct. 29, 2015, vol. 6: Article 248.
H. Khalili et al., "Fc-Fusion mimetics", Biomateerials Science, 2016, 4, 943, DOI: 10.1039/c6bm00077k.
Bastiaan L. Duivelshof et al., "Therapeutic Fc-fusion proteins: Current analytical strategies", Journal of Separation Science, 2021, 44:35-62, DOI: 10.1002/jssc.202000765.
Theo Rispens et al. "Antibodies to constant domains of therapeutic monoclonal antibodies: Angi-hinge antibodies in immunogenicity testing"; Journal of Immunological Methods 375 (2012) 93-99.
Rudge et al., VEGF Trap as a Novel Antiangiogenic Treatment Currently in Clinical Trials for Cancer and Eye Diseases, and VelociGene®-based Discovery of the Next Generation of Angiogenesis Targets (2005) CSH Symp Quant Biol, 70:411-418.
C.K. Osterland et al., "Anti-y-Globulin Factors in Human Sera Revealed by Enzymatic Splitting of Anti-Rh Antibodies", The Rockefeller Institute, New York, N. Y., Vox Sang. 8: 133-152 (1963).
Cheung et al., Poster: Intravitreal administration, but not systemic administration, of VEGF Mini-Trap effectively inhibits neovascularization in the Oxygen Induced Retinopathy (OIR) model in mice, Association for Research in Vision and Ophthalmology May 1-7, 2021.
Falkenburg et al., Anti-Hinge Antibodies Recognize IgG Subclass- and Protease-Restricted Neoepitopes, J Immunol. Jan. 1, 2017;198(1):82-93.Epub Nov. 18, 2016.
Brezski et al. (2008) Human anti-IgG1 hinge autoantibodies reconstitute the effector functions of proteolytically inactivated IgGs. J. Immunol. 181, 3183-3192.
Terness et al. (1995) The natural human IgG anti-F(ab')2 antibody recognizes a conformational IgG1 hinge epitope. J. Immunol. 154, 6446-6452.
Van Schie et al., (2015) Cross-reactive and pre-existing antibodies to therapeutic antibodies antibodies—Effects on treatment and immunogenicity. MAbs 7(4), 662-671.
Waller & Blaylock, (1966) Further studies on the anti-globulin factors in human serum to the pepsin digested fragment of the Ri anti-Rh antibody. J. Immunol. 97, 438-443.
George D. Yancopoulos et al., "Vascular-specific growth factors and blood vessel formation", 2000 Macmillan Magazines Ltd, Nature, vol. 407, Sep. 14, 2000.
Ruppel et al. (2016) Preexisting antibodies to an F(ab')2 antibody therapeutic and novel method for immunogenicity assessment. J. Immunol. Res. 2016, Article ID: 2921758 (special issue).
Kim et al., Evading pre-existing anti-hinge antibody binding by hinge engineering, MAbs, Nov./Dec. 2016;8(8):1536-1547. Epub Aug. 9, 2016.
Huang, T., et al. (2018) Molecular characterization of human anti-hinge antibodies derived from single-cell cloning of normal human B cells. J. Biol. Chem. 293, 906-919.
Leidich et al., Poster: An Aflibercept-Derived Mini-VEGF-Trap as a Potential Next-Generation VEGF Inhibitor, Association for Research in Vision and Ophthalmology May 1-7, 2021.
ARVO-2021 Abstracts.
Daly et al., "New York Inventors Develop Fusion Proteein", U.S. Fed News, Aug. 14, 2006.
Yano et al. (1995) Natural antibodies against the immunoglobulin F(ab')2 fragment cause elimination of antigens recognized by the F(ab')2 from the circulation. Eur. J. Immunol. 25, 3128-3133.

(56) References Cited

OTHER PUBLICATIONS

Ngo, in the Protein Folding Problem and Tertiary Structure prediction, Merz et al. (eds.), Birkhauser Boston; Boston, MA, pp. 433 and 492-495, 1994.
R Arshady: "Styrene based polymer supports developed by suspension polymerization" Chimica e L'Industria 70(9), 70-75 (1988).
Rudinger (in Peptide Hormones, Parsons (ed.), University Park Press: Baltimore, MD, pp. 1-7, 1976.
Shihong Li et al.,Chemical Instability of Protein Pharmaceuticals: Mechanisms of Oxidation and Strategies for Stabilization, 1995, Biotechnology and Bioengineering vol. 48:490-500.
Stellan Hjerten, "The Preparation of Agarose Spheres For Chromatography of Molecules and Particles", Biochimica Biophysica Acta 79(2), pp. 393-398 (1964).
Ultrafiltration Handbook, Munir Cheryan (Technomic Publishing, 1986; ISBN No. 87762-456-9) (BOOK).
Akira Mizoguchi et al.: "Changes in Asparagine-linked Sugar Chains of Human Promyelocytic Leukemic Cells HL-60) during Monocytoid Differentiation and Myeloid Differentiation. Appearance of High Mannose-Type Oligosaccharides in Neutral Fraction" J Biol Chem. Oct. 10, 1984;259(19):11943-8.
Alan P. Baker and Leonard M. Hillegass, Enhancement of UDP-Galactose:Mucin Galactosyltransferase Activity by Spermine, Archives of Biochemistry and Biophysics 165, pp. 597-603, 1974.
Arun Kumar Shukla et al: "Dimethylsulphoxide as a Tool to Increase Functional Expression of Heterologously Produced GPCRs in Mammalian Cells", Department of Molecular Membrane Biology, Available online Jun. 9, 2006, FEBS Letter 580 (2006) 4261-4256.
Kamilla Swiech et al: "Enhanced Production of Recombinant Rabies Virus Glycoprotein (rRVGP) by *Drosophila melanogaster* S2 cells through Control of Culture Conditions", Cytotechnolog (2008) 57:67-72 DOI 10.1007/S10616-008-91 34-3—Published online: Feb. 24, 2008.
Keen et al., "Development of a Serum-Free Culture Medium for the Large Scale Production of Recombinant Protein From a Chinese Hamster Ovary Cell Line," Cytotechnology 17: pp. 153-163, 1995.
Kyung Hwa Chang et al: "Dimethylsulfoxide and sodium butyrate enhance the production of recombinant cyclooxygenase 2 in stably transformed *Drosophila melanogaster* S2 cells", Biotechnology Letter 24: 1353-1359, 2002, Kluwer Academic Publishers.
Kyung Hwa Chang et al: "Improved Prodcution of Recombinant Tumstatin in Stably transformed Trishoplusia ni BTI Tn 5B1-4 Cells", Department of Genetic Engineering, Kyung Hee University, Republic of Korea, Protein Expression and Purification 35 (2004) 69-75.
Marie-Claire Biol-N'Garagba, Polyamine Participation in the Maturation of Glycoprotein Fucosylation, but Not Sialylation, in Rat Small Intestine, Pediatric Research, vol. 51, No. 5, 2002, pp. 625-634.
Melissa Hamm et al: "Characterization of N-Linked Glycosylation in a Monoclonal Antibody Produced in NS0 Cells Using Capillary Electrophoresis with Laser-Induced Fluorescence Detection", Pharmaceuticals (Basel). Mar. 21, 2013;6(3):393-406. doi: 10.3390/ph6030393.
Michael F Wahl et al: "Effects of Dimethyl Sulfoxide on Heavy Chain Monoclonal Antibody Production from Plant Cell Culture", Department of Chemical Engineering, Institute of Biological Chemistry Washington State University, Biotechnology Letters, vol. 17 No. 5 (May 1995) pp. 463-468.
Ricardo Gouveia et al: "Production and N-glycosylation of Recombinant Human Cell Adhesion Molecule L1 from Insect Cells using the Stable Expression System. Effect of dimethyl sulfoxide", Journal of Biotechnology, Jan. 15, 2010;145(2):130-8. doi: 10.1016/j.jbiotec.2009.10.018. Epub Nov. 14, 2009.
Sarah F Schillie et al: "Immune response of hepatitis B vaccine among persons with diabetes: a systematic review of the literature" Diabetes Care. Dec. 2012;35(12):2690-7.
Shields et al., "Lack of Fucose on Human IgG1 N-Linked Oligosaccharide Improves Binding to Human fcyRIII and Antibody-Dependent Celluar Toxicity," The Journal of Biological Chemistry, vol. 277, No. 30, pp. 26733-26740, 2002.
T. Shantha Raju and Robert E. Jordan, "Galastosylation Variations in Marketed Therapeutic Antibodies," mAbs 4:3, pp. 385-391, 2012.
Thomas Berg et al: "Purification and Characterization of Recombinant Human Lysosomal !-Mannosidase", Molecular Genetics and Metabolism 73, 18-29 (2001), DOI: 10.1006/mgme.2001.3173 available online at http:// www.idealibray.com.
Wenying Wang et al: "Gene Transcription Acceleration: Main Cause of Hepatitis B Surface Antigen Production Improvement by Dimethyl Sulfoxide in the Culture of Chinese Hamster Ovary Cells", State Key Laboratory of Bioreactor Engineering, East China University of Science and Technology, Biotechnol Bioeng. 2007; 97: 526-535.
Xia-Juan Xia et al: "Effects of inducers of differentiation on protein kinase C and CMP-N-acetylneuraminic acid: lactosylceramide sialyltransferase activities of HL-60 leukemia cells", Journal of Lipid Research, Feb. 1989;30 (2):181-8.
Xiao-Ling Li et al: "The preparation of HL-60 cells vaccine expressing BCG heat shock protein 70 and detection of its immunogenicity in vitro" Hum Vaccin Immunother. Oct. 1, 2012; 8(10): 1376-1381.
Cell Culture Catalogue BioConcept, 2004.
Anonymous: "Affinity Chromatography, vol. 1: Antibodies", GE Healthcare—Handbook, Apr. 1, 2016, XP55575328 [retrieved on Mar. 28, 2019].
Brian W. Pack et al., Modernization of Physical Appearance and Solution Color Tests Using Quantitative Tristimulus Colorimetry: Advantages, Harmonization, and Validation Strategies, J. Pharmaceutical Sci. 104: 3299-3313 (2015).
Buecheler, J.W., et al. (2018). High-throughput oxidation screen of antibody-drug conjugates by analytical protein A chromatography following IdeS digest. Journal of Pharmacy and Pharmacology. vol. 70, No. 5, pp. 625-635. Recuperado desde.
Butko Margaret et al: "Recombinant Antibody Color Resulting from Advanced Glycation End Product Modifications", Analytical Chemistry, vol. 86, No. 19, Sep. 11, 2014 (Sep. 11, 2014), pp. 9816-9823, ISSN: 0003-2700, DOI: 10.1021/ac5024099.
Darius Ghaderi et al., Production Platforms for Biotherapeutic Glycoproteins. Occurrence, impact, and challenges of non-human sialylation, Biotechnology and Genetic Engineering Review 2012, vol. 28:1, pp. 147-176.
David Reinhart et al: "Benchmarking of commercially available CHO cell culture media for antibody production", BMC Proceedings, Biomed Central Ltd, London UK, vol. 7, No. Suppl 6, Dec. 4, 2013 (Dec. 4, 2013), p. P13, SSN: 1753-6561, DOI: 10.1186/1753-6561-7-S6-P13.
Florian Krattenmacher: "Beyond chemically defined— Characterization of chemically defined cell culture medium for the cultivation of CHO cells", Dec. 1, 2019 (Dec. 1, 2019), XP055766822, Retrieved from the Internet: URL:https://pub.uni-bielefeld.de/download/2943695/2944336/FKrattenmacher 2020_Beyond ChemicallyDefinedCharacterizatio0fCDM PhD Thesis.pdf; retrieved on Jan. 10, 2021.
"K. Wenig et al: ""Structure of the streptococcal endopeptidase IdeS, acysteine proteinase with strict specificity for IgG""", Proceedings of the National Academy of Sciences, vol. 101, No. 50, Dec. 14, 2004 (Dec. 14, 2004), pp. 17371-17376".
Kim Do Yun et al: "Fed-batch CHO cell t-PA production and feed glutamine replacement to reduce ammonia production," Biotechnology Progress, Wiley-Blackwell Publishing, Inc., US, vol. 29, No. 1, Jan. 1, 2013, pp. 165-175.
Linda Switzar et al., Chapter 2, Protein digestion: An overview of the available techniques and recent developments, Journal of Proteome Research, 2013, vol. 12 (3), pp. 1067-1077.
Maeshima et al. "LC-MS/MS method development of aflibercept using Fab-selective proteolysis nSMOL technology" American Society for Mass Spectroscopy Meeting 2020, poster WP 487 (2020).
Microfiltration and Ultrafiltration—Principles and Applications, L. Zeman and A. Zydney (Marcel Dekker, Inc., New York, M.Y., 1996 (BOOK).
Natarajan Vijayasankaran et al., "Effect of Cell Culture Medium Components on Color of Formulated Monoclonal Antibody Drug

(56) References Cited

OTHER PUBLICATIONS

Substance," Biotechnology Prog. 2013, American Institute of Chemical Engineers, vol. 29, No. 5 pp. 1270-1277.

Nathan Brot and Herbert Weissbach, The biochemistry of methionine sulfoxide residues in proteins, 1982, Trends Biochem. Sci. 7: 137-139.

Nika Kruljec et al: "Alternative Affinity Ligands for Immunoglobulins," Bioconjugate Chemistry, vol. 28, No. 8, Aug. 16, 2017 (Aug. 16, 2017), pp. 2009-2030.

Novarra, S., et al. A hingeless Fc fusion system for site-specific cleavage by IdeS. MABS, 2016, 8(6):1118-1125.

Ping Xu et al: "Effects of glutamine and asparagine on recombinant antibody production using CHO-GS cell lines," Biotechnology Progress, vol. 30, No. 6, Nov. 8, 2014, pp. 1457-1468.

*Regeneron Pharmaceuticals, Inc., v. Mylan Pharmaceuticals Inc.*, Joint Claim Construction Chart, Case No. 1:22-v-00061-TSK, filed on Nov. 17, 2022, The United States District Court for the Northern District of West Virginia Clarksburg Division.

Review Report, pp. 1-63, Sep. 7, 2012, Evaluation and Administration Division, Pharmaceutical and Food Safety Bureau, Ministry of Health Labor and Welfare, [Retrieved on Oct. 19, 2022], http://www.nihs.go.jp/dbcb/reviews/Aflibercept.pdf.

Ritacco Frank V. et al: "Cell culture media for recombinant expression in Chinese hamster ovary (CHO) cells: History, key components, and optimization strategies," Biotechnology Progress, Wiley-Blackwell Publishing, Inc., US, vol. 34, No. 6, Nov. 1, 2018 (Nov. 1, 2018) pp. 1407-1426.

Rodrigues Maria Elisa et al: "Advances and Drawbacks of the Adaptation to Serum-Free Culture of CHO-K1 Cells for Monoclonal Antibody Production", Applied Biochemistry and Biotechnology, vol. 169, No. 4, Jan. 11, 2013 (Jan. 11, 2013), pp. 1279-1291, ISSN: 0273-2289, DOI: 10.1007/s12010-012-0068-z; Retrieved from the Internet:URL:http://link.springer.com/article/10.1007/s12010-012-0068-zffulltext.html.

Ryan J. Graham et al: "Consequences of trace metal variability and supplementation on Chinese hamster ovary (CHO) cell culture performance: A review of key mechanisms and considerations", Biotechnology and Bioengineering, vol. 116, No. 12, Aug. 30, 2019 (Aug. 30, 2019), pp. 3446-3456.

Shen et al. Analytical comparability assessment on glycosylation of ziv-aflibercept and biosimilar candidate, International Journal of Biological Macromolecules. Mar. 6, 2021, vol. 180. pp. 494-509. (2021).

Sivertsen et al. "Pharmaceutical compounding of aflibercept in prefilled syringes does not affect structural integrity, stability or VEGF and Fc binding properties" Scientific Reports 8:2101 (Year: 2018).

Unknown: "Antibody Affinity Resins," Sep. 28, 2018 (Sep. 28, 2018), XP055771552, Retrieved from the Internet: URL:https://www.thermofisher.com/documentconnect/document-connect.html?url=https%3A%2F%2Fassets.thermofisher.com%2FTFS-Assets%2FLSG%2Fmanuals%2FMAN0017191CapSelectAntibodyAffinityResins PI. pdf&tifle=UNJvalVjdCBJbmZvIFNoZWV00i6DVXBOdXJ1U2VsZWNOIEFudG1ib2R5IEFmZmluaXR5IFJ1c21ucw== retrieved on Feb. 2, 2021].

Unknown: "Assessment report Eylea aflibercept Procedure No. EMEA/HC/002392/," Sep. 20, 2012, retrieved From the Internet: URL:https://www.ema.europa.eu/en/documents/assessment-report/eylea-epar-public-assessment-report_en.pdf [retrieved on Jan. 18, 2021].

Wang-Gillam et al. "A phase I study of subcutaneously administered aflibercept (VEGF trap) in a new formulation in patients with advanced solid tumors" Invest. New Drugs 30:1958-1961 (Year: 2011).

Yan an et al., "A new tool for monoclonal antibody analysis: Application of IdeS proteolysis in IgG domain-specific characterization," MABS, vol. 6, No. 4, Apr. 7, 2014 (Apr. 7, 2014), pp. 879-893.

J Rodriguez et al: "Enhanced production of monomeric interferon-beta by CHO cells through the control of culture conditions" Department of Microbiology, Biotechnol Prog. Jan.-Feb. 2005;21(1)79-30. doi: 10.1021/bp049807b.

James N. Arnold et al., "The Impact of Glycosylation On the Biological Function and Structure of Human Immunoglobulins," Annu. Rev. Immunol. 2007, 25, pp. 21-50.

Jianxin Ye et al: "High-level protein expression in scalable CHO transient transfection" Biotechnol Bioeng. Jun. 15, 2009;103(3):542-51. doi: 10.1002/bit.22265.

Opinion of Dr. Ursula Kinkeldey of Sep. 6, 2019, as submitted previously in the opposition against EP 2 971 040.

Opposition to European Patent No. 2968549 (14 769 180.2) mailed Jan. 31, 2020.

Opposition to European Patent No. 2971040 (14 775 649.8) mailed Jun. 14, 2019.

Fxpert Declaration by Professor Dr. Henrik Clausen Jul. 10, 2019.

Zahra Sheikholeslami et al: "Elucidating the effects of postinduction glutamine feeding on the growth and productivity of CHO cells," Biotechnology Progress, vol. 30, No. 3, May 1, 2014 (May 1, 2014), pp. 535-546.

Kim et al., "Development of Serum-Free Medium for the Production of Humanized Antibody From Chinese Hamster Ovary Cells Using a Statistical Design," Vitro Cell. Dev. Biol.—Animal 34:7 Nov.-Dec. 1998, pp. 757-761.

Leos J. Zeman & Andrew L. Zydney, Microfiltration and ultrafiltration: principles and applications (1996) (BOOK).

Aparna S. Kolkekar et al., Peptidylglycine α-Hydroxylating Monooxygenase: Active Site Residues, Disulfide Linkages, and a Two-Domain Model of the Catalytic Core 1997, Biochemistry, 36: 10901-10909.

Chasin et al., Effect of gamma rays at the dihydrofolate reductase locus: Deletions and inversions, 1986, Somatic Cell Molecular Genetics, vol. 12 pp. 555-556.

Dafne Muller & Roland E. Kontermann, Bispecific Antibodies, Handbook of Therapeutic Antibodies 265-310 (2014).

F.L. Graham et al., Characteristics of a Human Cell Line Transformed by DNA from Human Adenovirus Type 5, Journal of General Virology, 1977, 36, pp. 59-72.

Gail Urlaub et al., Isolation of Chinese hamster cell mutants deficient in dihydrofolate reductase activity, Proceedings National Academy of Science, USA, vol. 77, No. 7, Jul. 1980, Genetics, pp. 4216-4220.

Jennie P. Mather, Culture of Testicular Cells in Hormone-Supplemented Serum-Free Medium Annals NY Academy Sciences, 1982, vol. 383; pp. 44-68.

Jennie P. Mather, Establishment and Characterization of Two Distinct Mouse Testicular Epithelial Cell Lines, Biology of Reproduction 23, 1980, pp. 243-253.

Kenneth M. Prentice et al., "Hydroxocobalamin Association During Cell Culture Results in Pink Therapeutic Proteins," mAbs 5:6, Nov./Dec. 2013; Landes Bioscience, pp. 974-981.

Sigma-Aldrich Cell Culture, Nutrient Mixture F-12 Ham Formulation, obtained from https://www.sigmaaldrich.com/life-science/cell-culture/learning-center/media-formulations/f-12-ham.printerview.html, pp. 1-6, 2023.

Liu, H.F., "Recovery and purification process development for monoclonal antibody productions recovery and purification process development for monoclonal antibody production", MAbs, LandesBioscience, vol. 2, No. 5, pp. 480-499. DOI: DOI: 10.4161/mabs.2.5.12645, 2010.

Natarajan Vijayasankaran et al., "Effect of Cell Culture Medium Additives on Color and Acidic Charge Variants of a Monoclonal Antibody," American Institute of Chemical Engineers Biotechnology Progress DOI 10.1002/btpr.2668, pp. 1-31, 2018.

Ute M. Kent, "Purification of Antibodies Using Protein A-Sepharose and FPLC," Methods in Molecular Biology, vol. 115: pp. 29-33, 1998.

Justin Bryan Goh and Say Kong Ng, "Impact of Host Cell Line Choice On Glycan Profile," Critical reviews in Biotechnology, 38:6, pp. 851-867, 2017.

Leidich, et al.; An Aflibercept-derived Mini-VEGF-Trap as a Potential Next-Generation VEGF Inhibitor. Invest. Ophthalmol; Vis. Sci.

(56) References Cited

OTHER PUBLICATIONS

2021; 62(8):204; Full Abstract e-published on Apr. 1, 2021 ARVO published through Online Planner/Program.

Cheung, et al., Intravitreal administration, but not systemic administration, of VEGF Mini-Trap effectively inhibits neovascularization in the Oxygen Induced Retinopathy (OIR) in mice; Invest. Ophthalmol. Vis. Sci. 2021; 62(8): 3293, Full Abstract e-published on Apr. 1, 2021 ARVO published through Online Planner/Program.

Khawli et al., Stable, Genetically Engineered F(ab')2 Fragments of Chimeric TNT-3 Expressed in Mammalian Cells, Hybridoma and Hybridomics 21(1): 11-18 (2002).

Leidich et al., An Aflibercept-derived Mini-VEGF-Trap as a Potential Next-Generation VEGF Inhibitor, ARVO 2021 Annual Meeting, Apr. 1, 2021—Abstract.

* cited by examiner

Figure 1

| VEGF Trap | VEGF mini Trap from IdeS cleavage | IgGs | IgG hinge amino acid sequence [//IdeS cleavage site] |
|---|---|---|---|
| REGN3 | REGN7483 | hIgG1 | DKTHTCPPCPAPELLG // GPSV (amino acids 6-25 of SEQ ID NO: 15) |
| REGN10104 | REGN10104 | hIgG1 stealth | DKTHTCPPCPAPPVA // GPSV (SEQ ID NO: 70) |
| REGN10102 | REGN10105 | hIgG2 w_2Cys | VECPPCPAPPVA // GPSV (amino acids 6-21 of SEQ ID NO: 18) |
| REGN10117 | REGN10103 | hIgG2 w_4Cys | ERKCCVECPPCPAPPVA // GPSV (amino acids 1-21 of SEQ ID NO: 18) |
| REGN10187 | REGN10187 | hIgG4 stealth | YGPPCPPCPAPPVA // GPSV (amino acids 4-21 of SEQ ID NO: 21) |
| REGN10511 | | hIgG1-2 chimera | DKTHTCPPCPAPPVA // GPSV (SEQ ID NO: 70) |
| REGN10512 | | hIgG1 Mut GGGF (SEQ ID NO: 92) | DKTHTCPPCPGGGFLG // GPSV (amino acids 6-25 of SEQ ID NO: 74) |
| REGN10513 | | hIgG1 Mut GGGG (SEQ ID NO: 93) | DKTHTCPPCPGGGGLG // GPSV (amino acids 6-25 of SEQ ID NO: 75) |
| REGN10514 | | hIgG1 mut GGGL (SEQ ID NO: 94) | DKTHTCPPCPGGGLLG // GPSV (amino acids 6-25 of SEQ ID NO: 76) |
| REGN10515 | | hIgG1 del (APE) | DKTHTCPPCPLLG // GPSV (amino acids 6-22 of SEQ ID NO: 77) |

Figure 3(A)

| Trap Mini Trap | Isotype | Common Name | Construct Descriptive name | MW (kDa) |
|---|---|---|---|---|
| REGN3 | | VEGF Trap hIgG1 Fc [Aflibercept] | Flt1 Ig Domain 2(S129-D231).hFLK1 Ig Domain 3(V226-K327).hIgG1_Fc_v2(D104-K330) | 97.18 |
| REGN7483 | Human IgG1 | Ides cleaved mini VEGF Trap hIgG1 Fc | Flt1 Ig Domain 2(S129-D231).hFLK1 Ig Domain 3(V226-K327).hFc DKTHTCPPCPAPELLG(D104-G119) ("DKTHTCPPCPAPELLG" disclosed as SEQ ID NO: 1) | 49.44 |
| REGN10104 | | VEGF Trap hIgG1 stealth Fc | Flt1 Ig Domain 2(S129-D231).hFLK1 Ig Domain 3(V226-K327).hIgG1_CH1 v1(D104-T108).hIgG2_Hinge(C106-A115).hIgG4_CH2(G117-G221).hIgG1_CH3(Q225-K330) | 96.82 |
| REGN10104 | Human IgG1 stealth | Ides cleaved mini VEGF Trap hIgG1 stealth Fc | Flt1 Ig Domain 2(S129-D231).hFLK1 Ig Domain 3(V226-K327).hIgG1 DKTHTCPPCPAPPVA ("DKTHTCPPCPAPPVA" disclosed as SEQ ID NO: 2) | |
| REGN10102 | Human IgG2 cl 2 Cys | VEGF Trap hIgG2 Fc w_2 cys | Flt1 Ig Domain 2(S129-D231).hFLK1 Ig Domain 3(V226-K327).hIgG2*01 Sapl(human) | 96.24 |

Figure 3(B)

| | | | | |
|---|---|---|---|---|
| REGN10105 | | Ides cleaved mini VEGF Trap hIgG2 Fc w_2 cys | Flt1 Ig Domain 2(S129-D231).hFLK1 Ig Domain 3(V226-K327).hIgG2_Fc w_2 cys CPPCPAPPVA(V104-A115) ("CPPCPAPPVA" disclosed as SEQ ID NO: 109) | 48.44 |
| REGN10105 | | Recombinant mini VEGF Trap hIgG2 Fc w_2 cys | | |
| REGN10117 | Human IgG2 c/ 4 Cys | VEGF Trap hIgG2 Fc w_4 cys | Flt1 Ig Domain 2(S129-D231).hFLK1 Ig Domain 3(V226-K327).hIgG2_Fc w_4 cys(E99-K326;S257A) | 97.48 |
| REGN10103 | | Ides cleaved mini VEGF Trap hIgG2 Fc w_4 cys | Flt1 Ig Domain 2(S129-D231).hFLK1 Ig Domain 3(V226-K327).hIgG2_Fc w_4 cys CPPCPAPPVA(E99-A115) ("CPPCPAPPVA" disclosed as SEQ ID NO: 109) | 49.68 |
| REGN10103 | | Recombinant mini VEGF Trap hIgG2 Fc w_4 cys | | |
| REGN10187 | Human IgG4 stealth | VEGF Trap hIgG4 stealth Fc | Flt1 Ig Domain 2(S129-D231).hFLK1 Ig Domain 3(V226-K327).hIgG4 (E99-P105)(E99-P105).hIgG2_Hinge(C106-A115).hIgG4_CH2-CH3(G117-K327) | 97.26 |
| REGN10187 | | Ides cleaved mini VEGF Trap hIgG4 stealth Fc | Flt1 Ig Domain 2(S129-D231).hFLK1 Ig Domain 3(V226-K327).hIgG4 YGPPCPPCPAPPVA ("YGPPCPPCPAPPVA" disclosed as SEQ ID NO: 115) | |
| REGN10511 | hIgG1-2 chimera | VEGF Trap hIgG1-2 Chimera Fc | Flt1 Ig Domain 2(S129-D231).hFLK1 Ig Domain 3(V226-K327).hIgG1 hinge(D102-P113)(D104- | 96.96 |

Figure 3 (C)

| | | | | |
|---|---|---|---|---|
| REGN10512 | hIgG1 mut | VEGF Trap hIgG1 Mut GGGF (SEQ ID NO: 92) Fc | Flt1 Ig Domain 2(S129-D231).hFLK1 Ig Domain 3(V226-K327).hIgG1 hinge(D102-P113)(D104-P113).hIgG2Fc (A111-K326)(A111-K326;S257A) | 97.0 |
| REGN10513 | hIgG1 mut | VEGF Trap hIgG1 Mut GGGG (SEQ ID NO: 93) Fc | Flt1 Ig Domain 2(S129-D231).hFLK1 Ig Domain 3(V226-K327).hIgG1 hinge(D102-P113)(D104-P113).hIgG2Fc (A111-K326)(A111-K326;S257A) | 96.82 |
| REGN10514 | hIgG1 mut | VEGF Trap hIgG1 Mut GGGL (SEQ ID NO: 94) Fc | Flt1 Ig Domain 2(S129-D231).hFLK1 Ig Domain 3(V226-K327).hIgG1 hinge(D102-P113)(D104-P113).GGGLLG(human).hIgG1 Fc (G120-K330) ("GGGLLG" disclosed as SEQ ID NO: 110) | 96.92 |
| REGN10515 | hIgG1 del | VEGF Trap hIgG1 Del (APE) Fc | AC14047 - Flt1 Ig Domain 2(S129-D231).hFLK1 Ig Domain 3(V226-K327).hIgG1 hinge(D102-P113)(D104-P113).hIgG1 Fc (L117-K330)(L117-K330) | 96.58 |

Figure 7(A)

1 -AFLIBERCEPT AND IdeS PROTEASE CLEAVED MINI TRAP (hIgG1)

VEGF Trap REGN3-hIgG1Fc

SDTGRPFVEM / YSEIPEIIHM / TEGRELVIPC / RVTSPNITVT / LKKFPLDTLI / PDGKRIIWDS / RKGFIISNAT / YKEIGLLTCE / ATVNGHLYKT / NYLTHRQTNT / IDWLSPSH / GIELSVGEKL / VLNCTARTEL / NVGIDFNWEY / PSSKHQHKKL / VARDLKTQSG / SEMKKFLSTL / TIDGVTRSDQ / GLYTCAASSG / LMTKKNSTFV / RVHEK / DKTHT CPPCPAPELL / GGPSVFLFPP / KPKDTLMISR / TPEVTCVVVD / VSHEDPEVKF / NWYVDGVEVH / NAKTKPREEQ / YNSTYRVVSV / LTVLHQDWLN / GKEYKCKVSN / KALPAPIEKT / ISKAKGQPRE / PQVYTLPPSR / DELTKNQVSL / TCLVKGFYPS / DIAVEWESNG / QPENNYKTTP / PVLDSDGSFF / LYSKLTVDKS / RWQQGNVFSC / SVMHEALHNH / YTQKSLSLSP / GK (SEQ ID NO: 69)

→ IdeS protease cleavage site

Mini Trap REGN7483 - generated from Fabricator cleavage of REGN3

SDTGRPFVEM / YSEIPEIIHM / TEGRELVIPC / RVTSPNITVT / LKKFPLDTLI / PDGKRIIWDS / RKGFIISNAT / YKEIGLLTCE / ATVNGHLYKT / NYLTHRQTNT / IDWLSPSH / GIELSVGEKL / VLNCTARTEL / NVGIDFNWEY / PSSKHQHKKL / VARDLKTQSG / SEMKKFLSTL / TIDGVTRSDQ / GLYTCAASSG / LMTKKNSTFV / RVHEK / DKTHT CPPCPAPELL / G (SEQ ID NO: 67)

CPPC (SEQ ID NO: 100)-core hinge

VEGFR1d2 domain
VEGFR2d3 domain
hIgG1Fc

Figure 7(B)

#2 - VEGF TRAP REGN10104 (hIgG1 STEALTH) AND IdeS PROTEASE CLEAVED MINI TRAP

VEGF Trap REGN10104 (hIgG1 stealth Fc)

SDTGRPFVEM / YSEIPEIIHM / TEGRELVIPC / RVTSPNITVT / LKKFPLDTLI / PDGKRIIWDS / RKGFIISNAT / YKEIGLLTCE
ATVNGHLYKT / NYLTHRQTNT / IDIWLSPSH - / GIELSVGEKL - VLNCTARTEL - NVGIDFNWEY - PSSKHQHKKLVARDLKTQSG
SEMKKFLSTL - TIDGVTRSDQ - GLYTCAASSG - LMTKKNSTFV - RVHEKDKTHT CPPCPAPPVA GPSVFLFPPK PKDTLMISRT
PEVTCVVVDV SQEDPEVQFN WYVDGVEVHN AKTKPREEQF NSTYRVVSVL TVLHQDWLNG KEYKCKVSNK GLPSSIEKTI
SKAKGQPREP QVYTLPPSRD ELTKNQVSLT CLVKGFYPSD IAVEWESNGQ PENNYKTTPP VLDSDGSFFL VSKLTVDKSR
WQQGNVFSCSVMHEALHNHY TQKSLSLSPGK (SEQ ID NO: 42)

↓ IdeS protease cleavage site miniTrap - generated from IdeS protease cleavage of REGN10104 (hIgG1 stealth Fc)

SDTGRPFVEM / YSEIPEIIHM / TEGRELVIPC / RVTSPNITVT / LKKFPLDTLI / PDGKRIIWDS / RKGFIISNAT / YKEIGLLTCE
ATVNGHLYKT / NYLTHRQTNT / IDIWLSPSH - / GIELSVGEKL · VLNCTARTEL · NVGIDFNWEYPSSKHQHKKL · VARDLKTQSG
SEMKKFLSTL - TIDGVTRSDQ · GLYTCAASSG · LMTKKNSTFV·RVHEKDKTHT CPPCPAPPVA (SEQ ID NO: 34)

- VEGFR1d2 domain
- VEGFR2d3 domain
- hIgG1 stealth Fc

Figure 7(C)

3 - VEGF TRAP REGN10102 (hIgG2 Cf2cys) AND IdeS PROTEASE CLEAVED MINI TRAP REGN10105

VEGF Trap REGN10102 (hIgG2 Fc w/2cys)

SDTGRPFVEM / YSEIPEIIHM / TEGRELVIPC / RVTSPNITVT / LKKFPLDTLI / PDGKRIIWDS - RKGFIISNAT / YKEIGLLTCE
ATVNGHLYKT / NYLTHRQTNT / IDWLSPSH - GIELSVGEKL - VLNCTARTEL - NVGIDFNWEY - PSSKHQHKKL-VNRDLKTQSG
SEMKKFLSTL - TIDGVTRSDQ - GLYTCAASSG - LMTKKNISTFV - RVHEKVE CPP CPAPPVAGPS / VFLFPPKPKD - TLMISRTPEV
TCVVVDVSHE - DPEVQFNWYV - DGVEVHNAKT - KPREEQFNST - FRVVSVLTVV - HQDWLNGKEY - KCKVSNKGLP - APIEKTISKT
KGQPREPQVYTLPPSREEMT KNQVSLTCLV - KGFYPSDIAV - EWESNGQPEN - NYKTTPPVMLD - SDGSFFLYSK - LTVDKSRWQQ
GNVFSCSVMH - EALHNHYTQK - SLSLSPGK (SEQ ID NO: 41)

→ IdeS protease cleavage site mini Trap REGN10105 - generated from IdeS protease cleavage of REGN10102 hIgG2 Fc w/2cys)

SDTGRPFVEM / YSEIPEIIHM / TEGRELVIPC / RVTSPNITVT / LKKFPLDTLI / PDGKRIIWDS - RKGFIISNAT / YKEIGLLTCE
ATVNGHLYKT / NYLTHRQTNT / IDWLSPSH - GIELSVGEKL - VLNCTARTEL - NVGIDFNWEYPSSKHQHKKL - VNRDLKTQSG
SEMKKFLSTL - TIDGVTRSDQ - GLYTCAASSG - LMTKKNSTFV RVHEKVE CPPPC PAPPVA (SEQ ID NO: 33)

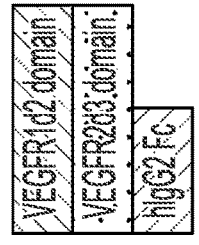

Figure 7(D)

4 - VEGF TRAP REGN10117 (hIgG2 Cl4cys) AND IdeS PROTEASE CLEAVED MINI TRAP REGN10103

VEGF Trap REGN10117 (hIgG2 Fc w/4cys)

SDTGRPFVEM / YSEIPEIIHM / TEGRELVIPC / RVTSPNITVT / LKKFPLDTLI / PDGKRIIWDS · RKGFIISNAT / YKEIGLLTCE
ATVNGHLYKT · NVLTHRQTNT / IDWLSPSH · · GIELSVGEKL · VLNCTARTEL · NVGIDFNWEY · PSSKHQHKKL · VNRDLKTQSG
SEMKKFLSTL · TIDGVTRSDQ · GLYTCAASSG · LMTKKNSTFV · RVHEKERKCC  VECPPPCPAPP  VAGPSVFLFP   PKPKDTLMIS
RTPEVTCVVV · DVSHEDPEVQ · FNWYVDGVEV · HNAKTKPREE · QFNSTFRVVS · VLTVVHQDWL · NGKEYKCKVS · NKGLPAPIEK
TISKTKGQPR · EPQVYTLPPS · REEMTKNQVS · LTCLVKGFYP · SDIAVEWESN · GQPENNYKTT · PPMLDSDGSF · FLYSKLTVDK
SRWQQGNVFS · CSVMHEALHN · HYTQKSLSLS · PGK (SEQ ID NO: 43)

→ IdeS protease cleavage site mini Trap REGN10103 - generated from IdeS protease cleavage of REGN10117 (hIgG2 Fc w/4cys)

SDTGRPFVEM / YSEIPEIIHM / TEGRELVIPC / RVTSPNITVT / LKKFPLDTLI / PDGKRIIWDS · RKGFIISNAT / YKEIGLLTCE
ATVNGHLYKT · NVLTHRQTNT / IDWLSPSH · · GIELSVGEKL · VLNCTARTEL · NVGIDFNWEY · PSSKHQHKKL · VNRDLKTQSG
SEMKKFLSTL · TIDGVTRSDQ · GLYTCAASSG · LMTKKNSTFV RVHEKERKCC  VECPPPCPAPP  VA (SEQ ID NO: 32)

VEGFR1d2 domain
VEGFR2d3 domain
hIgG2 Fc

Figure 7(E)

5 - VEGF TRAP REGN10187 (hIgG4 STEALTH) AND IdeS PROTEASE CLEAVED MINI TRAP

VEGF Trap REGN10187 (hIgG4 stealth Fc)

SDTGRPFVEM / YSEIPEIIHM / TEGRELVIPC / RVTSPNITVT / LKKFPLDTLI / PDGKRIIWDS / RKGFIISNAT / YKEIGLLTCE
ATVNGHLYKT / NYLTHRQTNT / IDWLSPSH... / GIELSVGEKL / VLNCTARTEL / NVGIDFNWEY / PSSKHQHKKL / VIRDLKTQSG
SEMKKFLSTL / TIDGVTRSDQ / ... GLYTCAASSG / LMTKKNSTFV / RVHEKEKSYG / PPCPPCPAPP / VAGPSVFLFP / PKPKDTLMIS
RTPEVTCVVV / DVSQEDPEVQ / FNWYVDGVEV / HNAKTKPREE / QFNSTFRVVS / VLTVLHQDWL / NGKEYKCKVS / NKGLPSSIEK
TISKAKGQPR / EPQVYTLPPS / QEEMTKNQVS / LTCLVKGFYP / SDIAVEWESN / GQPENNYKTT / PPVLDSDGSF / FLYSRLTVDK
SRWQEGNVFS / CSVMHEALHN / HYTQKSLSLS / LGK (SEQ ID NO: 44)

→ IdeS protease cleavage site mini Trap - generated from IdeS protease cleavage of REGN10187 (hIgG4 stealth Fc)

SDTGRPFVEM / YSEIPEIIHM / TEGRELVIPC / RVTSPNITVT / LKKFPLDTLI / PDGKRIIWDS / RKGFIISNAT / YKEIGLLTCE
ATVNGHLYKT / NYLTHRQTNT / IDWLSPSH... / GIELSVGEKL / VLNCTARTEL / NVGIDFNWEY / PSSKHQHKKL / VIRDLKTQSG
SEMKKFLSTLTIDGVTRSDQ / ... GLYTCAASSG / LMTKKNSTFV / RVHEKEKSYGPP / CPPCPAPP / VA (SEQ ID NO: 35)

VEGFR1d2.domain.
-VEGFR2d3.domain.
hIgG4.stealth.Fc

Figure 15

IgG4 with IgG2 lower hinge

Sequence of construct is boxed

Crossover identities underlined

```
                    |----- CH2 ->
IgG1   ...DKKAEPKSCD KTHTCPPCPA PELLGGPSVF LFPPKPKDTL MISRTPEVTC VVVDVSHEDP
IgG2   ...DKTVERKCC- --VECPPCPA PP-VAGPSVF LFPPKPKDTL MISRTPEVTC VVVDVSHEDP
IgG4   ...DKRVESKYGP ---PCPSCPA PEFLGGPSVF LFPPKPKDTL MISRTPEVTC VVVDVSQEDP
                             (Lower hinge)

IgG1   EVKFNWYVDG VEVHNAKTKP REEQYNSTYR VVSVLTVLHQ DWLNGKEYKC KVSNKALPAPI
IgG2   EVQFNWYVDG MEVHNAKTKP REEQFNSTFR VVSVLTVVHQ DWLNGKEYKC KVSNKGLPAPI
IgG4   EVQFNWYVDG VEVHNAKTKP REEQFNSTYR VVSVLTVLHQ DWLNGKEYKC KVSNKGLPSSI

|----- CH3 ->
IgG1   EKTISKAKG QPREPQVYTL PPSRDELTKN QVSLTCLVKG FYPSDIAVEW ESNGQPENNY
IgG2   EKTISKTKG QPREPQVYTL PPSREEMTKN QVSLTCLVKG FYPSDIAVEW ESNGQPENNY
IgG4   EKTISKAKG QPREPQVYTL PPSQEEMTKN QVSLTCLVKG FYPSDIAVEW ESNGQPENNY

IgG1   KTTPPVLDSD GSFFLYSKLT VDKSRWQQGN VFSCSVMHEA LHNHYTQKSL SLSPGK*
IgG2   KTTPPMLDSD GSFFLYSKLT VDKSRWQQGN VFSCSVMHEA LHNHYTQKSL SLSPGK*
IgG4   KTTPPVLDSD GSFFLYSRLT VDKSRWQEGN VFSCSVMHEA LHNHYTQKSL SLSLGK*
```

Figure 17

IgG1 with effectorless CH2

Sequence of construct is boxed

Crossover identities underlined

```
                         |----CH2 ->
IGG1  ...DKKAEPKSCD KTHTCPPCPA PELLGGPSVF LFPPKPFDTL MISRTPEVTC VVVDVSHEDP
IGG2  ...DKTVERKCC-  --VECPPCPA PP-VAGPSVF LFPPKPKDTL MISRTPEVTC VVVDVSHEDP
IGG4  ...DKRVESKYGP ---PCPSCPA PEFLGGPSVF LFPPKPKDTL MISRTPEVTC VVVDVSQEDP
                              (Lower hinge)

IGG1  EVKFNWYVDG VEVHNAKTKP REEQYNSTYR VVSVLTVLHQ DWLNGKEYKC KVSNKALPAPI
IGG2  EVQFNWYVDG MEVHNAKTKP REEQFNSTFR VVSVLTVVHQ DWLNGKEYKC KVSNKGLPAPI
IGG4  EVQFNWYVDG VEVHNAKTKP REEQFNSTYR VVSVLTVLHQ DWLNGKEYKC KVSNKGLPSSI

|----CH3 ->
IGG1  EKTISKAKG QPREPQVYTL PPSRDELTKN QVSLTCLVKG FYPSDIAVEW ESNGQPENNY
IGG2  EKTISKTKG QPREPQVYTL PPSREEMTKN QVSLTCLVKG FYPSDIAVEW ESNGQPENNY
IGG4  EKTISKAKG QPREPQVYTL PPSQEEMTKN QVSLTCLVKG FYPSDIAVEW ESNGQPENNY

IGG1  KTTPPVLDSD GSFFLYSKLT VDKSRWQQGN VFSCSVMHEA LHNHYTQKSL SLSPGK*
IGG2  KTTPPMLDSD GSFFLYSKLT VDKSRWQQGN VFSCSVMHEA LHNHYTQKSL SLSPGK*
IGG4  KTTPPVLDSD GSFFLYSRLT VDKSRWQEGN VFSCSVMHEA LHNHYTQKSL SLSLGK*
```

Figure 19 (C)

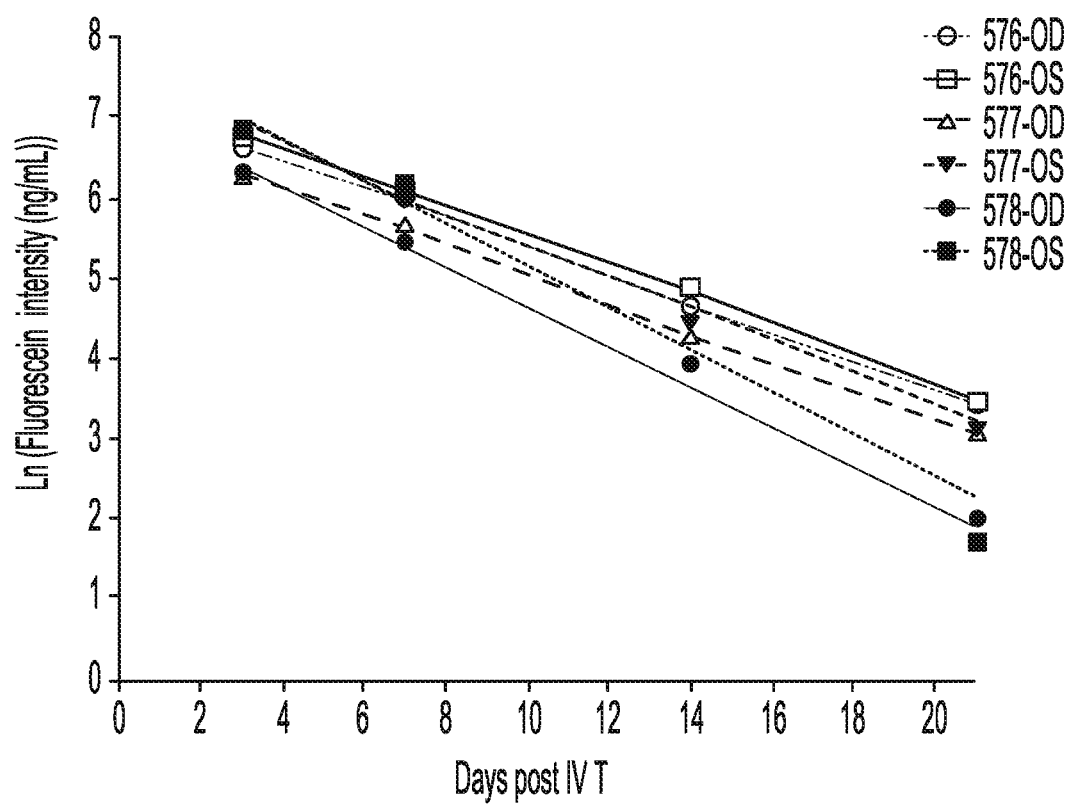

SEQUENCE LISTING

```
<160> NUMBER OF SEQ ID NOS: 116

<210> SEQ ID NO 1
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Asp Lys Thr His Thr Cys Pro Pro Cys Pro Ala Pro Glu Leu Leu Gly
1               5                   10                  15

<210> SEQ ID NO 2
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 2

Asp Lys Thr His Thr Cys Pro Pro Cys Pro Ala Pro Pro Val Ala
1               5                   10                  15

<210> SEQ ID NO 3
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Asp Lys Thr His Thr Cys Pro Pro Cys Pro Ala Pro Gly Gly Gly
1               5                   10                  15

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Glu Arg Lys Cys Cys Val Glu Cys Pro Pro Cys Pro Ala Pro Pro Val
1               5                   10                  15

Ala

<210> SEQ ID NO 5
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Val Glu Cys Pro Pro Cys Pro Ala Pro Pro Val Ala
1               5                   10

<210> SEQ ID NO 6
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Glu Pro Lys Ser Cys Asp Thr Pro Pro Cys Pro Pro Cys Pro Ala
1               5                   10                  15

Pro Glu Leu Leu Gly
            20

<210> SEQ ID NO 7
<211> LENGTH: 18
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 7

Glu Ser Lys Tyr Gly Pro Pro Cys Pro Pro Cys Pro Ala Pro Glu Phe
1               5                   10                  15

Leu Gly

<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Glu Ser Lys Tyr Gly Pro Pro Cys Pro Pro Cys Pro Ala Pro Pro Val
1               5                   10                  15

Ala

<210> SEQ ID NO 9
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Glu Ser Lys Tyr Gly Pro Pro Cys Pro Pro Cys Pro Ala Pro Gly Gly
1               5                   10                  15

Gly

<210> SEQ ID NO 10
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asp Lys Thr His Thr Cys Pro Pro Cys Pro Ala Pro Pro Val Ala
1               5                   10                  15

<210> SEQ ID NO 11
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Asp Lys Thr His Thr Cys Pro Pro Cys Pro Gly Gly Gly Phe Leu Gly
1               5                   10                  15

<210> SEQ ID NO 12
<211> LENGTH: 16
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Lys Thr His Thr Cys Pro Pro Cys Pro Gly Gly Gly Gly Leu Gly
1               5                   10                  15

<210> SEQ ID NO 13
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Asp Lys Thr His Thr Cys Pro Pro Cys Pro Gly Gly Gly Leu Leu Gly
1               5                   10                  15

<210> SEQ ID NO 14
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asp Lys Thr His Thr Cys Pro Pro Cys Pro Leu Leu Gly
1               5                   10

<210> SEQ ID NO 15
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr
        35

<210> SEQ ID NO 16
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Pro Lys Ser Cys Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30
```

Asp Thr

<210> SEQ ID NO 17
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Pro Lys Ser Cys Asp Lys Thr His Thr Cys Pro Pro Cys Pro Ala
1               5                   10                  15

Pro Gly Gly Gly Gly Pro Ser Val Phe Leu Phe Pro Pro Lys Pro Lys
            20                  25                  30

Asp Thr

<210> SEQ ID NO 18
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr
            20                  25                  30

<210> SEQ ID NO 19
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Pro Lys Ser Cys Asp Thr Pro Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr
        35

<210> SEQ ID NO 20
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Ser Lys Tyr Gly Pro Pro Cys Pro Cys Pro Ala Pro Glu Phe
1               5                   10                  15

Leu Gly Gly Pro Ser Val Phe Leu Phe Pro Pro Lys Pro Lys Asp Thr
            20                  25                  30

```
<210> SEQ ID NO 21
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr
            20                  25                  30

<210> SEQ ID NO 22
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Glu Ser Lys Tyr Gly Pro Pro Cys Pro Pro Cys Pro Ala Pro Gly Gly
1               5                   10                  15

Gly Gly Pro Ser Val Phe Leu Phe Pro Pro Lys Pro Lys Asp Thr
            20                  25                  30

<210> SEQ ID NO 23
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Gln Phe Asn Trp Tyr Val Asp Gly Val Glu Val
        35                  40                  45

His Asn Ala Lys Thr Lys Pro Arg Glu Glu Gln Phe Asn Ser Thr Phe
    50                  55                  60

Arg Val Val Ser Val Leu Thr Val Val His Gln Asp Trp Leu Asn Gly
65                  70                  75                  80

Lys Glu Tyr Lys Cys Lys Val Ser Asn Lys Gly Leu Pro Ala Pro Ile
                85                  90                  95

Glu Lys Thr Ile Ser Lys Thr Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160
```

```
Met Leu Asp Ser Asp Gly Ser Phe Phe Leu Tyr Ser Lys Leu Thr Val
            165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
            195                 200                 205

Pro Gly Lys
    210

<210> SEQ ID NO 24
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser Gln
            20                  25                  30

Glu Asp Pro Glu Val Gln Phe Asn Trp Tyr Val Asp Gly Val Glu Val
            35                  40                  45

His Asn Ala Lys Thr Lys Pro Arg Glu Glu Gln Phe Asn Ser Thr Tyr
        50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Gly Leu Pro Ser Ser Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Asp Glu Leu Thr Lys Asn Gln Val Ser
            115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Lys Leu Thr Val
            165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
            195                 200                 205

Pro Gly Lys
    210

<210> SEQ ID NO 25
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 25

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Gln Phe Asn Trp Tyr Val Asp Gly Val Glu Val
        35                  40                  45

His Asn Ala Lys Thr Lys Pro Arg Glu Glu Gln Phe Asn Ser Thr Phe
    50                  55                  60

Arg Val Val Ser Val Leu Thr Val Val His Gln Asp Trp Leu Asn Gly
65                  70                  75                  80

Lys Glu Tyr Lys Cys Lys Val Ser Asn Lys Gly Leu Pro Ala Pro Ile
                85                  90                  95

Glu Lys Thr Ile Ser Lys Thr Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Met Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Lys
    210

<210> SEQ ID NO 26
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser Gln
            20                  25                  30

Glu Asp Pro Glu Val Gln Phe Asn Trp Tyr Val Asp Gly Val Glu Val
        35                  40                  45

His Asn Ala Lys Thr Lys Pro Arg Glu Glu Gln Phe Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Gly Leu Pro Ser Ser Ile
                85                  90                  95

Glu Lys Thr Ile Ser Lys Ala Lys Gly Gln Pro Arg Glu Pro Gln Val
            100                 105                 110

```
Tyr Thr Leu Pro Pro Ser Gln Glu Met Thr Lys Asn Gln Val Ser
        115                 120                 125

Leu Thr Cys Leu Val Lys Gly Phe Tyr Pro Ser Asp Ile Ala Val Glu
        130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Arg Leu Thr Val
                165                 170                 175

Asp Lys Ser Arg Trp Gln Glu Gly Asn Val Phe Ser Cys Ser Val Met
                180                 185                 190

His Glu Ala Leu His Asn His Tyr Thr Gln Lys Ser Leu Ser Leu Ser
        195                 200                 205

Leu Gly Lys
    210

<210> SEQ ID NO 27
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Gln Phe Asn Trp Tyr Val Asp Gly Val Glu Val
        35                  40                  45

His Asn Ala Lys Thr Lys Pro Arg Glu Glu Gln Phe Asn Ser Thr Phe
    50                  55                  60

Arg Val Val Ser Val Leu Thr Val Val His Gln Asp Trp Leu Asn Gly
65                  70                  75                  80

Lys Glu Tyr Lys Cys Lys Val Ser Asn Lys Gly Leu Pro Ala Pro Ile
                85                  90                  95

Glu Lys Thr Ile Ser Lys Thr Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
        130                 135                 140

Trp Glu Ser Asn Gly Gln Pro Glu Asn Asn Tyr Lys Thr Thr Pro Pro
145                 150                 155                 160

Met Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
                180                 185                 190

His Glu Ala Leu His Asn His Tyr Thr Gln Lys Ser Leu Ser Leu Ser
        195                 200                 205

Pro Gly Lys
    210

<210> SEQ ID NO 28
<211> LENGTH: 211
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Asp Glu Leu Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Lys
    210

<210> SEQ ID NO 29
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80
```

```
Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Asp Glu Leu Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Lys
    210

<210> SEQ ID NO 30
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Asp Glu Leu Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205
```

-continued

```
Pro Gly Lys
        210

<210> SEQ ID NO 31
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
                20                  25                  30

Glu Asp Pro Glu Val Lys Phe Asn Trp Tyr Val Asp Gly Val Glu Val
            35                  40                  45

His Asn Ala Lys Thr Lys Pro Arg Glu Glu Gln Tyr Asn Ser Thr Tyr
        50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Asp Glu Leu Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Asp Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Lys
        210

<210> SEQ ID NO 32
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45
```

```
Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
                100                 105                 110

Glu Leu Ser Val Gly Glu Lys Leu Val Leu Asn Cys Thr Ala Arg Thr
                115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
                180                 185                 190

Thr Lys Lys Asn Ser Thr Phe Val Arg Val His Glu Lys Glu Arg Lys
                195                 200                 205

Cys Cys Val Glu Cys Pro Pro Cys Pro Ala Pro Val Ala
210                 215                 220
```

<210> SEQ ID NO 33
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

```
Ser Asp Thr Gly Arg Pro Phe Val Glu Met Tyr Ser Glu Ile Pro Glu
1                5                  10                  15

Ile Ile His Met Thr Glu Gly Arg Glu Leu Val Ile Pro Cys Arg Val
                 20                  25                  30

Thr Ser Pro Asn Ile Thr Val Thr Leu Lys Lys Phe Pro Leu Asp Thr
                 35                  40                  45

Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
                100                 105                 110

Glu Leu Ser Val Gly Glu Lys Leu Val Leu Asn Cys Thr Ala Arg Thr
                115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175
```

```
Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Val Glu Cys
        195                 200                 205

Pro Pro Cys Pro Ala Pro Val Ala
    210                 215

<210> SEQ ID NO 34
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Val Ala
    210                 215                 220

<210> SEQ ID NO 35
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Ser Asp Thr Gly Arg Pro Phe Val Glu Met Tyr Ser Glu Ile Pro Glu
1               5                   10                  15
```

```
Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Glu Ser Lys
            195                 200                 205

Tyr Gly Pro Pro Cys Pro Pro Cys Pro Ala Pro Val Ala
210                 215                 220

<210> SEQ ID NO 36
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
130                 135                 140
```

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Pro Val Ala
        210                 215                 220

<210> SEQ ID NO 37
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Gly Gly Gly Phe Leu Gly
        210                 215                 220

<210> SEQ ID NO 38
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Gly Gly Gly Leu Gly
    210                 215                 220
```

<210> SEQ ID NO 39
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125
```

Glu Leu Asn Val Gly Ile Asp Phe Asn Trp Glu Tyr Pro Ser Ser Lys
             130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Gly Gly Gly Leu Leu Gly
        210                 215                 220

<210> SEQ ID NO 40
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
            130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Leu Leu Gly
        210                 215

<210> SEQ ID NO 41
<211> LENGTH: 428
<212> TYPE: PRT
<213> ORGANISM: Artificial Sequence
<220> FEATURE:

-continued

```
<221> NAME/KEY: source
<223> OTHER INFORMATION: /note="Description of Artificial Sequence:
      Synthetic polypeptide"

<400> SEQUENCE: 41

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Val Glu Cys
        195                 200                 205

Pro Pro Cys Pro Ala Pro Pro Val Ala Gly Pro Ser Val Phe Leu Phe
    210                 215                 220

Pro Pro Lys Pro Lys Asp Thr Leu Met Ile Ser Arg Thr Pro Glu Val
225                 230                 235                 240

Thr Cys Val Val Val Asp Val Ser His Glu Asp Pro Glu Val Gln Phe
                245                 250                 255

Asn Trp Tyr Val Asp Gly Val Glu Val His Asn Ala Lys Thr Lys Pro
            260                 265                 270

Arg Glu Glu Gln Phe Asn Ser Thr Phe Arg Val Val Ser Val Leu Thr
        275                 280                 285

Val Val His Gln Asp Trp Leu Asn Gly Lys Glu Tyr Lys Cys Lys Val
    290                 295                 300

Ser Asn Lys Gly Leu Pro Ala Pro Ile Glu Lys Thr Ile Ser Lys Thr
305                 310                 315                 320

Lys Gly Gln Pro Arg Glu Pro Gln Val Tyr Thr Leu Pro Pro Ser Arg
                325                 330                 335

Glu Glu Met Thr Lys Asn Gln Val Ser Leu Thr Cys Leu Val Lys Gly
            340                 345                 350

Phe Tyr Pro Ser Asp Ile Ala Val Glu Trp Glu Ser Asn Gly Gln Pro
        355                 360                 365

Glu Asn Asn Tyr Lys Thr Thr Pro Pro Met Leu Asp Ser Asp Gly Ser
    370                 375                 380
```

-continued

```
Phe Phe Leu Tyr Ser Lys Leu Thr Val Asp Lys Ser Arg Trp Gln Gln
385                 390                 395                 400

Gly Asn Val Phe Ser Cys Ser Val Met His Glu Ala Leu His Asn His
            405                 410                 415

Tyr Thr Gln Lys Ser Leu Ser Leu Ser Pro Gly Lys
            420                 425

<210> SEQ ID NO 42
<211> LENGTH: 431
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Val Ala Gly Pro Ser Val
    210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser Gln Glu Asp Pro Glu
                245                 250                 255

Val Gln Phe Asn Trp Tyr Val Asp Gly Val Glu Val His Asn Ala Lys
            260                 265                 270

Thr Lys Pro Arg Glu Glu Gln Phe Asn Ser Thr Tyr Arg Val Val Ser
        275                 280                 285

Val Leu Thr Val Leu His Gln Asp Trp Leu Asn Gly Lys Glu Tyr Lys
    290                 295                 300
```

```
Cys Lys Val Ser Asn Lys Gly Leu Pro Ser Ser Ile Glu Lys Thr Ile
305                 310                 315                 320

Ser Lys Ala Lys Gly Gln Pro Arg Glu Pro Gln Val Tyr Thr Leu Pro
                325                 330                 335

Pro Ser Arg Asp Glu Leu Thr Lys Asn Gln Val Ser Leu Thr Cys Leu
                340                 345                 350

Val Lys Gly Phe Tyr Pro Ser Asp Ile Ala Val Glu Trp Glu Ser Asn
                355                 360                 365

Gly Gln Pro Glu Asn Asn Tyr Lys Thr Thr Pro Pro Val Leu Asp Ser
            370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys
            420                 425                 430

<210> SEQ ID NO 43
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
                35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
                100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
        130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Glu Arg Lys
        195                 200                 205

Cys Cys Val Glu Cys Pro Pro Cys Pro Ala Pro Pro Val Ala Gly Pro
    210                 215                 220
```

```
Ser Val Phe Leu Phe Pro Lys Pro Lys Asp Thr Leu Met Ile Ser
225                 230                 235                 240

Arg Thr Pro Glu Val Thr Cys Val Val Val Asp Val Ser His Glu Asp
            245                 250                 255

Pro Glu Val Gln Phe Asn Trp Tyr Val Asp Gly Val Glu Val His Asn
            260                 265                 270

Ala Lys Thr Lys Pro Arg Glu Glu Gln Phe Asn Ser Thr Phe Arg Val
        275                 280                 285

Val Ser Val Leu Thr Val Val His Gln Asp Trp Leu Asn Gly Lys Glu
290                 295                 300

Tyr Lys Cys Lys Val Ser Asn Lys Gly Leu Pro Ala Pro Ile Glu Lys
305                 310                 315                 320

Thr Ile Ser Lys Thr Lys Gly Gln Pro Arg Glu Pro Gln Val Tyr Thr
                325                 330                 335

Leu Pro Pro Ser Arg Glu Glu Met Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Met Leu
370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys

<210> SEQ ID NO 44
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125
```

```
Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Glu Ser Lys
        195                 200                 205

Tyr Gly Pro Pro Cys Pro Pro Cys Pro Ala Pro Val Ala Gly Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser Gln Glu Asp
                245                 250                 255

Pro Glu Val Gln Phe Asn Trp Tyr Val Asp Gly Val Glu Val His Asn
            260                 265                 270

Ala Lys Thr Lys Pro Arg Glu Glu Gln Phe Asn Ser Thr Tyr Arg Val
        275                 280                 285

Val Ser Val Leu Thr Val Leu His Gln Asp Trp Leu Asn Gly Lys Glu
    290                 295                 300

Tyr Lys Cys Lys Val Ser Asn Lys Gly Leu Pro Ser Ser Ile Glu Lys
305                 310                 315                 320

Thr Ile Ser Lys Ala Lys Gly Gln Pro Arg Glu Pro Gln Val Tyr Thr
                325                 330                 335

Leu Pro Pro Ser Gln Glu Glu Met Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Tyr Ser Arg Leu Thr Val Asp Lys
385                 390                 395                 400

Ser Arg Trp Gln Glu Gly Asn Val Phe Ser Cys Ser Val Met His Glu
                405                 410                 415

Ala Leu His Asn His Tyr Thr Gln Lys Ser Leu Ser Leu Ser Leu Gly
            420                 425                 430

Lys

<210> SEQ ID NO 45
<211> LENGTH: 431
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30
```

Thr Ser Pro Asn Ile Thr Val Thr Leu Lys Lys Phe Pro Leu Asp Thr
          35                  40                  45

Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
             100                 105                 110

Glu Leu Ser Val Gly Glu Lys Leu Val Leu Asn Cys Thr Ala Arg Thr
         115                 120                 125

Glu Leu Asn Val Gly Ile Asp Phe Asn Trp Glu Tyr Pro Ser Ser Lys
     130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Pro Val Ala Gly Pro Ser Val
    210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
                245                 250                 255

Val Gln Phe Asn Trp Tyr Val Asp Gly Val Glu Val His Asn Ala Lys
            260                 265                 270

Thr Lys Pro Arg Glu Glu Gln Phe Asn Ser Thr Phe Arg Val Val Ser
        275                 280                 285

Val Leu Thr Val Val His Gln Asp Trp Leu Asn Gly Lys Glu Tyr Lys
    290                 295                 300

Cys Lys Val Ser Asn Lys Gly Leu Pro Ala Pro Ile Glu Lys Thr Ile
305                 310                 315                 320

Ser Lys Thr Lys Gly Gln Pro Arg Glu Pro Gln Val Tyr Thr Leu Pro
                325                 330                 335

Pro Ser Arg Glu Glu Met Thr Lys Asn Gln Val Ser Leu Thr Cys Leu
            340                 345                 350

Val Lys Gly Phe Tyr Pro Ser Asp Ile Ala Val Glu Trp Glu Ser Asn
        355                 360                 365

Gly Gln Pro Glu Asn Asn Tyr Lys Thr Thr Pro Pro Met Leu Asp Ser
    370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys
            420                 425                 430

<210> SEQ ID NO 46
<211> LENGTH: 432

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Gly Gly Phe Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365
```

```
Asn Gly Gln Pro Glu Asn Asn Tyr Lys Thr Thr Pro Pro Val Leu Asp
        370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430
```

<210> SEQ ID NO 47
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Gly Gly Gly Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285
```

```
Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 48
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205
```

```
His Thr Cys Pro Pro Cys Pro Gly Gly Gly Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 49
<211> LENGTH: 429
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125
```

-continued

```
Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
                180                 185                 190

Thr Lys Lys Asn Ser Thr Phe Val Arg Val His Glu Lys Asp Lys Thr
            195                 200                 205

His Thr Cys Pro Pro Cys Pro Leu Leu Gly Gly Pro Ser Val Phe Leu
210                 215                 220

Phe Pro Pro Lys Pro Lys Asp Thr Leu Met Ile Ser Arg Thr Pro Glu
225                 230                 235                 240

Val Thr Cys Val Val Val Asp Val Ser His Glu Asp Pro Glu Val Lys
                245                 250                 255

Phe Asn Trp Tyr Val Asp Gly Val Glu Val His Asn Ala Lys Thr Lys
                260                 265                 270

Pro Arg Glu Glu Gln Tyr Asn Ser Thr Tyr Arg Val Val Ser Val Leu
            275                 280                 285

Thr Val Leu His Gln Asp Trp Leu Asn Gly Lys Glu Tyr Lys Cys Lys
290                 295                 300

Val Ser Asn Lys Ala Leu Pro Ala Pro Ile Glu Lys Thr Ile Ser Lys
305                 310                 315                 320

Ala Lys Gly Gln Pro Arg Glu Pro Gln Val Tyr Thr Leu Pro Pro Ser
                325                 330                 335

Arg Asp Glu Leu Thr Lys Asn Gln Val Ser Leu Thr Cys Leu Val Lys
                340                 345                 350

Gly Phe Tyr Pro Ser Asp Ile Ala Val Glu Trp Glu Ser Asn Gly Gln
            355                 360                 365

Pro Glu Asn Asn Tyr Lys Thr Thr Pro Pro Val Leu Asp Ser Asp Gly
370                 375                 380

Ser Phe Phe Leu Tyr Ser Lys Leu Thr Val Asp Lys Ser Arg Trp Gln
385                 390                 395                 400

Gln Gly Asn Val Phe Ser Cys Ser Val Met His Glu Ala Leu His Asn
                405                 410                 415

His Tyr Thr Gln Lys Ser Leu Ser Leu Ser Pro Gly Lys
                420                 425

<210> SEQ ID NO 50
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45
```

-continued

Thr Ser Val Trp Thr Lys Gly Val Thr Pro Pro Ala Asn Phe Thr Gln
 50                  55                  60

Gly Glu Asp Val Phe His Ala Pro Tyr Val Ala Asn Gln Gly Trp Tyr
 65                  70                  75                  80

Asp Ile Thr Lys Thr Phe Asn Gly Lys Asp Asp Leu Leu Cys Gly Ala
                 85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
        115                 120                 125

Phe Asn Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 51
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
            20                  25                  30

Ser Ala Asn Gln Glu Ile Arg Tyr Ser Glu Val Thr Pro Tyr His Val
        35                  40                  45

Thr Ser Val Trp Thr Lys Gly Val Thr Pro Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asp Gly Lys Asp Asp Leu Leu Cys Gly Ala
                85                  90                  95

Ala Thr Ala Gly Asn Met Leu His Trp Trp Phe Asp Gln Asn Lys Asp
                100                 105                 110

Gln Ile Lys Arg Tyr Leu Glu Glu His Pro Glu Lys Gln Lys Ile Asn
                115                 120                 125

Phe Asn Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
                180                 185                 190

Pro Thr Pro Val Lys Glu Gly Ser Lys Asp Pro Arg Gly Gly Ile Phe
                195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
                260                 265                 270

Ser Asn Gly Asn Leu Lys Ala Ile Tyr Val Thr Asp Ser Asp Ser Asn
                275                 280                 285

Ala Ser Ile Gly Met Lys Lys Tyr Phe Val Gly Val Asn Ser Ala Gly
                290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 52
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
                35                  40                  45

Thr Ser Val Trp Thr Lys Gly Val Thr Pro Pro Ala Asn Phe Thr Gln
         50                  55                  60

Gly Glu Asp Val Phe His Ala Pro Tyr Val Ala Asn Gln Gly Trp Tyr
 65                  70                  75                  80

Asp Ile Thr Lys Thr Phe Asn Gly Lys Asp Asp Leu Leu Cys Gly Ala
                 85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
            115                 120                 125

Phe Arg Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
            195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
            275                 280                 285

Ala Ser Ile Gly Met Lys Lys Tyr Phe Val Gly Val Asn Ser Ala Gly
290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 53
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Met Arg Lys Arg Cys Tyr Ser Thr Ser Ala Ala Val Leu Ala Ala Val
 1               5                  10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45

Thr Ser Val Trp Thr Lys Gly Val Thr Pro Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
            115                 120                 125

Phe Asn Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Leu Gly Tyr Arg Leu Ser Leu Thr Asn His Gly
            180                 185                 190

Pro Thr Pro Val Lys Glu Gly Ser Lys Asp Pro Arg Gly Gly Ile Phe
            195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
            275                 280                 285

Ala Ser Ile Gly Met Lys Lys Tyr Phe Val Gly Val Asn Ser Ala Gly
290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 54
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 54

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45

```
Thr Ser Val Trp Thr Lys Gly Val Thr Pro Pro Ala Asn Phe Thr Gln
 50                  55                  60

Gly Glu Asp Val Phe His Ala Pro Tyr Val Ala Asn Gln Gly Trp Tyr
 65                  70                  75                  80

Asp Ile Thr Lys Thr Phe Asn Gly Lys Asp Asp Leu Leu Cys Gly Ala
                 85                  90                  95

Ala Thr Ala Gly Asn Met Leu His Trp Trp Phe Asp Gln Asn Lys Asp
                100                 105                 110

Gln Ile Lys Arg Tyr Leu Glu Glu His Pro Glu Lys Gln Lys Ile Asn
                115                 120                 125

Phe Asn Gly Glu Gln Met Phe Asp Val Lys Glu Ala Ile Asp Thr Lys
                130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
                180                 185                 190

Pro Thr Pro Val Lys Glu Gly Ser Lys Asp Pro Arg Gly Gly Ile Phe
                195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
                260                 265                 270

Ser Asp Gly Asn Leu Lys Ala Ile Tyr Val Thr Asp Ser Asp Ser Asn
                275                 280                 285

Ala Ser Ile Gly Met Lys Lys Tyr Phe Val Gly Val Asn Ser Ala Gly
                290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 55
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Met Arg Lys Arg Cys Tyr Ser Thr Ser Ala Ala Val Leu Ala Ala Val
  1               5                  10                  15

Thr Leu Phe Val Leu Ser Val Asp Arg Gly Val Ile Ala Asp Ser Phe
                 20                  25                  30

Ser Ala Asn Gln Glu Ile Arg Tyr Ser Glu Val Thr Pro Tyr His Val
                 35                  40                  45
```

Thr Ser Val Trp Thr Lys Gly Val Thr Pro Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asp Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
        115                 120                 125

Phe Arg Gly Glu Gln Met Phe Asp Val Lys Glu Ala Ile Asp Thr Lys
    130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 56
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
            20                  25                  30

Ser Ala Asn Gln Glu Ile Arg Tyr Ser Glu Val Thr Pro Tyr His Val
        35                  40                  45

Thr Ser Val Trp Thr Lys Gly Val Thr Pro Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asp Gly Lys Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
            115                 120                 125

Phe Asn Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Leu Gly Tyr Arg Leu Ser Leu Thr Asn His Gly
            180                 185                 190

Pro Thr Pro Val Lys Glu Gly Ser Lys Asp Pro Arg Gly Gly Ile Phe
            195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
            275                 280                 285

Ala Ser Ile Gly Met Lys Lys Tyr Phe Val Gly Val Asn Ser Ala Gly
290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 57
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45

```
Thr Ser Val Trp Thr Lys Gly Val Thr Pro Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asp Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
        115                 120                 125

Phe Asn Gly Glu Gln Met Phe Asp Val Lys Glu Ala Ile Asp Thr Lys
    130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asp Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 58
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45
```

```
Thr Ser Val Trp Thr Lys Gly Val Thr Pro Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
        115                 120                 125

Phe Arg Gly Glu Gln Met Phe Asp Val Lys Glu Ala Ile Asp Thr Lys
    130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Leu Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 59
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45
```

Thr Ser Val Trp Thr Lys Gly Val Thr Pro Pro Ala Asn Phe Thr Gln
            50                  55                  60

Gly Glu Asp Val Phe His Ala Pro Tyr Val Ala Asn Gln Gly Trp Tyr
 65                  70                  75                  80

Asp Ile Thr Lys Thr Phe Asn Gly Lys Asp Asp Leu Leu Cys Gly Ala
                 85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
            115                 120                 125

Phe Arg Gly Glu Gln Met Phe Asp Val Lys Glu Ala Ile Asp Thr Lys
            130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
            195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
                260                 265                 270

Ser Asp Gly Asn Leu Lys Ala Ile Tyr Val Thr Asp Ser Asp Ser Asn
            275                 280                 285

Ala Ser Ile Gly Met Lys Lys Tyr Phe Val Gly Val Asn Ser Ala Gly
            290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 60
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Met Arg Lys Arg Cys Tyr Ser Thr Ser Ala Ala Val Leu Ala Ala Val
  1               5                  10                  15

Thr Leu Phe Val Leu Ser Val Asp Arg Gly Val Ile Ala Asp Ser Phe
                 20                  25                  30

Ser Ala Asn Gln Glu Ile Arg Tyr Ser Glu Val Thr Pro Tyr His Val
             35                  40                  45

```
Thr Ser Val Trp Thr Lys Gly Val Thr Pro Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
        115                 120                 125

Phe Asn Gly Glu Gln Met Phe Asp Val Lys Glu Ala Ile Asp Thr Lys
    130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Leu Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asp Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 61
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45
```

```
Thr Ser Val Trp Thr Lys Gly Val Thr Pro Pro Ala Asn Phe Thr Gln
     50                  55                  60

Gly Glu Asp Val Phe His Ala Pro Tyr Val Ala Asn Gln Gly Trp Tyr
 65                  70                  75                  80

Asp Ile Thr Lys Thr Phe Asp Gly Lys Asp Asp Leu Leu Cys Gly Ala
                 85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
        115                 120                 125

Phe Arg Gly Glu Gln Met Phe Asp Val Lys Glu Ala Ile Asp Thr Lys
    130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Leu Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 62
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Met Arg Lys Arg Cys Tyr Ser Thr Ser Ala Ala Val Leu Ala Ala Val
 1               5                  10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45
```

```
Thr Ser Val Trp Thr Lys Gly Val Thr Pro Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asp Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
        115                 120                 125

Phe Arg Gly Glu Gln Met Phe Asp Val Lys Glu Ala Ile Asp Thr Lys
    130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asp Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 63
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45
```

Thr Ser Val Trp Thr Lys Gly Val Thr Pro Pro Ala Asn Phe Thr Gln
        50                  55                  60

Gly Glu Asp Val Phe His Ala Pro Tyr Val Ala Asn Gln Gly Trp Tyr
65                  70                  75                  80

Asp Ile Thr Lys Thr Phe Asp Gly Lys Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
            115                 120                 125

Phe Asn Gly Glu Gln Met Phe Asp Val Lys Glu Ala Ile Asp Thr Lys
        130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Leu Gly Tyr Arg Leu Ser Leu Thr Asn His Gly
            180                 185                 190

Pro Thr Pro Val Lys Glu Gly Ser Lys Asp Pro Arg Gly Gly Ile Phe
            195                 200                 205

Asp Ala Val Phe Thr Arg Gly Asp Gln Ser Lys Leu Leu Thr Ser Arg
        210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asp Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
        290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 64
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45

Thr Ser Val Trp Thr Lys Gly Val Thr Pro Pro Ala Asn Phe Thr Gln
            50                  55                  60

Gly Glu Asp Val Phe His Ala Pro Tyr Val Ala Asn Gln Gly Trp Tyr
 65                  70                  75                  80

Asp Ile Thr Lys Thr Phe Asn Gly Lys Asp Asp Leu Leu Cys Gly Ala
                 85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
            115                 120                 125

Phe Arg Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Leu Gly Tyr Arg Leu Ser Leu Thr Asn His Gly
            180                 185                 190

Pro Thr Pro Val Lys Glu Gly Ser Lys Asp Pro Arg Gly Gly Ile Phe
            195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
                260                 265                 270

Ser Asp Gly Asn Leu Lys Ala Ile Tyr Val Thr Asp Ser Asp Ser Asn
            275                 280                 285

Ala Ser Ile Gly Met Lys Lys Tyr Phe Val Gly Val Asn Ser Ala Gly
            290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 65
<211> LENGTH: 339
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Met Arg Lys Arg Cys Tyr Ser Thr Ser Ala Ala Val Leu Ala Ala Val
 1               5                  10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45

Thr Ser Val Trp Thr Lys Gly Val Thr Pro Pro Ala Asn Phe Thr Gln
            50                  55                  60

Gly Glu Asp Val Phe His Ala Pro Tyr Val Ala Asn Gln Gly Trp Tyr
 65                  70                  75                  80

Asp Ile Thr Lys Thr Phe Asp Gly Lys Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
            115                 120                 125

Phe Arg Gly Glu Gln Met Phe Asp Val Lys Glu Ala Ile Asp Thr Lys
            130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Leu Gly Tyr Arg Leu Ser Leu Thr Asn His Gly
            180                 185                 190

Pro Thr Pro Val Lys Glu Gly Ser Lys Asp Pro Arg Gly Gly Ile Phe
            195                 200                 205

Asp Ala Val Phe Thr Arg Gly Asp Gln Ser Lys Leu Leu Thr Ser Arg
            210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asp Gly Asn Leu Lys Ala Ile Tyr Val Thr Asp Ser Asp Ser Asn
            275                 280                 285

Ala Ser Ile Gly Met Lys Lys Tyr Phe Val Gly Val Asn Ser Ala Gly
            290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 66
<211> LENGTH: 339
<212> TYPE: PRT
<213> ORGANISM: Streptococcus pyogenes

<400> SEQUENCE: 66

Met Arg Lys Arg Cys Tyr Ser Thr Ser Ala Ala Val Leu Ala Ala Val
 1               5                  10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45

Thr Ser Val Trp Thr Lys Gly Val Thr Pro Pro Ala Asn Phe Thr Gln
            50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
            115                 120                 125

Phe Asn Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
            195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
            275                 280                 285

Ala Ser Ile Gly Met Lys Lys Tyr Phe Val Gly Val Asn Ser Ala Gly
290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 67
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
            35                  40                  45

```
Leu Ile Pro Asp Gly Lys Arg Ile Ile Trp Asp Ser Arg Lys Gly Phe
    50                  55                  60
Ile Ile Ser Asn Ala Thr Tyr Lys Glu Ile Gly Leu Leu Thr Cys Glu
 65                  70                  75                  80
Ala Thr Val Asn Gly His Leu Tyr Lys Thr Asn Tyr Leu Thr His Arg
                 85                  90                  95
Gln Thr Asn Thr Ile Ile Asp Val Val Leu Ser Pro Ser His Gly Ile
            100                 105                 110
Glu Leu Ser Val Gly Glu Lys Leu Val Leu Asn Cys Thr Ala Arg Thr
        115                 120                 125
Glu Leu Asn Val Gly Ile Asp Phe Asn Trp Glu Tyr Pro Ser Ser Lys
    130                 135                 140
His Gln His Lys Lys Leu Val Asn Arg Asp Leu Lys Thr Gln Ser Gly
145                 150                 155                 160
Ser Glu Met Lys Lys Phe Leu Ser Thr Leu Thr Ile Asp Gly Val Thr
                165                 170                 175
Arg Ser Asp Gln Gly Leu Tyr Thr Cys Ala Ala Ser Ser Gly Leu Met
            180                 185                 190
Thr Lys Lys Asn Ser Thr Phe Val Arg Val His Glu Lys Asp Lys Thr
        195                 200                 205
His Thr Cys Pro Pro Cys Pro Ala Pro Glu Leu Leu Gly
    210                 215                 220

<210> SEQ ID NO 68
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Asp Lys Thr His Thr Cys Pro Leu Cys Pro Ala Pro Glu Leu Leu Gly
1               5                   10                  15

<210> SEQ ID NO 69
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Ser Asp Thr Gly Arg Pro Phe Val Glu Met Tyr Ser Glu Ile Pro Glu
1               5                   10                  15
Ile Ile His Met Thr Glu Gly Arg Glu Leu Val Ile Pro Cys Arg Val
             20                  25                  30
Thr Ser Pro Asn Ile Thr Val Thr Leu Lys Lys Phe Pro Leu Asp Thr
         35                  40                  45
```

Leu Ile Pro Asp Gly Lys Arg Ile Ile Trp Asp Ser Arg Lys Gly Phe
            50                   55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                    85                  90                  95

Gln Thr Asn Thr Ile Ile Asp Val Val Leu Ser Pro Ser His Gly Ile
                100                 105                 110

Glu Leu Ser Val Gly Glu Lys Leu Val Leu Asn Cys Thr Ala Arg Thr
            115                 120                 125

Glu Leu Asn Val Gly Ile Asp Phe Asn Trp Glu Tyr Pro Ser Ser Lys
        130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 70
<211> LENGTH: 19
<212> TYPE: PRT
<213> ORGANISM: Artificial Sequence
<220> FEATURE:

<220> FEATURE:
<221> NAME/KEY: source
<223> OTHER INFORMATION: /note="Description of Artificial Sequence:
      Synthetic peptide"

<400> SEQUENCE: 70

Asp Lys Thr His Thr Cys Pro Pro Cys Pro Ala Pro Pro Val Ala Gly
1               5                   10                  15

Pro Ser Val

<210> SEQ ID NO 71
<211> LENGTH: 669
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
agtgataccg gtagacctttt cgtagagatg tacagtgaaa tccccgaaat tatacacatg     60
actgaaggaa gggagctcgt cattccctgc cgggttacgt cacctaacat cactgttact    120
ttaaaaaagt ttccacttga cactttgatc cctgatggaa aacgcataat ctgggacagt    180
agaaagggct tcatcatatc aaatgcaacg tacaagaaa tagggcttct gacctgtgaa     240
gcaacagtca atgggcattt gtataagaca aactatctca cacatcgaca aaccaataca    300
atcatagatg tggttctgag tccgtctcat ggaattgaac tatctgttgg agaaaagctt    360
gtcttaaatt gtacagcaag aactgaacta aatgtgggga ttgacttcaa ctgggaatac    420
ccttcttcga agcatcagca taagaaactt gtaaaccgag acctaaaaac ccagtctggg    480
agtgagatga agaaattttt gagcacctta actatagatg gtgtaacccg gagtgaccaa    540
ggattgtaca cctgtgcagc atccagtggg ctgatgacca agaagaacag cacatttgtc    600
agggtccatg aaaaggagcg caaatgttgt gtcgagtgcc caccgtgccc agcaccacct    660
gtggcatga                                                            669

<210> SEQ ID NO 72
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72
agtgataccg gtagacctttt cgtagagatg tacagtgaaa tccccgaaat tatacacatg     60
actgaaggaa gggagctcgt cattccctgc cgggttacgt cacctaacat cactgttact    120
ttaaaaaagt ttccacttga cactttgatc cctgatggaa aacgcataat ctgggacagt    180
agaaagggct tcatcatatc aaatgcaacg tacaagaaa tagggcttct gacctgtgaa     240
gcaacagtca atgggcattt gtataagaca aactatctca cacatcgaca aaccaataca    300
atcatagatg tggttctgag tccgtctcat ggaattgaac tatctgttgg agaaaagctt    360
gtcttaaatt gtacagcaag aactgaacta aatgtgggga ttgacttcaa ctgggaatac    420
ccttcttcga agcatcagca taagaaactt gtaaaccgag acctaaaaac ccagtctggg    480
agtgagatga agaaattttt gagcacctta actatagatg gtgtaacccg gagtgaccaa    540

```
ggattgtaca cctgtgcagc atccagtggg ctgatgacca agaagaacag cacatttgtc    600
agggtccatg aaaaggtcga gtgcccaccg tgcccagcac cacctgtggc atga          654
```

<210> SEQ ID NO 73
<211> LENGTH: 666
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73

```
agtgataccg gtagaccttt cgtagagatg tacagtgaaa tccccgaaat tatacacatg     60
actgaaggaa gggagctcgt cattccctgc cgggttacgt cacctaacat cactgttact    120
ttaaaaaagt ttccacttga cactttgatc cctgatggaa aacgcataat ctgggacagt    180
agaaagggct tcatcatatc aaatgcaacg tacaaagaaa tagggcttct gacctgtgaa    240
gcaacagtca atgggcattt gtataagaca aactatctca cacatcgaca aaccaataca    300
atcatagatg tggttctgag tccgtctcat ggaattgaac tatctgttgg agaaaagctt    360
gtcttaaatt gtacagcaag aactgaacta aatgtgggga ttgacttcaa ctgggaatac    420
ccttcttcga agcatcagca taagaaactt gtaaaccgag acctaaaaac ccagtctggg    480
agtgagatga agaaattttt gagcaccttaa actatagatg gtgtaacccg gagtgaccaa    540
ggattgtaca cctgtgcagc atccagtggg ctgatgacca agaagaacag cacatttgtc    600
agggtccatg aaaaggacaa aactcacaca tgcccaccgt gcccaggcgg tggacttcta    660
gggtga                                                               666
```

<210> SEQ ID NO 74
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

```
Glu Pro Lys Ser Cys Asp Lys Thr His Thr Cys Pro Pro Cys Pro Gly
1               5                   10                  15

Gly Gly Phe Leu Gly Gly Pro Ser Val Phe Leu Phe Pro Pro Lys Pro
            20                  25                  30

Lys Asp Thr
        35
```

<210> SEQ ID NO 75
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

```
Glu Pro Lys Ser Cys Asp Lys Thr His Thr Cys Pro Pro Cys Pro Gly
1               5                   10                  15

Gly Gly Gly Leu Gly Gly Pro Ser Val Phe Leu Phe Pro Pro Lys Pro
            20                  25                  30
```

Lys Asp Thr
        35

<210> SEQ ID NO 76
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Glu Pro Lys Ser Cys Asp Lys Thr His Thr Cys Pro Pro Cys Pro Gly
1               5                   10                  15

Gly Gly Leu Leu Gly Gly Pro Ser Val Phe Leu Phe Pro Pro Lys Pro
            20                  25                  30

Lys Asp Thr
        35

<210> SEQ ID NO 77
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Glu Pro Lys Ser Cys Asp Lys Thr His Thr Cys Pro Pro Cys Pro Leu
1               5                   10                  15

Leu Gly Gly Pro Ser Val Phe Leu Phe Pro Pro Lys Pro Lys Asp Thr
            20                  25                  30

<210> SEQ ID NO 78
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

```
Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 79
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser Gln Glu
        35                  40                  45

Asp Pro Glu Val Gln Phe Asn Trp Tyr Val Asp Gly Val Glu Val His
    50                  55                  60

Asn Ala Lys Thr Lys Pro Arg Glu Glu Gln Phe Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Gly Leu Pro Ser Ser Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 80
<211> LENGTH: 228
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 81
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80
```

```
Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
            195                 200                 205

Met His Glu Ala Leu His Asn His Tyr Thr Gln Lys Ser Leu Ser Leu
        210                 215                 220

Ser Leu Gly Lys
225

<210> SEQ ID NO 82
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Gln Phe Asn Trp Tyr Val Asp Gly Val Glu Val His
    50                  55                  60

Asn Ala Lys Thr Lys Pro Arg Glu Glu Gln Phe Asn Ser Thr Phe Arg
65                  70                  75                  80

Val Val Ser Val Leu Thr Val Val His Gln Asp Trp Leu Asn Gly Lys
                85                  90                  95

Glu Tyr Lys Cys Lys Val Ser Asn Lys Gly Leu Pro Ala Pro Ile Glu
            100                 105                 110

Lys Thr Ile Ser Lys Thr Lys Gly Gln Pro Arg Glu Pro Gln Val Tyr
        115                 120                 125

Thr Leu Pro Pro Ser Arg Glu Glu Met Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Met
                165                 170                 175

Leu Asp Ser Asp Gly Ser Phe Phe Leu Tyr Ser Lys Leu Thr Val Asp
            180                 185                 190
```

```
Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
        210                 215                 220

Gly Lys
225

<210> SEQ ID NO 83
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Asp Lys Thr His Thr Cys Pro Pro Cys Pro Gly Gly Gly Phe Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 84
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 84

```
Asp Lys Thr His Thr Cys Pro Pro Cys Pro Gly Gly Gly Gly Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 85
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

```
Asp Lys Thr His Thr Cys Pro Pro Cys Pro Gly Gly Gly Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 86
<211> LENGTH: 224
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Asp Lys Thr His Thr Cys Pro Pro Cys Pro Leu Leu Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
        50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
            115                 120                 125

Pro Pro Ser Arg Asp Glu Leu Thr Lys Asn Gln Val Ser Leu Thr Cys
            130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
            195                 200                 205
```

```
Leu His Asn His Tyr Thr Gln Lys Ser Leu Ser Leu Ser Pro Gly Lys
    210                 215                 220
```

<210> SEQ ID NO 87
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

```
Asp Lys Thr His Thr Cys Pro Pro Cys Pro Pro Cys
1               5                   10
```

<210> SEQ ID NO 88
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

```
Asp Lys Thr His Thr Cys Pro Pro Cys Pro Pro Cys Pro Pro Cys
1               5                   10                  15
```

<210> SEQ ID NO 89
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

```
Asp Lys Thr His Thr Cys Pro Leu Cys Pro Ala Pro Glu Leu Leu Gly
1               5                   10                  15
```

<210> SEQ ID NO 90
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

```
Glu Leu Leu Gly
1
```

<210> SEQ ID NO 91
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

```
Ala Pro Glu Leu
1
```

```
<210> SEQ ID NO 92
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Gly Gly Phe
1

<210> SEQ ID NO 93
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Gly Gly Gly
1

<210> SEQ ID NO 94
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Gly Gly Gly Leu
1

<210> SEQ ID NO 95
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Glu Phe Leu Gly
1

<210> SEQ ID NO 96
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Pro Ser Val
1

<210> SEQ ID NO 97
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 97

Val Glu Cys Pro Pro Cys Pro Ala Pro Pro Val Ala Gly Pro Ser Val
1               5                  10                  15

<210> SEQ ID NO 98
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Glu Ser Lys Tyr
1

<210> SEQ ID NO 99
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Asp Lys Thr His Thr
1               5

<210> SEQ ID NO 100
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Cys Pro Pro Cys
1

<210> SEQ ID NO 101
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Cys Pro Ser Cys
1

<210> SEQ ID NO 102
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 102

Cys Pro Pro Cys Pro Ala Pro Glu Leu Leu Gly
1               5                   10

<210> SEQ ID NO 103
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Cys Pro Pro Cys Pro Ala Pro Gly Gly Gly
1               5                   10

<210> SEQ ID NO 104
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Cys Pro Pro Cys Pro Ala Pro Glu Phe Leu Gly
1               5                   10

<210> SEQ ID NO 105
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Cys Pro Pro Ala Pro Pro Ala Pro Pro Val Ala
1               5                   10

<210> SEQ ID NO 106
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Cys Pro Pro Ala Pro Ala Pro Pro Val Ala
1               5                   10

<210> SEQ ID NO 107
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

<400> SEQUENCE: 107

Asp Lys Thr His Thr Cys Pro Pro Cys Pro Ala Pro Glu Leu Leu Gly
1               5                   10                  15

Gly Pro Ser Val
            20

<210> SEQ ID NO 108
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Ala Pro Glu Leu Leu Gly
1               5

<210> SEQ ID NO 109
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Cys Pro Pro Cys Pro Ala Pro Pro Val Ala
1               5                   10

<210> SEQ ID NO 110
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Gly Gly Gly Leu Leu Gly
1               5

<210> SEQ ID NO 111
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Cys Pro Ser Cys Pro Ala Pro Glu Phe Leu Gly
1               5                   10

<210> SEQ ID NO 112
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

```
Asp Lys Lys Ala Glu Pro Lys Ser Cys Asp Lys Thr His Thr Cys Pro
1               5                   10                  15

Pro Cys Pro Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
130                 135                 140

Asp Glu Leu Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235
```

<210> SEQ ID NO 113
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 113

```
Asp Lys Thr Val Glu Arg Lys Cys Cys Val Glu Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Asn Trp Tyr Val
    50                  55                  60

Asp Gly Met Glu Val His Asn Ala Lys Thr Lys Pro Arg Glu Glu Gln
65                  70                  75                  80

Phe Asn Ser Thr Phe Arg Val Val Ser Val Leu Thr Val Val His Gln
                85                  90                  95

Asp Trp Leu Asn Gly Lys Glu Tyr Lys Cys Lys Val Ser Asn Lys Gly
            100                 105                 110
```

```
Leu Pro Ala Pro Ile Glu Lys Thr Ile Ser Lys Thr Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 114
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Asp Lys Arg Val Glu Ser Lys Tyr Gly Pro Pro Cys Pro Ser Cys Pro
1               5                   10                  15

Ala Pro Glu Phe Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220
```

```
Lys Ser Leu Ser Leu Ser Leu Gly Lys
225                 230
```

<210> SEQ ID NO 115
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

```
Tyr Gly Pro Pro Cys Pro Pro Cys Pro Ala Pro Pro Val Ala
1               5                   10
```

<210> SEQ ID NO 116
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Val Glu Cys
        195                 200                 205

Pro Pro Cys Pro Ala Pro Pro Val
    210                 215
```

VEGF TRAPS AND MINI-TRAPS AND METHODS FOR TREATING OCULAR DISORDERS AND CANCER

CROSS REFERENCE TO RELATED APPLICATIONS

This patent application claims priority to U.S. Provisional Application No. 63/022,178, filed May 8, 2020, the disclosure of each of which is herein incorporated by reference in its entirety.

SEQUENCE LISTING

The sequence listing of the present application is submitted electronically as an ASCII formatted sequence listing with a file name "REPLACEMENT_SL_03152023.txt", creation date of Mar. 15, 2023, and a size of 176,503 bytes. This sequence listing submitted is part of the specification and is herein incorporated by reference in its entirety.

FIELD OF THE INVENTION

The field of the present invention relates to VEGF trap and mini-trap molecules that are useful for treating cancer and angiogenic eye disorders as well as such treatment methods themselves.

BACKGROUND OF THE INVENTION

Several eye disorders are associated with pathological angiogenesis. For example, the development of age-related macular degeneration (AMD) is associated with a process called choroidal neovascularization (CNV). Leakage from the CNV causes macular edema and collection of fluid beneath the macula resulting in vision loss. Diabetic macular edema (DME) is another eye disorder with an angiogenic component. DME is the most prevalent cause of moderate vision loss in patients with diabetes and is a common complication of diabetic retinopathy, a disease affecting the blood vessels of the retina. Clinically significant DME occurs when fluid leaks into the center of the macula, the light-sensitive part of the retina responsible for sharp, direct vision. Fluid in the macula can cause severe vision loss or blindness. Yet another eye disorder associated with abnormal angiogenesis is central retinal vein occlusion (CRVO). CRVO is caused by obstruction of the central retinal vein that leads to a back-up of blood and fluid in the retina. The retina can also become ischemic, resulting in the growth of new, inappropriate blood vessels that can cause further vision loss and more serious complications. Release of vascular endothelial growth factor (VEGF) contributes to increased vascular permeability in the eye and inappropriate new vessel growth. Thus, inhibiting the angiogenic-promoting properties of VEGF is an effective strategy for treating angiogenic eye disorders.

Various VEGF inhibitors, such as the VEGF trap, Eylea (aflibercept), have been approved to treat such eye disorders. Fragments of VEGF traps, mini-traps, are also useful means by which to treat such angiogenic eye disorders. VEGF mini-traps, however, can suffer from the drawback of reactivity with anti-hinge antibodies (AHA) in the body of a patient. Such AHAs recognize the neoepitope created when C-terminal residues of an immunoglobulin Fc that has been truncated become exposed. Though AHAs have been identified in individuals with autoimmune diseases such as rheumatoid arthritis, the function of such antibodies is not well understood. Falkenburg et al., J. Immunol. 198: 82-93 (2017).

SUMMARY OF THE INVENTION

The present invention provides a VEGF mini-trap characterized by the domain structure:

[(VEGFR1 Ig2)-(VEGFR2 Ig3)]$_a$-multimerizing component (MC), or

[(VEGFR1 Ig2)-(VEGFR2 Ig3)-(VEGFR2 Ig4)]$_a$-multimerizing component (MC), wherein a=1, 2, 3, 4, 5, 6, 7, 8, 9 or 10; and
wherein the MC is a hinge region which is
an IgG1 hinge region comprising a stealth mutation (e.g., wherein residues ELLG (SEQ ID NO: 90) are mutated to PVA);
an IgG1 hinge region-IgG2 hinge region chimera (e.g., wherein the IgG1 residues ELLG (SEQ ID NO: 90) are mutated to PVA);
an IgG1 hinge region comprising an uber mutation (e.g., wherein residues ELLG (SEQ ID NO: 90) are mutated to GGG)
an IgG1 hinge region with residues APEL (SEQ ID NO: 91) mutated (e.g., mutated to GGGF (SEQ ID NO: 92), GGGG (SEQ ID NO: 93) or GGGL (SEQ ID NO: 94));
an IgG1 hinge with an APE residue deletion;
an IgG2 hinge region (e.g., with two or four cysteines which can form disulfide bridges);
an IgG3 hinge region;
an IgG4 hinge region;
an IgG4 hinge region comprising a stealth mutation (e.g., wherein IgG4 hinge residues EFLG (SEQ ID NO: 95) are mutated to PVA); or
an IgG4 hinge region comprising an uber mutation (e.g., wherein residues EFLG (SEQ ID NO: 95) are mutated to GGG)
e.g., wherein the hinge region comprises, consists of or consists essentially of the amino acid sequence:
DKTHTCPPCPAPPVA (SEQ ID NO: 2) (see VEGF mini-trap hIgG1 stealth Fc);
DKTHTCPPCPAPGGG (SEQ ID NO: 3) (see VEGF mini-trap hIgG1 uber Fc);
ERKCCVECPPCPAPPVA (SEQ ID NO: 4) (see VEGF mini-trap hIgG2 Fc w/4 Cys);
VECPPCPAPPVA (SEQ ID NO: 5) (see VEGF mini-trap hIgG2 Fc w/2 Cys);

(SEQ ID NO: 6)
EPKSCDTPPPCPPCPAPELLG or amino acids 6-21 thereof) (see VEGF mini-trap hIgG3 Fc);

(SEQ ID NO: 7)
ESKYGPPCPPCPAPEFLG or amino acids 4-18 thereof) (see VEGF mini-trap hIgG4 Fc);

(SEQ ID NO: 8)
ESKYGPPCPPCPAPPVA or amino acids 4-17 thereof) (see VEGF mini-trap hIgG4 stealth Fc);

ESKYGPPCPPCPAPGGG (SEQ ID NO: 9)

or amino acids 4-17 thereof) (see VEGF mini-trap hIgG4 uber Fc);
DKTHTCPPCPAPPVA (SEQ ID NO: 10) (see VEGF mini-trap hIgG1-2 Chimera Fc);
DKTHTCPPCPGGGFLG (SEQ ID NO: 11) (see VEGF mini-trap hIgG1 Mut GGGF (SEQ ID NO: 92) FC),
DKTHTCPPCPGGGGLG (SEQ ID NO: 12) (see VEGF mini-trap hIgG1 Mut GGGG (SEQ ID NO: 93) FC),
DKTHTCPPCPGGGLLG (SEQ ID NO: 13) (see VEGF mini-trap hIgG1 Mut GGGL (SEQ ID NO: 94) FC),
DKTHTCPPCPLLG (SEQ ID NO: 14) (see VEGF mini-trap hIgG1 Del (APE) Fc); or
DKTHTCPLCPAPELLG (SEQ ID NO: 68); or
any of SEQ ID Nos: 15-22 or 74-77 up to, but not including, the GPSV (SEQ ID NO: 96) IdeS cleavage site as set forth in FIG. 2.

The present invent also provides a VEGF trap characterized by the domain structure

[(VEGFR1 Ig2)-(VEGFR2 Ig3)]$_a$-multimerizing component (MC), or

[(VEGFR1 Ig2)-(VEGFR2 Ig3)-(VEGFR2 Ig4)]$_a$-multimerizing component (MC), wherein a=1, 2, 3, 4, 5, 6, 7, 8, 9 or 10; and
wherein the MC includes a hinge region and a protease cleavage site which is
- an IgG1 hinge region comprising a stealth mutation;
- an IgG1 hinge region-IgG2 hinge region chimera;
- an IgG1 hinge region with residues APEL (SEQ ID NO: 91) mutated (e.g., to GGGF (SEQ ID NO: 92), GGGG (SEQ ID NO: 93) or GGGL (SEQ ID NO: 94));
- an IgG1 hinge region with APE residues deleted;
- an IgG2 hinge region (e.g., including two or four cysteine residues that may form disulfide bridges);
- an IgG3 hinge region;
- an IgG4 hinge region; or
- an IgG4 hinge region comprising a stealth mutation;

e.g., wherein the MC includes the amino acid sequence:

EPKSCDKTHTCPPCPAPPVAGPSVFLFPPKPKDT, (SEQ ID NO: 16)

or a variant thereof) or amino acids 6-24 thereof (see VEGF trap hIgG1 stealth Fc);

EPKSCDKTHTCPPCPAPGGGGPSVFLFPPKPKDT, (SEQ ID NO: 17)

or a variant thereof) or amino acids 6-24 thereof (see VEGF trap hIgG1 uber Fc);

ERKCCVECPPCPAPPVAGPSVFLFPPKPKDT, (SEQ ID NO: 18)

or a variant thereof) or amino acids 1-21 or 6-21 (VECPPCPAPPVAGPSV (SEQ ID NO: 97)) thereof (see VEGF trap hIgG2 Fc w/2Cys or w/4Cys);

EPKSCDTPPPCPPCPAPELLGGPSVFLFPPKPKDT, (SEQ ID NO: 19)

or a variant thereof) or amino acids 6-25 thereof (see VEGF trap hIgG3 Fc);

ESKYGPPCPPCPAPEFLGGPSVFLFPPKPKDT, (SEQ ID NO: 20)

or a variant thereof) or amino acids 1-22 thereof (see VEGF trap hIgG4 Fc);

ESKYGPPCPPCPAPPVAGPSVFLFPPKPKDT, (SEQ ID NO: 21)

or a variant thereof) or amino acids 1-21 thereof (see VEGF trap hIgG4 stealth Fc);

ESKYGPPCPPCPAPGGGGPSVFLFPPKPKDT, (SEQ ID NO: 22)

or a variant thereof) or amino acids 1-21 thereof (see VEGF trap hIgG4 uber Fc);
DKTHTCPPCPAPPVAGPSV (SEQ ID NO: 70) (see VEGF trap hIgG1 stealth Fc or hIgG1-2 chimera Fc);
DKTHTCPPCPGGGFLGGPSV (amino acids 6-25 of SEQ ID NO: 74) (see VEGF trap hIgG1 mut GGGF (SEQ ID NO: 92) Fc);
DKTHTCPPCPGGGGLGGPSV (amino acids 6-25 of SEQ ID NO: 75) (see VEGF trap hIgG1 mut GGGG (SEQ ID NO: 93) Fc);
DKTHTCPPCPGGGLLGGPSV (amino acids 6-25 of SEQ ID NO: 76) (see VEGF trap hIgG1 mut GGGL (SEQ ID NO: 94) Fc); or
DKTHTCPPCPLLGGPSV (amino acids 6-22 of SEQ ID NO: 77) (see VEGF trap hIgG1 Del (APE) Fc).

In an embodiment of the invention, any of the VEGF traps or mini-traps set forth herein are characterized by any one or more of the following:
- Binds to human VEGF$_{165}$ with a K$_D$ of about 1-2 pM or a greater affinity at 25° C. wherein said affinity was measured by surface plasmon resonance;
- Has a homodimer molecular weight of less than 97 kDa (e.g., about 50 kDa, 49 kDa, 48 kDa, 47 kDa or 46 kDa; or less than any of the foregoing weights);
- Has an IC$_{50}$ of about $1-2\times10^{-11}$ M for blocking VEGF$_{121}$ and/or VEGF$_{165}$ activation of VEGFR1 and/or VEGFR2 as measured in HEK293 cells expressing the VEGF receptor extracellular domain fused to the intracellular domain of IL18Ralpha or IL18R beta and having an NFkappaB-luciferase-IRES-eGFP reporter gene;
- Exhibits less immunogenicity in monkey naïve serum samples and/or human AMD/DME baseline serum samples than that of REGN7483 (SDTGRPFVEMY-SEIPEIIHMTEGRELVIPCRVT-SPNITVTLKKFPLDTLIPDGKRIIWDSRKGFIIS-NATY KEIGLLTCEATVNGHLYKTNYLTHRQTNTI-IDVVLSP-SHGIELSVGEKLVLNCTARTELNVGIDFNWEYPS SKHQHKKLVNRDLKTQSGSEMKKFLSTLTI-DGVTRSDQGLYTCAASSGLMTKKN-STFVRVHEKDKTHTCPP CPAPELLG (SEQ ID NO: 67)) as measured by anti-drug antibody (ADA) assay;
- Forms a 1:1 complex with VEGF$_{165}$ homodimer;

Forms a 1:1:2 complex with $VEGF_{165}$ homodimer and an anti-VEGF Fab fragment (VEGF mini-trap:$VEGF_{165}$ homodimer: Fab fragment);

Reduces retinal neovascularization when dosed intravitreally in an Oxygen Induced Retinopathy (OIR) mouse model;

Exhibits a shorter intravitreal half-live than aflibercept in rabbit eyes when intravitreally injected;

Exhibits lower plasma levels of free molecule when injected intravitreally at 5.5 mg/eye, than aflibercept injected intravitreally at 4 mg/eye in a non-human primate;

Exhibits about 0.1 or 0.2 or 0.1-0.2 micrograms/ml (or less) concentration of free molecule in the plasma of a non-human primate about 336 hours after intravitreal injection of about 5.5 mg/eye;

Does not significantly accumulate in the eye of a non-human primate after four intravitreal injections about every 28 days of about 5.5 mg/eye.

In a composition comprising VEGF traps and/or VEGF mini-trap, such molecules are glycosylated with one or more fucose residues (e.g., about 43-45%), galactose residues (e.g., about 64-72%), sialic acid residues (e.g., about 20-27%), high mannose residues (e.g., Man5) (e.g., about 19-25%) and/or bisecting glycans (e.g., about 1.6-1.9%; i.e., N-glycan having an N-acetyl glucosamine between two regular branches, see e.g., FIG. 26(A)).

One or more histidines are oxidized to 2-oxo-histidine.
One or more tryptophans are deoxidated.
One or more asparagines thereof are glycosylated.
One more serines or threonines are O-glycosylated,
One or more asparagines are deamidated.
One or more Aspartate-Glycine motifs are converted to iso-aspartate-glycine and/or
Asn-Gly.
One or more methionines are oxidized.
One or more tryptophans are converted to N-formylkynurenin.
One or more arginines are converted to Arg 3-deoxyglucosone.
The C-terminal residue is not present.
There are one or more non-glycosylated glycosites.
Is xylosylated.
Is glycated at a lysine.
Comprises a cystine with a free-thiol group.
Comprises an intrachain disulfide bridge.
Comprises disulfide bridges in parallel or crossed orientation; and/or
Comprises a lysine or arginine which is carboxymethylated.

In an embodiment of the invention, the MC of any of the VEGF traps comprise the amino acid sequence:

(SEQ ID NO: 23)
GPSVFLFPPKPKDTLMISRTPEVTCVVVDVSHEDPEVQFNWYVDGVEVHN

AKTKPREEQFNSTFRVVSVLTVVHQDWLNGKEYKCKVSNKGLPAPIEKTI

SKTKGQPREPQVYTLPPSREEMTKNQVSLTCLVKGFYPSDIAVEWESNGQ

PENNYKTTPPMLDSDGSFFLYSKLTVDKSRWQQGNVFSCSVMHEALHNHY

TQKSLSLSPGK;

(SEQ ID NO: 24)
GPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTI

SKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHY

TQKSLSLSPGK;

(SEQ ID NO: 25)
GPSVFLFPPKPKDTLMISRTPEVTCVVVDVSHEDPEVQFNWYVDGVEVHN

AKTKPREEQFNSTFRVVSVLTVVHQDWLNGKEYKCKVSNKGLPAPIEKTI

SKTKGQPREPQVYTLPPSREEMTKNQVSLTCLVKGFYPSDIAVEWESNGQ

PENNYKTTPPMLDSDGSFFLYSKLTVDKSRWQQGNVFSCSVMHEALHNHY

TQKSLSLSPGK;

(SEQ ID NO: 26)
GPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTI

SKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHY

TQKSLSLSLGK;

(SEQ ID NO: 27)
GPSVFLFPPKPKDTLMISRTPEVTCVVVDVSHEDPEVQFNWYVDGVEVHN

AKTKPREEQFNSTFRVVSVLTVVHQDWLNGKEYKCKVSNKGLPAPIEKTI

SKTKGQPREPQVYTLPPSREEMTKNQVSLTCLVKGFYPSDIAVEWESNGQ

PENNYKTTPPMLDSDGSFFLYSKLTVDKSRWQQGNVFSCSVMHEALHNHY

TQKSLSLSPGK;

(SEQ ID NO: 28)
GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHY

TQKSLSLSPGK;

(SEQ ID NO: 29)
GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHY

TQKSLSLSPGK;

(SEQ ID NO: 30)
GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHY

TQKSLSLSPGK;

(SEQ ID NO: 31)
GPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHY

TQKSLSLSPGK;

(SEQ ID NO: 78)
VECPPCPAPPVAGPSVFLFPPKPKDTLMISRTPEVTCVVVDVSHEDPEVQ
FNWYVDGVEVHNAKTKPREEQFNSTFRVVSVLTVVHQDWLNGKEYKCKVS
NKGLPAPIEKTISKTKGQPREPQVYTLPPSREEMTKNQVSLTCLVKGFYP
SDIAVEWESNGQPENNYKTTPPMLDSDGSFFLYSKLTVDKSRWQQGNVFS
CSVMHEALHNHYTQKSLSLSPGK;

(SEQ ID NO: 79)
DKTHTCPPCPAPPVAGPSVFLFPPKPKDTLMISRTPEVTCVVVDVSQEDP
EVQFNWYVDGVEVHNAKTKPREEQFNSTYRVVSVLTVLHQDWLNGKEYKC
KVSNKGLPSSIEKTISKAKGQPREPQVYTLPPSRDELTKNQVSLTCLVKG
FYPSDIAVEWESNGQPENNYKTTPPVLDSDGSFFLYSKLTVDKSRWQQGN
VFSCSVMHEALHNHYTQKSLSLSPGK;

(SEQ ID NO: 80)
ERKCCVECPPCPAPPVAGPSVFLFPPKPKDTLMISRTPEVTCVVVDVSHE
DPEVQFNWYVDGVEVHNAKTKPREEQFNSTFRVVSVLTVVHQDWLNGKEY
KCKVSNKGLPAPIEKTISKTKGQPREPQVYTLPPSREEMTKNQVSLTCLV
KGFYPSDIAVEWESNGQPENNYKTTPPMLDSDGSFFLYSKLTVDKSRWQQ
GNVFSCSVMHEALHNHYTQKSLSLSPGK;

(SEQ ID NO: 81)
ESKYGPPCPPCPAPPVAGPSVFLFPPKPKDTLMISRTPEVTCVVVDVSQE
DPEVQFNWYVDGVEVHNAKTKPREEQFNSTYRVVSVLTVLHQDWLNGKEY
KCKVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSRWQE
GNVFSCSVMHEALHNHYTQKSLSLSLGK;

(SEQ ID NO: 82)
DKTHTCPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDIAVEWESNGQPENNYKTTPPMLDSDGSFFLYSKLTVDKSRWQQGN
VFSCSVMHEALHNHYTQKSLSLSPGK;

(SEQ ID NO: 83)
DKTHTCPPCPGGGFLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK;

(SEQ ID NO: 84)
DKTHTCPPCPGGGGLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK;

(SEQ ID NO: 85)
DKTHTCPPCPGGGLLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK;
or (SEQ ID NO: 86)
DKTHTCPPCPLLGGPSVFLFPPKPKDTLMISRTPEVTCVVVDVSHEDPEV
KFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVF
SCSVMHEALHNHYTQKSLSLSPGK.

In an embodiment of the invention, a VEGF mini-trap comprises the amino acid sequence:

(SEQ ID NO: 32)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDFNWEYPSSKHQHKKL
VNRDLKTQSGSEMKKELSTLTIDGVTRSDQGLYTCAASSGLMTKKNSTEV
RVHEKERKCCVECPPCPAPPVA;

(SEQ ID NO: 33)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKVECPPCPAPPVA;

(SEQ ID NO: 34)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKDKTHTCPPCPAPPVA;

(SEQ ID NO: 35)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKESKYGPPCPPCPAPPVA;

(SEQ ID NO: 36)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL

-continued

```
VNRDLKTQSGSEMKKELSTLTIDGVTRSDQGLYTCAASSGLMTKKNSTEV
RVHEKDKTHTCPPCPAPPVA;

(SEQ ID NO: 37)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKDKTHTCPPCPGGGFLG;

(SEQ ID NO: 38)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKDKTHTCPPCPGGGGLG;

(SEQ ID NO: 39)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKDKTHTCPPCPGGGLLG;
or
                                          (SEQ ID NO: 40)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKDKTHTCPPCPLLG.
```

In an embodiment of the invention, a VEGF Trap comprises the amino acid sequence:

```
                                          (SEQ ID NO: 41)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKVECPPCPAPPVAGPSVFLEPPKPKDTLMISRTPEVTCVVVDVSHE
DPEVQFNWYVDGVEVHNAKTKPREEQFNSTFRVVSVLTVVHQDWLNGKEY
KCKVSNKGLPAPIEKTISKTKGQPREPQVYTLPPSREEMTKNQVSLTCLV
KGFYPSDIAVEWESNGQPENNYKTTPPMLDSDGSFFLYSKLTVDKSRWQQ
GNVFSCSVMHEALHNHYTQKSLSLSPGK;

(SEQ ID NO: 42)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKDKTHTCPPCPAPPVAGPSVFLEPPKPKDTLMISRTPEVTCVVVDV
SQEDPEVQFNWYVDGVEVHNAKTKPREEQFNSTYRVVSVLTVLHQDWLNG
KEYKCKVSNKGLPSSIEKTISKAKGQPREPQVYTLPPSRDELTKNQVSLT
CLVKGFYPSDIAVEWESNGQPENNYKTTPPVLDSDGSFELYSKLTVDKSR
WQQGNVESCSVMHEALHNHYTQKSLSLSPGK;

(SEQ ID NO: 43)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKERKCCVECPPCPAPPVAGPSVFLEPPKPKDTLMISRTPEVTCVVV
DVSHEDPEVQFNWYVDGVEVHNAKTKPREEQFNSTFRVVSVLTVVHQDWL
NGKEYKCKVSNKGLPAPIEKTISKTKGQPREPQVYTLPPSREEMTKNQVS
LTCLVKGFYPSDIAVEWESNGQPENNYKTTPPMLDSDGSFELYSKLTVDK
SRWQQGNVESCSVMHEALHNHYTQKSLSLSPGK;

(SEQ ID NO: 44)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKESKYGPPCPPCPAPPVAGPSVFLEPPKPKDTLMISRTPEVTCVVV
DVSQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQVS
LTCLVKGFYPSDIAVEWESNGQPENNYKTTPPVLDSDGSFELYSRLTVDK
SRWQEGNVESCSVMHEALHNHYTQKSLSLSLGK;

(SEQ ID NO: 45)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKDKTHTCPPCPAPPVAGPSVFLEPPKPKDTLMISRTPEVTCVVVDV
SHEDPEVQFNWYVDGVEVHNAKTKPREEQFNSTFRVVSVLTVVHQDWLNG
KEYKCKVSNKGLPAPIEKTISKTKGQPREPQVYTLPPSREEMTKNQVSLT
CLVKGFYPSDIAVEWESNGQPENNYKTTPPMLDSDGSFELYSKLTVDKSR
WQQGNVESCSVMHEALHNHYTQKSLSLSPGK;

(SEQ ID NO: 46)
SDTGRPFVEMYSEIPEIIHMTEGRELVIPCRVTSPNITVTLKKFPLDTLI
PDGKRIIWDSRKGFIISNATYKEIGLLTCEATVNGHLYKTNYLTHRQTNT
IIDVVLSPSHGIELSVGEKLVLNCTARTELNVGIDENWEYPSSKHQHKKL
VNRDLKTQSGSEMKKELSTLTIDGVTRSDQGLYTCAASSGLMTKKNSTEV
RVHEKDKTHTCPPCPGGGFLGGPSVFLEPPKPKDTLMISRTPEVTCVVVD
VSHEDPEVKFNWYVDGVEVHNAKTKPREEQYNSTYRVVSVLTVLHQDWLN
```

-continued
GKEYKCKVSNKALPAPIEKTISKAKGQPREPQVYTLPPSRDELTKNQVSL

TCLVKGFYPSDIAVEWESNGQPENNYKTTPPVLDSDGSFELYSKLTVDKS

RWQQGNVESCSVMHEALHNHYTQKSLSLSPGK;

(SEQ ID NO: 47)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDENWEYPSSKHQHKKL

VNRDLKTQSGSEMKKELSTLTIDGVTRSDQGLYTCAASSGLMTKKNSTEV

RVHEKDKTHTCPPCPGGGLGGPSVFLEPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFELYSKLTVDKS

RWQQGNVESCSVMHEALHNHYTQKSLSLSPGK;

(SEQ ID NO: 48)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDENWEYPSSKHQHKKL

VNRDLKTQSGSEMKKELSTLTIDGVTRSDQGLYTCAASSGLMTKKNSTEV

RVHEKDKTHTCPPCPGGGLLGGPSVFLEPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFELYSKLTVDKS

RWQQGNVESCSVMHEALHNHYTQKSLSLSPGK;
or (SEQ ID NO: 49)
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDENWEYPSSKHQHKKL

VNRDLKTQSGSEMKKELSTLTIDGVTRSDQGLYTCAASSGLMTKKNSTEV

RVHEKDKTHTCPPCPLLGGPSVFLEPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVESCSVMHEALHNHYTQKSLSLSPGK.

In an embodiment of the invention, the VEGF trap or VEGF mini-trap is glycosylated, e.g., wherein said VEGF trap or VEGF mini-trap comprises N-linked glycans; said VEGF trap or VEGF mini-trap comprises O-linked glycans; said VEGF trap or VEGF mini-trap is sialylated, galactosylated and/or fusosylated at one or more residues; said VEGF trap or VEGF mini-trap comprises N-linked mannose-5 glycans (Man5) at one or more residues; and/or said VEGF trap or VEGF mini-trap comprises CHO cell glycosylation. The scope of the present invention includes a composition comprising a heterogeneous mixture of glycosylated variants of the VEGF trap or VEGF mini-trap set forth herein. For example, in an embodiment of the invention, about 47% of the VEGF traps or VEGF mini-traps are sialylated, about 70% of the VEGF traps or VEGF mini-traps are galactosylated, about 36% of the VEGF traps or VEGF mini-traps are fucosylated and/or about 11% of the VEGF traps or VEGF mini-traps are Man-5 glycosylated.

The present invention also includes a complex comprising the VEGF trap or mini-trap homodimer (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515) and VEGF; e.g., wherein VEGF is human VEGF such as human $VEGF_{165}$ or $VEGF_{121}$; and/or the complex includes an anti-VEGF antibody or Fab fragment thereof, e.g., which includes human VEGF and an anti-VEGF Fab fragment wherein the stoichiometric ratio is 1:1:2 (VEGF mini-trap: human VEGF: Fab); and/or wherein the complex is between VEGF mini-trap and VEGF and the stoichiometric ratio of VEGF mini-trap-to-VEGF is 1:1.

The present invention provides a pharmaceutical formulation (e.g., an aqueous pharmaceutical formulation) comprising a VEGF trap or VEGF mini-trap of the present invention (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515) and a pharmaceutically effective carrier.

The present invention also provides an isolated polynucleotide that encodes a VEGF trap or VEGF mini-trap of the present invention (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515), for example, SEQ ID NO: 71, 72 or 73; as well as vectors that include the polynucleotide.

The present invention also provides a host cell comprising the polynucleotide or vector of the present invention (e.g., a Chinese hamster ovary cell).

The present invention further provides an isolated polypeptide comprising, consisting or consisting essentially an amino acid sequence selected from the group consisting of SEQ ID Nos: 32-49.

The present invention also provides a vessel or injection device (e.g., syringe, a disposable syringe or a pre-filled syringe), e.g., which is sterile, comprising a VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515) or pharmaceutical formulation thereof of the present invention.

The present invention also provides a method for making a VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515) or pharmaceutical formulation thereof comprising contacting a VEGF trap of the present invention with a protease (e.g., IdeS, e.g., comprising the amino acid sequence of any of SEQ ID NOs: 50-65) that cleaves the MC of said VEGF trap and incubating the VEGF trap and protease under conditions that promotes cleavage, and, optionally, combining the VEGF mini-trap product of the cleavage with a pharmaceutically effective carrier.

The present invention also provides a method for making a VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515) or pharmaceutical formulation thereof comprising incubating a host cell containing a polynucleotide encoding the VEGF trap or VEGF mini-trap or a vector thereof in a culture medium under conditions that promote expression of the trap or mini-trap and, optionally, isolating the trap or mini-trap from the host cell and/or medium and, optionally, combining the VEGF trap or VEGF mini-trap product of the cleavage with a pharmaceutically effective carrier. Optionally, the method includes the step of contacting the VEGF trap with a protease that cleaves the MC of said VEGF trap and incubating the VEGF trap and protease under conditions that promotes cleavage. A VEGF trap or VEGF mini-trap that is the product of such a method also forms part of the present invention.

The present invention also provides a method for treating or preventing an angiogenic eye disorder (e.g., age-related macular degeneration, wet age-related macular degeneration, dry age-related macular degeneration, macular edema, macular edema following retinal vein occlusion, retinal vein occlusion (RVO), central retinal vein occlusion (CRVO), branch retinal vein occlusion (BRVO), retinopathy of prematurity (ROP), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, diabetic retinopathy in a subject with diabetic macular edema; diabetic retinopathy, non-proliferative diabetic retinopathy, and/or proliferative diabetic retinopathy), in a subject (e.g., a human), comprising administering (e.g., intraocularly or intravitreally) a therapeutically effective amount of VEGF trap or VEGF mini-trap of the present invention (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515) to the subject. In an embodiment of the invention, neovascularization of the retina is reduced in the subject's eye and/or vascular permeability of the retina is reduced in the subject's eye.

The present invention also provides a method for treating or preventing cancer (e.g., lung cancer, breast cancer, colorectal cancer, metastatic colorectal cancer, prostate cancer, skin cancer or stomach cancer), in a subject (e.g., a human), comprising administering (e.g., intravenously) a therapeutically effective amount of VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515) to the subject.

The present invention also provides a method for administering a VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515) or pharmaceutical formulation thereof of the present invention, to a subject (e.g., a human), comprising introducing (e.g., by injection, e.g., intravitreal injection) the VEGF trap or VEGF mini-trap or pharmaceutical formulation into the body of the subject.

The present invention also includes a method for reducing neovascularization of the retina and/or vascular permeability of the retina of a subject comprising administering a therapeutically effective amount of VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; and/or mREGN10515) or pharmaceutical formulation thereof as set forth herein to the subject.

The present invention encompasses any of the VEGF traps or mini-traps consisting of an amino acid sequence set forth herein except further including 1, 2, 3, 4, 5, 6, 7, 8, 9 or 10 (e.g., up to 10) additional amino acids, e.g., at the N-terminal or C-terminal end; as well as any of the related methods of use thereof.

BRIEF DESCRIPTION OF THE FIGURES

FIG. 1. Summary of VEGF traps and mini-traps with IgG hinge amino acids shown [//=IdeS cleavage site]. VEGF mini-trap from IdeS cleavage refers to the mini-trap generated by IdeS cleavage of the indicated VEGF trap. IgGs includes information concerning the form of IgG in the multimerizing component of the trap or mini-trap.

FIG. 3. Summary of VEGF traps and mini-traps with common and descriptive names and molecular weights indicated.

FIG. 15. Sequence of IgG4 with IgG2 lower hinge region sequence. Sequence of construct is boxed. IgG4/2 hybrid VEGF traps possessing an MC with the IgG2 boxed hinge sequence as shown in the figure (or starting at the IgG4 ESKY (SEQ ID NO: 98) motif) and mini-traps thereof (cleaved before the GPSV (SEQ ID NO: 96)) are part of the present invention. Figure discloses SEQ ID NOS 112-114, respectively, in order of appearance.

FIG. 17. Sequence of IgG1 with effectorless CH2 sequence. IgG1/2 hybrid VEGF traps possessing an MC with the IgG2 boxed hinge sequence as shown in the figure (or starting at the IgG1 DKTHT (SEQ ID NO: 99) motif) and mini-traps thereof (cleaved before the GPSV (SEQ ID NO: 96)) are part of the present invention. Figure discloses SEQ ID NOS 112-114, respectively, in order of appearance.

DETAILED DESCRIPTION OF THE INVENTION

The present invention provides VEGF traps and VEGF mini-traps which, relative to other mini-traps, exhibit superior stability and low viscosity—particularly at high concentrations. Such characteristics make the VEGF traps and mini-traps well suited for formulation at a high concentration which, in turn, facilitates high doses in a low volume and, thus, less frequent dosing. The anatomy and physiology of the eye makes it undesirable to inject a large volume intravitreally; thus, intravitreal injections should be done at a volume of no more than about 100 microliters. This combination of factors makes development of protein-based drugs, useful for intravitreal injection of a sufficient amount in a suitable volume, technically challenging. Maximizing the amount of drug delivered, so as to minimize the number of doses needed over a given time period, is an even greater challenge. The traps and mini-traps provided herein have overcome these technical hurdles.

The viscosity of aqueous compositions including VEGF mini-traps set forth herein, such as REGN10105, is low even relative to other VEGF mini-traps. The low viscosity allows intravitreal administration with higher gauge needles which minimizes patient discomfort and increases patient compliance.

Moreover, the VEGF mini-traps set forth herein, e.g., REGN10105 and REGN11095, exhibit greater stability (lower formation of high molecular weight species) than aflibercept under accelerated conditions. REGN10105 is also particularly photostability relative to other VEGF mini-traps such as REGN7483.

The level of potential systemic exposure following intravitreal administration of a VEGF mini-trap set forth herein, e.g., REGN10105, is also lower than that of aflibercept. Specifically, the half-life in the rabbit vitreous of REGN10105 is shorter leading to less likelihood of clearance from the eye into the rest of the body.

The VEGF mini-traps set forth herein, characterized, in vitro, as having less reactivity with pre-existing anti-hinge antibodies, have less potential for immunogenic reactions, when administered. For example, a VEGF mini-trap with an IgG2-based Fc hinge region lacks the PEL and T residues in IgG1-based Fc hinge regions (such as in REGN7483) that may be reactive with pre-existing anti-hinge antibodies.

VEGF Traps are VEGF receptor-based chimeric molecules which include two or more immunoglobulin (Ig)-like domains of a VEGF receptor such as VEGFR1 (also referred to as Flt1) (e.g., Ig2 domain of VEGFR1 (VEGFR1d2)) and/or VEGFR2 (also referred to as Flk1 or KDR) (e.g., Ig3 domain of VEGFR2 (VEGFR2d3)), preferably arranged as [(VEGFR1d2)-(VEGFR2d3)]$_n$ (e.g., wherein n=1) on each polypeptide chain of the VEGF trap, and also contain an Fc domain which facilitates the multimerization (e.g., dimerization) of two or more chimeric polypeptides).

Figure 2:
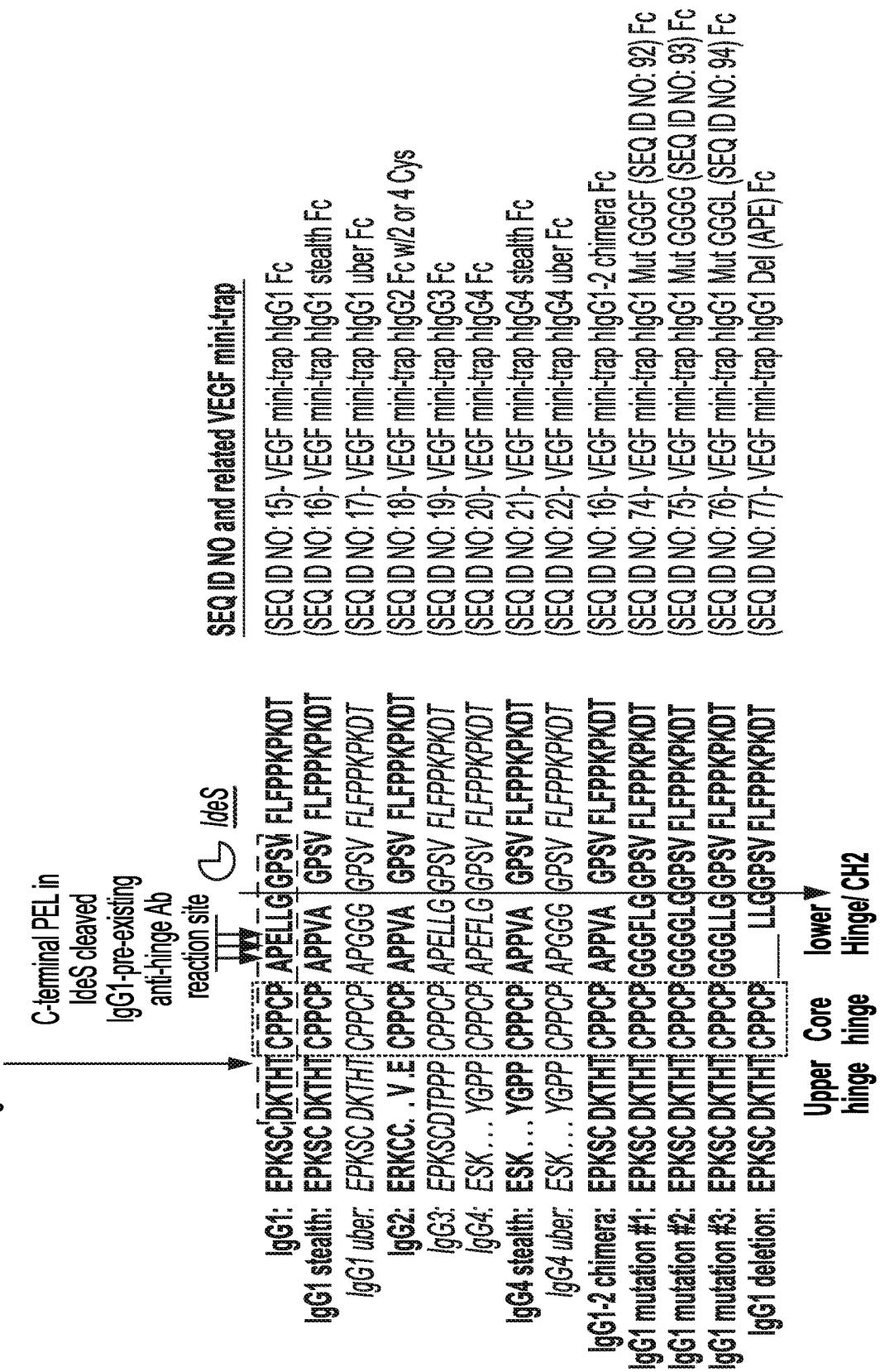
FIG. 2. VEGF Trap hinge region sequences with IdeS cleavage sites indicated. The location of residues in the Fc hinge region of an IgG1 (PEL and T) that may be reactive with pre-existing anti-hinge antibodies in the serum of a patient are indicated with arrows. Lower, core and upper hinge region residues are indicated with box. (SEQ ID Nos: 15-22, 16, 74-77, respectively)
Figure 4:
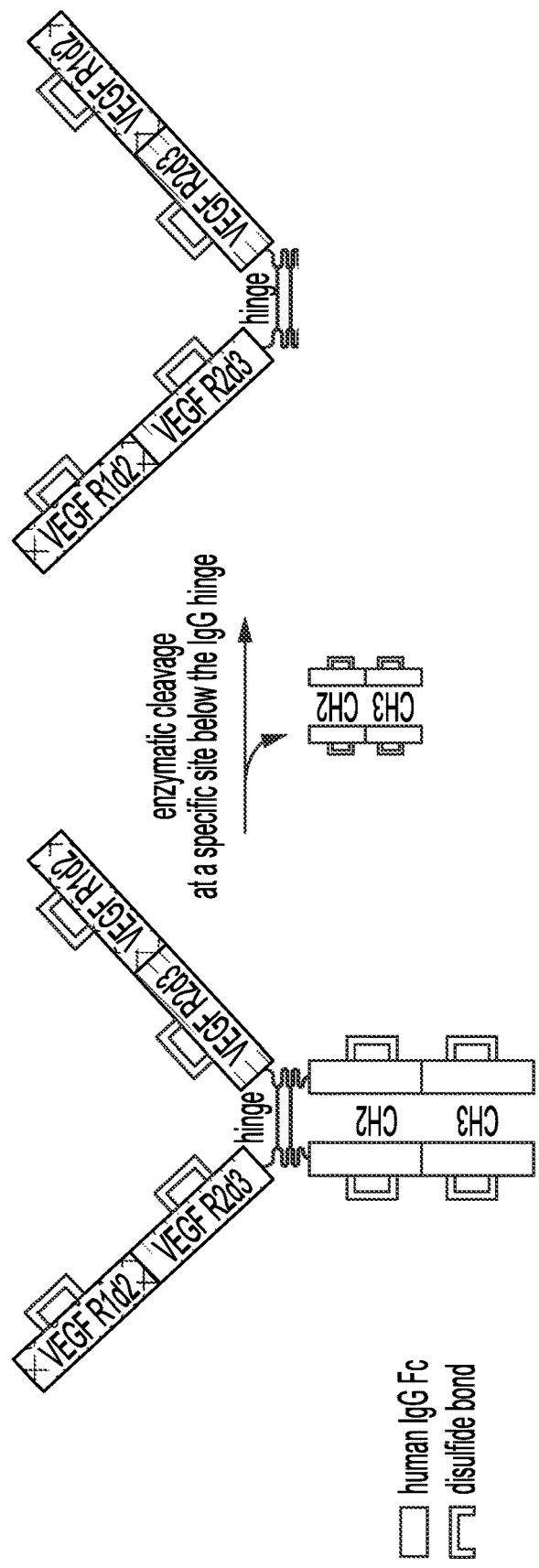
FIG. 4. Schematic representation of typical VEGF mini-trap formation resulting from IdeS cleavage of VEGF trap.

A VEGF mini-trap includes VEGF binding domains (e.g., VEGFR1 Ig domain 2 and VEGFR2 Ig domain 3, arranged in a manner similar to that of VEGF trap such as aflibercept) linked to a fragment of an Fc domain, preferably, the hinge region of the Fc domain (e.g., including the upper hinge region (sometimes beginning with a E-(P, S, or R)-K motif), the core hinge region and the lower hinge region), extending up to, but not including, the GPSV (SEQ ID NO: 96) cleavage site for IdeS protease (see e.g., FIG. 2). The hinge region preferably includes one or more (e.g., 2 or 4) cysteines that can form a cysteine bridge with another VEGF mini-trap polypeptide chain. Preferably, VEGF traps and mini-traps are homodimeric complexes of such polypeptides. VEGF traps and mini-traps may also be in composition including heterogeneous populations of such monomer polypeptides and homodimers. Such monomers, multimers and compositions form part of the present invention. The polypeptide homodimers can be bound together, for example, via disulfide bridges. A schematic of a VEGF trap and a VEGF mini-trap are set forth in FIG. 4.

The "Ig" domain of a VEGFR refers to the indicated immunoglobulin-like domain of the indicated VEGF receptor.

Standard methods in molecular biology are described Sambrook, Fritsch and Maniatis (1982 & 1989 $2^{nd}$ Edition, 2001 $3^{rd}$ Edition) Molecular Cloning, A Laboratory Manual, Cold Spring Harbor Laboratory Press, Cold Spring Harbor, N.Y.; Sambrook and Russell (2001) Molecular Cloning, $3^{rd}$ ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

General methods for protein purification including immunoprecipitation, chromatography, electrophoresis, centrifugation, and crystallization are described (Coligan et al. (2000) Current Protocols in Protein Science, Vol. 1, John Wiley and Sons, Inc., New York). Chemical analysis, chemical modification, post-translational modification, production of fusion proteins, glycosylation of proteins are described (see e.g., Coligan et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, N.Y., pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan et al. (2001) Current Protcols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan et al. (2001) Current Protocols in Immunology, Vol. 4, John Wiley, Inc., New York).

Methods for flow cytometry, including fluorescence activated cell sorting (FACS), are available (see, e.g., Owens et al. (1994) Flow Cytometry Principles for Clinical Laboratory Practice, John Wiley and Sons, Hoboken, N.J.; Givan (2001) Flow Cytometry, $2^{nd}$ ed.; Wiley-Liss, Hoboken, N.J.; Shapiro (2003) Practical Flow Cytometry, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see e.g., Muller-Harmelink (ed.) (1986) Human Thymus: Histopathology and Pathology, Springer Verlag, New York, N.Y.; Hiatt et al. (2000) Color Atlas of Histology, Lippincott, Williams, and Wilkins, Phila, Pa.; Louis et al. (2002) Basic Histology: Text and Atlas, McGraw-Hill, New York, N.Y.).

VEGF Mini-Traps and VEGF Traps

The VEGF mini-traps of the present invention exhibit superior VEGF neutralizing activity along with low immunogenicity and viscosity and high stability. Moreover, the VEGF Traps of the present invention are well suited for generation of such VEGF mini-traps insofar as they are cleavable with a protease such as IdeS protease (e.g., *Streptococcus pyogenes* IdeS).

The present invention provides VEGF mini-traps that comprise the following domain structure:

[(VEGFR1 Ig2)-(VEGFR2 Ig3)]$_a$-multimerizing component (MC), or

[(VEGFR1 Ig2)-(VEGFR2 Ig3)-(VEGFR2 Ig4)]$_a$-multimerizing component (MC), wherein a=1, 2, 3, 4, 5, 6, 7, 8, 9 or 10; and wherein the MC is a hinge region which is
- an IgG1 hinge region comprising a stealth mutation (e.g., wherein residues ELLG (SEQ ID NO: 90) are mutated to PVA);
- an IgG1 hinge region comprising an uber mutation (e.g., wherein residues ELLG (SEQ ID NO: 90) are mutated to GGG)
- an IgG1 hinge region-IgG2 hinge region chimera (e.g., wherein the IgG1 residues ELLG (SEQ ID NO: 90) are mutated to PVA);
- an IgG1 hinge region with residues APEL (SEQ ID NO: 91) mutated (e.g., mutated to GGGF (SEQ ID NO: 92), GGGG (SEQ ID NO: 93) or GGGL (SEQ ID NO: 94)),
- an IgG1 hinge with an APE residue deletion;
- an IgG2 hinge region (e.g., with two or four cysteines which can form disulfide bridges);
- an IgG3 hinge region;
- an IgG4 hinge region;
- an IgG4 hinge region comprising a stealth mutation (e.g., wherein IgG4 hinge residues EFLG (SEQ ID NO: 95) are mutated to PVA);
- an IgG4 hinge region comprising an uber mutation (e.g., wherein residues EFLG (SEQ ID NO: 95) are mutated to GGG) or
- the hinge region containing product of IdeS proteolytic cleavage of a human Fc; and multimers (e.g., homodimers) thereof.

In an embodiment of the invention, the VEGF mini-trap hinge region comprises, or consists essentially of, or consists of the amino acid sequence:
DKTHTCPPCPAPPVA (SEQ ID NO: 2) (see VEGF mini-trap hIgG1 stealth Fc);
DKTHTCPPCPAPGGG (SEQ ID NO: 3) (see VEGF mini-trap hIgG1 uber Fc);
ERKCCVECPPCPAPPVA (SEQ ID NO: 4) (see VEGF mini-trap hIgG2 Fc w/4 Cys);
VECPPCPAPPVA (SEQ ID NO: 5) (see VEGF mini-trap hIgG2 Fc w/2 Cys);

EPKSCDTPPPCPPCPAPELLG (SEQ ID NO: 6)

or amino acids 6-21 thereof (underscored)) (see VEGF mini-trap hIgG3 Fc);

ESKYGPPCPPCPAPEFLG (SEQ ID NO: 7)

or amino acids 4-18 thereof (underscored)) (see VEGF mini-trap hIgG4 Fc);

ESKYGPPCPPCPAPPVA (SEQ ID NO: 8)

or amino acids 4-18 thereof (underscored)) (see VEGF mini-trap hIgG4 stealth Fc);

ESKYGPPCPPCPAPGGG (SEQ ID NO: 9)

or amino acids 4-17 thereof (underscored)) (see VEGF mini-trap hIgG4 uber Fc);
DKTHTCPPCPAPPVA (SEQ ID NO: 10) (see VEGF mini-trap hIgG1-2 Chimera Fc);
DKTHTCPPCPGGGFLG (SEQ ID NO: 11) (see VEGF mini-trap hIgG1 Mut GGGF (SEQ ID NO: 92) FC);
DKTHTCPPCPGGGGLG (SEQ ID NO: 12) (see VEGF mini-trap hIgG1 Mut GGGG (SEQ ID NO: 93) FC);
DKTHTCPPCPGGGLLG (SEQ ID NO: 13) (see VEGF mini-trap hIgG1 Mut GGGL (SEQ ID NO: 94) FC),
DKTHTCPPCPLLG (SEQ ID NO: 14) (see VEGF mini-trap hIgG1 Del (APE) Fc); or
DKTHTCPLCPAPELLG (SEQ ID NO: 68).
or
the hinge region of any of the MCs set forth herein (e.g., any of SEQ ID NOs: 78-86) or any of those set forth in any of FIG. 1, 2, 3 5, 6, 7 or 13-17.

The IgG hinge region of aflibercept (REGN3) and REGN7483 comprise the amino acid sequence: DKTHTCPPCPAPELLG (SEQ ID NO: 1). In an embodiment of the invention, VEGF mini-traps and VEGF traps defined herein are with the proviso that the hinge region of the MC of aflibercept and/or the hinge region of REGN7483 is/are excluded.

The present invention also includes VEGF traps that comprise the following domain structure:

[(VEGFR1 Ig2)-(VEGFR2 Ig3)]$_a$-multimerizing component (MC), or

[(VEGFR1 Ig2)-(VEGFR2 Ig3)-(VEGFR2 Ig4)]$_a$-multimerizing component (MC), wherein a=1, 2, 3, 4, 5, 6, 7, 8, 9 or 10; and
wherein the MC is an immunoglobulin Fc polypeptide that includes a hinge region and a cleavage site for a protease such as IdeS (but, in an embodiment of the invention, the Fc is not wild-type human IgG1). In an embodiment of the invention the VEGF trap MC is a human Fc that includes:
- an IgG1 hinge region comprising a stealth or uber mutation;
- an IgG1 hinge region-IgG2 hinge region chimera;
- an IgG1 hinge region with residues APEL (SEQ ID NO: 91) mutated (e.g., mutated to GGGF (SEQ ID NO: 92), GGGG (SEQ ID NO: 93) or GGGL (SEQ ID NO: 94));
- an IgG1 APE residue deletion;
- an IgG2 hinge region (e.g., with two or four cysteines which can form disulfide bridges);
- an IgG3 hinge region;

an IgG4 hinge region;
an IgG4 hinge region comprising a stealth or uber mutation;
or
any of the MCs set forth herein.

In an embodiment of the invention, the VEGF trap MC includes the amino acid sequence (wherein \/ is an IdeS protease cleavage site):

(SEQ ID NO: 16)
EPKSCDKTHTCPPCPAPPVA˅GPSVFLFPPKPKDT, or a variant thereof) or amino acids 6-24 thereof (see VEGF trap hIgG1 stealth Fc);

(SEQ ID NO: 17)
EPKSCDKTHTCPPCPAPGGG˅GPSVFLFPPKPKDT, or a variant thereof) or amino acids 6-24 thereof (see VEGF trap hIgG1 uber Fc);

(SEQ ID NO: 18)
ERKCCVECPPCPAPPVA˅GPSVFLFPPKPKDT, or a variant thereof) or amino acids 1-21 or 6-21 (VECPPCPAPPVA\/GPSV (SEQ ID NO: 97)) thereof (see VEGF trap hIgG2 Fc w/2Cys or w/4Cys);

(SEQ ID NO: 19)
EPKSCDTPPPCPPCPAPELLG˅GPSVFLFPPKPKDT, or a variant thereof) or amino acids 6-25 thereof (see VEGF trap hIgG3 Fc);

(SEQ ID NO: 20)
ESKYGPPCPPCPAPEFLG˅GPSVFLFPPKPKDT, or a variant thereof) or amino acids 1-22 thereof (see VEGF trap hIgG4 Fc);

(SEQ ID NO: 21)
ESKYGPPCPPCPAPPVA˅GPSVFLFPPKPKDT, or a variant thereof) or amino acids 1-21 thereof (see VEGF trap hIgG4 stealth Fc);

(SEQ ID NO: 22)
ESKYGPPCPPCPAPGGG˅GPSVFLFPPKPKDT, or a variant thereof) or amino acids 1-21 thereof (see VEGF trap hIgG4 uber Fc);
DKTHTCPPCPAPPVA\/GPSV (SEQ ID NO: 70) (see VEGF trap hIgG1 stealth Fc or hIgG1-2 chimera Fc);
DKTHTCPPCPGGGFLG\/GPSV (amino acids 6-25 of SEQ ID NO: 74) (see VEGF trap hIgG1 mut GGGF (SEQ ID NO: 92) Fc);
DKTHTCPPCPGGGGLG\/GPSV (amino acids 6-25 of SEQ ID NO: 75) (see VEGF trap hIgG1 mut GGGG (SEQ ID NO: 93) Fc);
DKTHTCPPCPGGGLLG\/GPSV (amino acids 6-25 of SEQ ID NO: 76) (see VEGF trap hIgG1 mut GGGL (SEQ ID NO: 94) Fc); or
DKTHTCPPCPLLG\/GPSV (amino acids 6-22 of SEQ ID NO: 77) (see VEGF trap hIgG1 Del (APE) Fc).
See e.g., FIG. 2.

In an embodiment of the invention, the VEGF trap MC comprises the amino acid sequence:

(SEQ ID NO: 23)
GPSVFLFPPKPKDTLMISRTPEVTCVVVDVSHEDPEVQFNWYVDGVEVH
NAKTKPREEQFNSTFRVVSVLTVVHQDWLNGKEYKCKVSNKGLPAPIEK
TISKTKGQPREPQVYTLPPSREEMTKNQVSLTCLVKGFYPSDIAVEWES
NGQPENNYKTTPPMLDSDGSFFLYSKLTVDKSRWQQGNVFSCSVMHEAL
HNHYTQKSLSLSPGK;

(SEQ ID NO: 24)
GPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEK
TISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEAL
HNHYTQKSLSLSPGK;

(SEQ ID NO: 25)
GPSVFLFPPKPKDTLMISRTPEVTCVVVDVSHEDPEVQFNWYVDGVEVH
NAKTKPREEQFNSTFRVVSVLTVVHQDWLNGKEYKCKVSNKGLPAPIEK
TISKTKGQPREPQVYTLPPSREEMTKNQVSLTCLVKGFYPSDIAVEWES
NGQPENNYKTTPPMLDSDGSFFLYSKLTVDKSRWQQGNVFSCSVMHEAL
HNHYTQKSLSLSPGK;

(SEQ ID NO: 26)
GPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEAL
HNHYTQKSLSLSLGK;

(SEQ ID NO: 27)
GPSVFLFPPKPKDTLMISRTPEVTCVVVDVSHEDPEVQFNWYVDGVEVH
NAKTKPREEQFNSTFRVVSVLTVVHQDWLNGKEYKCKVSNKGLPAPIEK
TISKTKGQPREPQVYTLPPSREEMTKNQVSLTCLVKGFYPSDIAVEWES
NGQPENNYKTTPPMLDSDGSFFLYSKLTVDKSRWQQGNVFSCSVMHEAL
HNHYTQKSLSLSPGK;

(SEQ ID NO: 28)
GPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEAL
HNHYTQKSLSLSPGK;

(SEQ ID NO: 29)
GPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEK
TISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEAL
HNHYTQKSLSLSPGK;

-continued (SEQ ID NO: 30)
GPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEAL

HNHYTQKSLSLSPGK;
or (SEQ ID NO: 31)
GPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEAL

HNHYTQKSLSLSPGK.

In an embodiment of the invention, any of the VEGF mini-traps set forth herein do not include such a MC.

In an embodiment of the invention, a multimerizing component that includes an Fc domain hinge region or variant or fragment thereof (e.g., from IgG4) includes a S108P mutation, e.g., to promote dimer stabilization.

In an embodiment of the invention, a VEGF trap or VEGF mini-trap of the present invention comprises a modified Fc domain or fragment thereof (e.g., wherein the fragment includes the hinge region) having reduced effector function. As used herein, a "modified Fc domain having reduced effector function" means any Fc portion of an immunoglobulin that has been modified, mutated, truncated, etc., relative to a wild-type, naturally occurring Fc domain such that a molecule comprising the modified Fc exhibits a reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having reduced effector function" is an Fc domain with reduced or attenuated binding to an Fc receptor (e.g., FcγR).

In certain embodiments of the present invention, the modified Fc domain is a variant IgG1 Fc or a variant IgG4 Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504, the disclosure of which is hereby incorporated by reference in its entirety, as well as any functionally equivalent variants of the modified Fc regions set forth therein.

Other modified Fc domains and Fc modifications that can be used in the context of the present invention include any of the modifications as set forth in US 2014/0171623; U.S. Pat. No. 8,697,396; US 2014/0134162; WO 2014/043361, the disclosures of which are hereby incorporated by reference in their entireties.

Engineered IgG1 with a stealth mutation is based on the IgG1 framework but with replacement of both the hinge CPPCPAPELLG (amino acids 6-16 of SEQ ID NO: 1) to CPPCPAPPVA (amino acids 6-15 of SEQ ID NO: 2) and the IgG1 CH2 domain with that of IgG4. See e.g., FIG. 13, FIG. 14, FIG. 15, FIG. 16 and FIG. 17.

The engineered IgG4 with a stealth mutation has a three amino acid substitution (EFLG (SEQ ID NO: 95) to PVA) to resemble that of the hinge region of IgG2—which lacks the capacity to bind to FcγR1—in the framework of a hinge stabilized (CPPC (SEQ ID NO: 100) or CPSC (SEQ ID NO: 101)) IgG4, which lacks capacity to bind to C1q. See e.g., FIG. 13, FIG. 14, FIG. 15, FIG. 16 and FIG. 17.

In an embodiment of the invention, a VEGF trap or mini-trap has an IgG1 uber or uber stealth mutation in the hinge region making CPPCPAPELLG (SEQ ID NO: 102) to CPPCPAPGGG (SEQ ID NO: 103); or a VEGF trap or mini-trap has an IgG4 uber or uber stealth mutation in the hinge region making CPPCPAPEFLG (SEQ ID NO: 104) to CPPCPAPGGG (SEQ ID NO: 103).

VEGF trap or mini-trap with human IgG1 stealth Fc or human IgG4 stealth Fc replaces the amino acid residues in the hinge in VEGF Trap IgG1 that are prone to pre-existing anti-hinge antibody responses (PEL). Due to the sequence conservation between the IgG hinges of these chimeric Fc regions to that of human IgG2, they have low responses to pre-existing anti-hinge antibodies (AHA).

Chimeric IgG2/IgG4 Fc VEGF traps and mini-traps are part of the present invention. These molecules combine the favorable properties of both IgG2 and IgG4 isotypes- and possess minimal capacity for effector function. Different IgG isoforms are known to exert different types and levels of effector function. These differences are in large part due to each isoform's ability to interact with the various FcγRs, as well as with complement component C1q. Both the IgG2 and IgG4 isotypes demonstrate diminished capacity for generating Fc dependent effector function when compared to the IgG1 isotype.

The present invention also includes VEGF mini-traps which are the VEGF-binding product of proteolytic cleavage of a VEGF trap of the present invention wherein cleavage removes a portion of the MC. For example, in an embodiment of the invention, the proteolytic cleavage is with IdeS protease (or a variant thereof) or another protease which cleaves prior to GPSV (amino acids 218-221 of SEQ ID NO: 41).

In an embodiment of the invention, a VEGF mini-trap of the present invention comprises an amino acid sequence as set forth below:

REGN10103-VEGF mini-trap hIgG2 Fc w/4Cys
CPPAPPAPPVA (SEQ ID NO: 105)
(SEQ ID NO: 32)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDFNWEYPSSKHQH

KKLVNRDLKTQSGSEMKKFLSTLTIDGVTRSDQGLYTCAASSGLMTKKN

STFVRVHEKERKCCVECPPCPAPPVA;

REGN10105-VEGF mini-trap hIgG2 Fc w/2Cys
CPPAPAPPVA (SEQ ID NO: 106)
(SEQ ID NO: 33)
SDTGRPFVEMYSEIPEIIHMTEGRELVIPCRVTSPNITVTLKKFPLDTL

```
IPDGKRIIWDSRKGFIISNATYKEIGLLTCEATVNGHLYKTNYLTHRQT

NTIIDVVLSPSHGIELSVGEKLVLNCTARTELNVGIDFNWEYPSSKHQH

KKLVNRDLKTQSGSEMKKFLSTLTIDGVTRSDQGLYTCAASSGLMTKKN

STFVRVHEKVECPPCPAPPVA

Mini-REGN10104 (mREGN10104)-VEGF mini-Trap hIgG1
stealth Fc
                                        (SEQ ID NO: 34)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDFNWEYPSSKHQH

KKLVNRDLKTQSGSEMKKFLSTLTIDGVTRSDQGLYTCAASSGLMTKKN

STFVRVHEKDKTHTCPPCPAPPVA;

REGN10104 wherein Fc domain (or fragment thereof)
has been removed.

Mini-REGN10187 (mREGN10187)-VEGF mini-Trap hIgG4
stealth Fc
                                        (SEQ ID NO: 35)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDFNWEYPSSKHQH

KKLVNRDLKTQSGSEMKKFLSTLTIDGVTRSDQGLYTCAASSGLMTKKN

STFVRVHEKESKYGPPCPPCPAPPVA;

REGN10187 wherein Fc domain (or fragment thereof)
has been removed.

Mini-REGN10511 (mREGN10511)-VEGF mini-Trap
hIgG1-2 Chimera Fc
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDFNWEYPSSKHQH

KKLVNRDLKTQSGSEMKKFLSTLTIDGVTRSDQGLYTCAASSGLMTKKN

STFVRVHEKDKTHTCPPCPAPPVA
```

(SEQ ID NO: 36); REGN10511 wherein Fc domain (or fragment thereof) has been removed.

```
Mini-REGN10512 (mREGN10512)-VEGF mini-Trap hIgG1
Mut GGGF (SEQ ID NO: 92) Fc
                                        (SEQ ID NO: 37)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDENWEYPSSKHQH

KKLVNRDLKTQSGSEMKKFLSTLTIDGVTRSDQGLYTCAASSGLMTKKN

STFVRVHEKDKTHTCPPCPGGGFLG;

REGN10512 wherein Fc domain (or fragment thereof)
has been removed.

Mini-REGN10513 (mREGN10513)-VEGF mini-Trap hIgG1
Mut GGGG (SEQ ID NO: 93) Fc
                                        (SEQ ID NO: 38)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDENWEYPSSKHQH

KKLVNRDLKTQSGSEMKKFLSTLTIDGVTRSDQGLYTCAASSGLMTKKN

STFVRVHEKDKTHTCPPCPGGGGLG;

REGN10513 wherein Fc domain (or fragment thereof)
has been removed.

Mini-REGN10514 (mREGN10514 or REGN11095)-VEGF
mini-Trap hIgG1 Mut GGGL (SEQ ID NO: 94) Fc
                                        (SEQ ID NO: 39)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDENWEYPSSKHQH

KKLVNRDLKTQSGSEMKKFLSTLTIDGVTRSDQGLYTCAASSGLMTKKN

STFVRVHEKDKTHTCPPCPGGGLLG;

REGN10514 wherein Fc domain (or fragment thereof)
has been removed.

Mini-REGN10515 (mREGN10515)-VEGF mini-Trap hIgG1
Del (APE) Fc
                                        (SEQ ID NO: 40)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDENWEYPSSKHQH

KKLVNRDLKTQSGSEMKKFLSTLTIDGVTRSDQGLYTCAASSGLMTKKN

STFVRVHEKDKTHTCPPCPLLG;

REGN10515 wherein Fc domain (or fragment thereof)
has been removed.
```

See FIG. 7.

In an embodiment of the invention, a VEGF trap of the present invention comprises an amino acid sequence as set forth below:

```
REGN10102-VEGF trap hIgG2 Fc w/2Cys
                                        (SEQ ID NO: 41)
SDTGRPFVEMYSEIPEIIHMTEGRELVIPCRVTSPNITVTLKKFPLDTLIPDGKRIIWDSRKGFIISNATYKEIGLL

TCEATVNGHLYKTNYLTHRQTNTIIDVVLSPSHGIELSVGEKLVLNCTARTELNVGIDENWEYPSSKHQHKKLVNRD

LKTQSGSEMKKFLSTLTIDGVTRSDQGLYTCAASSGLMTKKNSTFVRVHEKVECPPCPAPPVAGPSVFLFPPKPKDT

LMISRTPEVTCVVVDVSHEDPEVQFNWYVDGVEVHNAKTKPREEQFNSTFRVVSVLTVVHQDWLNGKEYKCKVSNKG

LPAPIEKTISKTKGQPREPQVYTLPPSREEMTKNQVSLTCLVKGFYPSDIAVEWESNGQPENNYKTTPPMLDSDGSF

FLYSKLTVDKSRWQQGNVFSCSVMHEALHNHYTQKSLSLSPGK
```

REGN10104-VEGF Trap hIgG1 stealth Fc (SEQ ID NO: 42)
<u>SDTGRPFVEMYSEIPEIIHMTEGRELVIPCRVTSPNITVTLKKFPLDTLIPDGKRIIWDSRKGFIISNATYKEIGLL</u>

<u>TCEATVNGHLYKTNYLTHRQTNTIID</u>VVLSPSHGIELSVGEKLVLNCTARTELNVGIDENWEYPSSKHQHKKLVNRD

LKTQSGSEMKKFLSTLTIDGVTRSDQGLYTCAASSGLMTKKNSTFVRVHEKDKTHTCPPCPAPPVAGPSVFLFPPKP

KDTLMISRTPEVTCVVVDVSQEDPEVQFNWYVDGVEVHNAKTKPREEQFNSTYRVVSVLTVLHQDWLNGKEYKCKVS

NKGLPSSIEKTISKAKGQPREPQVYTLPPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

REGN10117-VEGF Trap hIgG2 Fc w/4 Cys (SEQ ID NO: 43)
<u>SDTGRPFVEMYSEIPEIIHMTEGRELVIPCRVTSPNITVTLKKFPLDTLIPDGKRIIWDSRKGFIISNATYKEIGLL</u>

<u>TCEATVNGHLYKTNYLTHRQTNTIID</u>VVLSPSHGIELSVGEKLVLNCTARTELNVGIDENWEYPSSKHQHKKLVNRD

LKTQSGSEMKKFLSTLTIDGVTRSDQGLYTCAASSGLMTKKNSTFVRVHEKERKCCVECPPCPAPPVAGPSVFLFPP

KPKDTLMISRTPEVTCVVVDVSHEDPEVQFNWYVDGVEVHNAKTKPREEQFNSTFRVVSVLTVVHQDWLNGKEYKCK

VSNKGLPAPIEKTISKTKGQPREPQVYTLPPSREEMTKNQVSLTCLVKGFYPSDIAVEWESNGQPENNYKTTPPMLD

SDGSFFLYSKLTVDKSRWQQGNVFSCSVMHEALHNHYTQKSLSLSPGK

REGN10187-VEGF Trap hIgG4 stealth Fc (SEQ ID NO: 44)
<u>SDTGRPFVEMYSEIPEIIHMTEGRELVIPCRVTSPNITVTLKKFPLDTLIPDGKRIIWDSRKGFIISNATYKEIGLL</u>

<u>TCEATVNGHLYKTNYLTHRQTNTIID</u>VVLSPSHGIELSVGEKLVLNCTARTELNVGIDENWEYPSSKHQHKKLVNRD

LKTQSGSEMKKFLSTLTIDGVTRSDQGLYTCAASSGLMTKKNSTFVRVHEKESKYGPPCPPCPAPPVAGPSVFLFPP

KPKDTLMISRTPEVTCVVVDVSQEDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

REGN10511-VEGF Trap hIgG1-2 Chimera Fc (SEQ ID NO: 45)
<u>SDTGRPFVEMYSEIPEIIHMTEGRELVIPCRVTSPNITVTLKKFPLDTLIPDGKRIIWDSRKGFIISNATYKEIGLL</u>

<u>TCEATVNGHLYKTNYLTHRQTNTIID</u>VVLSPSHGIELSVGEKLVLNCTARTELNVGIDENWEYPSSKHQHKKLVNRD

LKTQSGSEMKKFLSTLTIDGVTRSDQGLYTCAASSGLMTKKNSTFVRVHEKDKTHTCPPCPAPPVAGPSVFLFPPKP

KDTLMISRTPEVTCVVVDVSHEDPEVQFNWYVDGVEVHNAKTKPREEQFNSTFRVVSVLTVVHQDWLNGKEYKCKVS

NKGLPAPIEKTISKTKGQPREPQVYTLPPSREEMTKNQVSLTCLVKGFYPSDIAVEWESNGQPENNYKTTPPMLDSD

GSFFLYSKLTVDKSRWQQGNVFSCSVMHEALHNHYTQKSLSLSPGK

REGN10512-VEGF Trap hIgG1 Mut GGGF (SEQ ID NO: 92) Fc (SEQ ID NO: 46)
<u>SDTGRPFVEMYSEIPEIIHMTEGRELVIPCRVTSPNITVTLKKFPLDTLIPDGKRIIWDSRKGFIISNATYKEIGLL</u>

<u>TCEATVNGHLYKTNYLTHRQTNTIID</u>VVLSPSHGIELSVGEKLVLNCTARTELNVGIDENWEYPSSKHQHKKLVNRD

LKTQSGSEMKKFLSTLTIDGVTRSDQGLYTCAASSGLMTKKNSTFVRVHEKDKTHTCPPCPGGGFLGGPSVFLFPPK

PKDTLMISRTPEVTCVVVDVSHEDPEVKFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

REGN10513-VEGF Trap hIgG1 Mut GGGG (SEQ ID NO: 93) Fc (SEQ ID NO: 47)
<u>SDTGRPFVEMYSEIPEIIHMTEGRELVIPCRVTSPNITVTLKKFPLDTLIPDGKRIIWDSRKGFIISNATYKEIGLL</u>

<u>TCEATVNGHLYKTNYLTHRQTNTIID</u>VVLSPSHGIELSVGEKLVLNCTARTELNVGIDENWEYPSSKHQHKKLVNRD

LKTQSGSEMKKFLSTLTIDGVTRSDQGLYTCAASSGLMTKKNSTFVRVHEKDKTHTCPPCPGGGGLGGPSVFLFPPK

PKDTLMISRTPEVTCVVVDVSHEDPEVKFNWYVDGVEVHNAKTKPREEQYNSTYRVVSVLTVLHQDWLNGKEYKCKV

```
                                              -continued
SNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVESCSVMHEALHNHYTQKSLSLSPGK

REGN10514-VEGF Trap hIgG1 Mut GGGL (SEQ ID NO: 94) Fc
                                                                         (SEQ ID NO: 48)
SDTGRPFVEMYSEIPEIIHMTEGRELVIPCRVTSPNITVTLKKFPLDTLIPDGKRIIWDSRKGFIISNATYKEIGLL

TCEATVNGHLYKTNYLTHRQTNTIIDVVLSPSHGIELSVGEKLVLNCTARTELNVGIDENWEYPSSKHQHKKLVNRD

LKTQSGSEMKKFLSTLTIDGVTRSDQGLYTCAASSGLMTKKNSTFVRVHEKDKTHTCPPCPGGGLLGGPSVFLFPPK

PKDTLMISRTPEVTCVVVDVSHEDPEVKFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVESCSVMHEALHNHYTQKSLSLSPGK

REGN10515-VEGF Trap hIgG1 Del (APE) Fc
                                                                         (SEQ ID NO: 49)
SDTGRPFVEMYSEIPEIIHMTEGRELVIPCRVTSPNITVTLKKFPLDTLIPDGKRIIWDSRKGFIISNATYKEIGLL

TCEATVNGHLYKTNYLTHRQTNTIIDVVLSPSHGIELSVGEKLVLNCTARTELNVGIDENWEYPSSKHQHKKLVNRD

LKTQSGSEMKKFLSTLTIDGVTRSDQGLYTCAASSGLMTKKNSTFVRVHEKDKTHTCPPCPLLGGPSVFLFPPKPKD

TLMISRTPEVTCVVVDVSHEDPEVKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESNGQPENNYKTTPPVLDSDGS

FFLYSKLTVDKSRWQQGNVESCSVMHEALHNHYTQKSLSLSPGK
```

Such VEGF Traps are cleavable by IdeS protease. VEGF mini-traps that are the product of such a cleavage are part of the present invention. See FIG. 7.

Figure 5A:
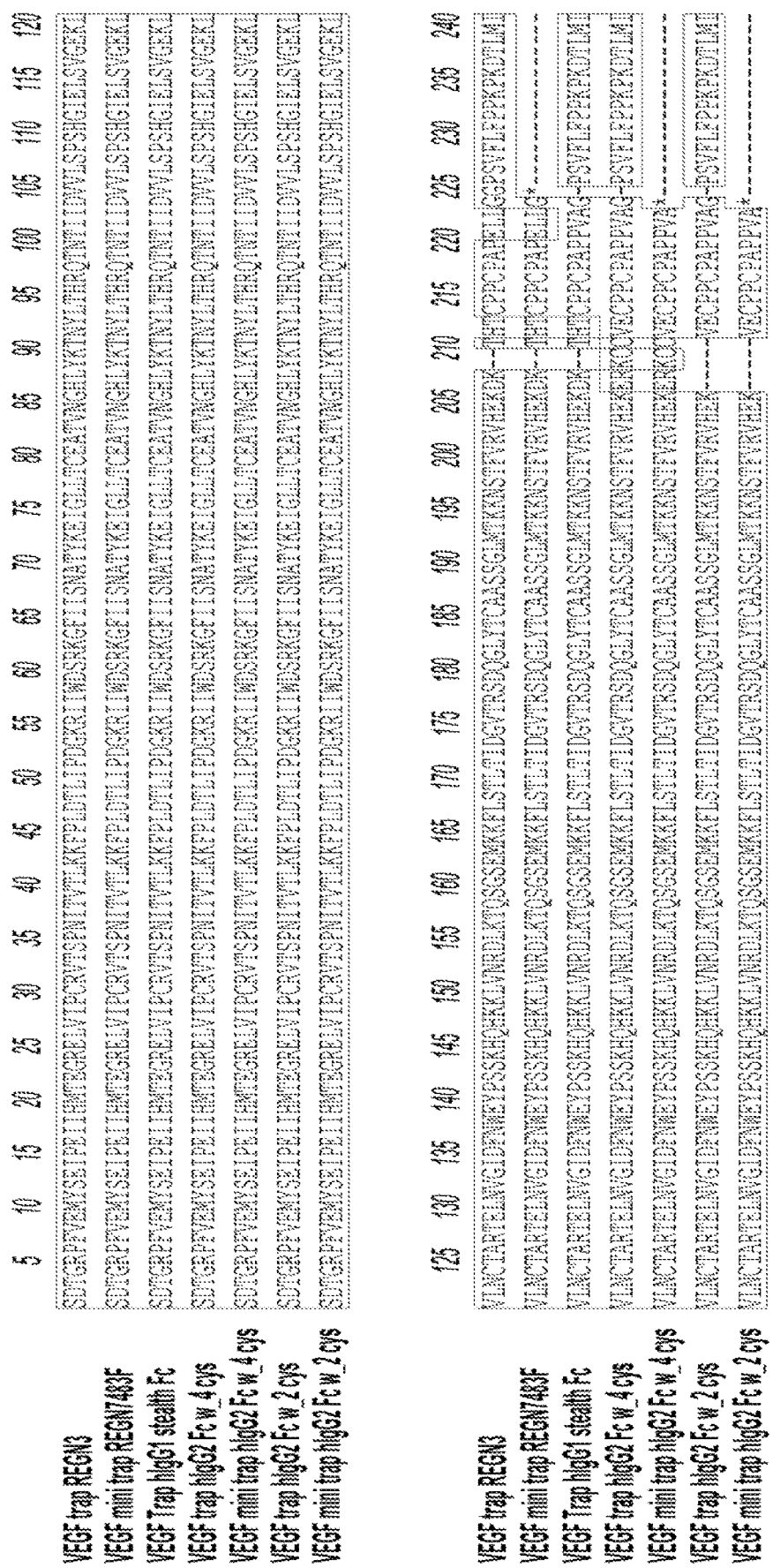
FIG. 5. Sequence comparison between aflibercept (REGN3), VEGF mini-trap derived from REGN3 (REGN7483$^F$), VEGF trap hIgG1 stealth Fc, VEGF trap hIgG2 Fc with 4 cys, VEGF mini-trap hIgG2 with 4 cys, VEGF trap hIgG2 Fc with 2 cys, and VEGF mini-trap hIgG2 with 2 cys.
Figure 5B:
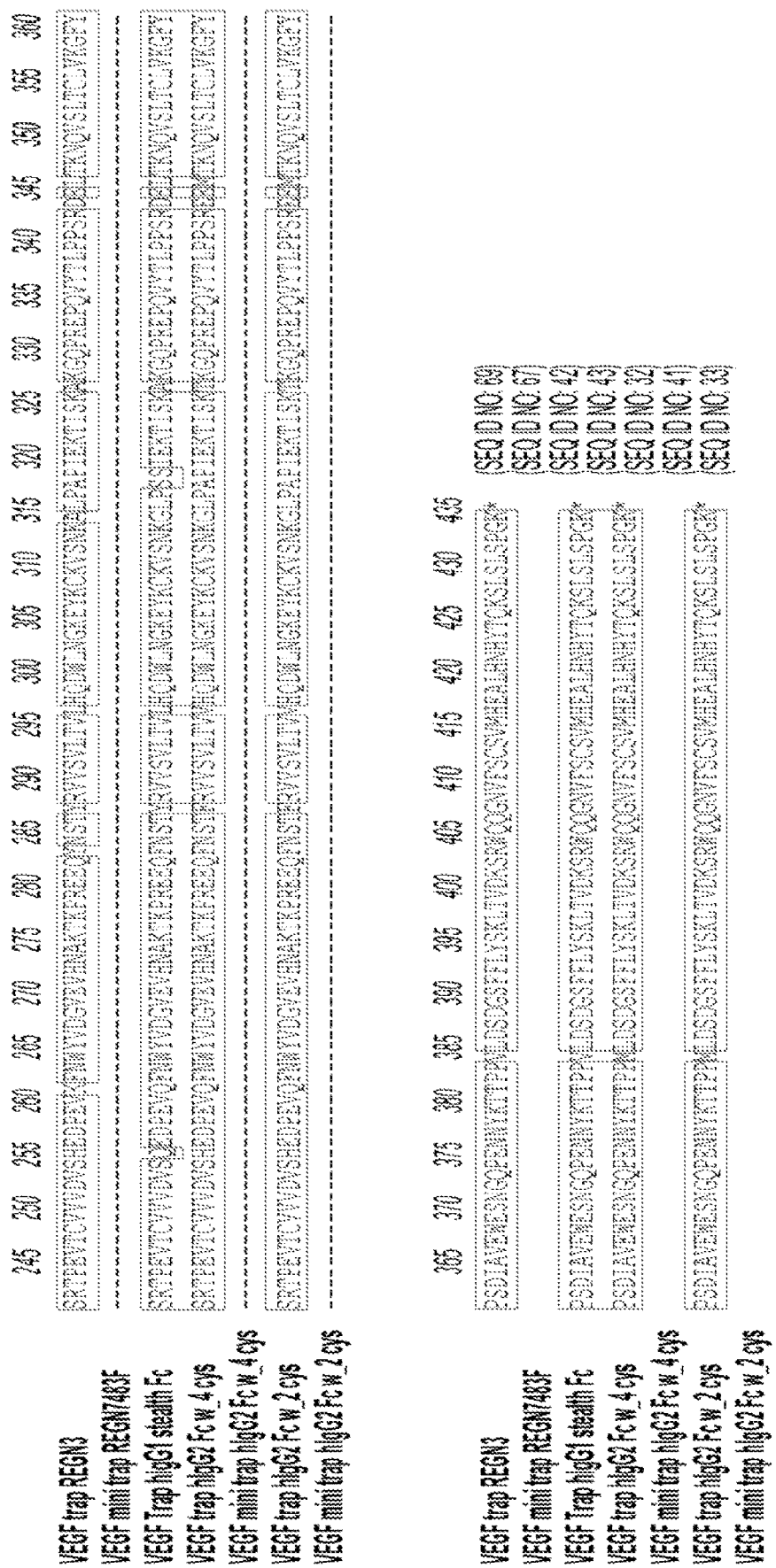
Figure 6A:
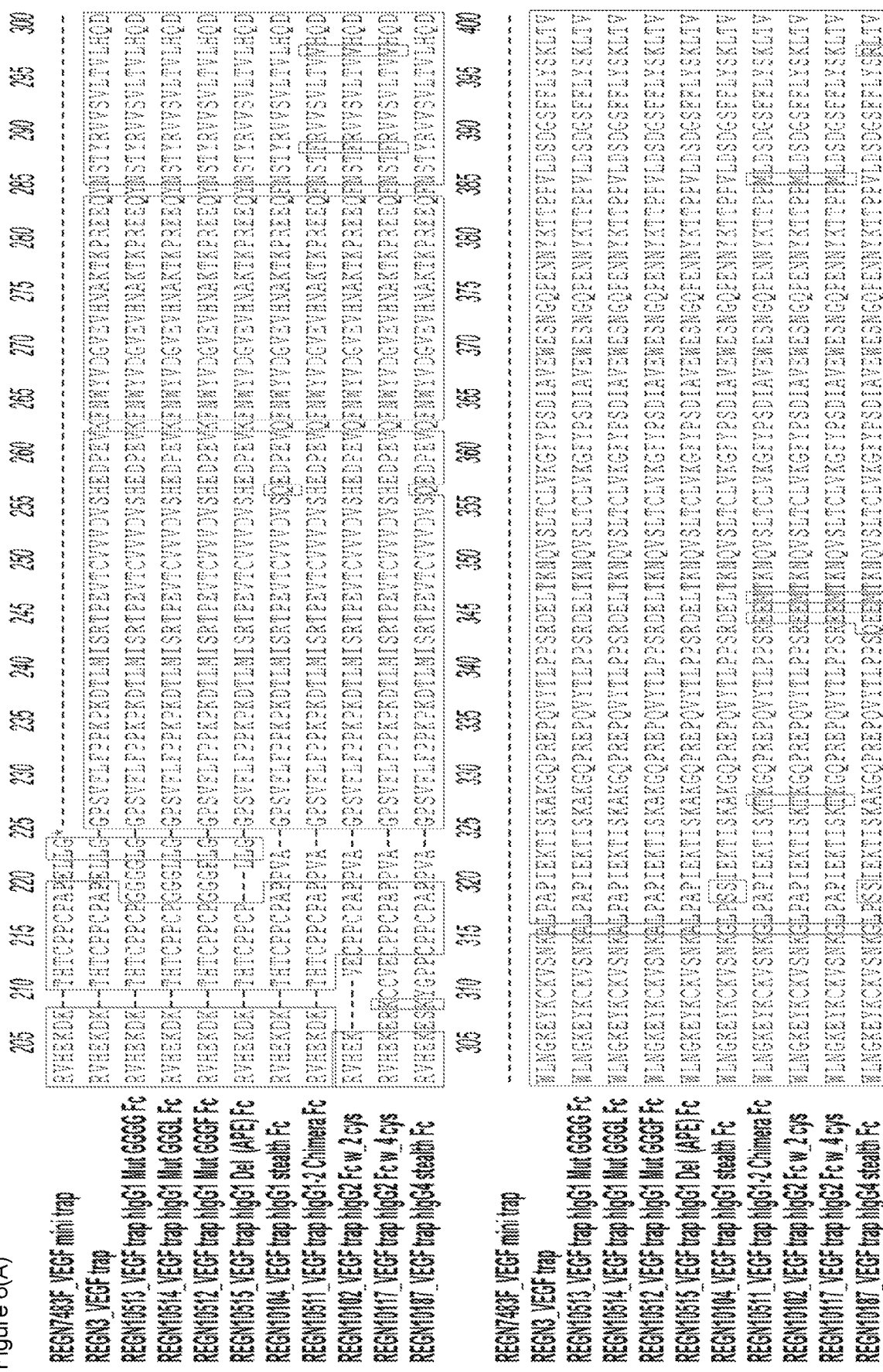
FIG. 6. Sequence comparison between aflibercept (REGN3), VEGF mini-trap derived from REGN3 (REGN7483$^F$), REGN10513, REGN10514, REGN10512, REGN10515, REGN10104, REGN10511, REGN10102, REGN10117, and REGN10187. Figure discloses "GGGF", "GGGG", and "GGGL" as SEQ ID NOS 92-94, respectively.
Figure 6:
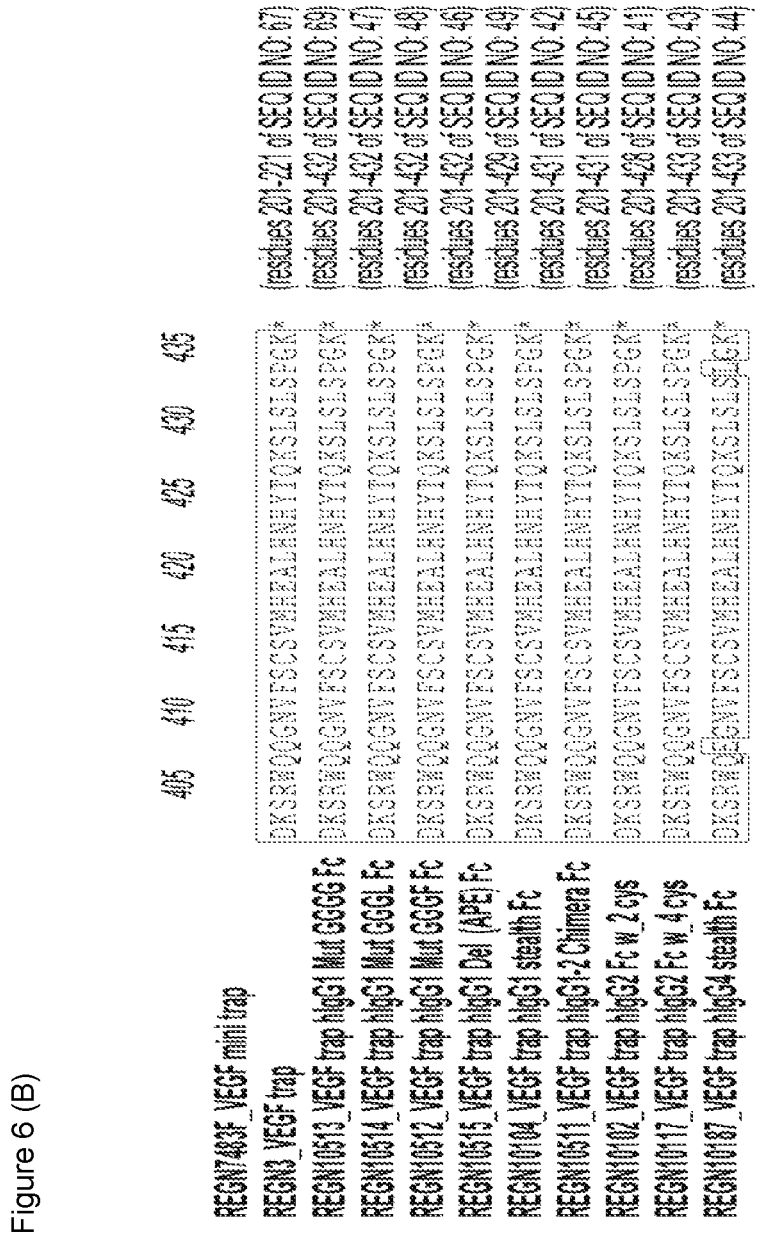
Figure 7F:
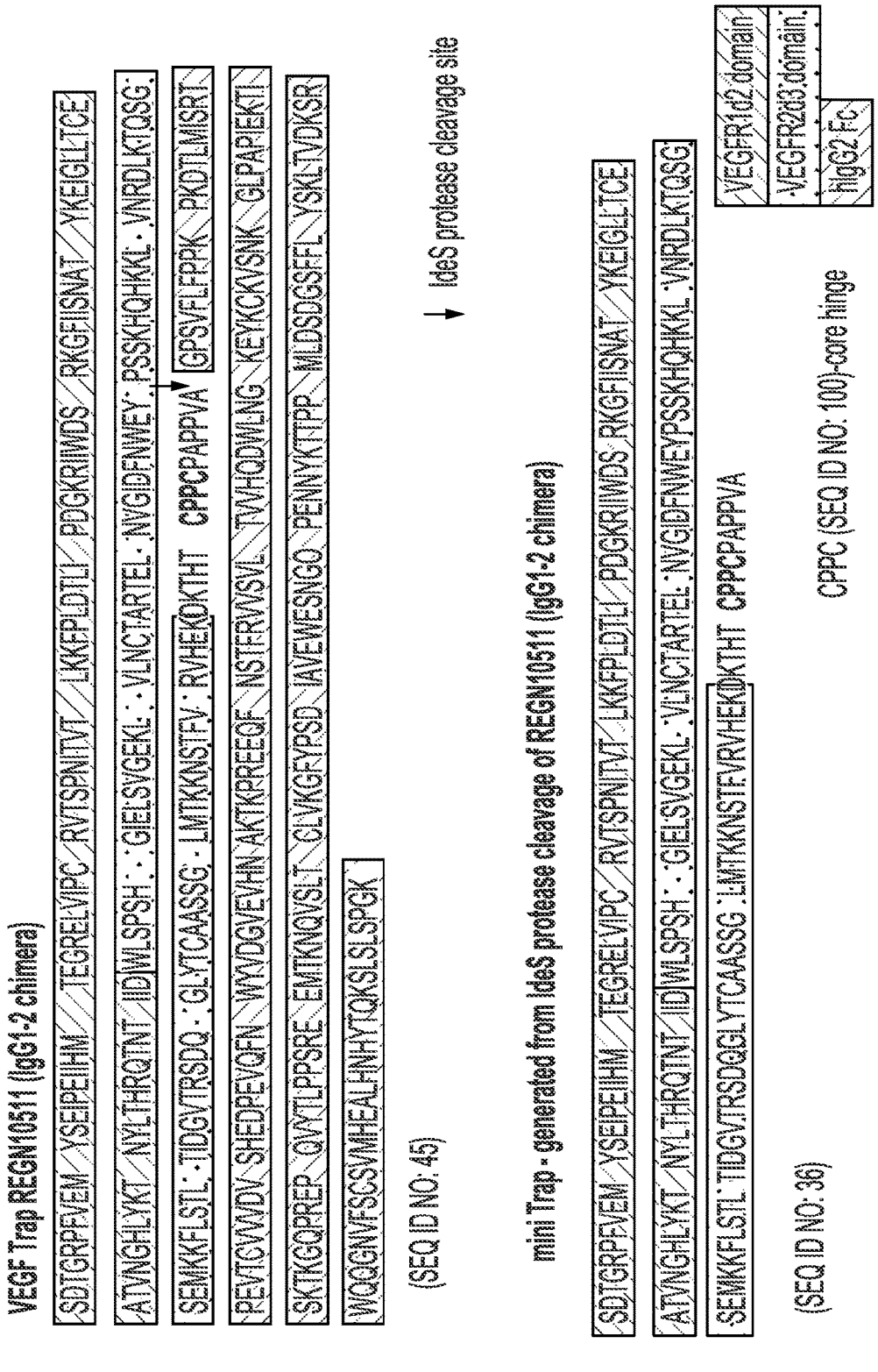
FIGS. 7 (A-J). Amino acid sequences of VEGF traps and VEGF mini-traps (A) REGN3, REGN7483, (B) REGN10104, mREGN10104, (C) REGN10102, REGN10105, (D) REGN1017, REGN10103, (E) REGN10187, mREGN10187, (F) REGN10511, mREGN10511, (G) REGN10512, mREGN10512, (H) REGN10513, mREGN10513, (I) REGN10514, REGN11095, and (J) REGN10515, mREGN10515. IdeS protease cleavage sites in VEGF traps are indicated by an arrow. N-terminal VEGFR1 domain 2 is dark shaded and VEGFR2 domain 3 is light shaded and boxed. C-terminal Fc domain in VEGF traps are dark shaded. Hinge regions of VEGF traps and VEGF mini-traps are unshaded. Figure discloses "GGGF", "GGGG", and "GGGL" as SEQ ID NOS 92-94, respectively.
Figure 7G:
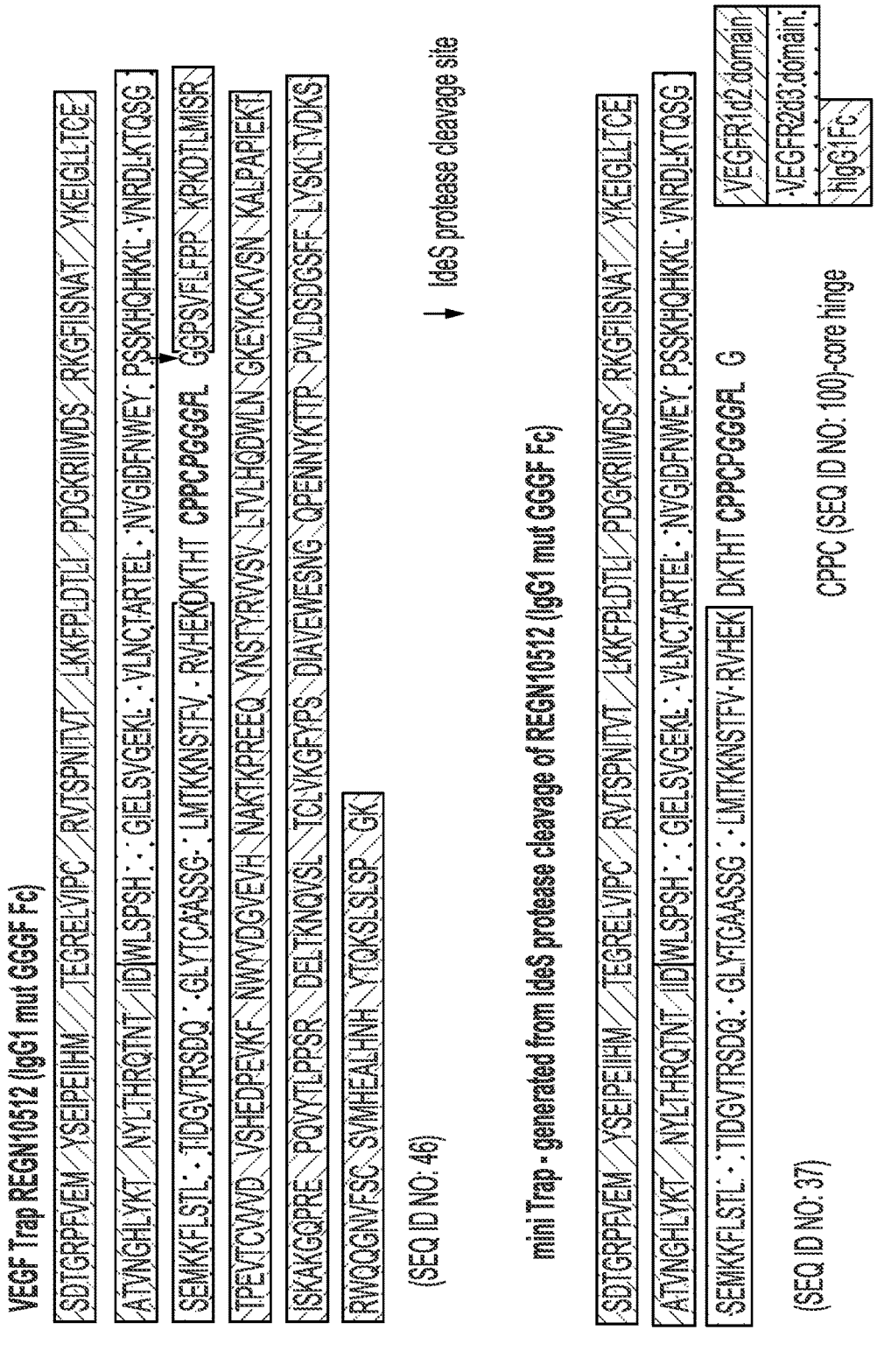
Figure 7H:
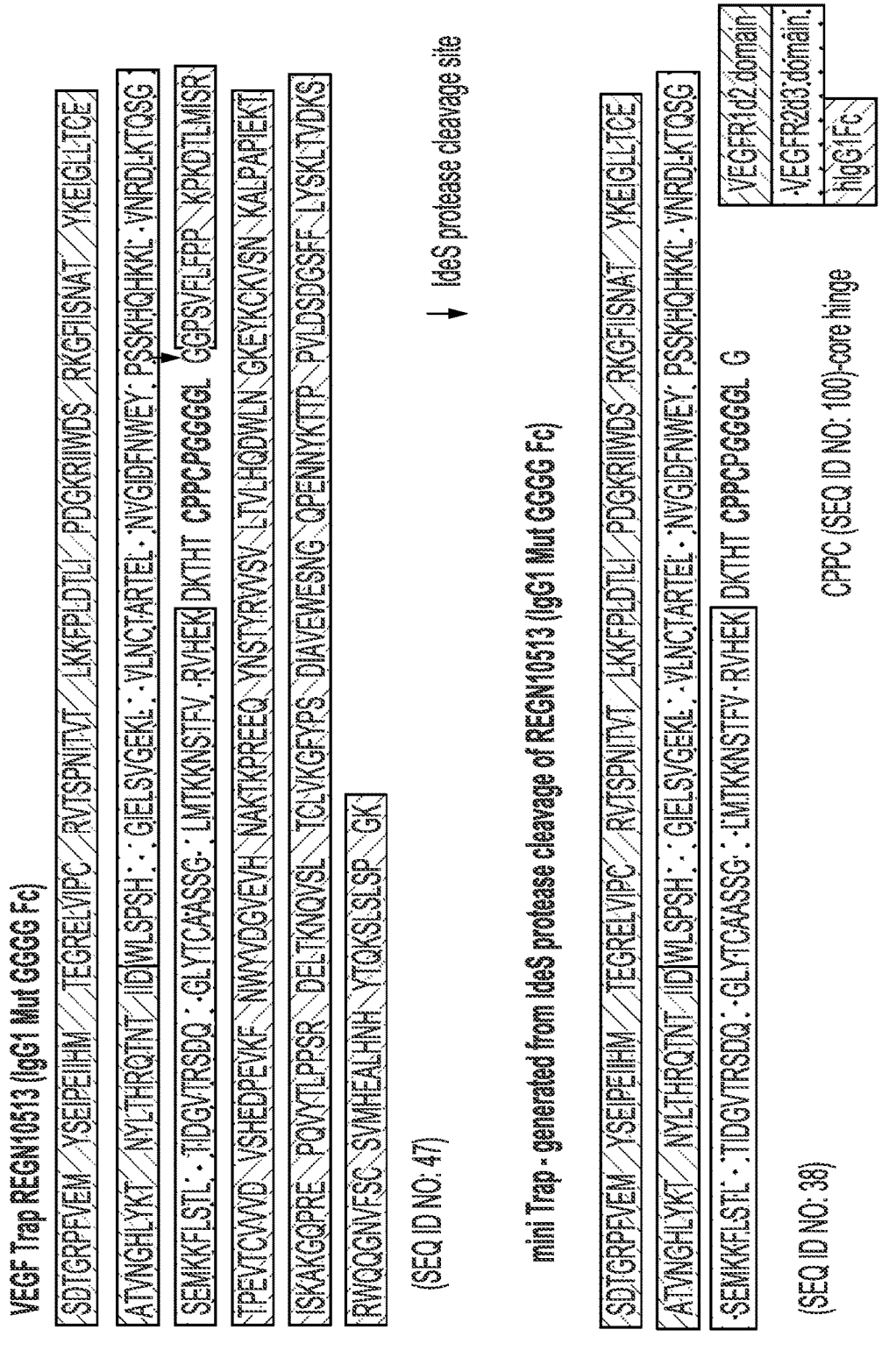
Figure 7I:
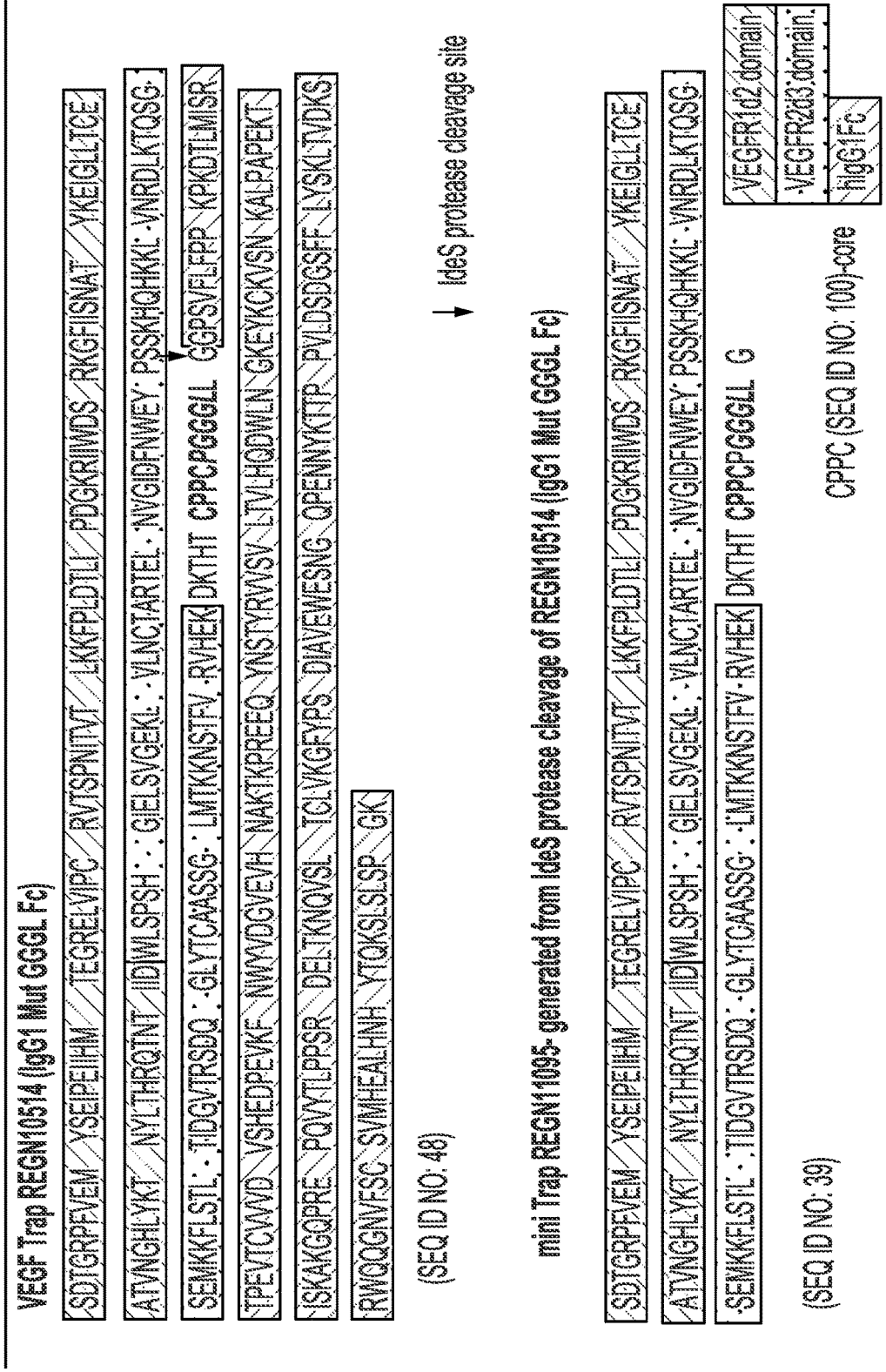
Figure 7J:
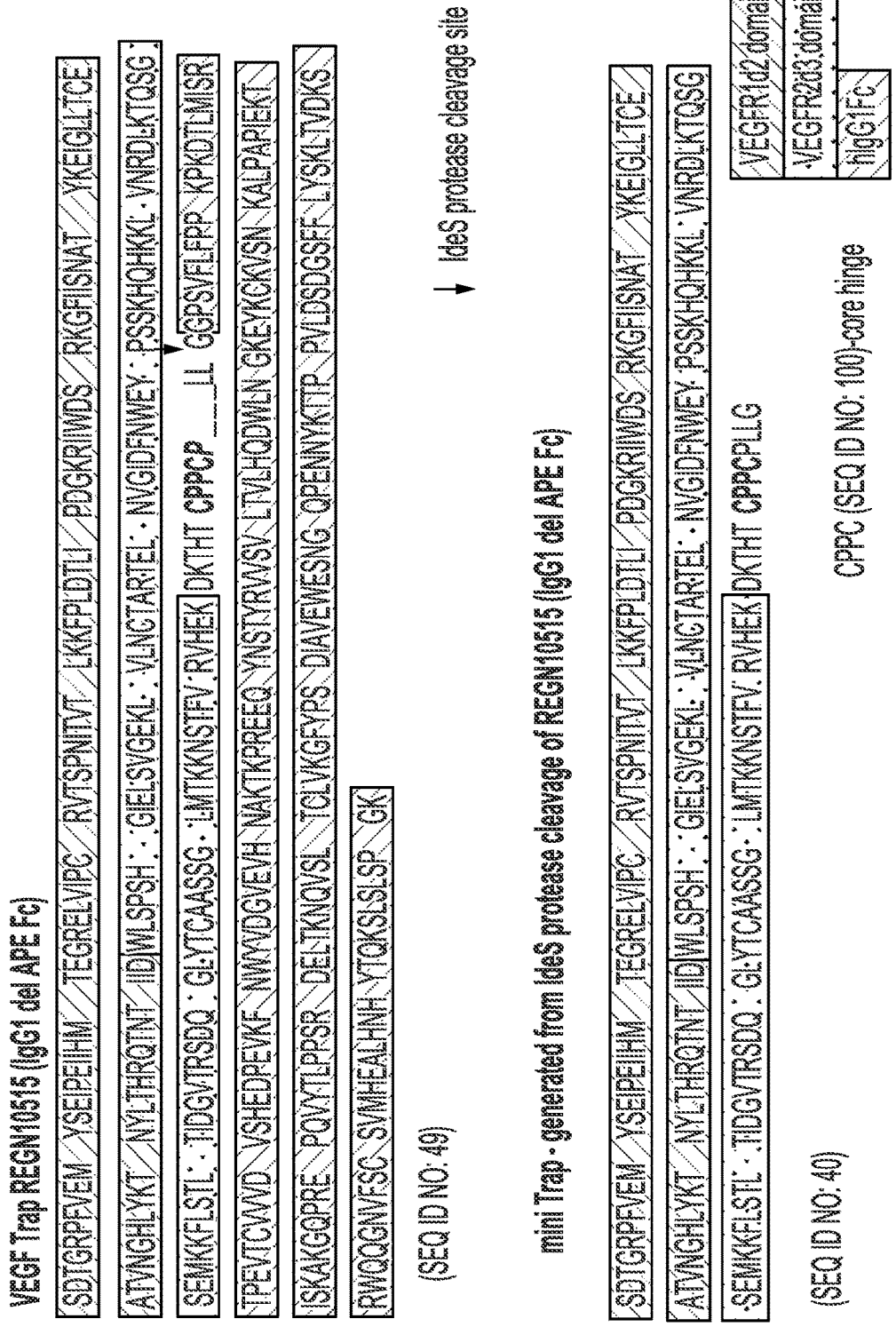
Figure 8A:
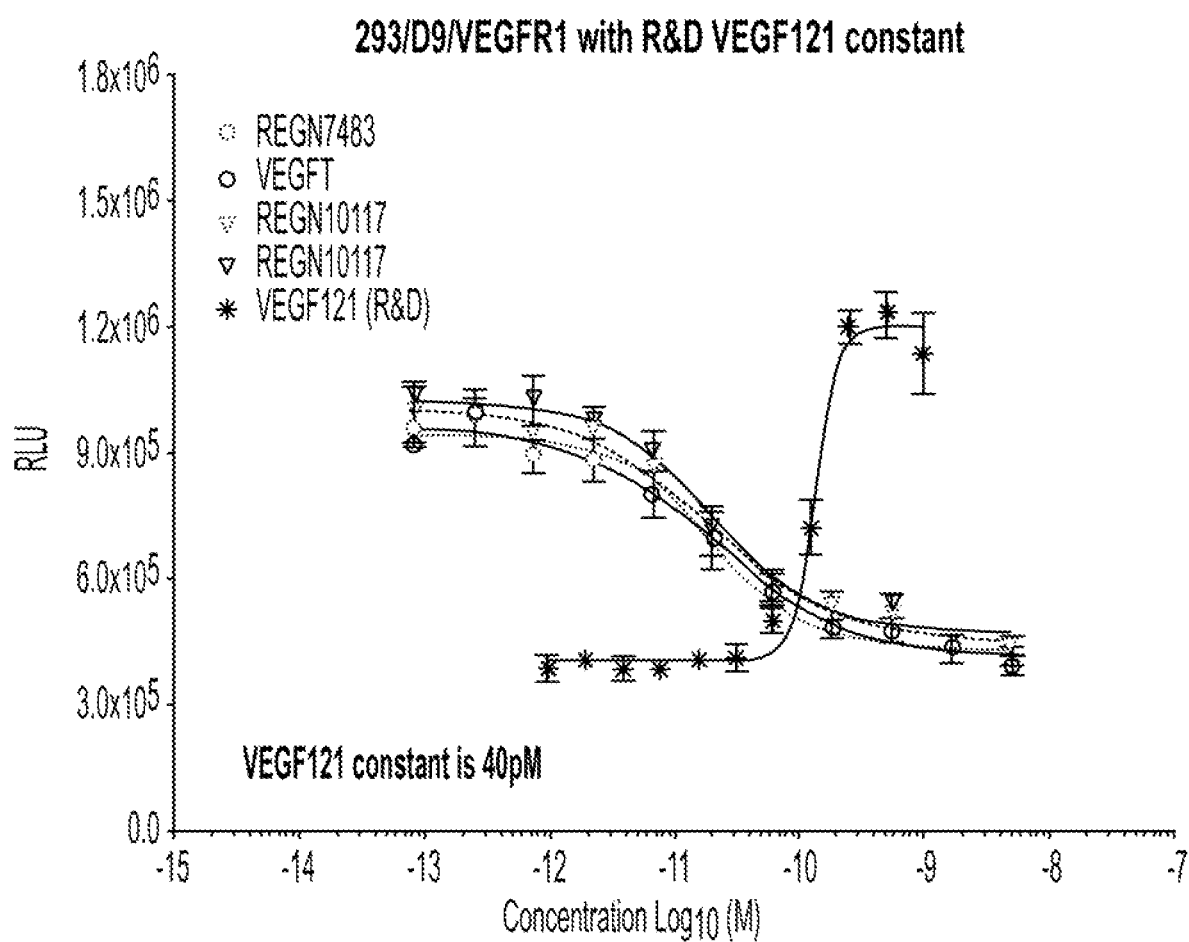
FIGS. 8 (A-E). Bioassay activity of VEGF traps and VEGF mini-traps (REGN10117 (A), REGN10104 and mREGN10104 (B), REGN10102 (C), REGN10187 and mREGN10187 (D); and REGN10103 and REGN10105 (E); along with controls REGN7483, REGN3 (VEGFT) and $VEGF_{121}$ in each) blocking $VEGF_{121}$ activation ($VEGF_{121}$ at 40 pM) of VEGFR1 expressing cells (293/D9/VEGFR1).
Figure 8B:
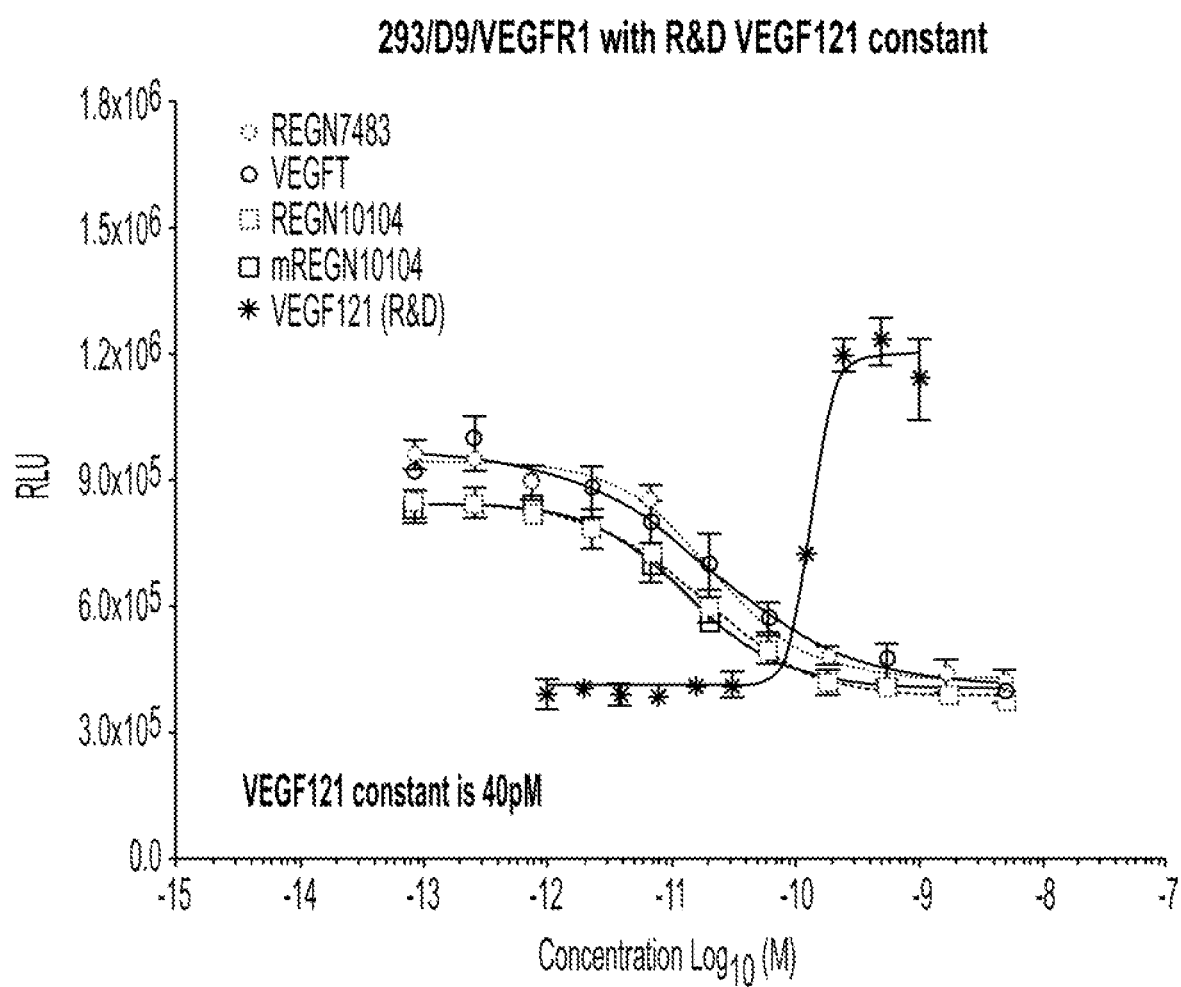
Figure 8C:
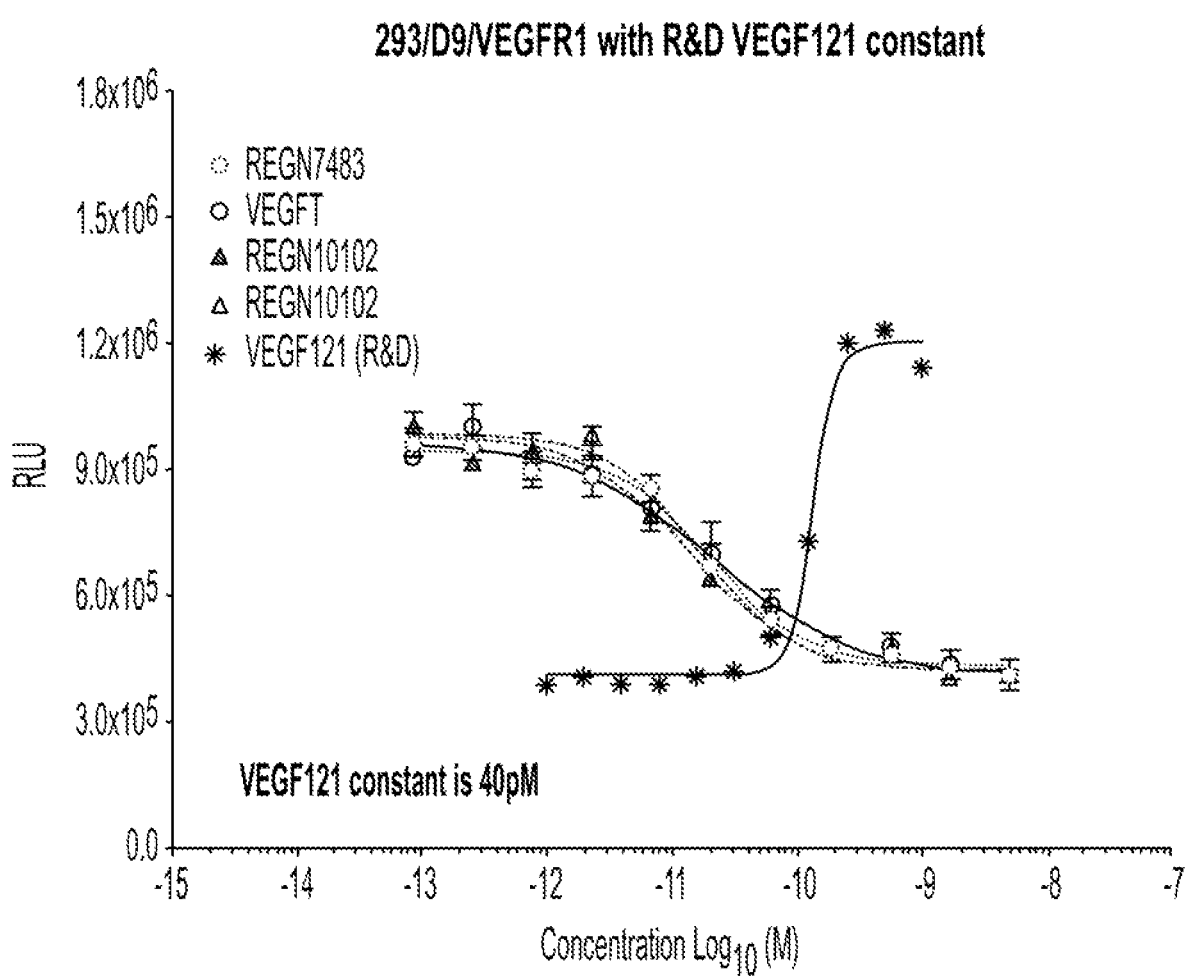
Figure 8D:
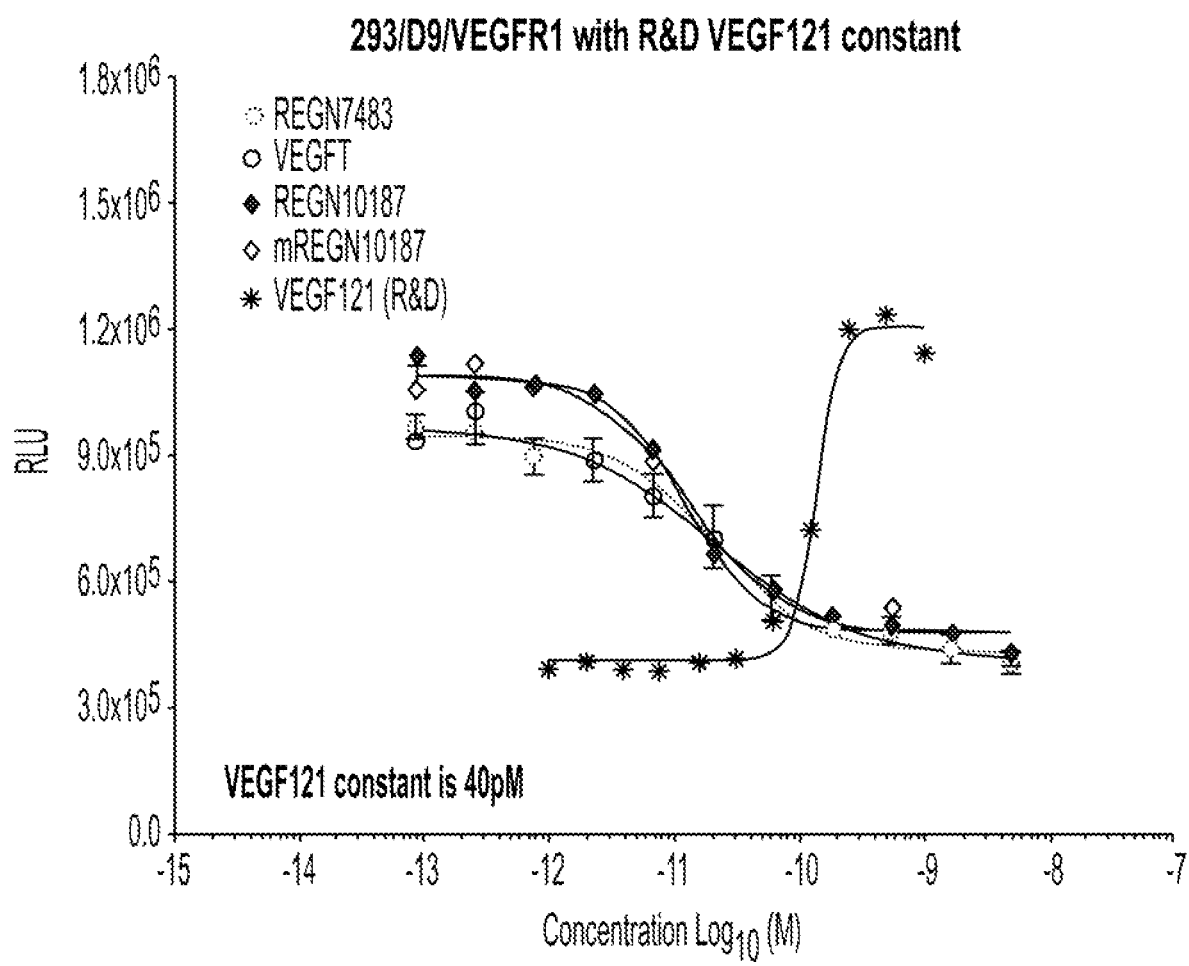
Figure 8E:
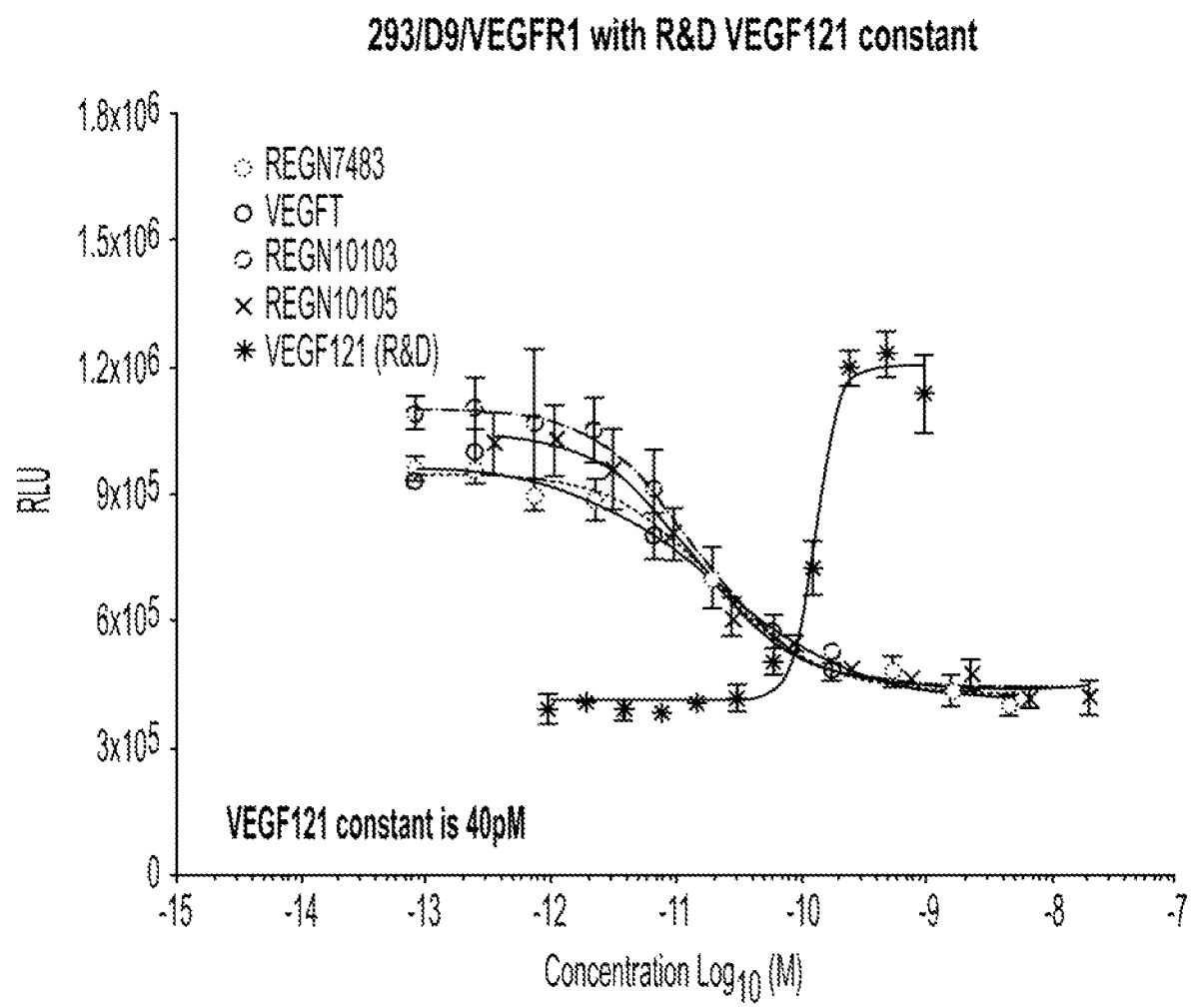
Figure 9A:
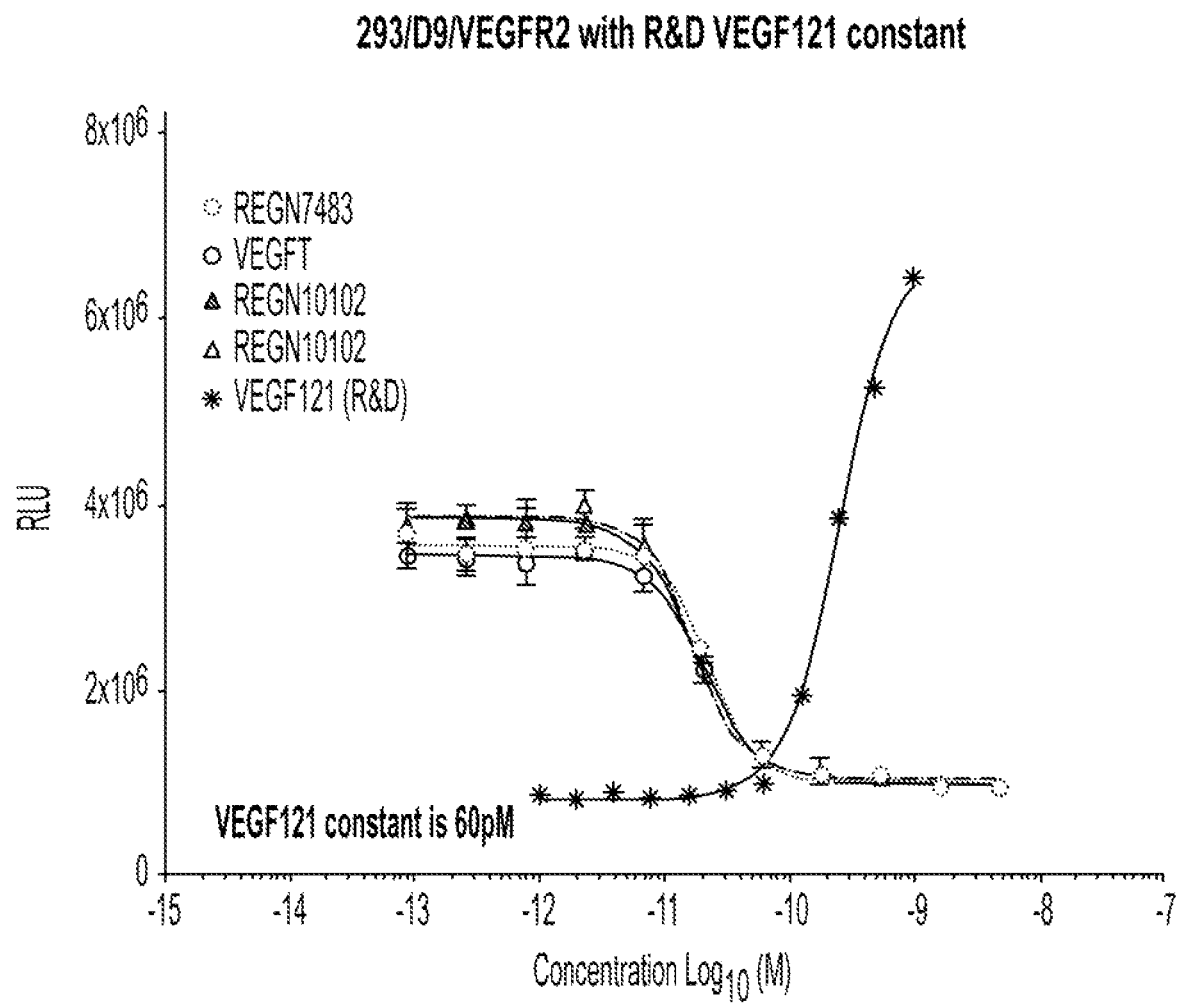
FIGS. 9 (A-E). Bioassay activity of VEGF traps and VEGF mini-traps (REGN10102 (A), REGN10104 and mREGN10104 (B) REGN10117(C), REGN10187 (D) REGN10187 and mREGN10187 (D); and REGN10103 and REGN101005 (E); along with controls REGN7483, REGN3 (VEGFT) and $VEGF_{121}$ in each) blocking $VEGF_{121}$ activation ($VEGF_{121}$ at 60 pM) of VEGFR2 expressing cells (293/D9/VEGFR2).
Figure 9B:
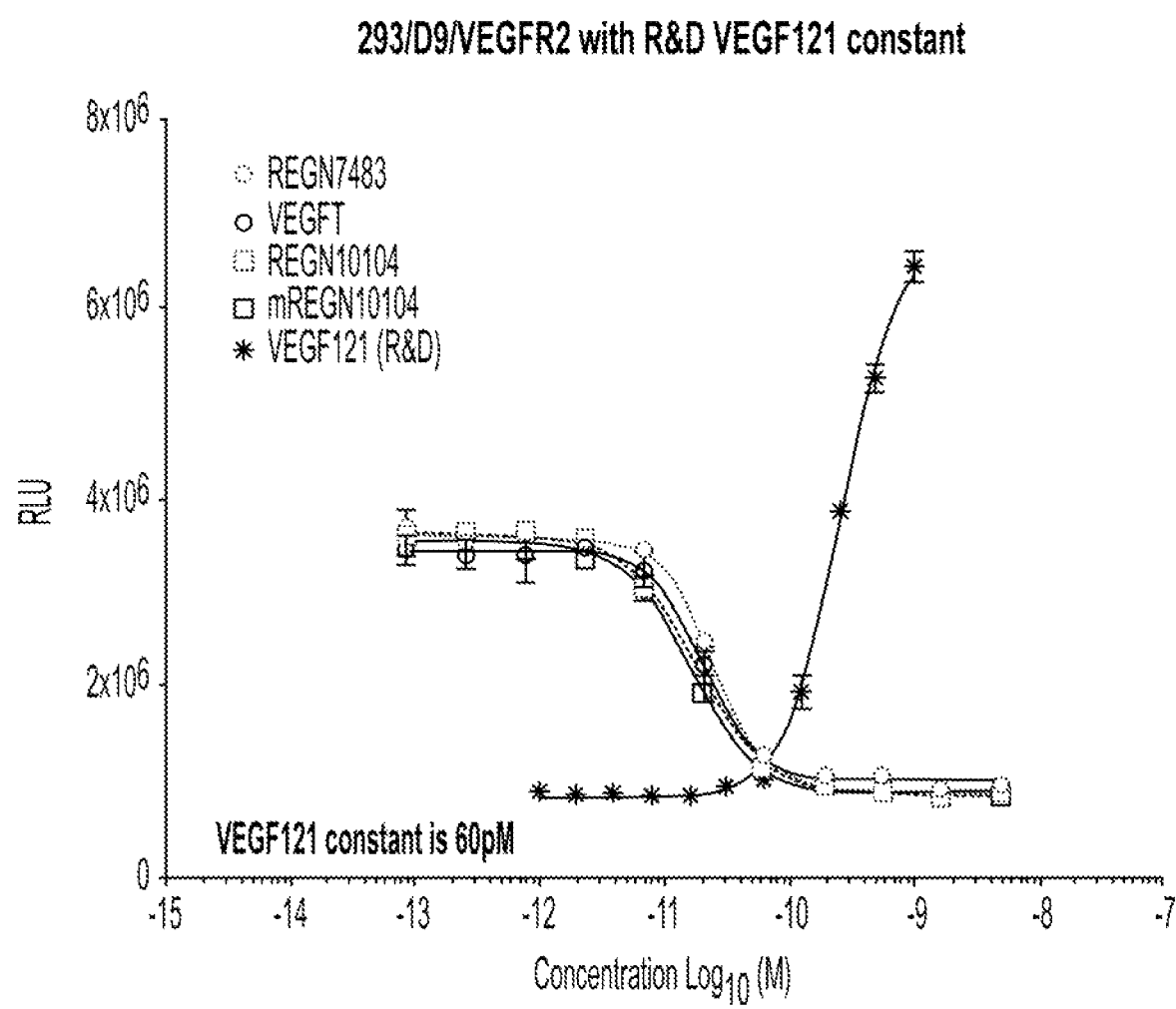
Figure 9C:
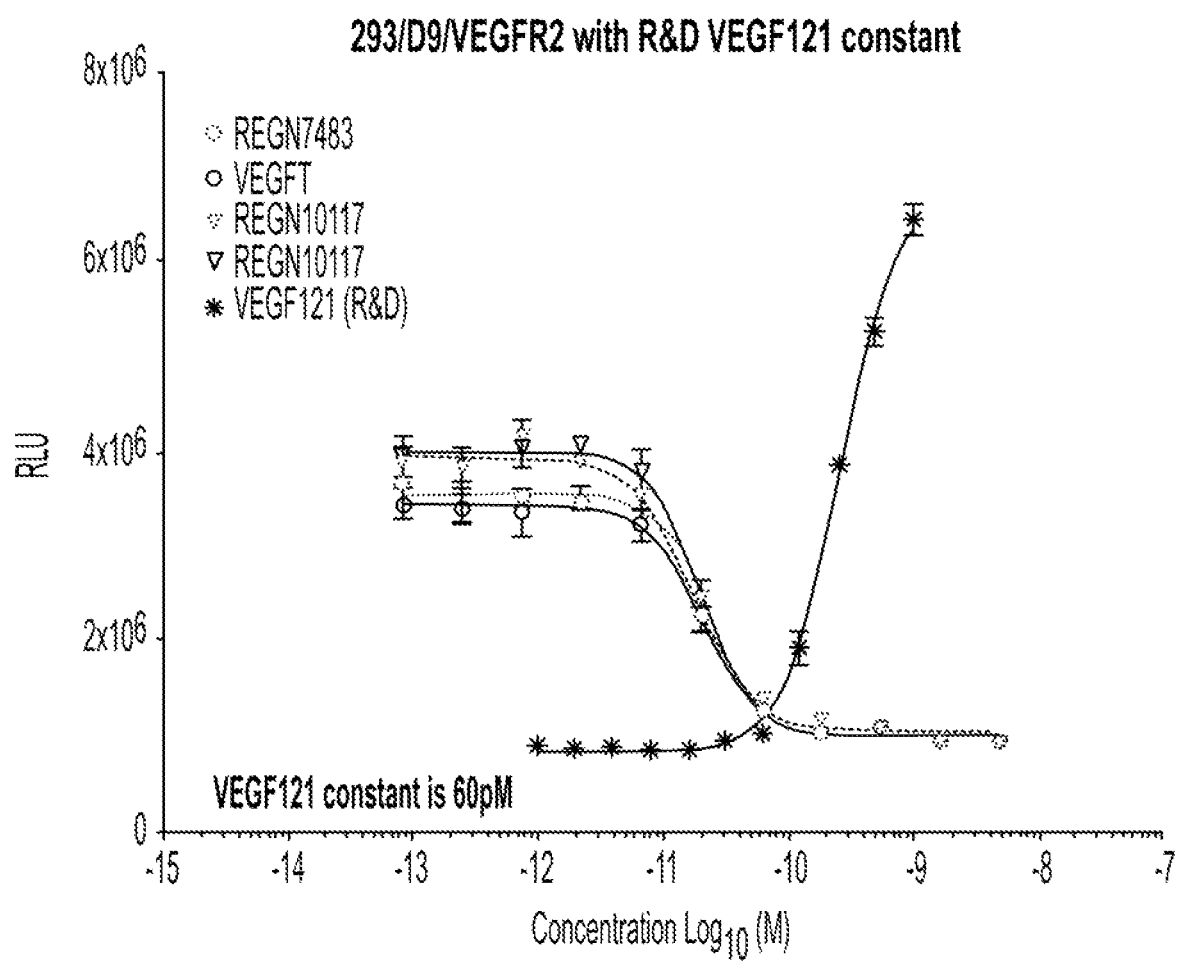
Figure 9D:
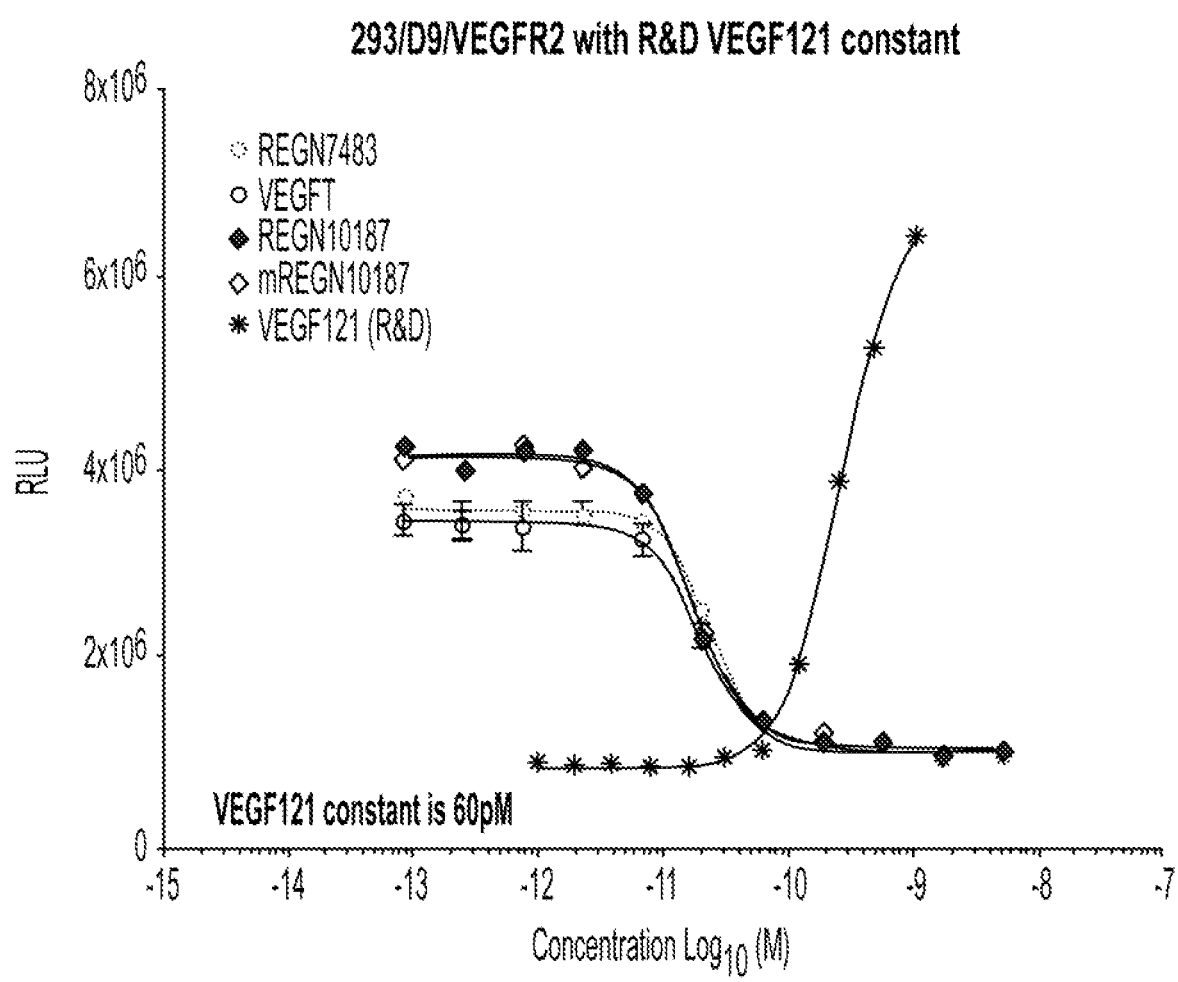
Figure 9E:
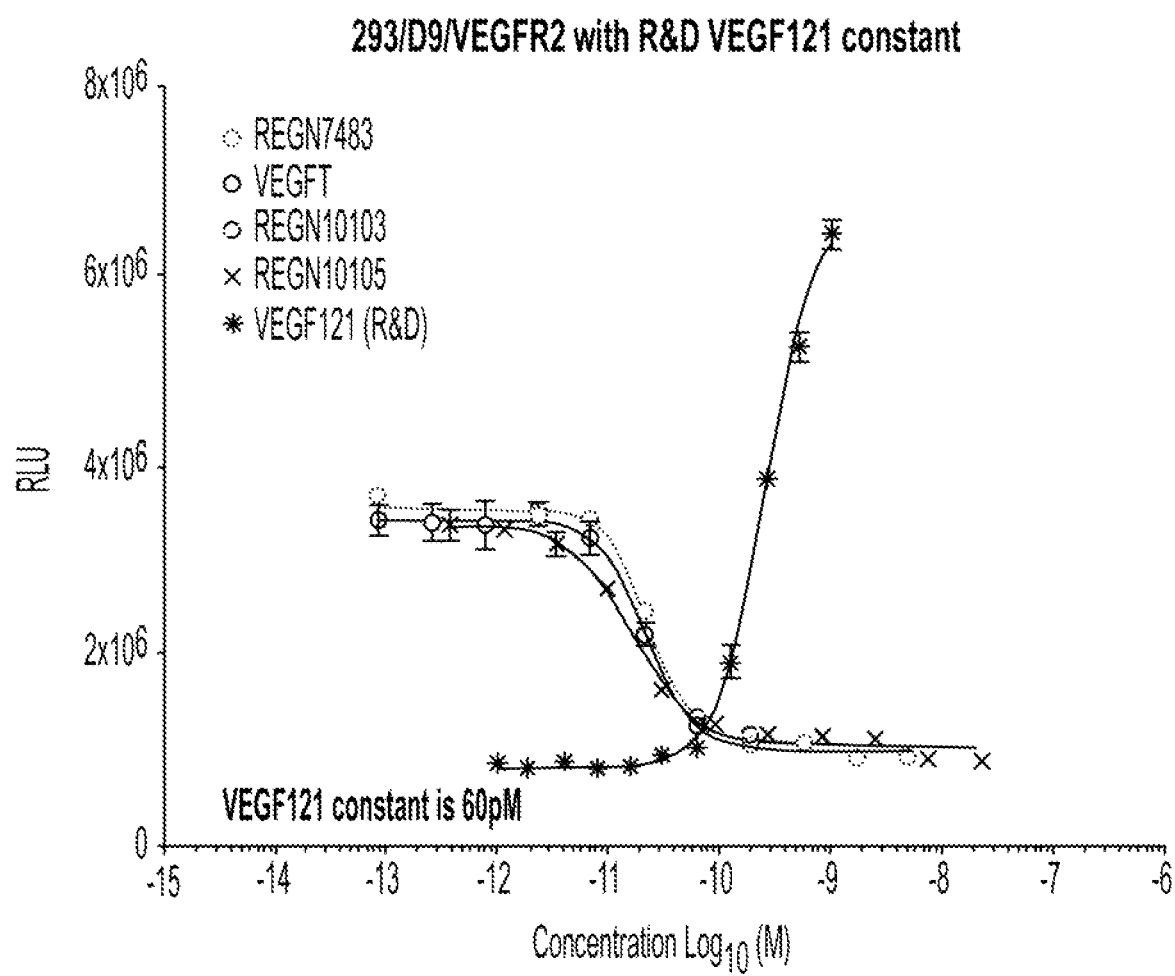
Figure 10A:
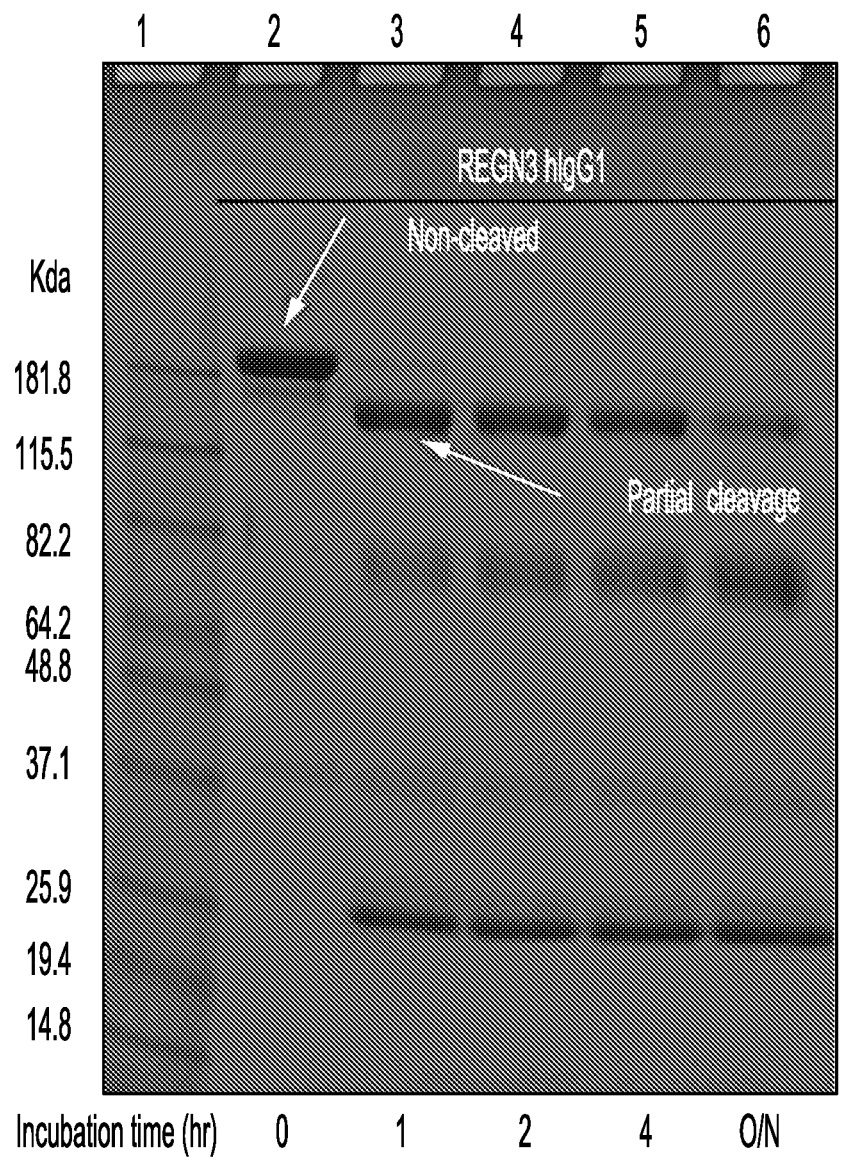
FIGS. 10 (A-F). Non-reducing SDS-PAGE analysis of Ides protease-mediated cleavage of various VEGF Traps (REGN3 (A), REGN10102 (B), REGN10511 (C), REGN10512 (D), REGN10514 (E) and REGN10515 (F)) over time (after incubation for 0, 1, 2 or 4 hours or overnight (0/N)). Figure discloses "GGGF" and "GGGL" as SEQ ID NOS 92 and 94, respectively.
Figure 10B:
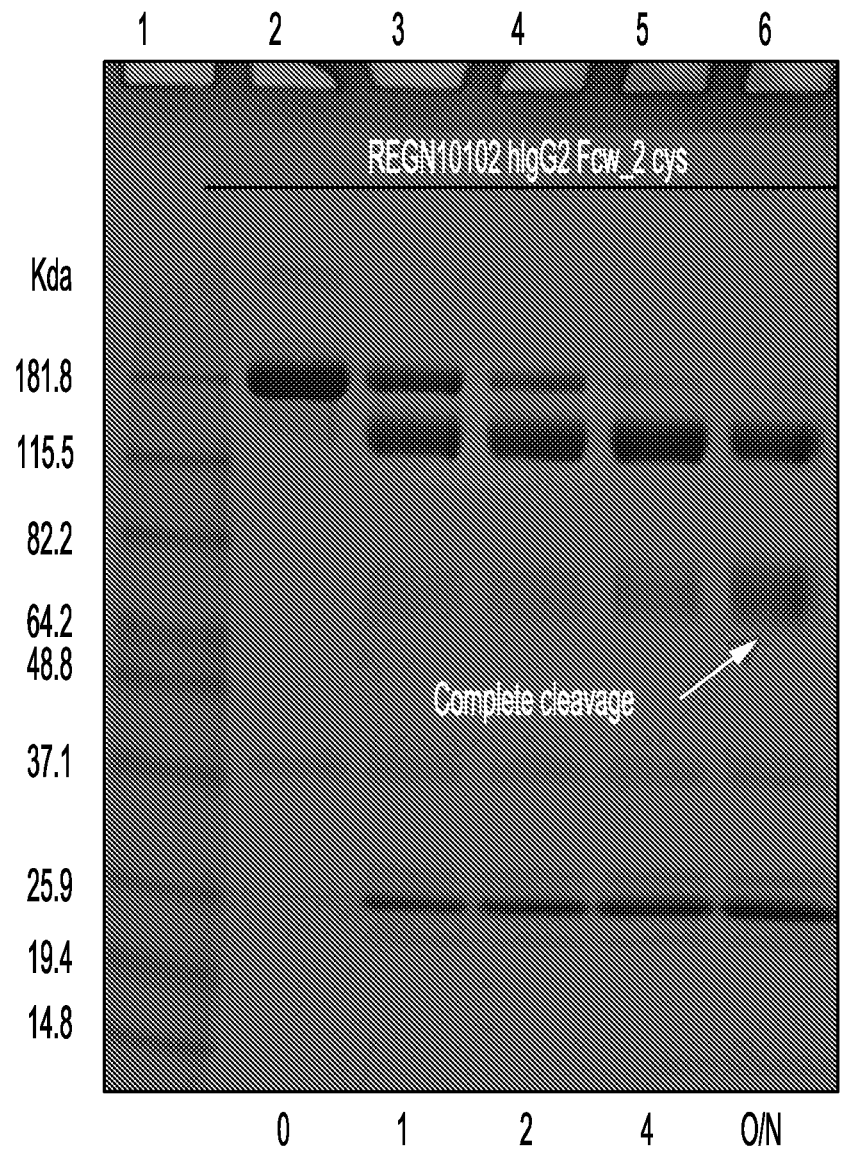
Figure 10C:
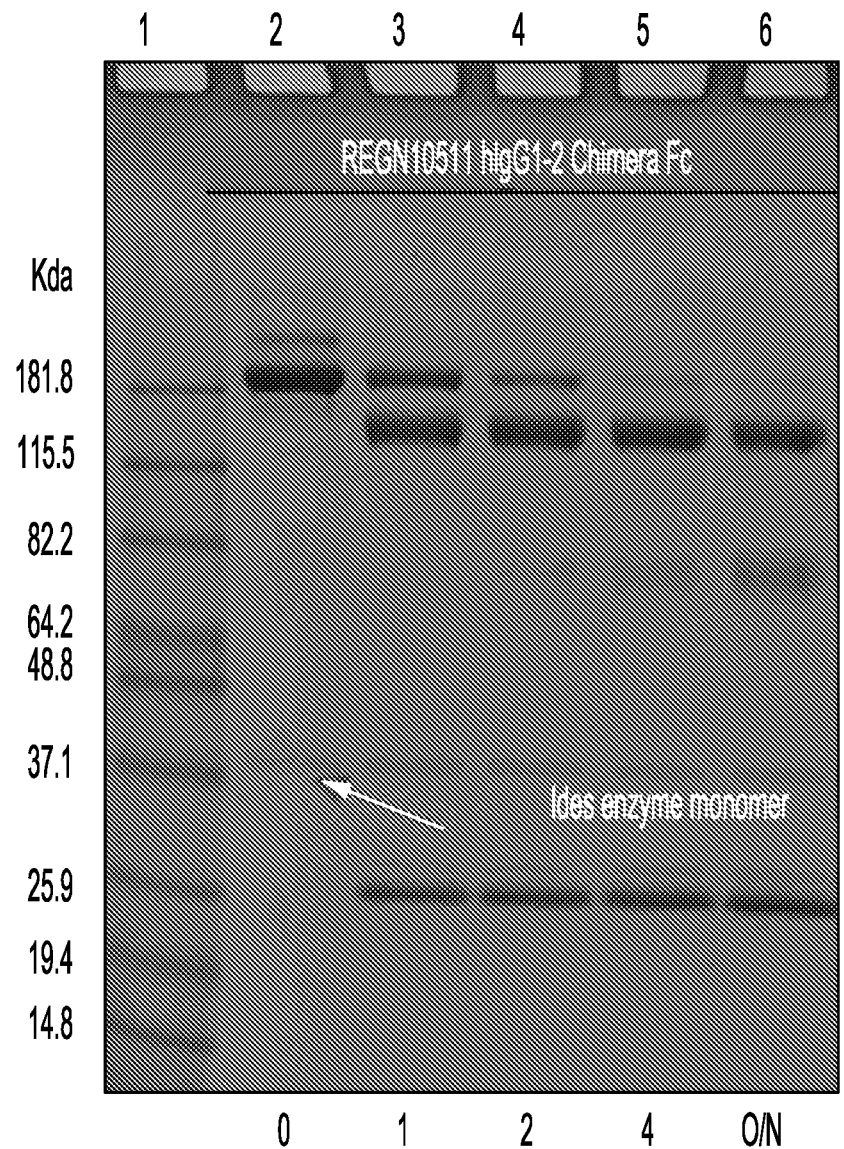
Figure 10D:
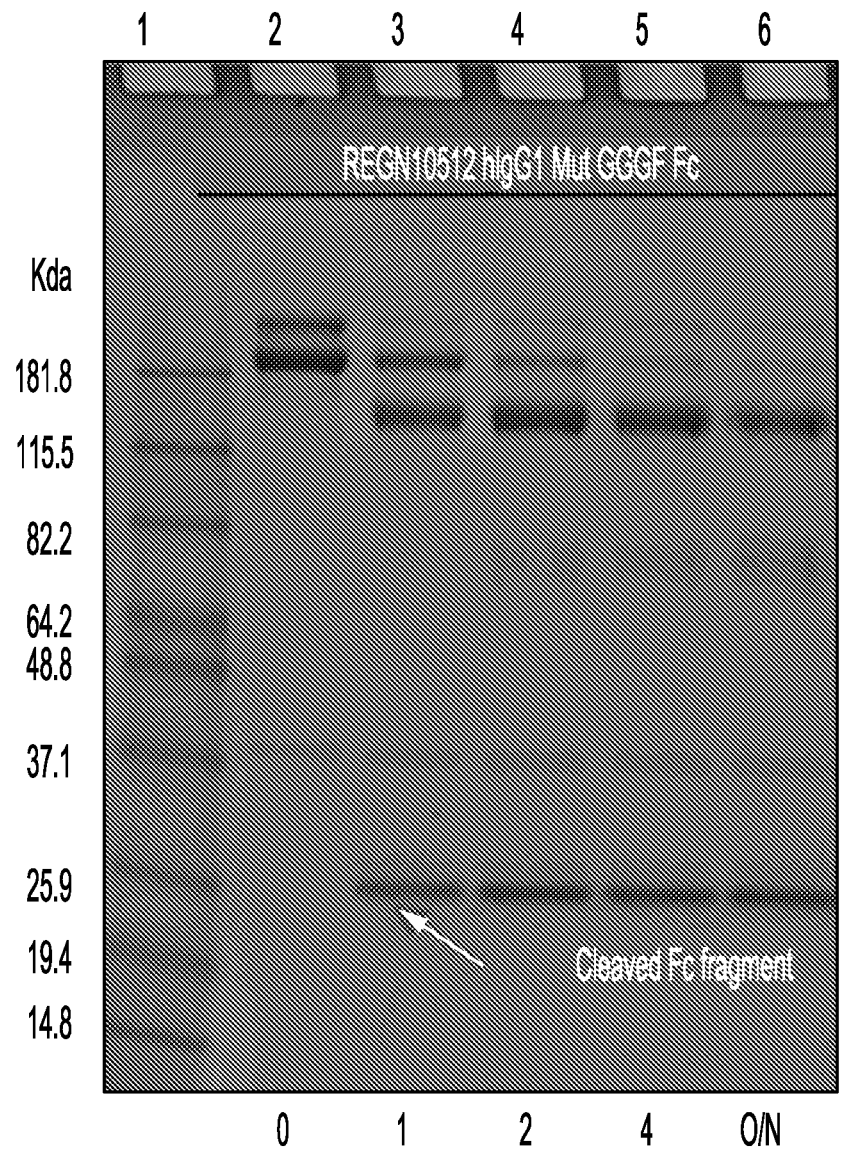
Figure 10E:
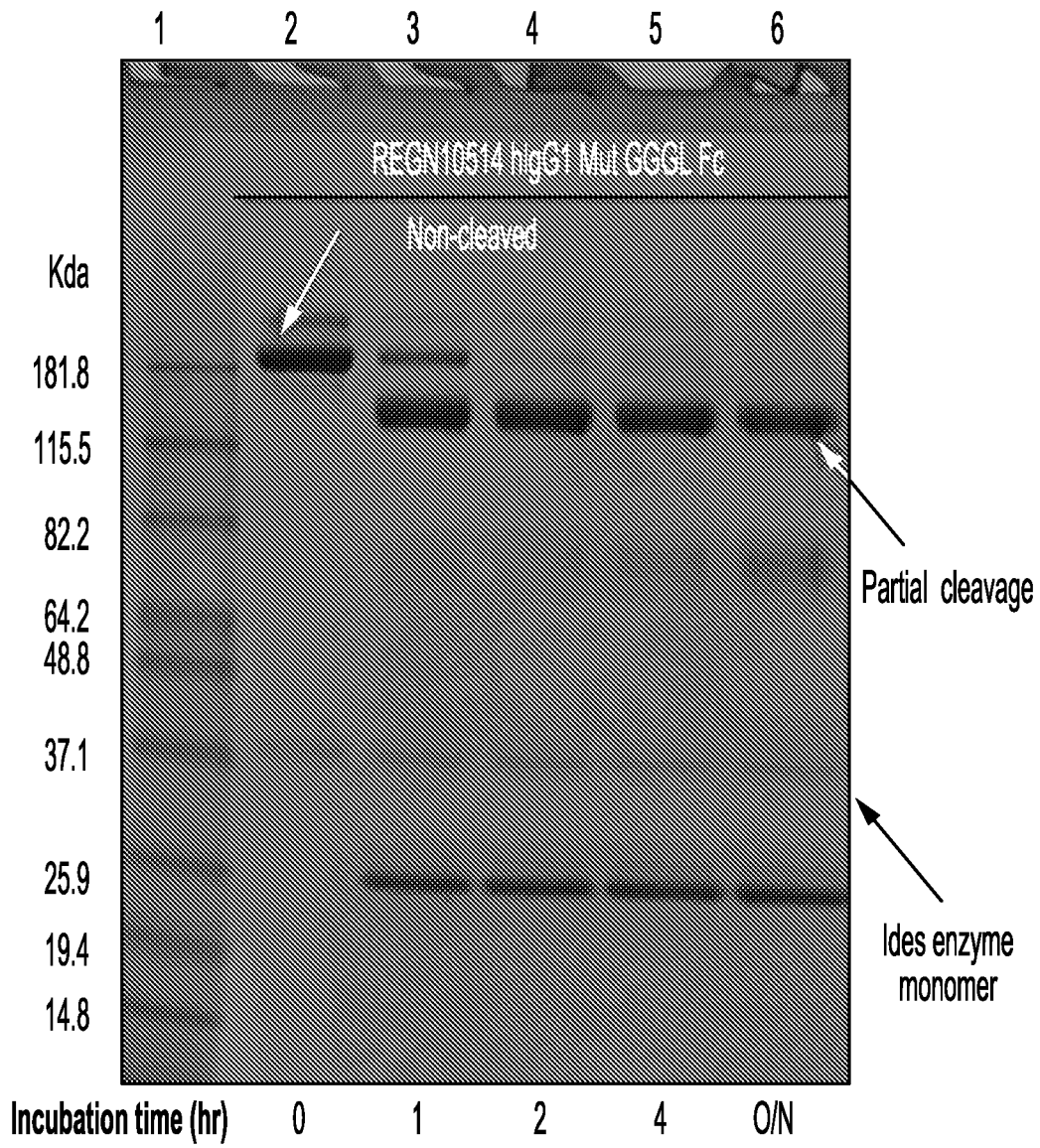
Figure 10F:
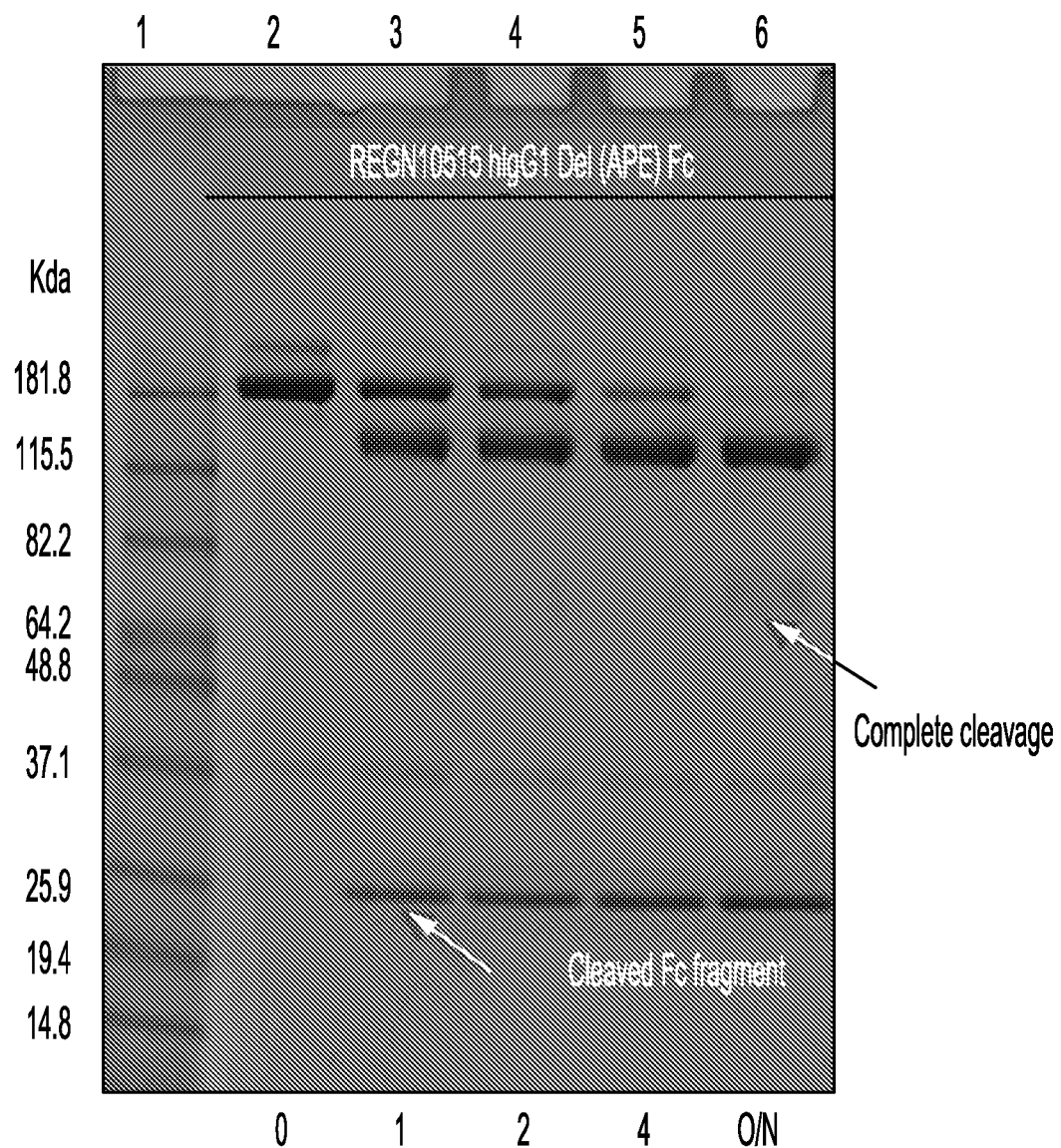

Sequence comparisons between various VEGF traps and VEGF mini-traps are set forth in FIGS. 5 and 6.

A "variant" of a polypeptide (e.g., a variant of a polypeptide including the amino acid sequence of any of SEQ ID Nos: 32-49) refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a reference amino acid sequence that is set forth herein; when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment). In an embodiment of the invention, a variant of a polypeptide refers to a polypeptide comprising about 1, 2, 3, 4, 5, 6, 7, 8, 9 or 10 point mutations (e.g., amino acid substitutions, deletions and/or insertions) relative to that of a reference amino acid sequence that is set forth herein. VEGF traps and mini-traps having amino acid sequences that are variants of any of those set forth herein are part of the present invention.

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

As set forth herein, the terms "REGN10104", "mREGN10104"; "REGN10102", "REGN10105", "REGN10117", "REGN10103", "REGN10187", "mREGN10187"; "REGN10511", "mREGN10511"; "REGN10512", "mREGN10512"; "REGN10513", "mREGN10513"; "REGN10514", "REGN11095", "REGN10515", "mREGN10515" refer to the respective VEGF traps and VEGF mini-traps including polypeptides that include the amino acid sequences described herein under these names as well as variants thereof; and/or multimers (e.g., homodimers) including two or more of such polypeptides.

In an embodiment of the invention, a VEGF mini-trap as set forth herein is characterized according to any one or more of the following:

Binds to human $VEGF_{165}$ or $VEGF_{121}$, e.g., to $VEGF_{165}$ with a $K_D$ of about 1 or 2 or 1-2 pM (e.g., about 0.74 pM, 0.8, 0.86, 0.865 pM, 1 pM, 1.1 pM, 1.08 pM, 1.78 pM, 2.6 pM, 1.89 pM, 1.37 pM, 1.08 pM, 1.82 pM or 1.37 pM) or a greater affinity, e.g., at 25° C., e.g., wherein said affinity was measured by surface plasmon resonance, e.g., in the presence of about 2.5 nM to about 0.078 pM human $VEGF_{165}$.

Has an $IC_{50}$ of about $1-2\times10^{-11}M$ for blocking $VEGF_{121}$ and/or $VEGF_{165}$ activation of VEGFR1 and/or VEGFR2, e.g., as measured in HEK293 cells expressing the VEGF receptor (e.g., wherein the extracellular domain is fused to the cytoplasmic domain of IL18Ralpha or IL18Rbeta), e.g., also having an NFkappaB-luciferase-IRES-eGFP reporter gene. For example, an $IC_{50}$ of about $1-2.5\times10-11M$ for blocking (i) $VEGF_{165}$ (at 40 pM) activation of VEGFR1 (e.g., about $1.06\times10^{-11}M$ or about $2.19\times10^{-11}M$); (ii) $VEGF_{165}$ (at 20 pM) activation of VEGFR2 (e.g., about $2.46\times10^{-11}M$ or about $2.39\times10^{-11}M$); (iii) $VEGF_{121}$ (at 40 pM) activation of VEGFR1 (e.g., about $1.74\times 10^{-11}M$ or about $2.16\times10^{-11}M$); (iv) $VEGF_{121}$ (at 60 pM) activation of VEGFR2 (e.g., about $1.80\times10^{-11}$ M or about $2.30\times10^{-11}M$).

Figure 11A:
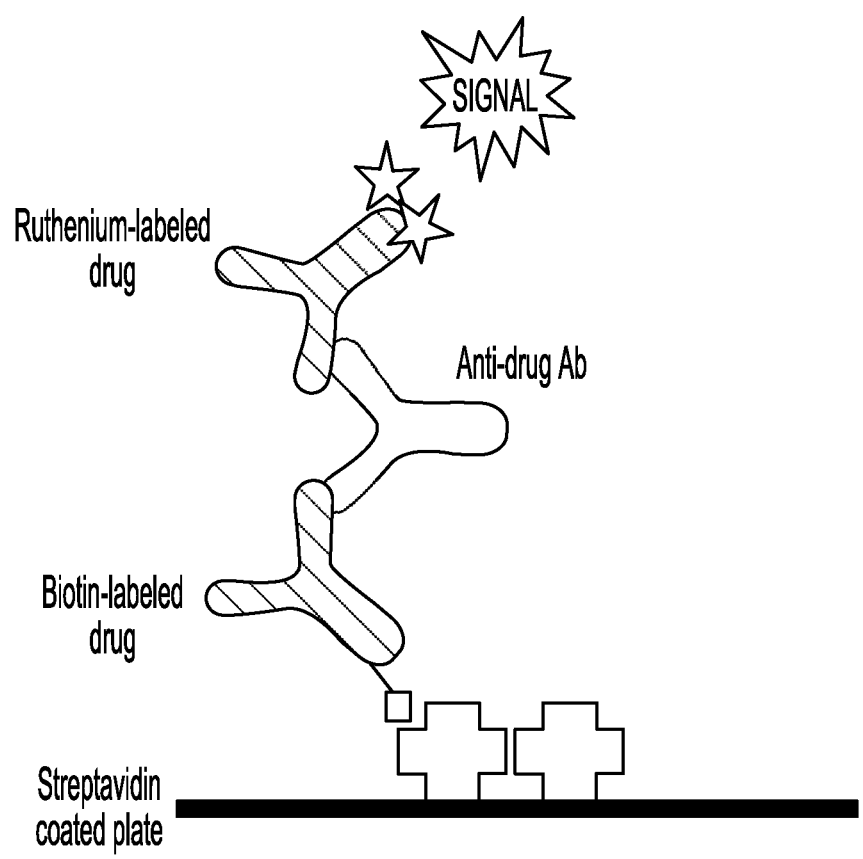
FIGS. 11 (A-B). Anti-drug antibody electrochemiluminescent immunoassay (ECL)—Bridging Format. (A) diagram of assay format. (B) Assay of REGN7483$^F$, REGN10105 (from IdeS cleaved VEGF trap with IgG2 Fc with 2 Cys), mREGN10104 (IdeS cleaved from REGN10104), REGN10105 (recombinantly expressed in CHO cells), REGN10103 (from IdeS cleaved from VEGF trap with IgG2 Fc with 4 Cys) and mREGN10187 for pre-existing anti-hinge antibodies (AHA) responses in naïve monkey serum samples.
Figure 11B:
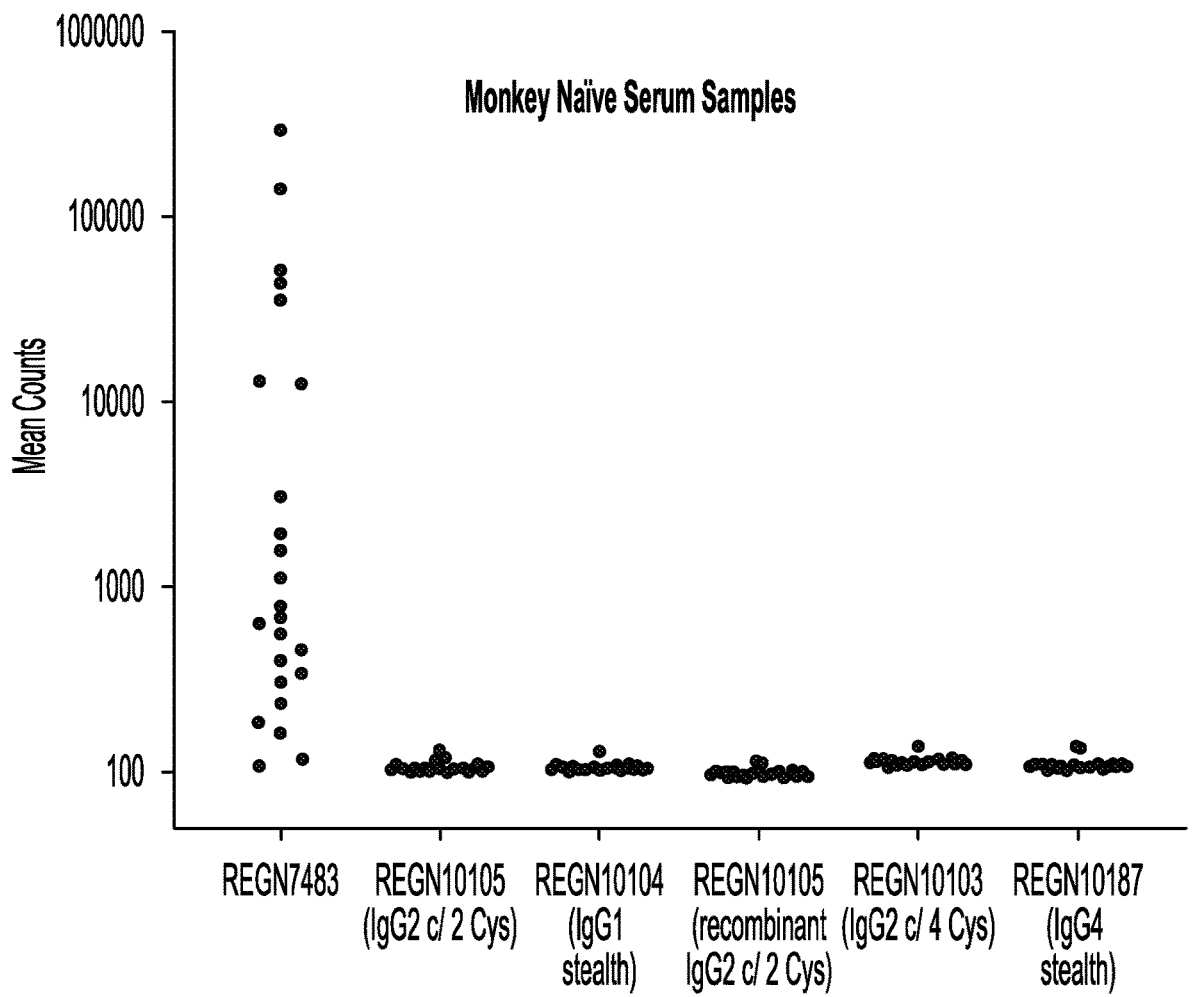

Exhibits less immunogenicity in monkey naïve serum samples and/or human AMD/DME baseline serum samples than that of REGN7483, e.g., as measured by anti-drug antibody (ADA) assay, e.g., electrochemiluminescent immunoassay bridging assay, e.g., wherein said VEGF mini-traps are labeled with biotin and ruthenium, e.g., wherein ADA binds Biotin- and Ruthenium-labeled VEGF mini-trap, forming a bridge, wherein the biotin labeled VEGF mini-trap is bound to a streptavidin-coated plate surface, e.g., wherein an electric current activates Ruthenium-labeled drug to produce an electrochemiluminescent signal that indicates the presence of the complex. See assay format summary in FIG. 11 (A).

Forms a 1:1 complex with $VEGF_{165}$ homodimer (REGN10105:$VEGF_{165}$ homodimer or REGN11095:$VEGF_{165}$ homodimer) (e.g., at 6 µM:2 µM, 2 µM:2 µM or 2 µM:6 µM ratio of the VEGF mini-trap:$VEGF_{165}$ homodimer).

Forms a 1:1:2 complex with $VEGF_{165}$ homodimer and REGN18 anti-VEGF Fab (REGN10105:$VEGF_{165}$ homodimer:REGN18).

Reduces retinal neovascularization when dosed (e.g., at about 0.125, 0.025, 0.25 or 2.5 micrograms per eye) intravitreally in an OIR mouse model (e.g., relative to that of mice dosed with human Fc), e.g., as measured under a retinal flat mount.

Exhibits faster intravitreal half-live (e.g., of about 3.4 or 3.9 days) than aflibercept in rabbit (e.g., New Zealand White rabbits) eyes when intravitreally injected (e.g., at about 0.115, 0.146 or 0.147 micrograms per eye), e.g., wherein the VEGF mini-trap is formulated in 10 mM histidine, e.g., wherein the VEGF mini-trap is conjugated with AF488 dye.

Exhibits less systemic exposure (e.g., plasma levels of free molecule) when injected intravitreally, e.g., at 5.5 mg/eye, than aflibercept (e.g., at 4 mg/eye) (e.g., in non-human primates (NHPs)). For example, having about 0.1 or 0.2 or 0.1-0.2 micrograms/ml (or less) concentration of free molecule in the plasma, e.g., of a NHP, about 336 hours after injection (e.g., a single injection) of about 5.5 mg/eye.

Does not accumulate in the plasma (e.g., as free or VEGF bound molecule), e.g., of a non-human primate, after multiple intravitreal injections (e.g., 4, e.g., about every 28 days), e.g., of about 5.5 mg/eye.

Exhibits greater stability than aflibercept under stress conditions such as elevated temperature, e.g., 37° C., e.g., for 4 weeks under approximately equimolar conditions. For example, at 90 mg/ml develops about 3-4% (e.g., 3.5, 3.6, 3.7, 3.74, 4.0 or 4.1) high molecular weight species (HMW) per week (e.g., for 4 weeks at 37° C.); and/or at 120 mg/ml develops about 5-6% (e.g., 5.0, 5.1, 5.2, 5.3, 5.5, 5.7 or 5.9) high molecular weight species (HMW) per week (e.g., for 4 weeks at 37° C.); for example, whereas aflibercept at 140 mg/ml develops about 5.6% high molecular weight species (HMW) per week (e.g., for 4 weeks at 37° C.); or, for example, whereas $REGN7483^F$ develops about 5-6% (e.g., 5.4, 5.45, 5.5, 5.6) HMW species/week (e.g., for 4 weeks at 37° C.) at 90 mg/ml. $REGN7483^F$ mini-trap is generated by FabRICATOR cleavage of aflibercept.

Exhibits no significant change in aggregation levels after about 15 minutes of agitation at about 1000 rpm and/or two free-thaw cycles (e.g., at about 90 mg/ml or 120 mg/ml).

Exhibits less viscosity than REGN7483, e.g., about 5.8 at 90 mg/ml or 12.1 cP at 120 mg/ml (e.g., at 20° C.); for example, whereas REGN7483 has a viscosity of about 6.9 cP at 90 mg/ml, or 12.1 cP at 120 mg/ml, or, for example, whereas REGN7483 has a viscosity of about 14.5 cP at 120 mg/ml (e.g., in the presence of histidine at 20° C.)—e.g., wherein the VEGF mini-trap is REGN10105.

Exhibits greater photostability than REGN7483, e.g., developing about 8.7% HMW increase (relative to dark control samples)/M lux*hrs (e.g., wherein the VEGF mini-trap is REGN10105), whereas, for example, REGN7483 exhibits about 9.5% HMW increase (relative to dark control samples)/M lux*hrs, e.g., at about 10 mg/ml concentration, e.g., wherein light is cool white light and/or ultraviolet light.

In a composition comprising VEGF traps and/or VEGF mini-trap (e.g., having an IgG2 hinge region), such molecules are glycosylated with N-glycans (e.g., fucosylated, sialylated, galactosylated, mannosylated or modified with bisecting N-glycan) such that about 43-45% of total N-glycans have a core fucose residue, about 64-72% of total N-glycans have at least one galactose residue, about 20-27% of total N-glycans have at least one sialic acid residue, about 19-25% are identified as having high mannose (e.g., Man5) and/or about 1.6-1.9% of total N-glycans are bisecting glycans; e.g., wherein such molecules are glycosylated with N-glycans such that about 43.3% of total N-glycans have a core fucose residue, about 64.4% of total N-glycans have at least one galactose residue, about 20% of total N-glycans have at least one sialic acid residue, about 25.2% are identified as having high mannose (e.g., Man5) and/or about 1.6% of total N-glycans are bisecting glycans (e.g., wherein the VEGF mini-trap is REGN10103); or such molecules are glycosylated with N-glycans such that about 44.8% of total N-glycans have a core fucose residue, about 71.6% of total N-glycans have at least one galactose residue, about 26.5% of total N-glycans have at least one sialic acid residue, about 18.6% are identified as having high mannose (e.g., Man5) and/or about 1.9% of total N-glycans are bisecting glycans (e.g., wherein the VEGF mini-trap is REGN10105).

one more serines or threonines of the VEGF trap or mini-trap are O-glycosylated;

one or more asparagines of the VEGF trap or mini-trap are deamidated;

one or more Aspartate-Glycine motifs of the VEGF trap or mini-trap are converted to iso-aspartate-glycine and/or Asn-Gly;

one or more methionines of the VEGF trap or mini-trap are oxidized;

one or more tryptophans of the VEGF trap or mini-trap are converted to N-formylkynurenin;

one or more arginines of the VEGF trap or mini-trap are converted to Arg 3-deoxyglucosone;

the C-terminal residue (e.g., glycine or alanine) of the VEGF trap or mini-trap is not present;

there are one or more non-glycosylated glycosites in the VEGF trap or mini-trap;

the VEGF trap or mini-trap is xylosylated;

the VEGF trap or mini-trap is glycated at a lysine;

the VEGF trap or mini-trap comprises a cystine with a free-thiol group;

the VEGF trap or mini-trap comprises an intrachain disulfide bridge;

the VEGF trap or mini-trap comprises disulfide bridges in parallel or crossed orientation; and/or the VEGF trap or mini-trap comprises a lysine or arginine which is carboxymethylated.

See e.g., Guidance for Industry Q1B Photostability Testing of New Drug Substances and Products, U.S. Department of Health and Human Services, Food and Drug Administration, Center for Drug Evaluation and Research (CDER), Center for Biologics Evaluation and Research (CBER), November 1996.

The VEGF traps and VEGF mini-traps set forth herein (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) may also be glycosylated (e.g., with N-linked and/or O-linked glycans). For example, in an embodiment of the invention, the VEGF trap or mini-trap is sialylated, galactosylated and/or fusosylated at one or more sites. In an embodiment of the invention, the VEGF trap or mini-trap has one or more N-linked mannose-5 glycans (Man5). In an embodiment of the invention, the VEGF trap or VEGF mini-trap includes glycosylation that is typically added to a molecule which is expressed in a Chinese hamster ovary (CHO) cell (CHO cell glycosylation). See e.g., Carillo et al., Glycosylation Analysis of Therapeutic Glycoproteins Produced in CHO Cells, Methods Mol Biol. 2017; 1603: 227-241; or Hossler et al., Optimal and consistent protein glycosylation in mammalian cell culture, Glycobiology 19(9): 936-949 (2009). In an embodiment of the invention, the VEGF trap or VEGF mini-trap is a composition including a heterogeneous mixture of glycosylated variants of the Trap or mini-trap. Individual molecules of VEGF trap or VEGF mini-trap may differ from others in the composition with respect to their particular glycosylation pattern. For example, about 47% of the molecules may be sialyalted, about 70% of the molecules may be galactosylated, about 36% of the molecules may be fucosylated and/or about 11% of the molecules may be Man-5 glycosylated. In an embodiment of the invention, a composition comprising VEGF traps and/or VEGF mini-trap, has the glycan profile of about 43.3% fucosylated, about 64.4% galactosylated, about 20% sialylated, about 25.2% with high mannose glycans and about 1.6% bisecting N-glycans (e.g., wherein the VEGF mini-trap is REGN10103), or having the glycan profile of about 44.8% fucosylated, about 71.6% galactosylated, about 26.5% sialylated, about 18.6% with high mannose glycans and about 1.9% bisecting N-glycans (e.g., wherein the VEGF mini-trap is REGN10105).

See e.g., Yu et al., Production, characterization, and pharmacokinetic properties of antibodies with N-linked mannose-5 glycans, MAbs. July-August 2012; 4(4):475-87.

In an embodiment of the invention, REGN10105 is N-glycosylated (e.g., as described herein) at one or more of the underscored N residues indicated below: SDTGRPFVE-MYSEIPEIIHMTEGRELVIPCRVT-SPNITVTLKKFPLDTLIPDGKRIIWDSRKGFIIS-NATYKEIGLL TCEATVNGHLYKTNYLTHRQTNTIIDVVLSP-SHGIELSVGEKLVLNCTARTELNVGIDFNWEY-PSSKHQHKKLVNRD LKTQSGSEMKKFLSTLTI-DGVTRSDQGLYTCAASSGLMTKKNSTFVRVHEKVE-CPPCPAPPVA (SEQ ID NO: 33). Corresponding N residues in the other VEGF traps and mini-traps set forth herein may be similarly N-glycosylated.

In an embodiment of the invention, one or more histidines in a VEGF trap or mini-trap as set forth herein is a 2-oxo-histidine.

Two chemical versions of 2-oxo-histidine (2-oxo-his) can be produced,

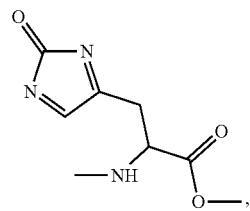

having a 13.98 Da increase in molecular weight relative to histidine (13.98 Da version); or

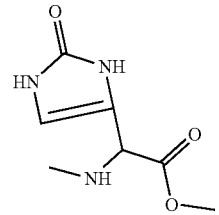

having a 15.99 Da increase in molecular weight relative to histidine (15.99 Da version); wherein the 13.98 Da version of 2-oxo-histidine is the predominant moiety observed in mini-trap expressed in CDM. The content of the 13.98 Da version of 2-oxo-histidine in a peptide can be evaluated spectrophotometrically since this moiety has an enhanced absorbance of light at 350 nM wavelength whereas the 15.99 Da version does not have such an enhanced absorbance. Formation of the 13.98 Da version of 2-oxo-histidine in mini-trap may be catalyzed by light whereas formation of the 15.99 Da version may be catalyzed by metal such as copper ($Cu^{2+}$).

Oxidation of tryptophan can give a complex mixture of products. The primary products can be N-formylkynurenine and kynurenine along with mono-oxidation, di-oxidation and/or tri-oxidation products. Peptides bearing oxidized Trp modifications generally exhibit mass increases of 4, 16, 32 and 48 Da, corresponding to the formation of kynurenine (KYN), hydroxytryptophan ($W_{ox1}$), and N-formylkynurenine/dihydroxytryptophan (NFK/W$_{ox2}$, referred to also as "doubly oxidized Trp"), trihydroxytryptophan (W$_{ox3}$; referred to also as "triply oxidized Trp"), and their combinations, such as hydroxykynurenine (KYN$_{ox1}$, +20 Da). Oxidation to hydroxytryptophan (W$_{ox1}$) (Mass spectrometric identification of oxidative modifications of tryptophan residues in proteins: chemical artifact or post-translational modification? J Am Soc Mass Spectrom. 2010 July; 21(7): 1114-1117). Similar to tryptophan, oxidation of tyrosine primarily yields 3,4-dihydroxyphenylalanine (DOPA) and dityrosine (Li, S, C Schoneich, and R T. Borchardt. 1995. Chemical Instability of Protein Pharmaceuticals: Mechanisms of Oxidation and Strategies for Stabilization. Biotechnol. Bioeng. 48:490-500).

The scope of the present invention includes compositions wherein about 0.1-2% (or less, e.g., 0.1% or less, or 0.05% or 0.01%) of histidines in the VEGF mini-traps or traps in the composition are 2-oxo-histidine.

Ides and Variants Thereof

The present invention includes VEGF mini-traps and compositions thereof that have been produced by proteolytic digestion of aflibercept with *Streptococcus pyogenes* IdeS (FabRICATOR) and variants thereof. FabRICATOR is commercially available from Genovis, Inc.; Cambridge, Mass.; Lund, Sweden.

In one embodiment, the IdeS polypeptide comprises an amino acid sequence with at least 70% sequence identity over a full length of the isolated an amino acid sequence as set forth in the group consisting of SEQ ID NO: 50-65. In one aspect, the isolated an amino acid sequence has at least about 80% sequence identity over a full length of the isolated an amino acid sequence. In another aspect, the isolated an amino acid sequence has at least about 90% sequence identity over a full length of the isolated an amino acid sequence. In another aspect, the isolated an amino acid sequence has about 100% sequence identity over a full length of the isolated an amino acid sequence. In one aspect, the polypeptide can be capable of cleaving a target protein into fragments. In a particular aspect, the target protein is an IgG. In another particular aspect, the target protein is a fusion protein. In yet another particular aspect, the fragments can comprise a Fab fragment and/or a Fc fragment.

In one embodiment, the IdeS amino acid sequence comprises a parental amino acid sequence defined by MRKRCYSTSAAVLAAVTLFVLSVDRGVIADSFSANQEIRYSEVTPYHVTSVWTKGVTPP ANFTQGEDVFHAPYVANQGWYDITKTFNGKDDLLCGAATAGNMLHWWFDQNKDQIK RYLEEHPEKQKINFNGEQMFDVKEAIDTKNHQLDSKLFEYFKEKAFPYLSTKHLGVFPD HVIDMFINGYRLSLTNHGPTPVKEGSKDPRGGI FDAVFTRGDQSKLLTSRHDFKEKNLK EISDLIKKELTEGKALGLSHTYANVRINHVINLWGADFDSNGNLKAIYVTDSDSNASIGM KKYFVGVNSAGKVAISAKEIKEDNIGAQVLGLFTLSTGQDSWNQTN (SEQ ID NO: 66), but having an asparagine residue at position 87, 130, 182 and/or 274 mutated to an amino acid other than asparagine. In one aspect, the mutation can confer an increased chemical stability at alkaline pH-values compared to the parental amino acid sequence. In another aspect, the mutation can confer an increase in chemical stability by 50% at alkaline pH-values compared to the parental amino acid sequence. In one aspect, the amino acid can be selected from aspartic acid, leucine, and arginine. In a particular aspect, the asparagine residue at position 87 is mutated to aspartic acid residue. In another particular aspect, the asparagine residue at position 130 is mutated to arginine residue. In a yet another particular aspect, the asparagine residue at position 182 is mutated to a leucine residue. In a yet another particular aspect, the asparagine residue at position 274 is mutated to aspartic acid residue. In a yet another particular aspect, the asparagine residue at position 87 and 130 are mutated. In a yet another particular aspect, the asparagine residue at position 87 and 182 are mutated. In a yet another particular aspect, the asparagine residue at position 87 and 274 are mutated. In a yet another particular aspect, the asparagine residue at position 130 and 182 are mutated. In a yet another particular aspect, the asparagine residue at position 130 and 274 are mutated. In a yet another particular aspect, the asparagine residue at position 182 and 274 are mutated. In a yet another particular aspect, the asparagine residue at position 87, 130 and 182 are mutated. In a yet another particular aspect, the asparagine residue at position 87, 182 and 274 are mutated. In a yet another particular aspect, the asparagine residue at position 130, 182 and 274 are mutated. In a yet another particular aspect, the asparagine residue at position 87, 130, 182 and 274 are mutated.

Aflibercept or another VEGF trap can be cleaved by IdeS that has been immobilized to a solid support, e.g., a chromatography bead. For example, a sample including VEGF trap in a buffered aqueous solution (in a cleavage buffer) can be applied to the immobilized IdeS, e.g., in a chromatography column. The column can be incubated, e.g., for 30 minutes, e.g., at about 18° C. The column can then be washed with the cleavage buffer. After cleavage, the digestion and wash solutions can be applied to a protein A column to capture cleaved Fc by-product wherein mini-trap product is retained in the flow-through fraction. In an embodiment of the invention, the cleavage buffer and/or the protein-A column equilibration and wash solutions are at pH 7, e.g., 40 mM Tris, 54 mM Acetate pH 7.0±0.1. Such methods for making a VEGF mini-trap are part of the present invention.

In an embodiment of the invention, an IdeS variant includes an amino acid sequence set forth below:

(SEQ ID NO: 50)
MRKRCYSTSAAVLAAVTLFVLSVDRGVIADSFSANQEIRYSEVTPYHVTSVWTKGVTPPANFTQGEDVFHAPYVANQ

GWYDITKTFNGKDDLLCGAATAGNMLHWWFDQNKDQIKRYLEEHPEKQKINENGEQMFDVKEAIDTKNHQLDSKLFE

YEKEKAFPYLSTKHLGVFPDHVIDMFINGYRLSLTNHGPTPVKEGSKDPRGGIFDAVFTRGDQSKLLTSRHDFKEKN

LKEISDLIKKELTEGKALGLSHTYANVRINHVINLWGADFDSNGNLKAIYVTDSDSNASIGMKKYFVGVNSAGKVAI

SAKEIKEDNIGAQVLGLFTLSTGQDSWNQTN;

(SEQ ID NO: 51)
MRKRCYSTSAAVLAAVTLFVLSVDRGVIADSFSANQEIRYSEVTPYHVTSVWTKGVTPPANFTQGEDVFHA
PYVANQGWYDITKTFDGKDDLLCGAATAGNMLHWWFDQNKDQIKRYLEEHPEKQKINENGEQMFDVKEAIDTKNHQL
DSKLFEYFKEKAFPYLSTKHLGVFPDHVIDMFINGYRLSLTNHGPTPVKEGSKDPRGGIFDAVFTRGDQSKLLTSRH
DFKEKNLKEISDLIKKELTEGKALGLSHTYANVRINHVINLWGADFDSNGNLKAIYVTDSDSNASIGMKKYFVGVNS
AGKVAISAKEIKEDNIGAQVLGLFTLSTGQDSWNQTN;

(SEQ ID NO: 52)
MRKRCYSTSAAVLAAVTLFVLSVDRGVIADSFSANQEIRYSEVTPYHVTSVWTKGVTPPANFTQGEDVFHA
PYVANQGWYDITKTFNGKDDLLCGAATAGNMLHWWFDQNKDQIKRYLEEHPEKQKINFRGEQMFDVKEAIDTKNHQL
DSKLFEYFKEKAFPYLSTKHLGVFPDHVIDMFINGYRLSLTNHGPTPVKEGSKDPRGGIFDAVFTRGDQSKLLTSRH
DFKEKNLKEISDLIKKELTEGKALGLSHTYANVRINHVINLWGADFDSNGNLKAIYVTDSDSNASIGMKKYFVGVNS
AGKVAISAKEIKEDNIGAQVLGLFTLSTGQDSWNQTN;

(SEQ ID NO: 53)
MRKRCYSTSAAVLAAVTLFVLSVDRGVIADSFSANQEIRYSEVTPYHVTSVWTKGVTPPANFTQGEDVFHA
PYVANQGWYDITKTFNGKDDLLCGAATAGNMLHWWFDQNKDQIKRYLEEHPEKQKINENGEQMFDVKEAIDTKNHQL
DSKLFEYFKEKAFPYLSTKHLGVFPDHVIDMFILGYRLSLTNHGPTPVKEGSKDPRGGIFDAVFTRGDQSKLLTSRH
DFKEKNLKEISDLIKKELTEGKALGLSHTYANVRINHVINLWGADFDSNGNLKAIYVTDSDSNASIGMKKYFVGVNS
AGKVAISAKEIKEDNIGAQVLGLFTLSTGQDSWNQTN;

(SEQ ID NO: 54)
MRKRCYSTSAAVLAAVTLFVLSVDRGVIADSFSANQEIRYSEVTPYHVTSVWTKGVTPPANFTQGEDVFHA
PYVANQGWYDITKTFNGKDDLLCGAATAGNMLHWWFDQNKDQIKRYLEEHPEKQKINENGEQMFDVKEAIDTKNHQL
DSKLFEYFKEKAFPYLSTKHLGVFPDHVIDMFINGYRLSLTNHGPTPVKEGSKDPRGGIFDAVFTRGDQSKLLTSRH
DFKEKNLKEISDLIKKELTEGKALGLSHTYANVRINHVINLWGADFDSDGNLKAIYVTDSDSNASIGMKKYFVGVNS
AGKVAISAKEIKEDNIGAQVLGLFTLSTGQDSWNQTN;

(SEQ ID NO: 55)
MRKRCYSTSAAVLAAVTLFVLSVDRGVIADSFSANQEIRYSEVTPYHVTSVWTKGVTPPANFTQGEDVFHA
PYVANQGWYDITKTFDGKDDLLCGAATAGNMLHWWFDQNKDQIKRYLEEHPEKQKINFRGEQMFDVKEAIDTKNHQL
DSKLFEYFKEKAFPYLSTKHLGVFPDHVIDMFINGYRLSLTNHGPTPVKEGSKDPRGGIFDAVFTRGDQSKLLTSRH
DFKEKNLKEISDLIKKELTEGKALGLSHTYANVRINHVINLWGADFDSNGNLKAIYVTDSDSNASIGMKKYFVGVNS
AGKVAISAKEIKEDNIGAQVLGLFTLSTGQDSWNQTN;

(SEQ ID NO: 56)
MRKRCYSTSAAVLAAVTLFVLSVDRGVIADSFSANQEIRYSEVTPYHVTSVWTKGVTPPANFTQGEDVFHA
PYVANQGWYDITKTFDGKDDLLCGAATAGNMLHWWFDQNKDQIKRYLEEHPEKQKINFNGEQMFDVKEAIDTKNHQL
DSKLFEYFKEKAFPYLSTKHLGVFPDHVIDMFILGYRLSLTNHGPTPVKEGSKDPRGGIFDAVFTRGDQSKLLTSRH
DFKEKNLKEISDLIKKELTEGKALGLSHTYANVRINHVINLWGADFDSNGNLKAIYVTDSDSNASIGMKKYFVGVNS
AGKVAISAKEIKEDNIGAQVLGLFTLSTGQDSWNQTN;

(SEQ ID NO: 57)
MRKRCYSTSAAVLAAVTLFVLSVDRGVIADSFSANQEIRYSEVTPYHVTSVWTKGVTPPANFTQGEDVFHA
PYVANQGWYDITKTFDGKDDLLCGAATAGNMLHWWFDQNKDQIKRYLEEHPEKQKINFNGEQMFDVKEAIDTKNHQL
DSKLFEYFKEKAFPYLSTKHLGVFPDHVIDMFINGYRLSLTNHGPTPVKEGSKDPRGGIFDAVFTRGDQSKLLTSRH
DFKEKNLKEISDLIKKELTEGKALGLSHTYANVRINHVINLWGADFDSDGNLKAIYVTDSDSNASIGMKKYFVGVNS
AGKVAISAKEIKEDNIGAQVLGLFTLSTGQDSWNQTN;

-continued (SEQ ID NO: 58)
MRKRCYSTSAAVLAAVTLFVLSVDRGVIADSFSANQEIRYSEVTPYHVTSVWTKGVTPPANFTQGEDVFHA
PYVANQGWYDITKTFNGKDDLLCGAATAGNMLHWWFDQNKDQIKRYLEEHPEKQKINFRGEQMFDVKEAIDTKNHQL
DSKLFEYFKEKAFPYLSTKHLGVFPDHVIDMFILGYRLSLTNHGPTPVKEGSKDPRGGIFDAVFTRGDQSKLLTSRH
DFKEKNLKEISDLIKKELTEGKALGLSHTYANVRINHVINLWGADFDSNGNLKAIYVTDSDSNASIGMKKYFVGVNS
AGKVAISAKEIKEDNIGAQVLGLFTLSTGQDSWNQTN;

(SEQ ID NO: 59)
MRKRCYSTSAAVLAAVTLFVLSVDRGVIADSFSANQEIRYSEVTPYHVTSVWTKGVTPPANFTQGEDVFHA
PYVANQGWYDITKTFNGKDDLLCGAATAGNMLHWWFDQNKDQIKRYLEEHPEKQKINFRGEQMFDVKEAIDTKNHQL
DSKLFEYFKEKAFPYLSTKHLGVFPDHVIDMFINGYRLSLTNHGPTPVKEGSKDPRGGIFDAVFTRGDQSKLLTSRH
DFKEKNLKEISDLIKKELTEGKALGLSHTYANVRINHVINLWGADFDSDGNLKAIYVTDSDSNASIGMKKYFVGVNS
AGKVAISAKEIKEDNIGAQVLGLFTLSTGQDSWNQTN;

(SEQ ID NO: 60)
MRKRCYSTSAAVLAAVTLFVLSVDRGVIADSFSANQEIRYSEVTPYHVTSVWTKGVTPPANFTQGEDVFHA
PYVANQGWYDITKTFNGKDDLLCGAATAGNMLHWWFDQNKDQIKRYLEEHPEKQKINFRGEQMFDVKEAIDTKNHQL
DSKLFEYFKEKAFPYLSTKHLGVFPDHVIDMFILGYRLSLTNHGPTPVKEGSKDPRGGIFDAVFTRGDQSKLLTSRH
DFKEKNLKEISDLIKKELTEGKALGLSHTYANVRINHVINLWGADFDSDGNLKAIYVTDSDSNASIGMKKYFVGVNS
AGKVAISAKEIKEDNIGAQVLGLFTLSTGQDSWNQTN;

(SEQ ID NO: 61)
MRKRCYSTSAAVLAAVTLFVLSVDRGVIADSFSANQEIRYSEVTPYHVTSVWTKGVTPPANFTQGEDVFHA
PYVANQGWYDITKTFDGKDDLLCGAATAGNMLHWWFDQNKDQIKRYLEEHPEKQKINFRGEQMFDVKEAIDTKNHQL
DSKLFEYFKEKAFPYLSTKHLGVFPDHVIDMFILGYRLSLTNHGPTPVKEGSKDPRGGIFDAVFTRGDQSKLLTSRH
DFKEKNLKEISDLIKKELTEGKALGLSHTYANVRINHVINLWGADFDSNGNLKAIYVTDSDSNASIGMKKYFVGVNS
AGKVAISAKEIKEDNIGAQVLGLFTLSTGQDSWNQTN;

(SEQ ID NO: 62)
MRKRCYSTSAAVLAAVTLFVLSVDRGVIADSFSANQEIRYSEVTPYHVTSVWTKGVTPPANFTQGEDVFHA
PYVANQGWYDITKTFDGKDDLLCGAATAGNMLHWWFDQNKDQIKRYLEEHPEKQKINFRGEQMFDVKEAIDTKNHQL
DSKLFEYFKEKAFPYLSTKHLGVFPDHVIDMFINGYRLSLTNHGPTPVKEGSKDPRGGIFDAVFTRGDQSKLLTSRH
DFKEKNLKEISDLIKKELTEGKALGLSHTYANVRINHVINLWGADFDSDGNLKAIYVTDSDSNASIGMKKYFVGVNS
AGKVAISAKEIKEDNIGAQVLGLFTLSTGQDSWNQTN;

(SEQ ID NO: 63)
MRKRCYSTSAAVLAAVTLFVLSVDRGVIADSFSANQEIRYSEVTPYHVTSVWTKGVTPPANFTQGEDVFHA
PYVANQGWYDITKTFDGKDDLLCGAATAGNMLHWWFDQNKDQIKRYLEEHPEKQKINFNGEQMFDVKEAIDTKNHQL
DSKLFEYFKEKAFPYLSTKHLGVFPDHVIDMFILGYRLSLTNHGPTPVKEGSKDPRGGIFDAVFTRGDQSKLLTSRH
DFKEKNLKEISDLIKKELTEGKALGLSHTYANVRINHVINLWGADFDSDGNLKAIYVTDSDSNASIGMKKYFVGVNS
AGKVAISAKEIKEDNIGAQVLGLFTLSTGQDSWNQTN;

(SEQ ID NO: 64)
MRKRCYSTSAAVLAAVTLFVLSVDRGVIADSFSANQEIRYSEVTPYHVTSVWTKGVTPPANFTQGEDVFHAPYVANQ
GWYDITKTFNGKDDLLCGAATAGNMLHWWFDQNKDQIKRYLEEHPEKQKINFRGEQMFDVKEAIDTKNHQLDSKLFE
YFKEKAFPYLSTKHLGVFPDHVIDMFILGYRLSLTNHGPTPVKEGSKDPRGGIFDAVFTRGDQSKLLTSRHDFKEKN
LKEISDLIKKELTEGKALGLSHTYANVRINHVINLWGADFDSDGNLKAIYVTDSDSNASIGMKKYFVGVNSAGKVAI
SAKEIKEDNIGAQVLGLFTLSTGQDSWNQTN;

or (SEQ ID NO: 65)
MRKRCYSTSAAVLAAVTLFVLSVDRGVIADSFSANQEIRYSEVTPYHVTSVWTKGVTPPANFTQGEDVFHA

PYVANQGWYDITKTFDGKDDLLCGAATAGNMLHWWFDQNKDQIKRYLEEHPEKQKINFRGEQMFDVKEAIDTKNHQL

DSKLFEYFKEKAFPYLSTKHLGVFPDHVIDMFILGYRLSLTNHGPTPVKEGSKDPRGGIFDAVFTRGDQSKLLTSRH

DFKEKNLKEISDLIKKELTEGKALGLSHTYANVRINHVINLWGADFDSDGNLKAIYVTDSDSNASIGMKKYFVGVNS

AGKVAISAKEIKEDNIGAQVLGLFTLSTGQDSWNQTN.

Such IdeS variants possess an increased chemical stability at alkaline pH-values compared to the parental amino acid sequence (SEQ ID NO: 66).

The present invention includes compositions including a VEGF mini-trap as set forth herein and the corresponding VEGF trap which was used to generate the VEGF mini-trap product through IdeS cleavage. The VEGF trap in the mixture is undigested or yet-to-be digested reactant for proteolysis by IdeS. For example, the composition may include:

- VEGF Trap REGN10102 and VEGF mini-trap REGN10105,
- VEGF Trap REGN10104 and VEGF mini-trap mREGN10104;
- VEGF Trap REGN10117 and VEGF mini-trap REGN10103,
- VEGF Trap REGN10187 and VEGF mini-trap mREGN10187;
- VEGF Trap REGN10511 and VEGF mini-trap mREGN10511;
- VEGF Trap REGN10512 and VEGF mini-trap mREGN10512;
- VEGF Trap REGN10513 and VEGF mini-trap mREGN10513;
- VEGF Trap REGN10514 and VEGF mini-trap REGN11095; and/or
- VEGF Trap REGN10515 and VEGF mini-trap mREGN10515.

In an embodiment of the invention, there is more (e.g., moles or grams) of the VEGF mini-trap than the VEGF trap, for example, 2, 5, 10 or 15 times more. Such a composition may further include IdeS or a variant thereof, e.g., as set forth herein. IdeS may be either absent or only be present at trace amounts, e.g., 0.04 ppm (or less) or less than 0.3 ppm. The composition may also include a buffer and/or other components conducive to protease cleavage.

Polynucleotides, Vectors, Host Cells and Methods of Making

An isolated polynucleotide encoding any VEGF trap or VEGF mini-trap polypeptides set forth herein forms part of the present invention as does a vector comprising the polynucleotide and/or a host cell (e.g., Chinese hamster ovary (CHO) cell) comprising the polynucleotide, vector, VEGF trap or VEGF mini-trap and/or a polypeptide set forth herein. Such host cells also form part of the present invention.

A polynucleotide includes DNA and RNA. The present invention includes any polynucleotide of the present invention, for example, encoding a VEGF trap or VEGF mini-trap polypeptide set forth herein (e.g., any of SEQ ID NOs: 32-49). Optionally, the polynucleotide is operably linked to a promoter or other expression control sequence. In an embodiment of the invention, a polynucleotide of the present invention is fused to a secretion signal sequence. Polypeptides encoded by such polynucleotides are also within the scope of the present invention.

In an embodiment of the invention, the polynucleotide encoding REGN10103 comprises the nucleotide sequence:

(SEQ ID NO: 71)
AGTGATACCGGTAGACCTTTCGTAGAGATGTACAGTGAAATCCCCGAAA

TTATACACATGACTGAAGGAAGGGAGCTCGTCATTCCCTGCCGGGTTAC

GTCACCTAACATCACTGTTACTTTAAAAAAGTTTCCACTTGACACTTTG

ATCCCTGATGGAAAACGCATAATCTGGGACAGTAGAAAGGGCTTCATCA

TATCAAATGCAACGTACAAAGAAATAGGGCTTCTGACCTGTGAAGCAAC

AGTCAATGGGCATTTGTATAAGACAAACTATCTCACACATCGACAAACC

AATACAATCATAGATGTGGTTCTGAGTCCGTCTCATGGAATTGAACTAT

CTGTTGGAGAAAAGCTTGTCTTAAATTGTACAGCAAGAACTGAACTAAA

TGTGGGGATTGACTTCAACTGGGAATACCCTTCTTCGAAGCATCAGCAT

AAGAAACTTGTAAACCGAGACCTAAAAACCCAGTCTGGGAGTGAGATGA

AGAAATTTTTGAGCACCTTAACTATAGATGGTGTAACCCGGAGTGACCA

AGGATTGTACACCTGTGCAGCATCCAGTGGGCTGATGACCAAGAAGAAC

AGCACATTTGTCAGGGTCCATGAAAAGGAGCGCAAATGTTGTGTCGAGT

GCCCACCGTGCCCAGCACCACCTGTGGCATGA

In an embodiment of the invention, the polynucleotide encoding REGN10105 comprises the nucleotide sequence:

(SEQ ID NO: 72)
AGTGATACCGGTAGACCTTTCGTAGAGATGTACAGTGAAATCCCCGAAA

TTATACACATGACTGAAGGAAGGGAGCTCGTCATTCCCTGCCGGGTTAC

GTCACCTAACATCACTGTTACTTTAAAAAAGTTTCCACTTGACACTTTG

ATCCCTGATGGAAAACGCATAATCTGGGACAGTAGAAAGGGCTTCATCA

TATCAAATGCAACGTACAAAGAAATAGGGCTTCTGACCTGTGAAGCAAC

AGTCAATGGGCATTTGTATAAGACAAACTATCTCACACATCGACAAACC

AATACAATCATAGATGTGGTTCTGAGTCCGTCTCATGGAATTGAACTAT

CTGTTGGAGAAAAGCTTGTCTTAAATTGTACAGCAAGAACTGAACTAAA

TGTGGGGATTGACTTCAACTGGGAATACCCTTCTTCGAAGCATCAGCAT

AAGAAACTTGTAAACCGAGACCTAAAAACCCAGTCTGGGAGTGAGATGA

AGAAATTTTTGAGCACCTTAACTATAGATGGTGTAACCCGGAGTGACCA

-continued

```
AGGATTGTACACCTGTGCAGCATCCAGTGGGCTGATGACCAAGAAGAAC

AGCACATTTGTCAGGGTCCATGAAAAGGTCGAGTGCCCACCGTGCCCAG

CACCACCTGTGGCATGA
```

In an embodiment of the invention, the polynucleotide encoding REGN11095 comprises the nucleotide sequence:

```
                                              (SEQ ID NO: 73)
AGTGATACCGGTAGACCTTTCGTAGAGATGTACAGTGAAATCCCCGAAA

TTATACACATGACTGAAGGAAGGGAGCTCGTCATTCCCTGCCGGGTTAC

GTCACCTAACATCACTGTTACTTTAAAAAAGTTTCCACTTGACACTTTG

ATCCCTGATGGAAAACGCATAATCTGGGACAGTAGAAAGGGCTTCATCA

TATCAAATGCAACGTACAAAGAAATAGGGCTTCTGACCTGTGAAGCAAC

AGTCAATGGGCATTTGTATAAGACAAACTATCTCACACATCGACAAACC

AATACAATCATAGATGTGGTTCTGAGTCCGTCTCATGGAATTGAACTAT

CTGTTGGAGAAAAGCTTGTCTTAAATTGTACAGCAAGAACTGAACTAAA

TGTGGGGATTGACTTCAACTGGGAATACCCTTCTTCGAAGCATCAGCAT

AAGAAACTTGTAAACCGAGACCTAAAAACCCAGTCTGGGAGTGAGATGA

AGAAATTTTTGAGCACCTTAACTATAGATGGTGTAACCCGGAGTGACCA

AGGATTGTACACCTGTGCAGCATCCAGTGGGCTGATGACCAAGAAGAAC

AGCACATTTGTCAGGGTCCATGAAAAGGACAAAACTCACACATGCCCAC

CGTGCCCAGGCGGTGGACTTCTAGGGTGA
```

In general, a "promoter" or "promoter sequence" is a DNA regulatory region capable of binding an RNA polymerase in a cell (e.g., directly or through other promoter-bound proteins or substances) and initiating transcription of a coding sequence. A promoter may be operably linked to other expression control sequences, including enhancer and repressor sequences and/or with a polynucleotide of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the beta-lactamase promoter (VIIIa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal4 promoter, the ADC (alcohol dehydrogenase) promoter, PGK (phosphoglycerol kinase) promoter or the alkaline phosphatase promoter.

A polynucleotide encoding a polypeptide is "operably linked" to a promoter or other expression control sequence when, in a cell or other expression system, the sequence directs RNA polymerase mediated transcription of the coding sequence into RNA, preferably mRNA, which then may be RNA spliced (if it contains introns) and, optionally, translated into a protein encoded by the coding sequence.

The present invention includes polynucleotides encoding VEGF trap or VEGF mini-trap polypeptide chains which are variants of those whose amino acid sequence is specifically set forth herein (e.g., any of SEQ ID NOs: 32-49).

Eukaryotic and prokaryotic host cells, including mammalian cells, may be used as hosts for expression of a VEGF trap or VEGF mini-trap polypeptide (e.g., any of SEQ ID NOs: 32-49). Such host cells are well known in the art and many are available from the American Type Culture Collection (ATCC). These host cells include, inter alia, Chinese hamster ovary (CHO) cells, CHO K1, EESYR, NICE, NS0, Sp2/0, embryonic kidney cells and BHK cells. Host cells include fungal cells such as *Pichia*, e.g., *Pichia pastoris* or bacterial cells, e.g., *E. coli*. The present invention includes an isolated host cell (e.g., a CHO cell or any type of host cell set forth above) comprising one or more VEGF trap or VEGF mini-trap polypeptides (or variant thereof) and/or a polynucleotide encoding such a polypeptide(s) (e.g., as discussed herein). A polynucleotide encoding a VEGF trap or VEGF mini-trap, or vector thereof, may be ectopic or chromosomally integrated into the chromosomal DNA or the host cell.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455. Thus, the present invention includes recombinant methods for making a VEGF trap or VEGF mini-trap comprising the steps of:
  (i) culturing the host cell (e.g., CHO or *Pichia* or *Pichia pastoris*) under conditions favorable to expression of a polynucleotide encoding a VEGF trap or VEGF mini-trap (e.g., in a bioreactor, e.g., in chemically defined medium (CDM) or non-CDM) and,
  (ii) optionally, isolating the VEGF trap or VEGF mini-trap or chain thereof from the host cell and/or medium in which the host cell is grown.

In an embodiment of the invention, the method includes the step of introducing, into a host cell, one or more polynucleotides encoding a VEGF trap or VEGF mini-trap polypeptide (e.g., including the amino acid sequence set forth in any one of SEQ ID NOs: 32-49), for example, wherein the polynucleotide is in a vector; and/or integrates into the host cell chromosome and/or is operably linked to a promoter. When making a VEGF trap or VEGF mini-trap that includes two or more polypeptide chains, co-expression of the chains in a single host cell leads to association of the chains, e.g., in the cell or on the cell surface or outside the cell if such chains are secreted, so as to form homodimeric VEGF mini-trap. The present invention also includes VEGF traps or VEGF mini-traps which are the product of the production methods set forth herein, and, optionally, the purification methods set forth herein.

Recombinant VEGF traps and VEGF mini-traps (e.g., any of SEQ ID NOs: 32-49) are part of the present invention, e.g., that are the product of such a method.

See e.g., Ling et al., Development and manufacturability assessment of chemically-defined medium for the production of protein therapeutics in CHO cells, Biotechnol Prog September-October 2015; 31(5):1163-71.

The present invention also provides a method for making a VEGF trap or VEGF mini-trap (e.g., a homodimeric VEGF mini-trap) set forth herein, from a VEGF trap, comprising, consisting of or consisting essentially of proteolyzing VEGF Trap with a protease which cleaves the VEGF Trap in the immunoglobulin Fc multimerizing component below (to the C-terminal side of) the Fc hinge domain such that the lower hinge or a portion thereof is part of the VEGF mini-trap product. For example, the proteolysis can be done with *S. pyogenes* IdeS (e.g., FabRICATOR protease; Genovis, Inc.; Cambridge, Mass.; Lund, Sweden) or *Streptococcus equi* subspecies *zooepidemicus* IdeZ (New England Biolabs; Ipswich, Mass.). In an embodiment of the invention, such a method lacks any steps that include significant modification of the amino acid residues of such VEGF mini-trap polypeptide (e.g., directed chemical modification such as PEGylation or iodoacetamidation) and/or disulfide bridge reduction. A VEGF mini-trap product of such a method for making is also part of the present invention.

Such a method for making a VEGF mini-trap may be followed by a method for purifying VEGF mini-trap, e.g., from contaminants such as an Fc fragment, proteolytic enzyme or other material. In an embodiment of the invention, the method for purifying is done under conditions promoting the formation of homodimeric VEGF mini-trap (e.g., under non-reducing conditions, e.g., in the absence of reducing agents such as dithiothreitol (DTT) or beta-mercaptoethanol). The VEGF mini-trap product of such a method for making and/or a method for purifying is also part of the present invention. In an embodiment of the invention, purification is performed by a method including chromatographic purification.

Also provided by the present invention is an isolated polypeptide comprising, consisting or consisting essentially an amino acid sequence selected from the group consisting of SEQ ID Nos: 32-49. Compositions comprising such polypeptides, e.g., in which all or a portion of such polypeptides are associated, e.g., into homodimeric VEGF trap or VEGF mini-trap complexes which can bind to VEGF are part of the present invention. Such compositions may include, for example, one or more of host cells, protease (e.g., IdeS) and culture medium.

Bioreactors, such as tank bioreactors or single-use bioreactors, may be used to culture host cells for expression of a VEGF trap or VEGF mini-trap. Such bioreactors may include an impellor (e.g., turbine, marine or spiral design) for culture mixing and means for controlling temperature, pH, oxygen and/or nitrogen content in the culture medium. Bioreactor volumes may be research scale (e.g., 250 mL or 2 liters) or manufacturing scale (e.g., 2000 liters or 10000 liters). The present invention includes a tank bioreactor that comprises a VEGF trap and/or VEGF mini-trap of the invention (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) and, optionally, host cells (e.g., as discussed herein) and/or culture medium (e.g., CDM). See e.g., Innovations in Cell Culture, BioProcess Vol. 12(suppl 5) (September 2014).

Combinations and Pharmaceutical Formulations

The present invention provides compositions that include VEGF traps or VEGF mini-traps (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) in association with one or more ingredients; as well as methods of use thereof and methods of making such compositions. Pharmaceutic formulations comprising a VEGF mini-trap and a pharmaceutically acceptable carrier or excipient are part of the present invention. In an embodiment of the invention, a pharmaceutical formulation of the present invention has a pH of approximately 5.5, 5.6, 5.7, 5.8, 5.9, 6.0, 6.1 or 6.2.

To prepare pharmaceutical formulations of the VEGF traps or VEGF mini-traps (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515), the mini-traps are admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, N.Y.; Weiner and Kotkoskie (2000) Excipient Toxicity and Safety, Marcel Dekker, Inc., New York, N.Y. In an embodiment of the invention, the pharmaceutical formulation is sterile. Such compositions are part of the present invention.

Pharmaceutical formulations of the present invention include a VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) and a pharmaceutically acceptable carrier including, for example, water, buffering agents, preservatives and/or detergents.

The scope of the present invention includes desiccated, e.g., freeze-dried, compositions comprising a VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) or a pharmaceutical formulation thereof that includes a pharmaceutically acceptable carrier but substantially lacks water.

In a further embodiment of the invention, a further therapeutic agent that is administered to a subject in association with a VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) disclosed herein is administered to the subject in accordance with the Physicians' Desk Reference 2003 (Thomson Healthcare; 57th edition (Nov. 1, 2002)).

The present invention provides a vessel (e.g., a plastic or glass vial, e.g., with a cap or a chromatography column, hollow bore needle or a syringe cylinder) comprising any of the VEGF traps or VEGF mini-traps (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) or a pharmaceutical formulation comprising a pharmaceutically acceptable carrier thereof. The present invention also provides an injection device comprising a VEGF trap or VEGF mini-trap or formulation set forth herein, e.g., a syringe, a pre-filled syringe or an autoinjector. In an embodiment of the invention, a vessel is tinted (e.g., brown or green) to block out light.

The present invention includes combinations including a VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) in association with one or more further therapeutic agents. The VEGF trap or VEGF mini-trap and the further therapeutic agent can be in a single composition or in separate compositions. For example, in an embodiment of the invention, the further therapeutic agent is an oligonucleotide (e.g., an oligonucleotide that reduces expression of VEGF, for example, an anti-sense oligonucleotide), Ang-2 inhibitor (e.g., nesvacumab), a Tie-2 receptor activator, an anti-PDGF antibody or antigen-binding fragment thereof, an anti-PDGF receptor or PDGF receptor beta antibody or antigen-binding fragment thereof and/or an additional VEGF antagonist such as aflibercept, conbercept, bevacizumab, ranibizumab, an anti-VEGF aptamer such as pegaptanib (e.g., pegaptanib sodium), a single chain (e.g., VL-VH) anti-VEGF antibody such as brolucizumab, an anti-VEGF DARPin such as the Abicipar Pegol DARPin, a bispecific anti-VEGF antibody, e.g., which also binds to ANG2, such as RG7716, or a soluble form of human vascular endothelial growth factor receptor-3 (VEGFR-3) comprising extracellular domains 1-3, expressed as an Fc-fusion protein.

Administration and Treatment

The present invention provides methods for treating or preventing a cancer (e.g., whose growth and/or metastasis is mediated, at least in part, by VEGF, e.g., VEGF-mediated angiogenesis) or an angiogenic eye disorder, in a subject, comprising administering a therapeutically effective amount of VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) to the subject.

The present invention also provides a method for treating cancer (e.g., whose growth and/or metastasis is mediated, at least in part, by VEGF, e.g., VEGF-mediated angiogenesis) or an angiogenic eye disorder in a subject in need thereof, the method comprising administering a therapeutically effective amount of VEGF traps or VEGF mini-trap set forth herein, and optionally a further therapeutic agent, to the body of the subject, e.g., into an eye of the subject. The expression "angiogenic eye disorder," as used herein, means any disease of the eye which is caused by or associated with the growth or proliferation of blood vessels or by blood vessel leakage. In an embodiment of the invention, administration is done by intravitreal injection. Non-limiting examples of angiogenic eye disorders that are treatable or preventable using the methods herein, include:

- age-related macular degeneration (AMD) (e.g., wet or dry, preferably wet),
- macular edema,
- macular edema following retinal vein occlusion,
- retinal vein occlusion (RVO),
- central retinal vein occlusion (CRVO),
- branch retinal vein occlusion (BRVO),
- diabetic macular edema (DME),
- choroidal neovascularization (CNV),
- iris neovascularization,
- neovascular glaucoma,
- post-surgical fibrosis in glaucoma,
- proliferative vitreoretinopathy (PVR),
- optic disc neovascularization,
- corneal neovascularization,
- retinal neovascularization,
- vitreal neovascularization,
- pannus,
- pterygium,
- vascular retinopathy,
- diabetic retinopathy in a subject with diabetic macular edema; and
- diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in a subject that does not suffer from DME or center-involved DME).

The term "treat" or "treatment" refers to a therapeutic measure that reverses, stabilizes or eliminates an undesired disease or disorder (e.g., an angiogenic eye disorder or cancer), for example, by causing the regression, stabilization or elimination of one or more symptoms or indicia of such disease or disorder by any clinically measurable degree, e.g., with regard to an angiogenic eye disorder, by causing a reduction in or maintenance of diabetic retinopathy severity score (DRSS), by improving or maintaining vision (e.g., in best corrected visual acuity e.g., as measured by an increase in ETDRS letters), increasing or maintaining visual field and/or reducing or maintaining central retinal thickness and, with respect to cancer, stopping or reversing the growth, survival and/or metastasis of cancer cells in the subject. Typically, the therapeutic measure is administration of one or more doses of a therapeutically effective amount of VEGF trap or VEGF mini-trap to the subject with the disease or disorder.

An effective or therapeutically effective amount of VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) for treating or preventing cancer (e.g., which is mediated, at least in part, by angiogenesis) or an angiogenic eye disorder refers to the amount of the VEGF trap or VEGF mini-trap sufficient to cause the regression, stabilization or elimination of the cancer or angiogenic eye disorder, e.g., by regressing, stabilizing or eliminating one or more symptoms or indicia of the cancer or angiogenic eye disorder by any clinically measurable degree, e.g., with regard to an angiogenic eye disorder, by causing a reduction in or maintenance of diabetic retinopathy severity score (DRSS), by improving or maintaining vision (e.g., in best corrected visual acuity e.g., as measured by an increase in ETDRS letters), increasing or maintaining visual field and/or reducing or maintaining central retinal thickness and, with respect to cancer, stopping or reversing the growth, survival and/or metastasis of cancer cells in the subject. In an embodiment of the invention, an effective or therapeutically effective amount of VEGF trap or VEGF mini-trap for treating or preventing an angiogenic eye disorder is about 0.5-25 mg, e.g., in no more than about 100 μl. The amount may vary depending upon the age and the size of a subject to be administered, target disease, conditions, route of administration, and the like. In certain embodiments, the initial dose may be followed by administration of a second or a plurality of subsequent doses of VEGF trap or VEGF mini-trap in an amount that can be approximately the same or less or more than that of the initial dose, wherein the subsequent doses are separated by about 1 to about 8 weeks.

The mode of administration of a VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) or composition thereof can vary. Routes of administration include parenteral, non-parenteral, oral, rectal, transmucosal, intestinal, intramuscular, subcutaneous, intradermal, intramedullary, intrathecal, direct intraventricular, intravenous, intraperitoneal, intranasal, intraocular, inhalation, insufflation, topical, cutaneous, intraocular, intravitreal, transdermal or intra-arterial.

The present invention provides methods for administering a VEGF trap or VEGF mini-trap (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515) to a subject, comprising introducing the VEGF trap or VEGF mini-trap or a pharmaceutical formulation thereof into the body of the subject. For example, in an embodiment of the invention, the method comprises piercing the body of the subject, e.g., with a needle of a syringe, and injecting the VEGF trap or VEGF mini-trap or a pharmaceutical formulation thereof into the body of the subject, e.g., into the eye, vein, artery, muscular tissue or subcutis of the subject.

In an embodiment of the invention, intravitreal injection of a pharmaceutical formulation of the present invention (which includes a VEGF trap or VEGF mini-trap of the present invention (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515)) includes the step of piercing the eye with a syringe and needle (e.g., 30-gauge injection needle) containing the formulation and injecting the formulation (e.g., less than or equal to about 100 microliters) into the vitreous of the eye (e.g., with a sufficient volume as to deliver a therapeutically effective amount as set forth herein, e.g., of about 0.5-20 mg VEGF mini-trap). Optionally, the method includes the steps of administering a local anesthetic (e.g., proparacaine, lidocaine or tetracaine), an antibiotic (e.g., a fluoroquinolone), antiseptic (e.g., povidone-iodine) and/or a pupil dilating agent to the eye being injected. In an embodiment of the invention, a sterile field around the eye to be injected is established before the injection. In an embodiment of the invention, following intravitreal injection, the subject is monitored for elevations in intraocular pressure, inflammation and/or blood pressure.

The term "in association with" indicates that components, a VEGF trap or VEGF mini-trap of the present invention (e.g., REGN10104; mREGN10104; REGN10102; REGN10105; REGN10117; REGN10103; REGN10187; mREGN10187; REGN10511; mREGN10511; REGN10512; mREGN10512; REGN10513; mREGN10513; REGN10514; REGN11095; REGN10515; or mREGN10515), along with another agent such as anti-ANG2; can be formulated into a single composition, e.g., for simultaneous delivery, or formulated separately into two or more compositions (e.g., a kit including each component). Components administered in association with each another can be administered to a subject at a different time than when the other component is administered; for example, each administration may be given non-simultaneously (e.g., separately or sequentially) at intervals over a given period of time. Separate components administered in association with each another may also be administered essentially simultaneously (e.g., at precisely the same time or separated by a non-clinically significant time period) during the same administration session. Moreover, the separate components administered in association with each another may be administered to a subject by the same or by a different route As used herein, the term "subject" refers to a mammal (e.g., rat, mouse, cat, dog, cow, sheep, horse, goat, rabbit), preferably a human, for example, in need of prevention and/or treatment of a cancer or an angiogenic eye disorder. The subject may have cancer or angiogenic eye disorder or be predisposed to developing cancer or angiogenic eye disorder.

In an embodiment of the invention, any method including the step of intravitreally injecting a VEGF trap or VEGF mini-trap of the present invention, e.g., for treating or preventing an angiogenic eye disorder, does not lead to a significant increase in intraocular pressure and/or blood pressure.

EXAMPLES

These examples are intended to exemplify the present invention are not a limitation thereof. Compositions and methods set forth in the Examples form part of the present invention.

Example 1: Binding Kinetic Analysis of VEGF Traps and VEGF Mini-Traps and VEGF on Receptor Captured Surface The binding characteristics of various VEGF traps and VEGF mini-traps was evaluated.

TABLE 1-1

| VEGF traps and VEGF mini-traps | |
|---|---|
| REGN# | VEGF trap or mini-trap |
| REGN110 | Human VEGF$_{165}$ |
| REGN3 | VEGF Trap hIgG1 Fc (aflibercept) |
| REGN7483 | VEGF mini-trap hIgG1 Fc |
| REGN10104 | VEGF Trap hIgG1 Stealth Fc |
| mREGN10104 | VEGF mini-trap hIgG1 Stealth Fc |
| REGN10102 | VEGF Trap hIgG2 Fc w_2 Cys |
| REGN10105 | VEGF mini-trap hIgG2 Fc w_2 Cys |
| REGN10117 | VEGF Trap hIgG2 Fc w_4 Cys |
| REGN10103 | VEGF mini-trap hIgG2 Fc w_4 Cys |

TABLE 1-1-continued

VEGF traps and VEGF mini-traps

| REGN# | VEGF trap or mini-trap |
|---|---|
| REGN10187 | VEGF Trap hIgG4 Stealth Fc |
| mREGN10187 | VEGF mini-trap hIgG4 Stealth Fc |
| REGN10514 | VEGF Trap hIgG1 Mut GGGL (SEQ ID NO: 94) Fc |
| REGN11095 | VEGF mini-trap hIgG1 Mut GGGL (SEQ ID NO: 94) Fc |

REGN3 =
(SEQ ID NO: 69)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDFNWEYPSSKHQH

KKLVNRDLKTQSGSEMKKFLSTLTIDGVTRSDQGLYTCAASSGLMTKKN

STFVRVHEKDKTHTCPPC240PAPELLGGPSVFLFPPKPKDTLMISRTP

EVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSR

DELTKNQVSLTCLVKGFYPSDIAVEWESNGQPENNYK403TTPPVLDSD

GSFFLYSKLTVDKSRWQQGNVESCSVMHEALHNHYTQKSLSLSPGK

Experimental Procedure (include description of relevant cell lines, proteins, reagents, and instrument type and model).

Equilibrium dissociation constants ($K_D$ values) for human $VEGF_{165}$ binding to various purified VEGF mini-trap constructs were determined using a real-time surface plasmon resonance biosensor using a Biacore 3000 instrument. All binding studies were performed in 10 mM HEPES, 150 mM NaCl, 3 mM EDTA, and 0.05% v/v Surfactant Tween-20; pH 7.4 (HBS-ET) running buffer at 25° C. The Biacore sensor surface was first derivatized by amine coupling with a monoclonal mouse anti-VEGFR1 antibody (REGN18) to capture VEGF mini-trap constructs. Binding studies were performed on the following human VEGF reagents: human $VEGF_{165}$. Different concentrations of $VEGF_{165}$ reagent were prepared in HBS-ET running buffer (2.5 nM-0.078 pM; 2-fold serial dilution for human $VEGF_{165}$) and then injected over anti-VEGFR1 captured VEGF mini-trap constructs surface for 108 seconds at a flow rate of 90 μL/minute. Dissociation of bound $VEGF_{165}$ reagent from VEGF mini-trap constructs was monitored for 60 minutes in HBS-ET running buffer. Kinetic association (ka) and dissociation (kd) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = \frac{kd}{ka}, \text{ and } t\frac{1}{2}(\min) = \frac{\ln(2)}{60 \cdot kd}$$

The binding kinetic parameters for human VEGF165 binding to different VEGF mini-trap constructs at 25° C. are shown in Table 1-2 and Table 1-3. All VEGF mini-traps showed comparable binding kinetics as aflibercept REGN3.

TABLE 1-2

Binding Kinetic Parameters of Human $VEGF_{165}$ Binding to Different VEGF Mini-Trap Constructs at 25° C.

| VEGF Trap or mini-trap | REGN# | Human IgG | Trap / mini-trap Capture Level (RU) | 2.5 nM $hVEGF_{165}$ Bound (RU) | ka(1/Ms) | kd(1/s) | $K_D$(M) | t½(min) |
|---|---|---|---|---|---|---|---|---|
| Trap | REGN3 | IgG1 | 15.8 ± 0.1 | 4.7 | 9.70E+06 | 1.70E−05 | 1.80E−12 | 679 |
| mini-trap | REGN7483 | IgG1 | 17.0 ± 0.1 | 9.37 | 1.01E+07 | 1.95E−05 | 1.90E−12 | 591 |
| Trap | REGN10104 | IgG1 stealth | 21.1 ± 0.2 | 7.3 | 9.20E+06 | 1.01E−05 | 1.10E−12 | 1149 |
| mini-trap | mREGN10104 | IgG1 stealth | 20.7 ± 0.1 | 12.2 | 9.50E+06 | 1.70E−05 | 1.78E−12 | 681 |
| Trap | REGN10102 | IgG2 w_2cys | 18.6 ± 0.2 | 6.6 | 1.06E+07 | 2.77E−05 | 2.60E−12 | 417 |
| mini-trap | REGN10105 | IgG2 w_2cys | 19.7 ± 0.2 | 10.5 | 7.62E+06 | 1.44E−05 | 1.89E−12 | 801 |
| Trap | REGN10117 | IgG2 w_4cys | 14.7 ± 0.1 | 4.2 | 7.30E+06 | ≤1e−5 | 1.37E−12 | ≥1155 |
| mini-trap | REGN10103 | IgG2 w_4cys | 23.9 ± 0.3 | 14.8 | 9.30E+06 | ≤1e−5 | 1.08E−12 | ≥1155 |
| Trap | REGN10187 | IgG4 stealth | 26.4 ± 0.3 | 10.5 | 9.50E+06 | 1.73E−05 | 1.82E−12 | 668 |
| mini-trap | mREGN10187 | IgG4 stealth | 25.1 ± 0.3 | 14.3 | 7.30E+06 | ≤1e−5 | 1.37E−12 | ≥1155 |
| Trap | REGN10514 | hIgG1-GGGL (SEQ ID NO: 94) | | | | | | |
| mini-trap | REGN11095 | hIgG1-GGGL (SEQ ID NO: 94) | | | | | | |

TABLE 1-3

Binding Kinetic Parameters of Human VEGF$_{165}$ Binding to Different VEGF
Mini-Trap Constructs at 25° C. (Additional Measurements) ("GGGL" disclosed as SEQ
ID NO: 94 and "CPPAPAPPVA" disclosed as SEQ ID NO: 106)

| VEGF Trap/mini-trap | Construct | VEGF Trap captured (RU) | 2 nM VEGF$_{165}$ Bound (RU) | ka (1/Ms) | kd (1/s) | KD (M) | t½ (min) |
|---|---|---|---|---|---|---|---|
| REGN11095 | VEGF mini Trap hIgG1 | 30 + 0.5 | 19.4 | 1.16E+07 | ≤1e-5 | 8.60E-13 | ≥1155 |
| REGN11095 (Alexa 488) | Mut GGGL (cleaved) | 24 + 0.2 | 14.9 | 1.16E+07 | ≤1e-5 | 8.65E-13 | ≥1155 |
| REGN10105 | VEGF mini Trap hIgG2 Fc w_2 cys | 29 + 0.2 | 20.4 | 9.30E+06 | ≤1e-5 | 1.08E-12 | ≥1155 |
| REGN10105 (Alexa 488) | CPPAPAPPVA (cleaved) | 24 + 0.1 | 18.0 | 1.36E+07 | ≤1e-5 | 7.40E-13 | ≥1155 |
| REGN3 | VEGF-Trap | 32 + 0.6 | 12.0 | 9.98E+06 | ≤1e-5 | 1.00E-12 | ≥1155 |

Example 2: Evaluation of the Ability of VEGF Mini-Traps to Block the Activation of VEGFR1 and VEFGR2 by VEGF$_{165}$ or VEGF$_{121}$ in a Luciferase Bioassay The ability of various VEGF traps and VEGF mini-traps to block VEGFR activation was evaluated.

TABLE 2-1

VEGF Traps and VEGF Mini-Traps

| REGN# | Description |
|---|---|
| REGN110 | Human VEGF$_{121}$ |
| | Human VEGF$_{165}$ |
| REGN3 | VEGF Trap hIgG1 Fc (aflibercept) |
| REGN7483 | VEGF mini-trap hIgG1 Fc |
| REGN10104 | VEGF Trap hIgG1 Fc Stealth |
| mREGN10104 | VEGF mini-trap hIgG1 Fc Stealth |
| REGN10102 | VEGF Trap hIgG2 Fc w_2 Cys |
| REGN10105 | VEGF mini-trap hIgG2 Fc w_2 Cys |
| REGN10117 | VEGF Trap hIgG2 Fc w_4 Cys |
| REGN10103 | VEGF mini-trap hIgG2 Fc w_4 Cys |
| REGN10187 | VEGF Trap hIgG4 Stealth Fc |
| mREGN10187 | VEGF mini-trap hIgG4 Stealth Fc |
| REGN10514 | VEGF Trap hIgG1 Mut GGGL (SEQ ID NO: 94) Fc |
| REGN11095 | VEGF mini-trap hIgG1 Mut GGGL (SEQ ID NO: 94) Fc |

Experimental Procedure (include description of relevant cell lines, proteins, reagents, and instrument type and model).

Cell Line

Two cell lines were generated to measure the ligand signaling pathway through VEGFR1 and VEGFR2 respectively. For VEGFR1, HEK293/D9/Flt(1-7)-IL18Rα/Flt-IL18Rβ clone V3H9 was constructed by two chimeric receptors incorporating the VEGFR1 extracellular domain Flt1(1-7) fused to the cytoplasmic domain of either IL18Rα or IL18Rβ. The chimeric receptors were transfected into a cell line with an integrated NFκB-luciferase-IRES-eGFP reporter gene. The extracellular VEGFR1 is dimerized upon binding VEGF, resulting in interaction of the IL18Rα and IL18Rβ intracellular domains, NFκB signaling, and subsequent luciferase production. Similarly, for VEGFR2, HEK293/D9/Flk(1-7)-IL18Rα/Flt-IL18Rβ was constructed by two chimeric receptors incorporating the VEGFR2 extracellular domain Flk1(1-7) fused to the cytoplasmic domain of either IL18Rα or IL18Rβ.

Assay Procedure

HEK293/D9/Flt-IL18Rα/Flt-ILI 8Rβ (VEGFR1) or HEK293/D9/Flk(1-7)-IL18Rα/Flt-IL18Rβ (VEGFR2) cells were plated in 96-well white opaque plates (Nunc, Cat #136101) at 10,000 cells/well in OptiMEM (INVITROGEN, Cat #31985) with 0.5% FBS (Seradigm, Cat #1500-500) and incubated at 37° C., 5% CO$_2$ overnight. The next day, cells were differentially treated with a 1:3 serial dilution of VEGF Trap or Mini Trap proteins ranging in concentration from 5000 pM to 0.085 pM, followed by the addition of a fixed concentration of VEGF$_{121}$ (R&D SYSTEMS Cat #4644-VS) or VEGF$_{165}$ (REGN110) ligand protein at 40 pM and incubated for 6 hours at 37° C., 5% CO$_2$. One-Glo luciferase substrate (PROM EGA, Cat #E6130) was then added to the cells and luminescence was measured using a VICTOR™ X5 Multilabel plate reader (PerkinElmer, Model 2030-0050). Data were analyzed using a 4-parameter logistic equation over an 11-point response curve with GraphPad Prism software to determine EC$_{50}$ and IC$_{50}$ values.

Results Summary and Conclusions

VEGF$_{121}$ activates HEK293/D9/Flt-IL18Rα/Flt-IL18Rβ (VEGFR1) or HEK293/D9/Flk(1-7)-IL18Rα/Flt-IL18Rβ (VEGFR2) cells with EC$_{50}$ values of ~30 pM (FIG. 8 and FIG. 9 and Table 2-2).

All VEGF mini-traps inhibited 20 pM of VEGF$_{121}$ mediated activation of VEGFR1 or VEGFR2 with similar IC$_{50}$ values to that observed with full length VEGF trap REGN3 (FIG. 8 and FIG. 9 and Table 2-2 and Table 2-3).

TABLE 2-2

Bioassay Activity of VEGF mini-traps Blocking VEGF$_{121}$ or VEGF$_{165}$ in VEGFR1 and VEGFR2 Cells

| VEGF Trap or mini-trap | REGN# | Human IgG | Inhibition of 20 pM VEGF$_{121}$ IC50 (M) | | Inhibition of 20 pM VEGF$_{165}$ IC50 (M) | |
|---|---|---|---|---|---|---|
| | | | VEGFR1 assay | VEGFR2 assay | VEGFR1 assay | VEGFR2 assay |
| Trap | REGN3 | IgG1 | 2.15E-11 | 2.14E-11 | 3.10E-11 | 3.21E-11 |
| mini-trap | REGN7483 | IgG1 | 2.09E-11 | 2.37E-11 | 3.36E-11 | 4.03E-11 |
| Trap | REGN10104 | IgG1 stealth | 1.91E-11 | 1.77E-11 | | |

TABLE 2-2-continued

Bioassay Activity of VEGF mini-traps Blocking $VEGF_{121}$ or $VEGF_{165}$ in VEGFR1 and VEGFR2 Cells

| VEGF Trap or mini-trap | REGN# | Human IgG | Inhibition of 20 pM $VEGF_{121}$ IC50 (M) | | Inhibition of 20 pM $VEGF_{165}$ IC50 (M) | |
|---|---|---|---|---|---|---|
| | | | VEGFR1 assay | VEGFR2 assay | VEGFR1 assay | VEGFR2 assay |
| mini-trap | mREGN10104 | IgG1 stealth | 1.34E−11 | 1.60E−11 | | |
| Trap | REGN10102 | IgG2 w_2cys | 1.43E−11 | 1.72E−11 | | |
| mini-trap | REGN10105 | IgG2 w_2cys | 1.68E−11 | 1.79E−11 | | |
| Trap | REGN10117 | IgG2 w_4cys | 2.02E−11 | 1.82E−11 | | |
| mini-trap | REGN10103 | IgG2 w_4cys | 2.11E−11 | 2.02E−11 | | |
| Trap | REGN10187 | IgG4 stealth | 1.25E−11 | 1.64E−11 | | |
| mini-trap | mREGN10187 | IgG4 stealth | 1.32E−11 | 1.63E−11 | | |
| Trap | REGN10514 | hIgG1-GGGL (SEQ ID NO: 94) | | | | |
| mini-trap | REGN11095 | hIgG1-GGGL (SEQ ID NO: 94) | | | | |

TABLE 2-3

Bioassay Activity of VEGF mini-traps Blocking $VEGF_{121}$ or $VEGF_{165}$ in VEGFR1 and VEGFR2 Cells (Additional Measurements) IC50 Table (M)

| | VEGFR1 40 pM VEGF165 (REGN110) | VEGFR1 40 pM R&D VEGF121 | VEGFR2 20 pM VEGF165 (REGN110) | VEGFR2 60 pM R&D VEGF121 |
|---|---|---|---|---|
| REGN3 | 1.49E−11 | 1.12E−11 | 2.16E−11 | 1.52E−11 |
| REGN10105 | 1.06E−11 | 1.74E−11 | 2.46E−11 | 1.80E−11 |
| REGN11095 | 2.19E−11 | 2.16E−11 | 2.39E−11 | 2.30E−11 |
| IgG1 Isotype | ND | ND | ND | ND |

Example 3: Determine Relative Cleavage Efficiency of VEGF-Trap Variants Mediated by Ides Protease Using SDS-PAGE Analysis The ability of various VEGF traps to be cleaved by IdeS protease was determined.

TABLE 3-1

| VEGF Traps and VEGF Mini-Traps | | |
|---|---|---|
| REGN# | Construct Details | |
| REGN3 | Full-length VEGF Trap, aflibercept | VEGF trap hIgG1 isotype |
| REGN10102 | Full-length VEGF trap | VEGF trap hIgG2 Fc w_2 cys |
| REGN10511 | Full-length VEGF trap | VEGF trap hIgG1-2 Chimera Fc |
| REGN10512 | Full-length VEGF trap | VEGF trap hIgG1 Mut GGGF (SEQ ID NO: 92) Fc |
| REGN10514 | Full-length VEGF trap | VEGF trap hIgG1 Mut GGGL (SEQ ID NO: 94) Fc |
| REGN10515 | Full-length VEGF trap | VEGF trap hIgG1 Del (APE) Fc |

Experimental Procedure (include description of relevant cell lines, proteins, reagents, and instrument type and model)

Relative cleavage efficiency of various VEGF trap constructs mediated by Ides protease was determined using SDS-PAGE analysis. All cleavage studies were performed in 10 mM sodium phosphate, 40 mM sodium chloride, 0.03% polysorbate 20, and 5% sucrose, pH 6.2 buffer at room temperature. The various VEGF trap constructs were first normalized to 0.1 mg/mL at a scale of 0.1 mg. For each VEGF trap construct, 100 uL sample aliquots were prepared from the normalized stock in replicates of 5. Stock Ides protease (0.1 mg/mL) was then added to all samples at a ratio of 5 ng protease/ug VEGF trap. Samples were allowed to incubate for periods of 0, 1, 2, 4, and 24 hr. Cleavage was stopped at each time point by addition of 0.1 mL of a stock amine based pH2.8 buffer. Sample timepoints collected were grouped by VEGF trap variant type, and 2 ug of each digest sample was then analyzed by SDS-PAGE using a 4-20% Tris-Glycine gel under non-reducing conditions. Each gel was run for a period of 1 hr at constant 300 mA. Simply-Blue Safe-Stain was used for subsequent staining of each gel. The de-stained gels were analyzed visually to ascertain relative cleavage efficiency of each VEGF trap variant over incubation time as mediated by Ides protease. Extent of cleavage efficiency was determined by comparison of relative levels of non-cleaved VEGF trap dimer, partially cleaved VEGF trap dimer, fully cleaved VEGF trap dimer (VEGF mini-trap), and Fc monomer fragment. A ranking of relative cleavage efficiency among the VEGF trap variants was then determined based on extent of Ides mediated cleavage observed.

SDS-PAGE analysis of IdeS protease mediated cleavage of each VEGF trap variant tested is shown in FIG. 10 (A-F).

Example 4: Assay of VEGF Mini-Traps for Reactivity with Pre-Existing Anti-Hinge Antibodies (AHA)

The reactivity of various VEGF mini-traps to pre-existing human and monkey anti-hinge antibodies was determined.

TABLE 3-1

VEGF Mini-Traps

| Mini-Trap | Human IgG | Details |
|---|---|---|
| REGN7483 | IgG1 | Enzymatically cleaved from aflibercept |
| mREGN10104 | IgG1 stealth | Enzymatically cleaved from VEGF trap-IgG1s |
| REGN10105 | IgG2 (2Cys) | Recombinantly expressed in CHO |
| REGN10105 | IgG2 (2Cys) | Enzymatically cleaved from VEGF trap-IgG2 |
| REGN10103 | IgG2 (4Cys) | Enzymatically cleaved from VEGF trap-IgG2 |
| mREGN10187 | IgG4 stealth | Enzymatically cleaved from VEGF trap-IgG4s |

Experimental Procedure (include description of relevant cell lines, proteins, reagents, and instrument type and model)

The potential immunogenicity of VEGF mini-traps towards pre-existing anti-hinge antibodies (AHA) was evaluated in an Anti-Drug Antibody (ADA) assay. See the illustration of the assay format in FIG. 11(A) This ADA assay is an Electrochemiluminescent Immunoassay (ECL) bridging assay, using Biotin- and Ruthenium-labeled drugs (mini-traps) to form a bridge. Anti-drug antibody binds Biotin- and Ruthenium-labeled drugs (VEGF mini-trap) forming a bridged complex, which is then captured by the streptavidin-coated plate surface. Electric current activates Ruthenium-labeled drug to produce an electrochemiluminescent signal.

Figure 12:
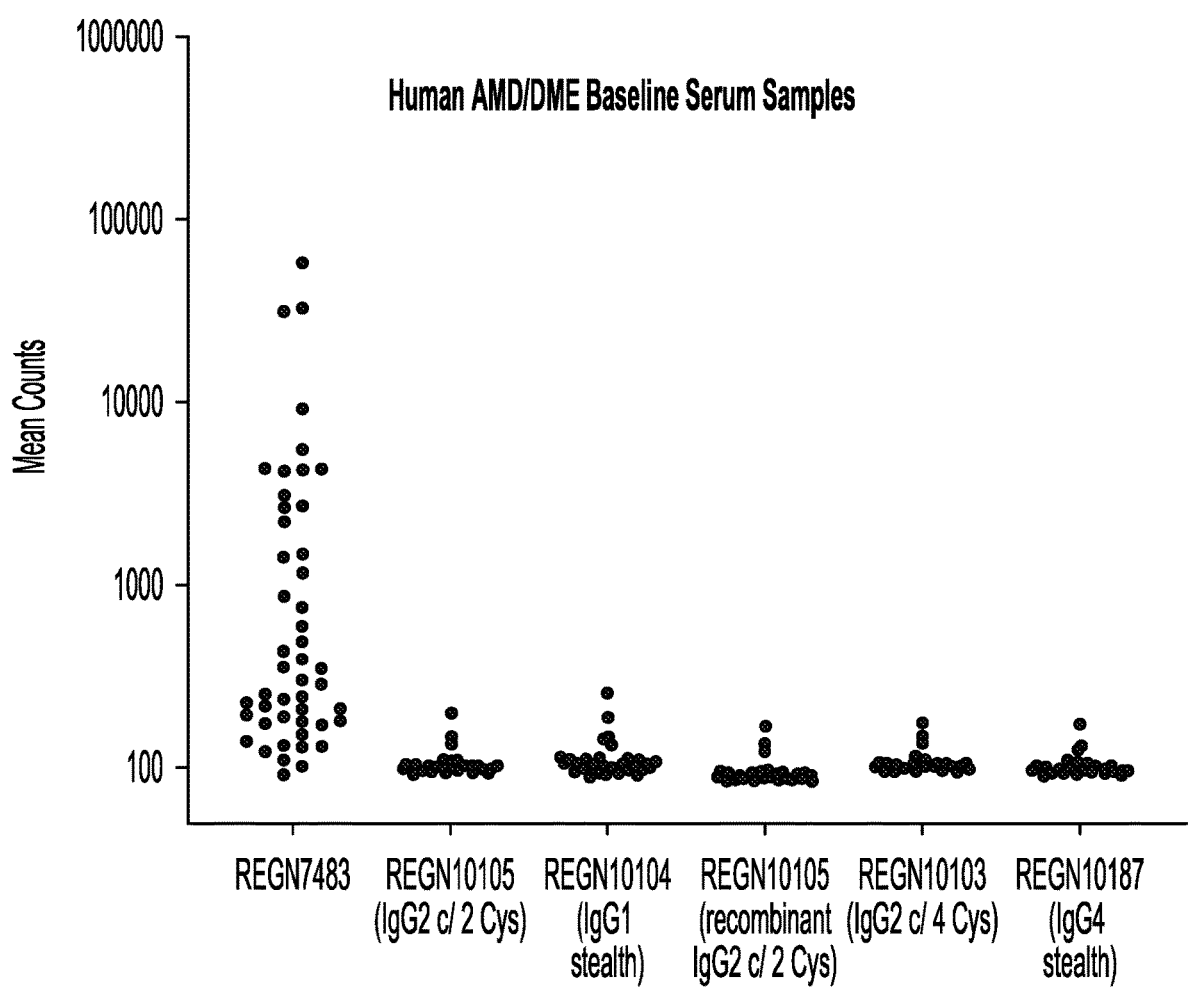
FIG. 12. Anti-drug antibody electrochemiluminescent immunoassay (ECL)—Bridging Format. Assay of REGN7483$^F$, REGN10105 (from IdeS cleaved VEGF trap with IgG2 Fc with 2 Cys), mREGN10104 (IdeS cleaved from REGN10104), REGN10105 (recombinantly expressed in CHO cells), REGN10103 (IdeS cleaved from VEGF trap with IgG2 Fc with 4 Cys) and mREGN10187 for pre-existing anti-hinge antibodies (AHA) responses in human AMD/DME serum samples.
Figure 13:
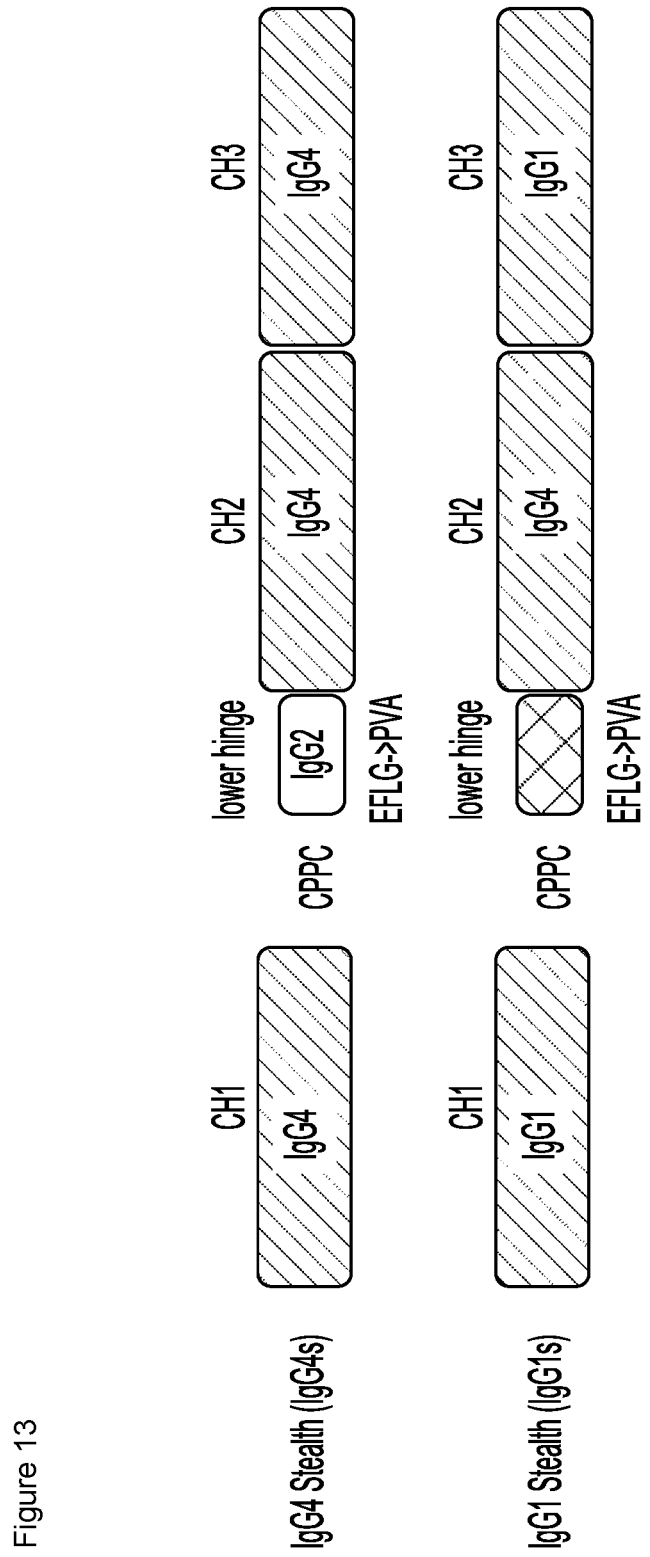
FIG. 13. Schematic diagram of human IgG4 stealth and human IgG1 stealth for reduction of effector functions. Figure discloses "CPPC" and "EFLG" as SEQ ID NOS 100 and 95, respectively.
Figure 14:
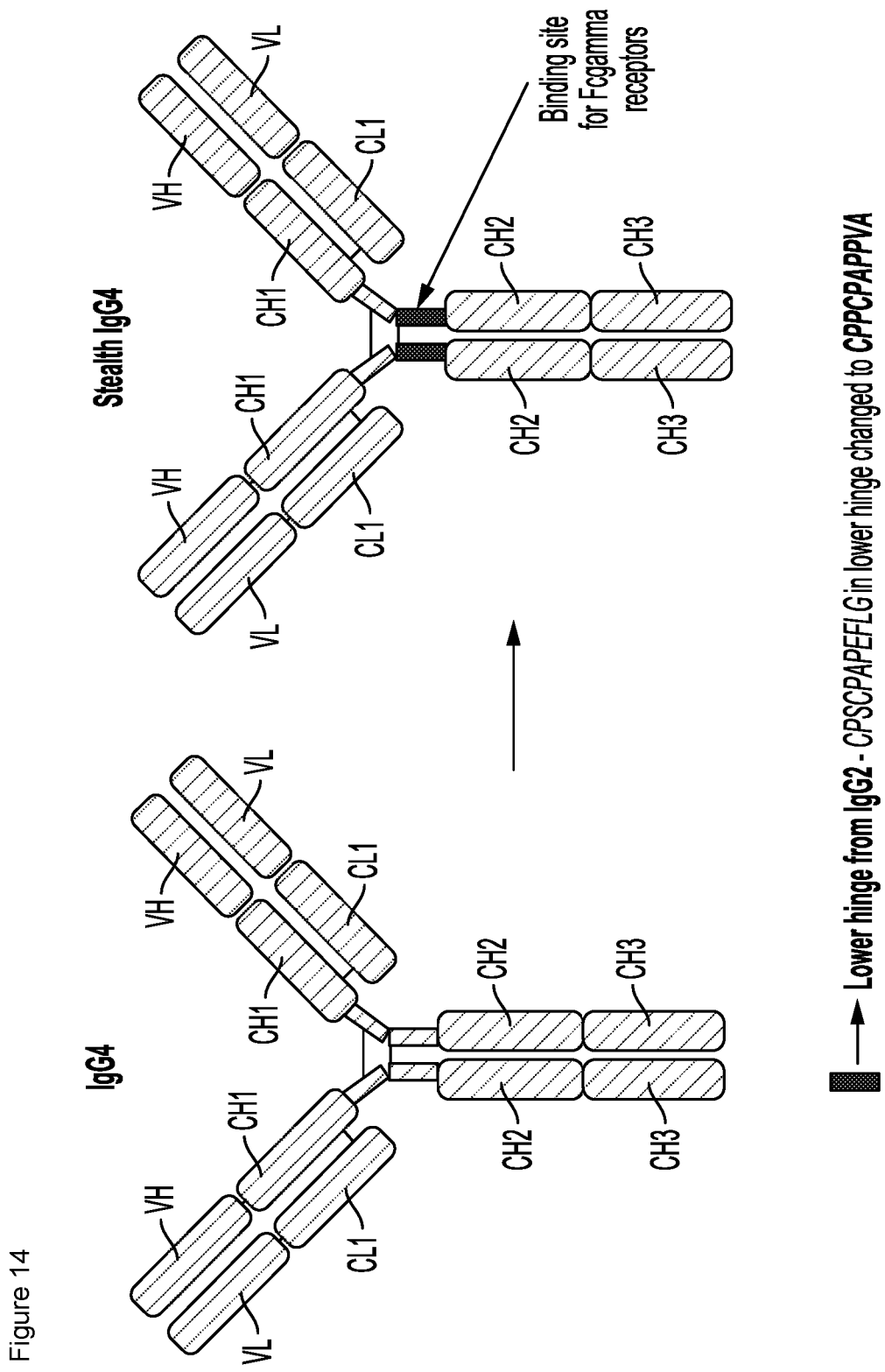
FIG. 14. Schematic diagram of IgG4 antibody possessing stealth mutations (SEQ ID NOS 111 and 109, respectively, in order of appearance).
Figure 16:
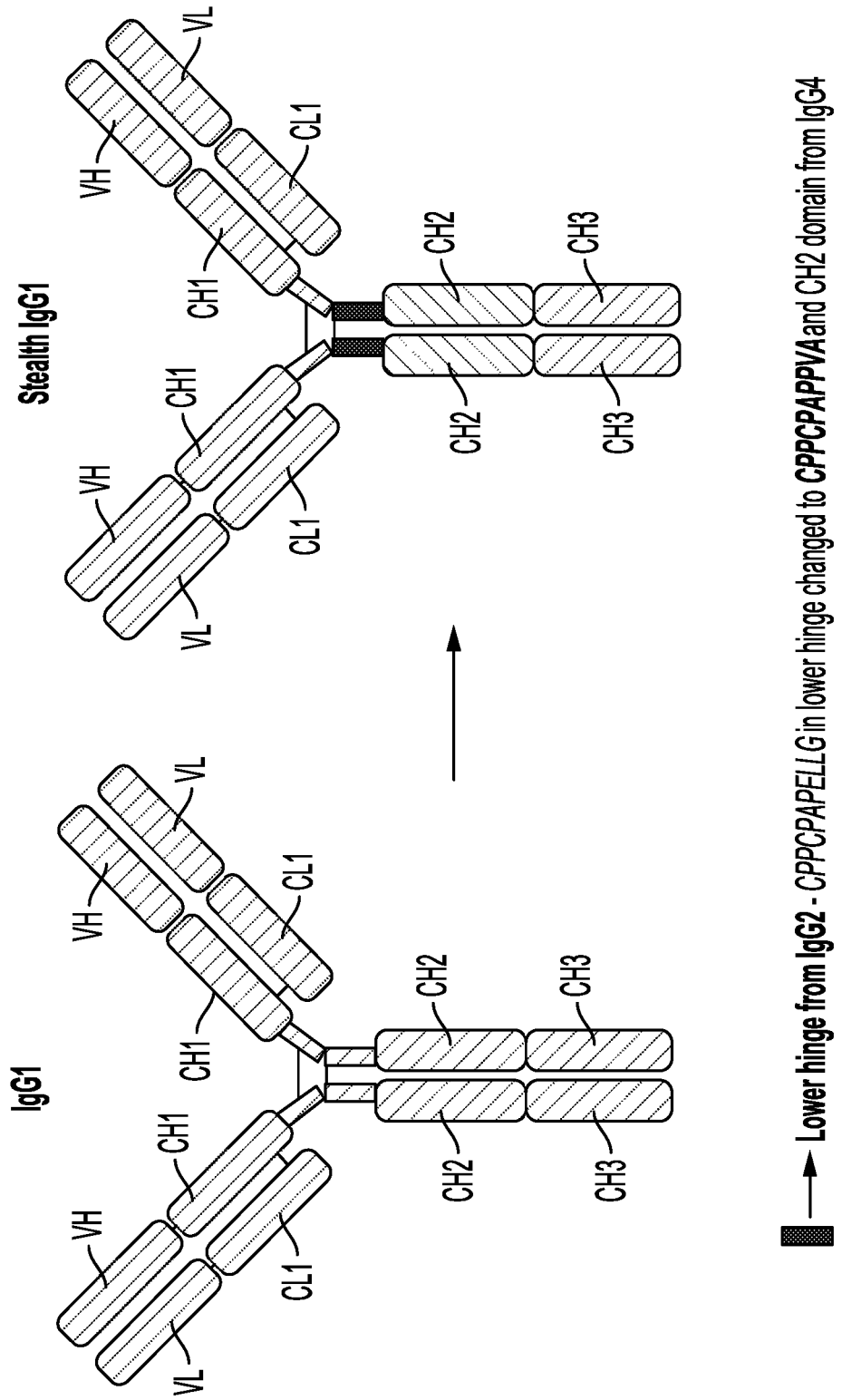
FIG. 16. Schematic diagram of IgG1 antibody possessing stealth mutations (SEQ ID NOS 102 and 109, respectively, in order of appearance).

Six VEGF mini-traps were tested in this assay using 48 human AMD/DME baseline serum samples and 24 monkey naïve serum samples. An anti-VEGFR1 monoclonal antibody (REGN18) was used as positive control. Results are summarized in FIG. 11(B) and FIG. 12.

Results Summary and Conclusions

Data showed that pre-existing anti-hinge antibodies (AHA) in naïve monkey serum samples or human AMD/DME baseline serum samples did not recognize the VEGF mini-trap constructs, except REGN7483 (hIgG1) which showed variable range of counts. Positive control anti-VEGFR1 mAb showed mean counts in the range of 6858-15055.

Example 5: Size Analysis of In Vitro Complexes Formed Between VEGF Mini-Traps (REGN10105 And REGN11095) and Recombinant Human VEGF$_{165}$ (REGN110) by Size Exclusion Chromatography Coupled to Multi-Angle Laser Light Scattering (SEC-MALS)

The stoichiometry of two VEGF mini-traps (REGN10105 and REGN11095) for binding to human VEGF$_{165}$ (hVEGF$_{165}$; REGN110) was determined.

Materials and Equipment

TABLE 5-1

Instrumentation List

| Instrumentation | Source |
|---|---|
| Waters Quaternary Solvent manager | Waters Corporation, Milford, MA |
| Waters Column Compartment | |
| Waters Sample Manager | |
| Waters UV detector | |
| Waters ACQUITY UPLC BEH ®200 SEC column (2.5 µm, 4.6 mm × 300 mm) | |

TABLE 5-1-continued

Instrumentation List

| Instrumentation | Source |
|---|---|
| microDawn light scattering detector | Wyatt Technology, Santa Barbara, CA |
| Optilab ® UT-rEX refractive index detector | |

TABLE 5-2

Reagent and Materials

| Reagent | Source |
|---|---|
| 10X Dulbecco's Phosphate Buffered Saline | Gibco |
| HPLC grade water | J. T. Baker |
| Sodium Phosphate Dibasic Heptahydrate | J. T. Baker |
| Sodium phosphate monobasic, monohydrate | J. T. Baker |
| Sodium Perchlorate | Sigma Aldrich |

Methods

SEC-MALS Mobile Phase Buffer. The mobile phase buffer (10 mM sodium phosphate, 500 mM sodium chloride, pH 7.0±0.1) was prepared by combining 1.4 g sodium phosphate monobasic monohydrate, 10.7 g sodium phosphate dibasic heptahydrate, and 500 mL 5 M sodium chloride; the solution was then brought to a volume to 5.0 L with HPLC grade water. The final measured pH of the buffer was 7.0. The mobile phase buffer was filtered (0.2 µm) before use.

SEC-MALS. The SEC-MALS system was composed of an UPLC connected to ultraviolet (UV), light scattering (LS), and refractive index (RI) detectors. The detectors were connected in series in the following order: UV-LS-RI. LS and RI detectors were calibrated according to instructions provided by Wyatt Technology. A BEH®200 SEC column size exclusion column was connected to the SEC-MALS system and pre-equilibrated in 10 mM sodium phosphate, 500 mM sodium chloride, pH 7.0 (SEC mobile phase buffer) with a flow rate of 0.3 mL/min prior to injection of samples. Defined amounts of mini-traps were each combined with hVEGF$_{165}$ (REGN110) and diluted in 1×DPBS, pH 7.4 to yield different ratios. All samples were incubated at ambient temperature for 2 hours and maintained unfiltered at 4° C. prior to injection. Bovine serum albumin (BSA; 2 mg/mL; 10 µg sample load) was injected separately and included as a system suitability control.

MALS Data Analysis. Data were analyzed using ASTRA V software (version 7.3.1.9, Wyatt Technology). The data were fit to the equation that relates the excess scattered light to the solute concentration and weight-average molar mass, Mw, (Kendrick et al., Online Size-Exclusion High-Performance Liquid Chromatography Light Scattering and Differential Refractometry Methods to Determine Degree of Polymer Conjugation to Proteins and Protein-Protein or Protein-Ligand Association States". (2001). Anal Biochem. 299(2), 136-46; Wyatt (1993) Anal. Chim. Acta 272(1), 1-40, Light Scattering and the Absolute Characterization of Macromolecules):

$$\frac{K*c}{R(\theta,c)} = \frac{1}{MwP(\theta)} + 2A_2c \qquad \text{Equation 1}$$

where c is the solute concentration, R(θ,c) is the excess Raleigh ratio from the solute as a function of scattering angle and concentration, Mw is the molar mass, P(θ) describes the angular dependence of scattered light (~1 for particles with radius of gyration <50 nm), $A_2$ is the second virial coefficient in the expansion of osmotic pressure (which can be neglected since measurements are performed on dilute solutions) and $$K^* = \frac{4\pi^2 n_0^2}{N_A \lambda_0^4}\left(\frac{dn}{dc}\right)^2 \quad \text{Equation 2}$$

where $n_o$ represents the solvent refractive index, $N_A$ is Avogadro's number, $\lambda_0$ is the wavelength of the incident light in a vacuum, and dn/dc represents the specific refractive index increment for the solute.

The molar mass of BSA monomer served to evaluate the calibration constants of the light scattering and differential refractive index detectors during data collection (system suitability check). The relative standard deviation (% RSD) of the average molar mass of BSA determined from the UV and RI detectors was ≤5.0%.

The normalization coefficients for the light scattering detectors, inter-detector delay volume and band broadening terms were calculated from the BSA chromatograms collected for the SEC-MALS condition employed. These values were applied to the data files collected for all the other samples to correct for these terms.

The dn/dc value and the extinction coefficient at 280 nm (corrected for glycosylation) were experimentally determined using the protein conjugate analysis provided in the Astra software. The corrected extinction coefficient and dn/dc value was used to analyze all protein-protein complex samples.

Results

The stoichiometry of two individual mini-traps (REGN10105 and REGN11095) binding to human VEGF165 (hVEGF$_{165}$; REGN110) was determined from SEC-MALS analysis of mini-trap in the presence and absence of varying concentrations of ligand. Under equivalent binding conditions, the stoichiometry of binding to hVEGF$_{165}$ was equivalent for each mini-trap tested. The stoichiometries of the resulting complexes from all samples analyzed are presented in FIG. 18 (A), and FIG. 18 (B) and are summarized in Table 5-3 and Table 5-4.

Figure 18:
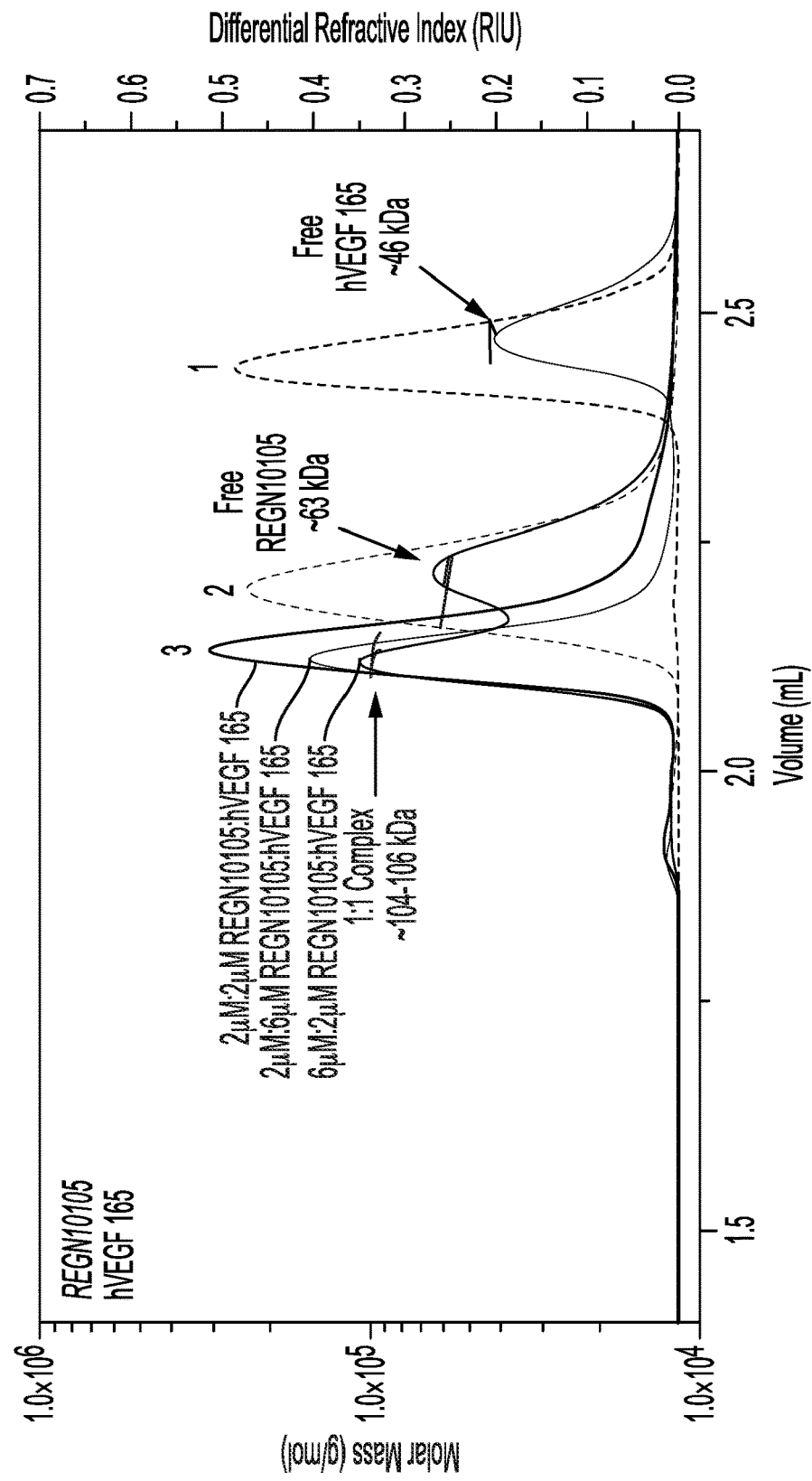
FIGS. 18 (A-B). Analysis of (A) REGN10105: hVEGF165 and (B) REGN11095: $hVEGF_{165}$ complexes (solid lines) by size exclusion chromatography coupled to multi-angle laser light scattering (SEC-MALS). Chromatograms from individual samples of REGN10105 or REGN11095 (grey dashed line) and $hVEGF_{165}$ (black dashed line) are also overlaid. Relative refractive index as a function of retention volume is shown for each sample and the measured molar masses of resolved peaks are indicated.
Figure 18:
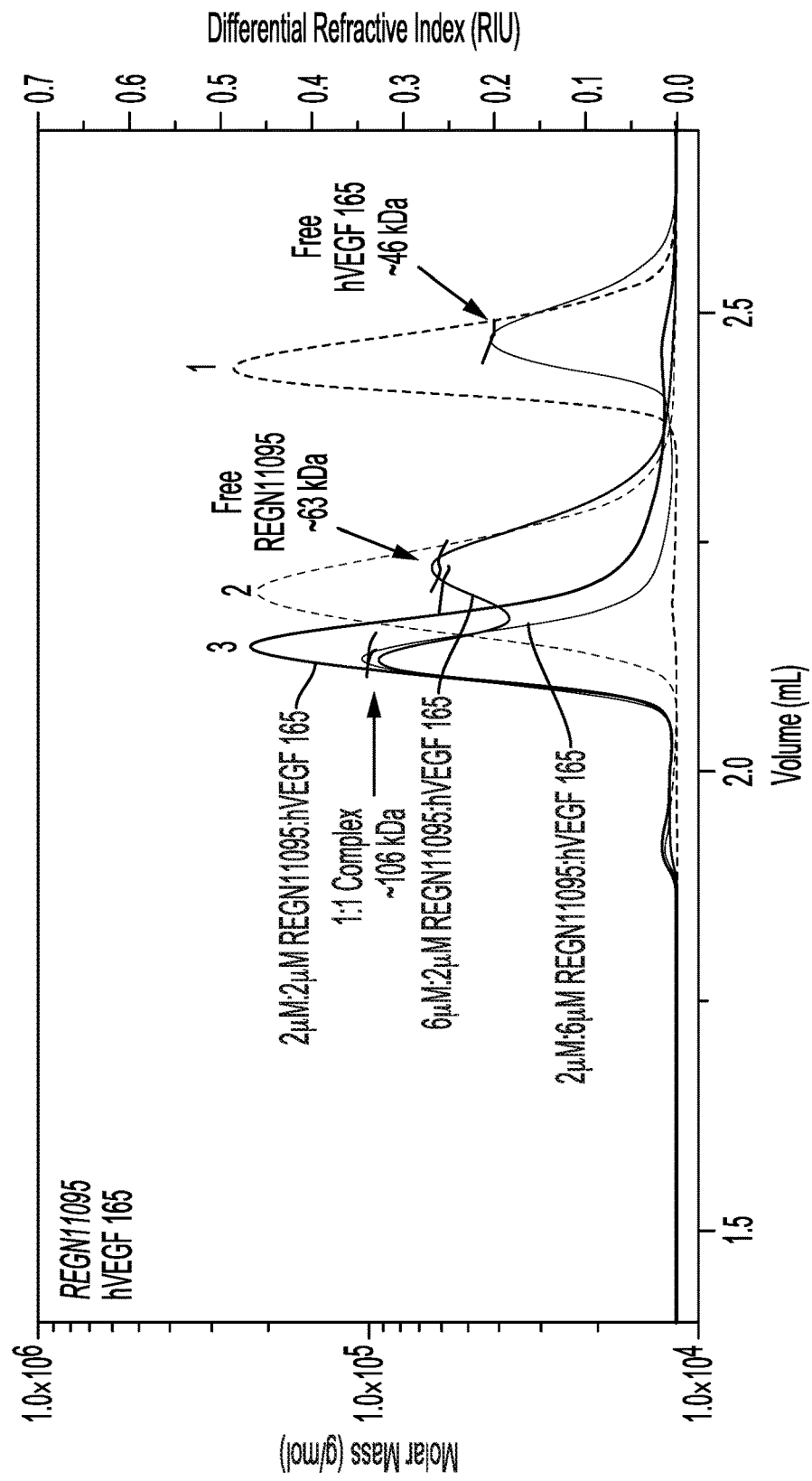

Representative overlaid chromatograms corresponding to 3:1, 1:1, and 1:3 molar ratios of each mini-trap to hVEGF$_{165}$ are shown in FIG. 18 (A) and 18 (B). The chromatograms of free hVEGF$_{165}$ and free mini-trap are also overlaid for comparison. The annotated peak numbers correspond to free hVEGF$_{165}$ (peak 1), free mini-trap (peak 2), and mini-trap-hVEGF$_{165}$ complexes (peak 3). The molar masses for each of the observed peaks are superimposed on the individual peaks for each chromatogram.

The measured molar masses of peak 1 and peak 2 were approximately 46 kDa and 63 kDa corresponding to free hVEGF$_{165}$ and free mini-trap, respectively. Based on the calculated molar masses of free hVEGF$_{165}$ and free mini-trap, the theoretical molar mass for a 1:1 complex of mini-trap:hVEGF$_{165}$ is predicted to be 109 kDa. Therefore, the chromatogram peak 3 most likely corresponds to a 1:1 mini-trap:hVEGF$_{165}$ complex based on a calculated average molar mass of approximately 106 kDa (Tables 5-3 and 5-4). Additionally, little to no higher molecular weight complexes were reliably detected for either sample under any of the tested conditions, indicating that each mini-trap binds to hVEGF$_{165}$ without higher-order multimerization. Taken together, the results demonstrate that each mini-trap exhibited equivalent binding stoichiometry to hVEGF$_{165}$, with each mini-trap molecule capable of binding one molecule of hVEGF$_{165}$ ligand.

TABLE 5-3

Summary of Molar Masses and Retention Tim of hVEGF$_{165}$ (REGN110) Complexes with REGN10105

| | | Peak 1 Free hVEGF$_{165}$ | | Peak 2 Free Mini-Trap | | Peak 3 [Mini-Trap]$_1$: [hVEGF$_{165}$]$_1$ Complex | |
|---|---|---|---|---|---|---|---|
| hVEGF$_{165}$ | Molar Ratio (mol:mol) | R$_t$, min | M$_w$, kDa | R$_t$, min | M$_w$, kDa | R$_t$, min | M$_w$, kDa |
| hVEGF$_{165}$ | — | 2.4 | 45.7 | ND | ND | ND | ND |
| REGN10105 | — | ND | ND | 2.2 | 63.1 | ND | ND |
| REGN10105:hVEGF$_{165}$ 3:1 | | ND | ND | 2.2 | 62.7 | 2.1 | 104.1 |
| REGN10105:hVEGF$_{165}$ 1:1 | | ND | ND | ND | ND | 2.1 | 104.4 |
| REGN10105:hVEGF$_{165}$ 1:3 | | 2.5 | 45.5 | ND | ND | 2.1 | 106.2 |

R$_t$: Retention Time; M$_w$: weight average molar mass; NA: Not Applicable; min: minutes; kDa: kiloDaltons;

TABLE 5-4

Summary of Molar Masses and Retention Time of hVEGF$_{165}$ (REGN110) Complexes with REGN11095

| | | Peak 1 Free hVEGF$_{165}$ | | Peak 2 Free Mini-Trap | | Peak 3 [Mini-Trap]$_1$: [hVEGF$_{165}$]$_1$ Complex | |
|---|---|---|---|---|---|---|---|
| Sample | Molar Ratio (mol:mol) | R$_t$, min | M$_w$, kDa | R$_t$, min | M$_w$, kDa | R$_t$, min | M$_w$, kDa |
| hVEGF$_{165}$ | — | 2.4 | 45.7 | ND | ND | ND | ND |
| REGN11095 | — | ND | ND | 2.2 | 63.4 | ND | ND |
| REGN11095:hVEGF$_{165}$ 3:1 | | ND | ND | 2.2 | 65.8 | 2.1 | 106.4 |

TABLE 5-4-continued

Summary of Molar Masses and Retention Time of hVEGF$_{165}$ (REGN110) Complexes with REGN11095

| | | Peak 1 Free hVEGF$_{165}$ | | Peak 2 Free Mini-Trap | | Peak 3 [Mini-Trap]$_1$: [hVEGF$_{165}$]$_1$ Complex | |
|---|---|---|---|---|---|---|---|
| Sample | Molar Ratio (mol:mol) | R$_t$, min | M$_w$, kDa | R$_t$, min | M$_w$, kDa | R$_t$, min | M$_w$, kDa |
| REGN11095:hVEGF$_{165}$ 1:1 | | ND | ND | ND | ND | 2.1 | 106.2 |
| REGN11095:hVEGF$_{165}$ 1:3 | | 2.5 | 45.8 | ND | ND | 2.1 | 106.6 |

R$_t$: Retention Time; M$_w$: weight average molar mass; NA: Not Applicable; min: minutes; kDa: kiloDaltons;

Example 6: Cryogenic Electron Microscopy (Cryo-EM) Structural Analysis of VEGF Mini-Trap REGN10105 in Complex with VEGF and Anti-VEGF Fab (REGN18)

Cryogenic electron microscopy was used to analyze the binding of REGN10105 to VEGF along with a Fab molecule. REGN18 is the anti-human VEGFR1-d2 mAb that is a non-blocker of VEGF binding which was added to increase the size of the complex to make the sample more suitable for Cryo-EM study.

Fab fragment preparation. The anti-hVEGFR1 domain 2 antibody REGN18 was cleaved into F(ab')$_2$ and Fc fragments using Fabricator enzyme (Genovis) following standard protocols from the manufacturer. F(ab')$_2$ was reduced into Fab using 2-mercaptoethylamine (2-MEA, ThermoFisher) followed by Fc fragment removal using CaptureSelect IgG-Fc (ms) affinity resin (ThermoFisher). Fab fragments were further purified by injection into a size exclusion chromatography (SEC) column (Superdex 200 Increase 15/300 GL, GE healthcare) connected to an AKTA Avant 25 chromatography system (GE healthcare). Running buffer contained 50 mM Tris-HCl pH 7.5, 150 mM NaCl. Peak fractions were pooled and concentrated in a 10 kDa cutoff centrifugal filter (Millipore Sigma) for subsequent use in complex preparation.

Complex preparation. 100 µg of purified mini-Trap (REGN10105-L3) was mixed with 200 µg REGN18 Fab and 160 µg hVEGF (REGN110-L9) and incubated at 4° C. overnight. The mixture was injected into an SEC column (Superdex 200 Increase 15/300 GL, GE) connected to an AKTA chromatography system (GE healthcare) and a Multi-Angle Light Scattering (MALS) detector (Wyatt Technology). SEC running buffer contained 50 mM Tris-HCl pH 7.5, 150 mM NaCl. Fractions from the peak corresponding to the REGN10105-REGN110-REGN18 Fab complex with an estimated molecular weight of 210 kDa were pooled and concentrated in a 30 kDa cutoff centrifugal filter (Millipore Sigma) to a concentration of 3.2 mg/mL measured using a Nanodrop instrument (ThermoFisher). See FIG. 19 (A). REGN18 is a non-blocker of VEGF binding and was added to increase the size of the REGN10105-REGN110 complex so as to make the sample more suitable for subsequent Cryo-EM study.

Cryo-EM sample preparation and data collection. Freshly purified REGN10105-REGN110-REGN18 Fab complex was mixed with 0.15% PMAL-C8 Amphipol detergent before pipetting 3.5 µL of the mixture onto a UltrAufoil R1.2/1.3, 300 mesh grid (Quantifoil). Excess liquid was blotted away using filter paper and the grid was plunge frozen into liquid ethane cooled by liquid nitrogen using a Vitrobot Mark IV (ThermoFisher) operated at 4° C. and 100% humidity. The grid was then loaded into a Titan Krios G3i microscope (ThermoFisher) equipped with a K3 camera (Gatan). 13,248 movies were collected in counted mode at a nominal magnification of 105,000× (0.85 Å pixel size). Each movie contained 46 dose fractions over a 2 second exposure, and the total acquired dose per Å$^2$ was ~40 electrons.

Cryo-EM data processing and map generation. Cryo-EM data were processed using Cryosparc v2.14.2. Movies were motion corrected by Patch motion correction and CTF parameters were estimated by Patch CTF estimation. Particles were initially picked using Blob picker to generate 2D class averages for template picking. 633,335 particles were left after running several rounds of 2D classification to remove junk particles. After ab initio reconstruction and Heterogenous refinement, 125,447 particles corresponding to the REGN10105-REGN110-REGN18 Fab complex were identified and further refined to 3.4 Å resolution reconstruction using Non-uniform refinement.

Results. Complex formation between REGN10105, hVEGF and REGN18 was determined. REGN10105 formed a 1:1 complex with hVEGF dimer (58 kDa+46 kDa=104 kDa). REGN10105, VEGF dimer and REGN18 Fab form a 1:1:2 complex (104 kDa+48 kDa*2=210 kDa). There was some REGN18 F(ab')$_2$ contamination in the sample. See FIG. 19 (A).

The 2-dimensional structure of the REGN10105/VEGF/REGN18 complex was characterized by visualization under cryogenic electron microscopy. The 2D classes showed secondary structure features and some of them show clear 2-fold symmetry. The VEGFR2 domain 3 density is visible in many views, but it is quite blurry (arrow pointed) compared with the rest of the complex, suggesting that this domain is flexible. The VEGFR2 domain 3 density is even blurrier at the distal end.

A 3.4 Å Cryo-EM map of REGN10105-VEGF-REGN18 complex showed poor density at the VEGFR2-domain 3 C-terminal end. There was very clear density for VEGFR1 domain 2; VEGF and the REGN18 Fab variable domain; and poor density for the REGN18 Fab constant domain due to flexibility of this region. VEGFR2 domain 3 was resolved where the main chain and some side chains could be traced, but the Cryo-EM density is quite weak at the C-terminal end of R2-d3, likely due to high flexibility of this region. See FIG. 19 (B-D).

Figure 19:
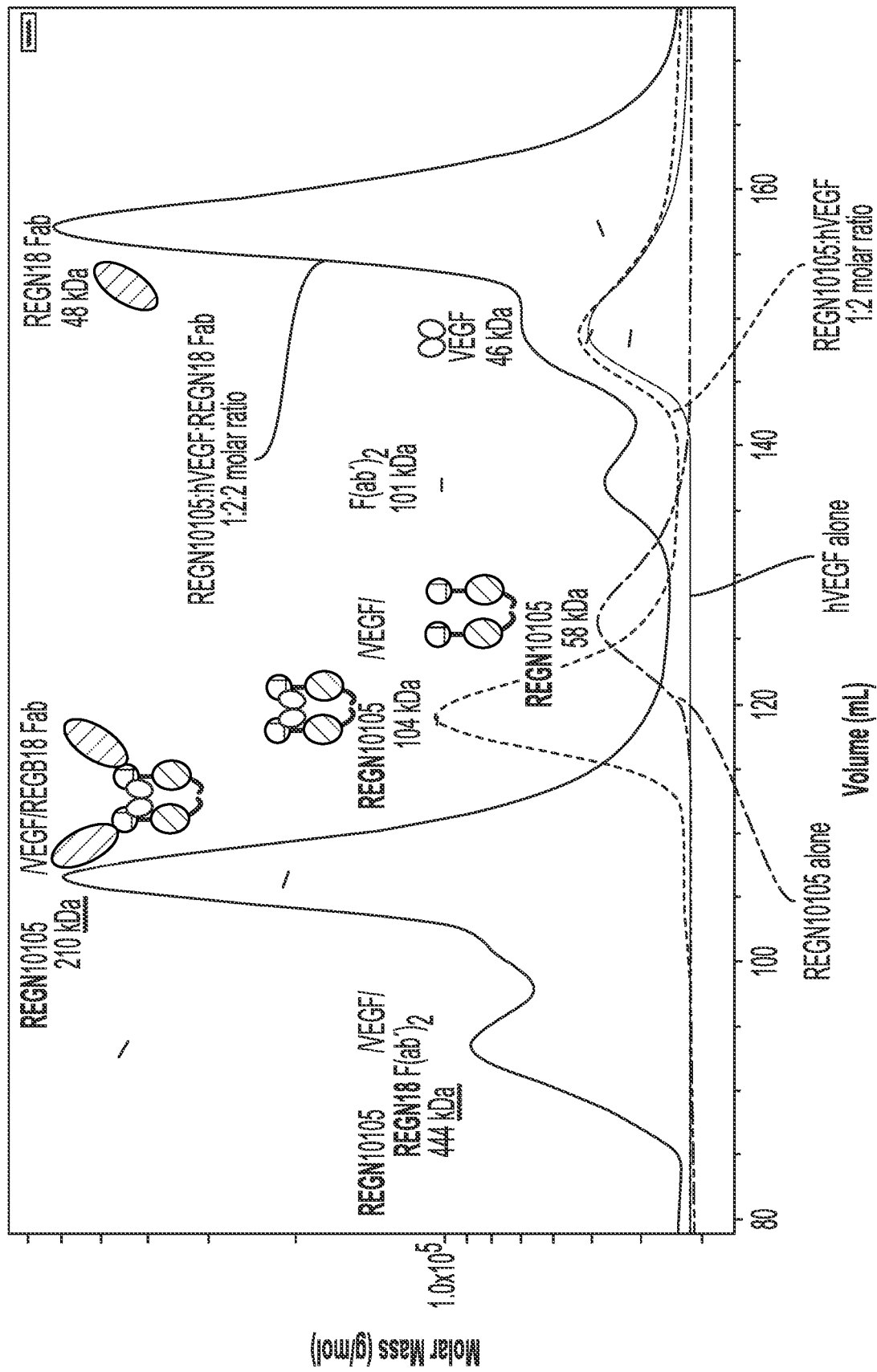
FIGS. 19 (A-D). Cryo-EM analyses of structure of VEGF mini-trap REGN10105 in complex with VEGF and REGN18 Fab. Samples of hVEGF alone, REGN10105 alone, REGN10105 with hVEGF or REGN10105, hVEGF and REGN18 Fab were analyzed. (A) SEC-MALS chromatogram of REGN10105/VEGF/REGN18 Fab mixture. (B) raw Cryo-EM image, complexes/particles circled. (C) selection of 2D class averages; arrows indicate VEGFR2 domain 3. (D) individual 2D classes; arrow indicates VEGF or VEGFR2 domain 3.
Figure 19:
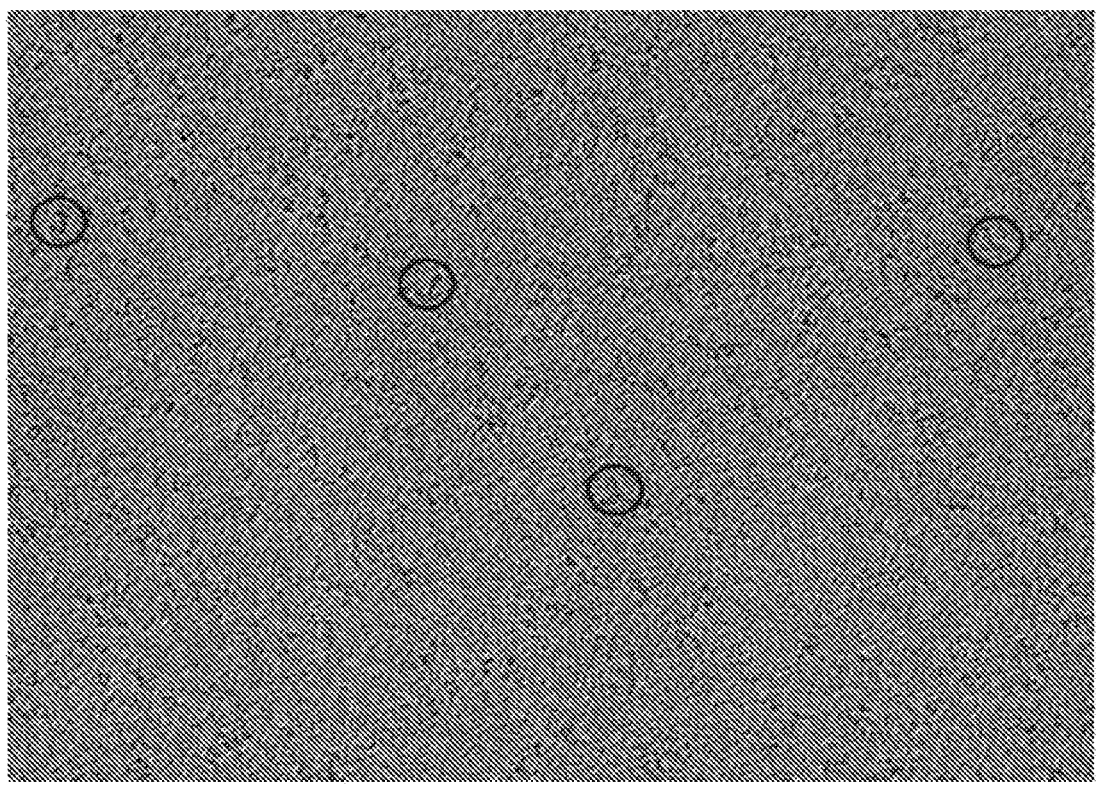
Figure 19C:
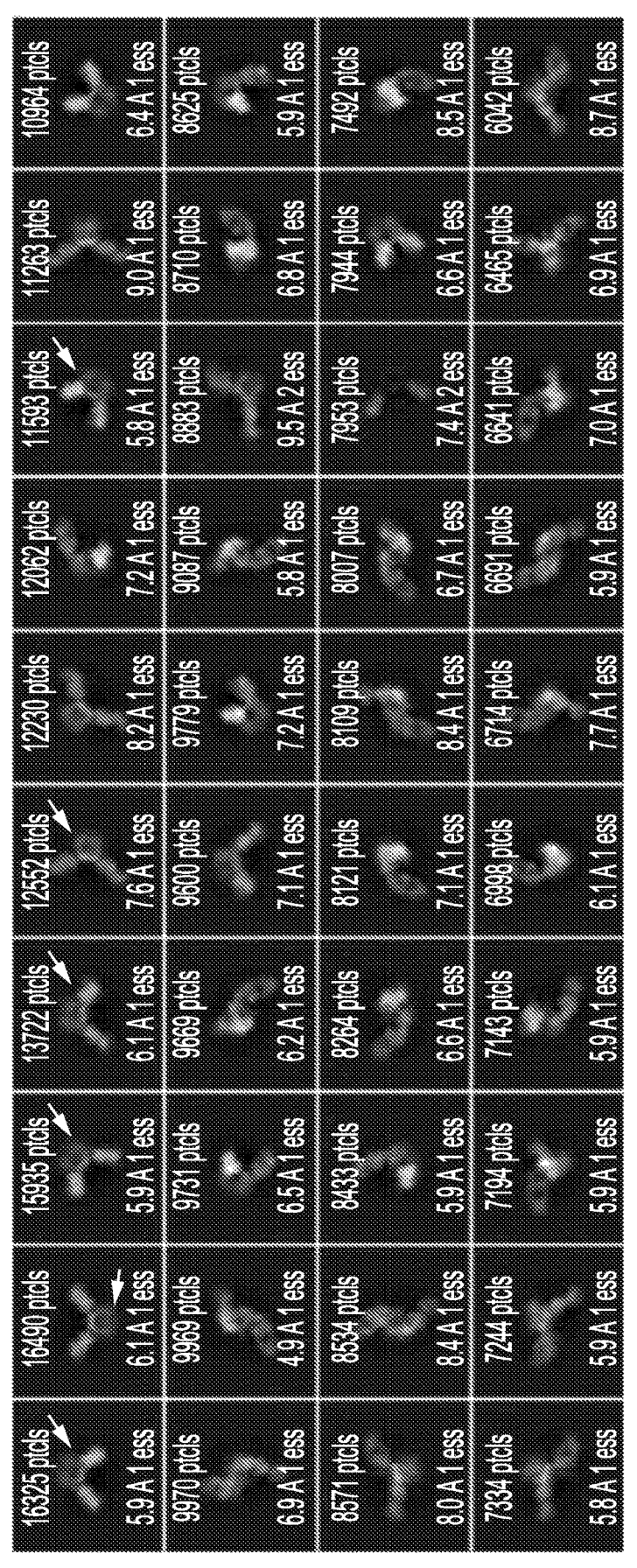
Figure 19:
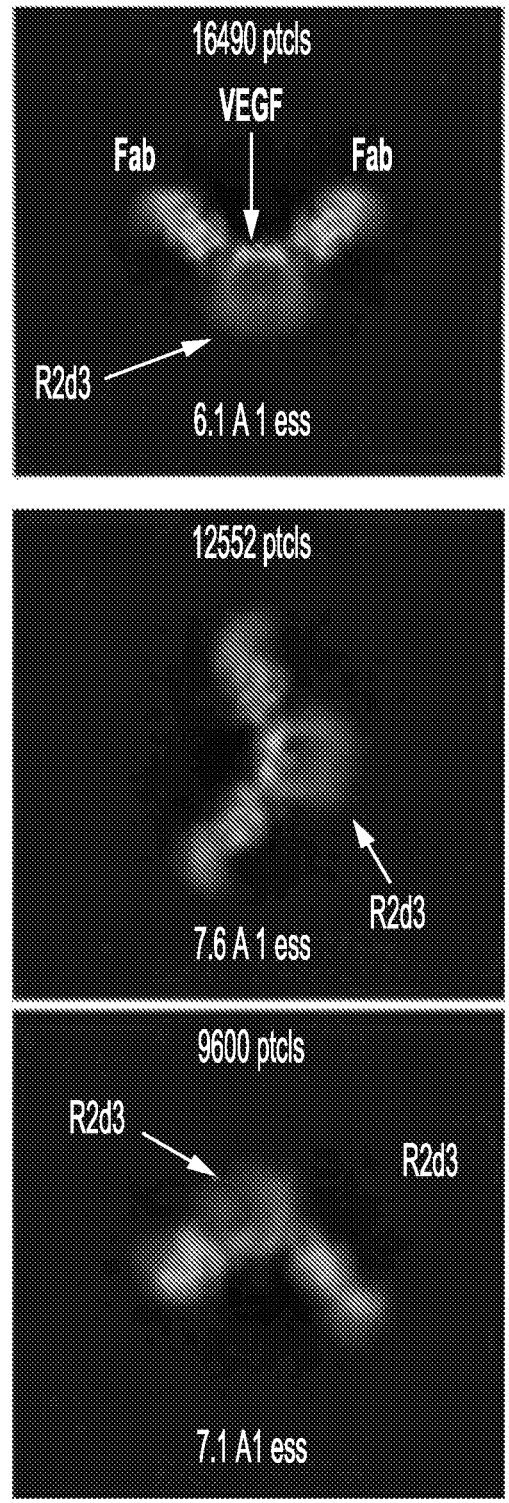

REGN10105 that forms a complex essentially as depicted in FIG. 19 (C-D) when complexed with human VEGF$_{165}$ and an anti-VEGF Fab, when visualized by Cryo-EM is part of the present invention.

Example 7: Effect of Mini-Traps REGN10105 and REGN11095 in Oxygen Induced Retinopathy (OIR) Mouse Model The effects of systemic and intravitreal REGN11095 and REGN10015 on retinal vasculature in an OIR mouse model was determined.

In the Oxygen Induced Retinopathy (OIR) model in mice, Taconic C57131/6 mouse pups were placed in a hyperoxic environment (75% $O_2$) at postnatal day (P)6 and returned to room air at P11. Study 1 (Intravitreal (IVT) Injection Equimolar Screen Study): OIR pups were injected IVT with human (h)Fc (hFc) 0.125 µg, aflibercept 0.25 µg, REGN10105 0.125 µg, REGN11095 0.125 µg respectively, at P13 and collected at P16. Study 2 (IVT Dose Response Study): OIR mice were injected IVT with hFc at 0.25 µg, REGN10105 at 0.025 µg, 0.25 µg, and 2.5 µg, or aflibercept at 0.05 µg, 0.5 µg, and 5 µg at P13 and collected at P16. Study 3 (Equimolar Systemic (IP) Study): OIR mice were injected IP with hFc at 5 mg/kg, aflibercept at 10 mg/kg, REGN10105 at 5 mg/kg, or REGN11095 at 5 mg/ml, respectively, at P12 and collected at P16. Retinas were fixed, dissected, and stained with FITC-labeled *Griffornia simplicifolia* lectin I (GS Lectin I) to label retinal vasculature (Vector Laboratories) and NG2 (Millipore) with secondary Alexa Fluor594 (Thermo Scientific) to label neovascular tufts.

Mice pups were placed in a chamber at the 75% $O_2$ at postnatal (P)6 to P11. After 5 days in an oxygen chamber, they were placed back in room air (21% $O_2$). For Intravitreal (IVT) studies, mice were injected with reagents at P13 and eyes collected at P16. For systemic (IP) studies, mice were injected with reagents at P12 and eyes were collected at P16.

Study 1: Intravitreal (IVT) Aflibercept and VEGF mini-Trap Equimolar Dose studies
Aflibercept (REGN3): 0.25 µg/eye
REGN11095: 0.125 µg/eye
REGN10105: 0.125 µg/eye
Vehicle (hFc): 0.125 µg/eye
3 mice per group; left and right eyes injected In the Oxygen Induced Retinopathy (OIR) model in mice, Taconic C57Bl/6 mouse pups were placed in a hyperoxic environment (75% $O_2$) at postnatal day (P)6 and returned to room air at P11.

Study 1 (IVT Equimolar Screen Study): OIR pups were injected IVT with human Fc (hFc) 0.125 µg, aflibercept 0.25 µg, REGN10105 0.125 µg, REGN11095 0.125 µg respectively, at P13 and collected at P16.

Figure 20A:
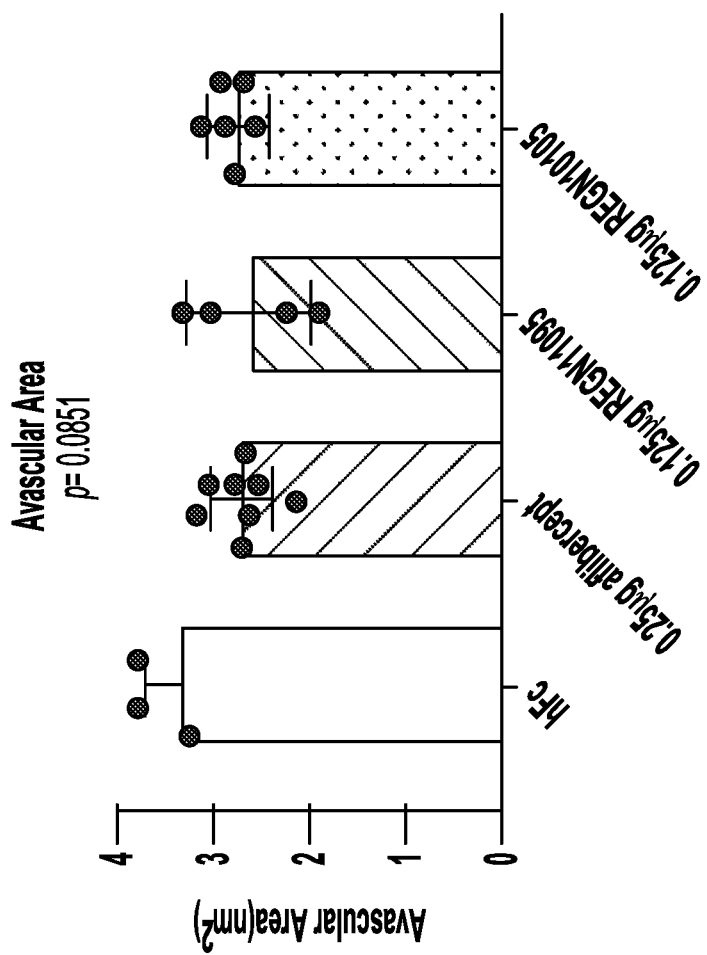
FIGS. 20 (A-B). Summary of (A) avascular and (B) abnormal areas observed in retinas from oxygen-induced retinopathy mouse models intravitreally treated with human Fc, aflibercept, REGN11095 or REGN10105. Retinal flat mounts stained with GS Lectin I (for avascular area study) or NG2 (for abnormal area study) were analyzed.
Figure 20B:
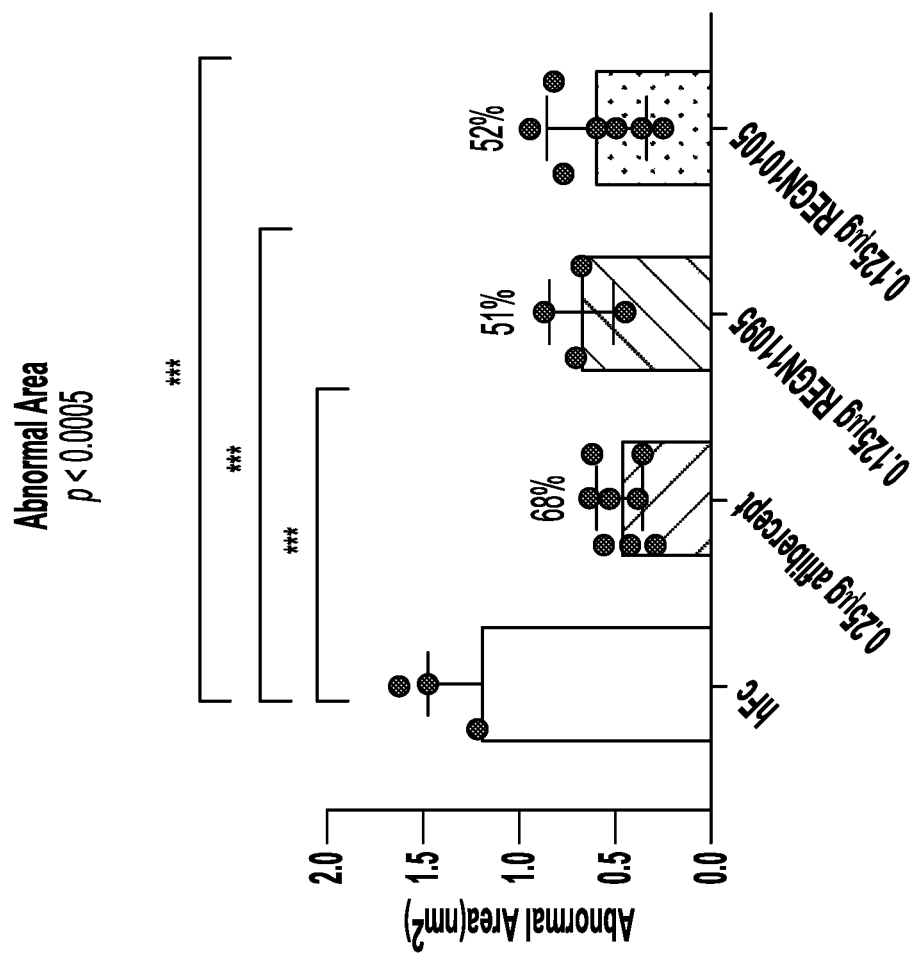

Retinas were fixed, dissected, and stained with FITC-labeled *Griffornia simplicifolia* lectin 1 (GS Lectin 1) to label retinal vasculature (Vector Laboratories) and NG2 (Millipore) with secondary Alexa Fluor594 (Thermo Scientific) to label neovascular tufts. Avascular area of mouse retinas are summarized in FIG. 20 (A). The abnormal area of the mouse retinas are summarized in FIG. 20 (B).

Study 2: Intravitreal (IVT) Equimolar Aflibercept and VEGF mini-Trap Dose Response studies
Aflibercept (REGN3): 0.05 µg/eye, 0.5 µg/eye, and 5 µg/eye
REGN10105: 0.025 µg/eye, 0.25 µg/eye, and 2.5 µg/eye
Vehicle (hFc): 0.25 µg/eye 3-4 mice per group; only left eyes injected In the Oxygen Induced Retinopathy (OIR) model in mice, Taconic C57Bl/6 mouse pups were placed in a hyperoxic environment (75% $O_2$) at postnatal day (P)6 and returned to room air at P11.

Study 2 (IVT Dose Response Study): OIR mice were injected IVT with hFc at 0.25 µg, REGN10105 at 0.025 µg, 0.25 µg, and 2.5 µg, or aflibercept at 0.05 µg, 0.5 µg, and 5 µg at P13 and collected at P16.

Retinas were fixed, dissected, and stained with FITC-labeled *Griffornia simplicifolia* lectin 1 (GS Lectin 1) to label retinal vasculature (Vector Laboratories) and NG2 (Millipore) with secondary Alexa Fluor594 (Thermo Scientific) to label neovascular tufts.

Figure 21:
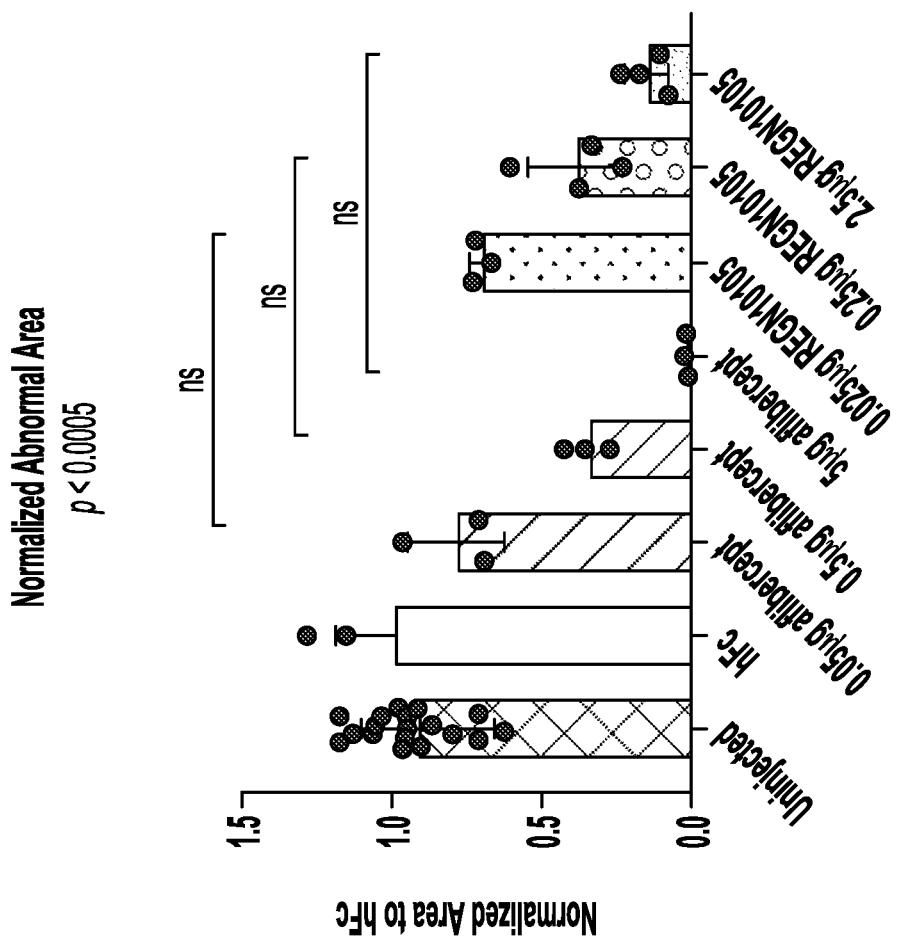
FIG. 21. Summary of normalized (to hFc treated) abnormal areas observed in retinas from oxygen-induced retinopathy mouse models uninjected, or intravitreally treated with human Fc, aflibercept (0.05, 0.5 or 5 micrograms) or REGN10105 (0.025, 0.25 or 2.5 micrograms). Retinal flat mounts stained with or NG2 were analyzed. Data were normalized to the Fc treated group.

The area of abnormal retinal area, which is normalized to that of mice dosed with hFc only, is set forth in FIG. 21.

Study 3: Systemic Aflibercept and VEGF mini-Trap Equimolar studies
Aflibercept (REGN3): 10 mg/kg
REGN10105 5 mg/kg
REGN11095 5 mg/kg
Vehicle (hFc): 5 mg/kg
* Experiment done 2 times
3 mice per group; left and right eyes analyzed In the Oxygen Induced Retinopathy (OIR) model in mice, Taconic C57Bl/6 mouse pups were placed in a hyperoxic environment (75% $O_2$) at postnatal day (P)6 and returned to room air at P11.

Study 3 (Equimolar Systemic (IP) Study): OIR mice were injected IP with hFc at 5 mg/kg, aflibercept at 10 mg/kg, REGN10105 at 5 mg/kg, or REGN11095 at 5 mg/ml, respectively, at P12 and collected at P16.

Retinas were fixed, dissected, and stained with FITC-labeled *Griffornia simplicifolia* lectin 1 (GS Lectin 1) to label retinal vasculature (Vector Laboratories) and NG2 (Millipore) with secondary Alexa Fluor594 (Thermo Scientific) to label neovascular tufts.

Figure 22A:
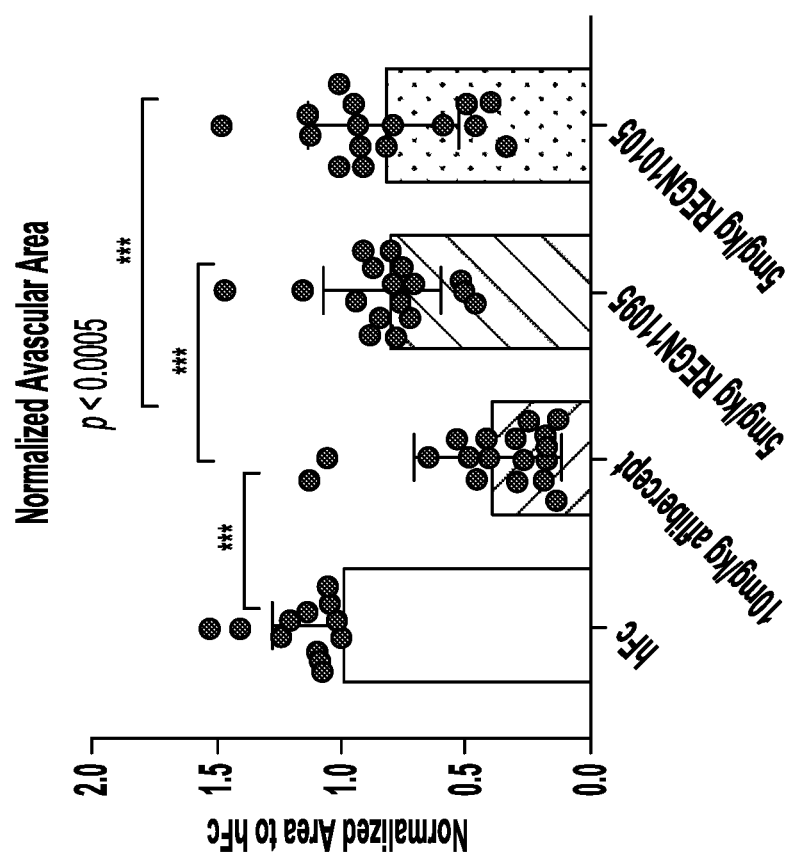
FIGS. 22 (A-B). Summary of (A) avascular and (B) abnormal areas (normalized to hFc treated) observed in retinas from oxygen-induced retinopathy mouse models systemically administered human Fc, aflibercept, REGN11095 or REGN10105. Retinal flat mounts stained with GS Lectin I (for avascular area study) or NG2 (for abnormal area study) were analyzed.
Figure 22B:
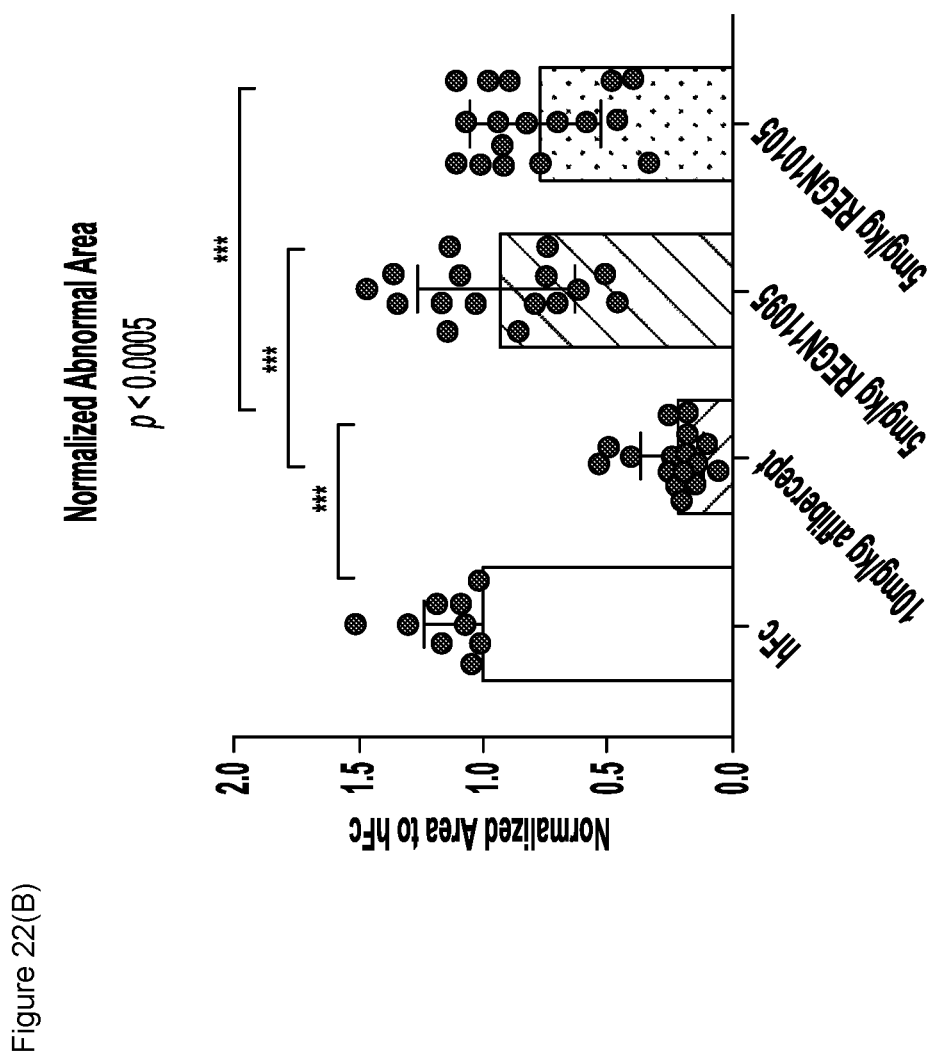

The avascular area of mouse retinas, normalized to that of mice dosed with hFc only, are summarized in FIG. 22 (A). The abnormal area of the mouse retinas, normalized to that of mice dosed with hFc only, are summarized in FIG. 22 (B).

Example 8: VEGF Trap and Mini-Trap (REGN10105; REGN11095 and REGN3) In Vivo Pharmacokinetics (PK) in Rabbits The pharmacokinetics of REGN10105 and REGN11095 in rabbits was investigated.

This PK study showed that the half-lives of the VEGF mini-traps (REGN10105 and REGN11095)) were shorter than that of VEGF Trap (REGN3) in NZW rabbit vitreous, the VEGF mini-traps persistence was about 22% and 32% shorter, respectively (5.0 days vs 3.9 and 3.4 days).

TABLE 8-1

| VEGF Traps and VEGF Mini-Traps Tested | | |
|---|---|---|
| REGN# | Common name | IgG hinge amino acid sequence |
| REGN3 | VEGF Trap hIgG1 Fc | DKTHT CPPCP APELLGGPSV (SEQ ID NO: 107) |
| REGN10105 | VEGF mini-trap hIgG2 Fc w_2 cys | VE CPPCP APPVA (SEQ ID NO: 5) |
| REGN11095 | VEGF mini-trap hIgG1 Mut GGGL (SEQ ID NO: 94) | DKTHT CPPCP GGGLLG (SEQ ID NO: 13) |

Experimental procedures. VEGF Trap (REGN3) and two new VEGF mini-traps (REGN10105; and REGN11095)

were molecules tagged with Alexa Fluor 488 (AF488) through amine conjugation. Protein concentrations, endotoxin levels, and Degree of Labeling (DOL) are provided in Table 8-2. Bilateral intravitreal (IVT) injections were made to 6 male New Zealand White (NZW) rabbits (6 eyes/3 rabbits/molecule). All eyes were examined for vitreous baseline fluorescence with OcuMetrics Fluorotron fluorophotometer (Mountain View, Calif.) before injection, and followed up for vitreous fluorescence intensity post injection at Day 3, 7, 14 and 21. General ocular examination included intraocular pressure (IOP), inflammation signs, corneal and conjunctival edema, hemorrhages, floaters in anterior chamber, pupil size and shape, cataract, and retinal detachment before and 30 minutes after IVT injection, and at each follow-up time point. Fluorescence intensity and position information were extracted and imported in GraphPad Prism for graphical display and analysis. The data were fitted to a first order, single compartment model.

TABLE 8-2

Half-life ($t_{1/2}$) of VEGF Trap and VEGF Mini-Trap in Intravitreal Photofluorimetry PK in Rabbits

| Test article | Conjugation | Conc. mg/ml | Endotoxin (EU/mL) | DOL (Degree of AF488 Labeling) | Volume (uL)/eye | $t_{1/2}$ (Std) Days |
|---|---|---|---|---|---|---|
| REGN3 (aflibercept) | AF488 | 2.29 | <5 | 2.38 | 50 | 5.0 (0.4) |
| REGN10105 | AF488 | 2.92 | <1.05 | 2.87 | 50 | 3.9 (0.3) |
| REGN11095 | AF488 | 2.93 | <1.05 | 2.65 | 50 | 3.4 (0.5) |

Figure 23:
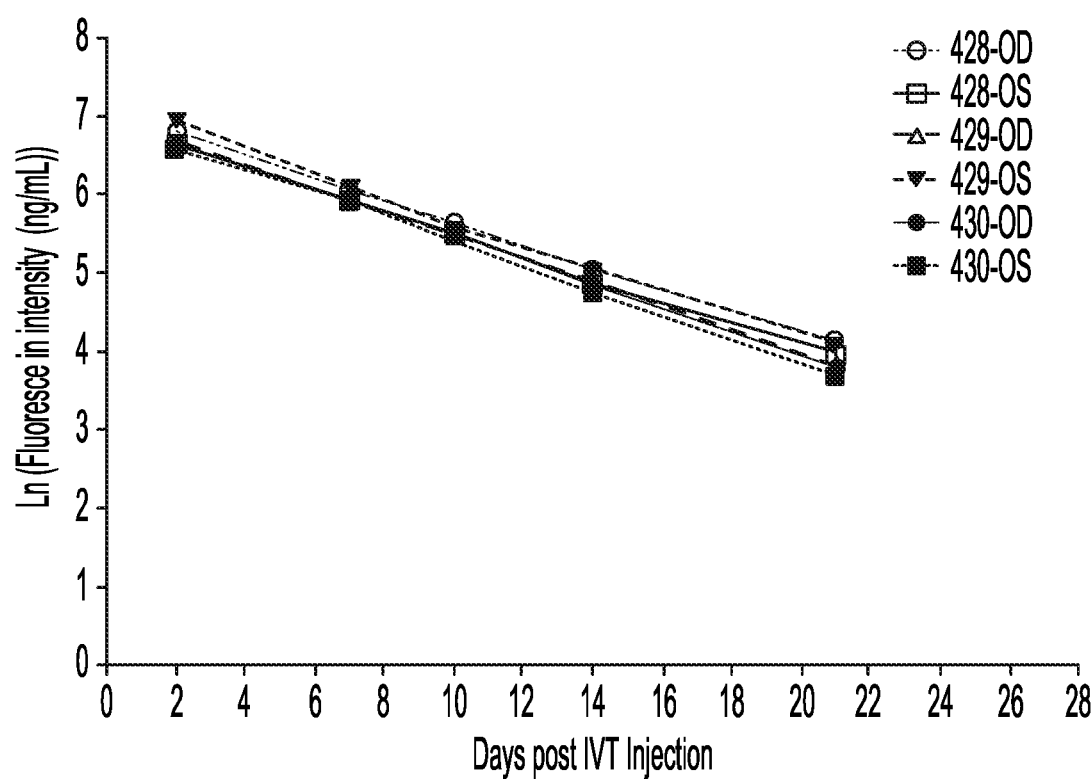
FIGS. 23 (A-F). Decay analysis of VEGF traps in vitreous of New Zealand White rabbits. (A) REGN3 (animals 428, 429 and 430), (B) REGN7483 (animals 434, 435 and 436), (C) REGN3 (animals 570, 571 and 572), (D) REGN10105 (animals 573, 574 and 575) and (E) REGN11095 (animals 576, 577 and 578). OS=oculus sinister, OD=oculus dexter. (F) intraocular pressure (IOP) (mmHg) before and after IVT injection of REGN3, REGN10105 or REGN11095.
Figure 23:
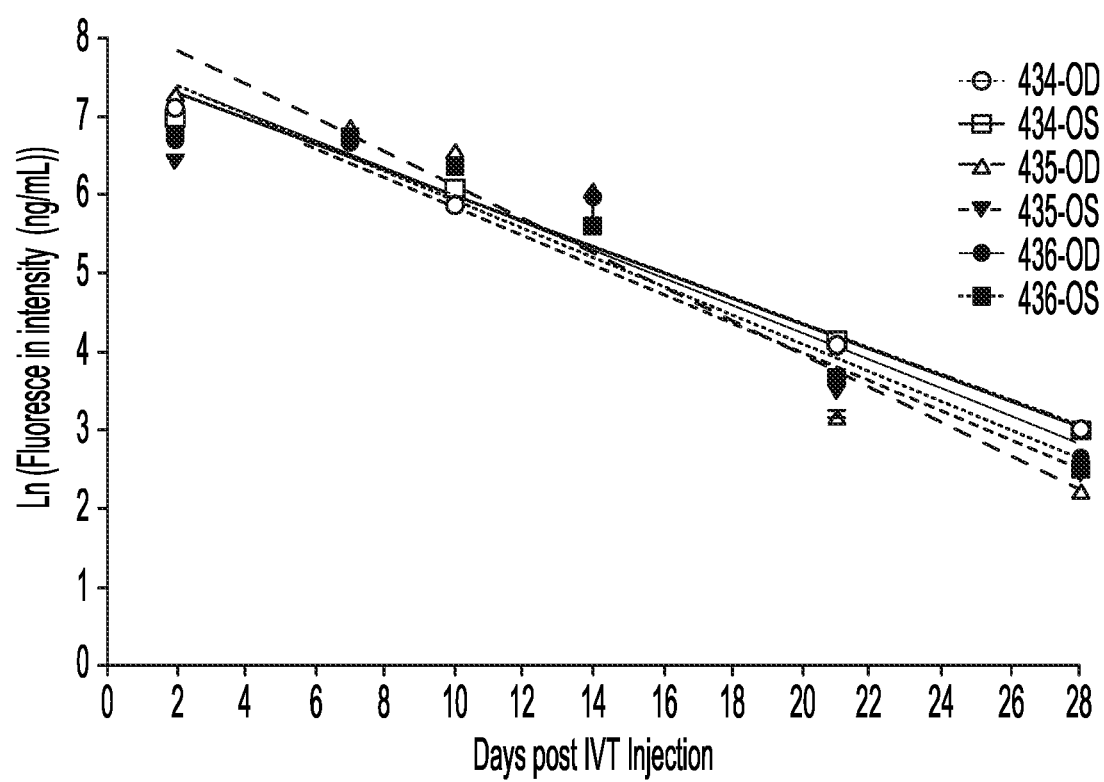
Figure 23:
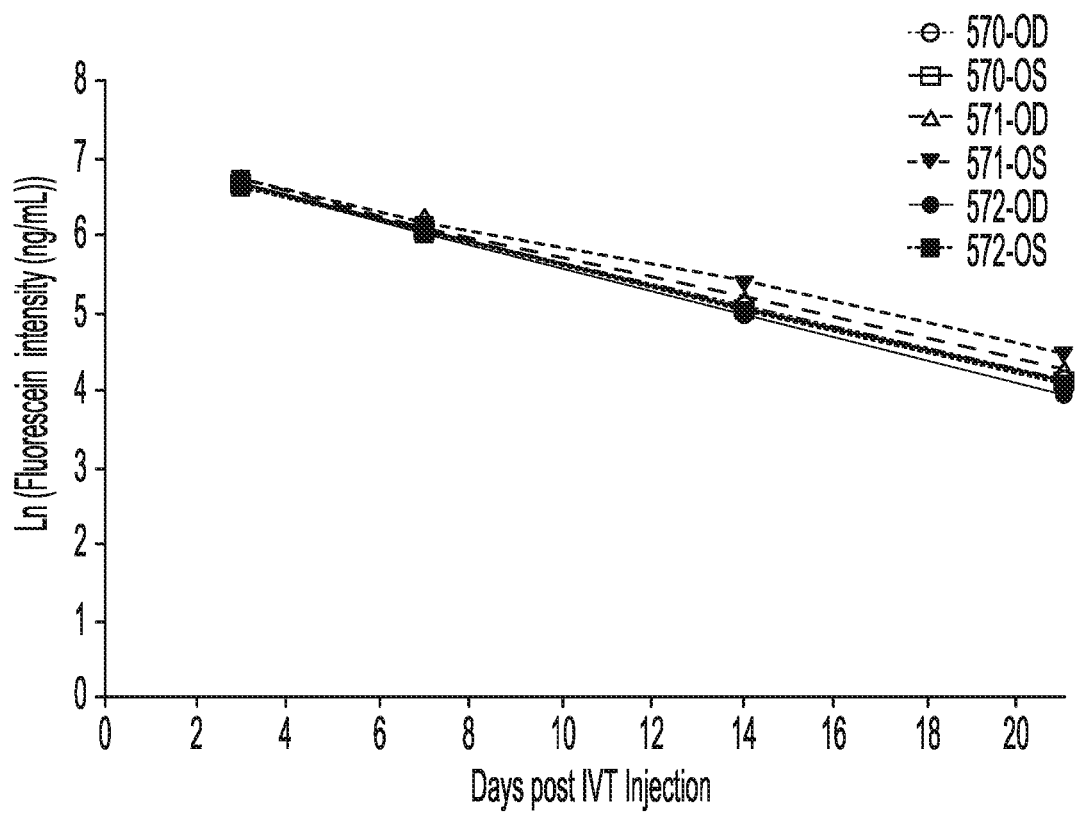
Figure 23:
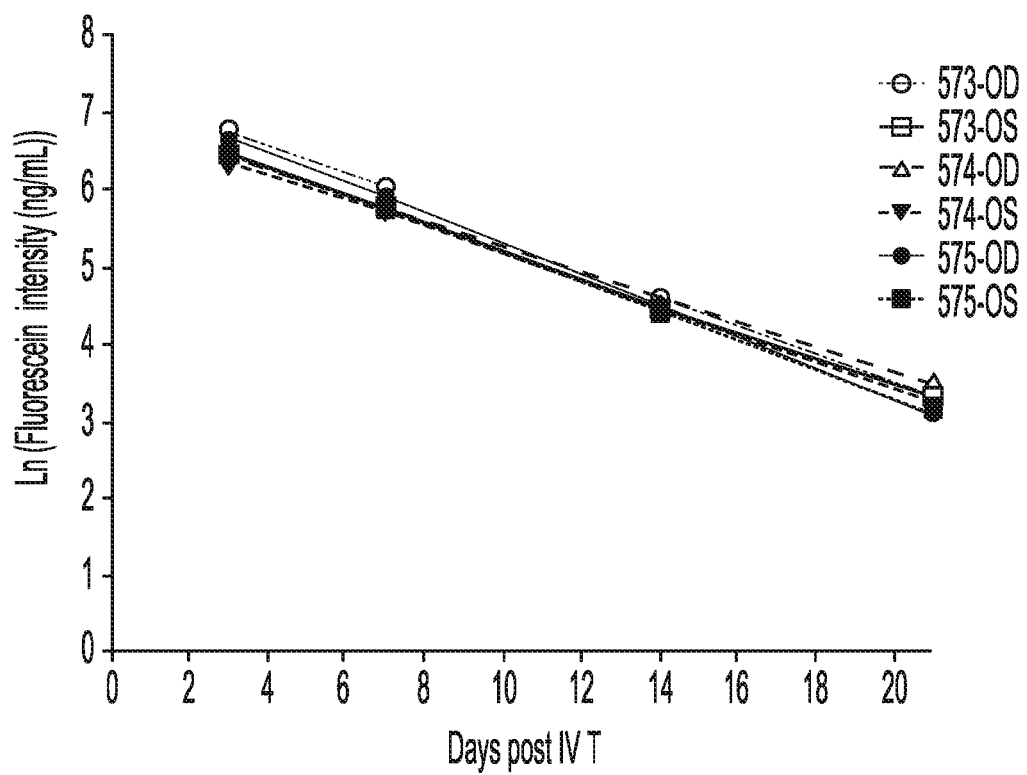
Figure 23:
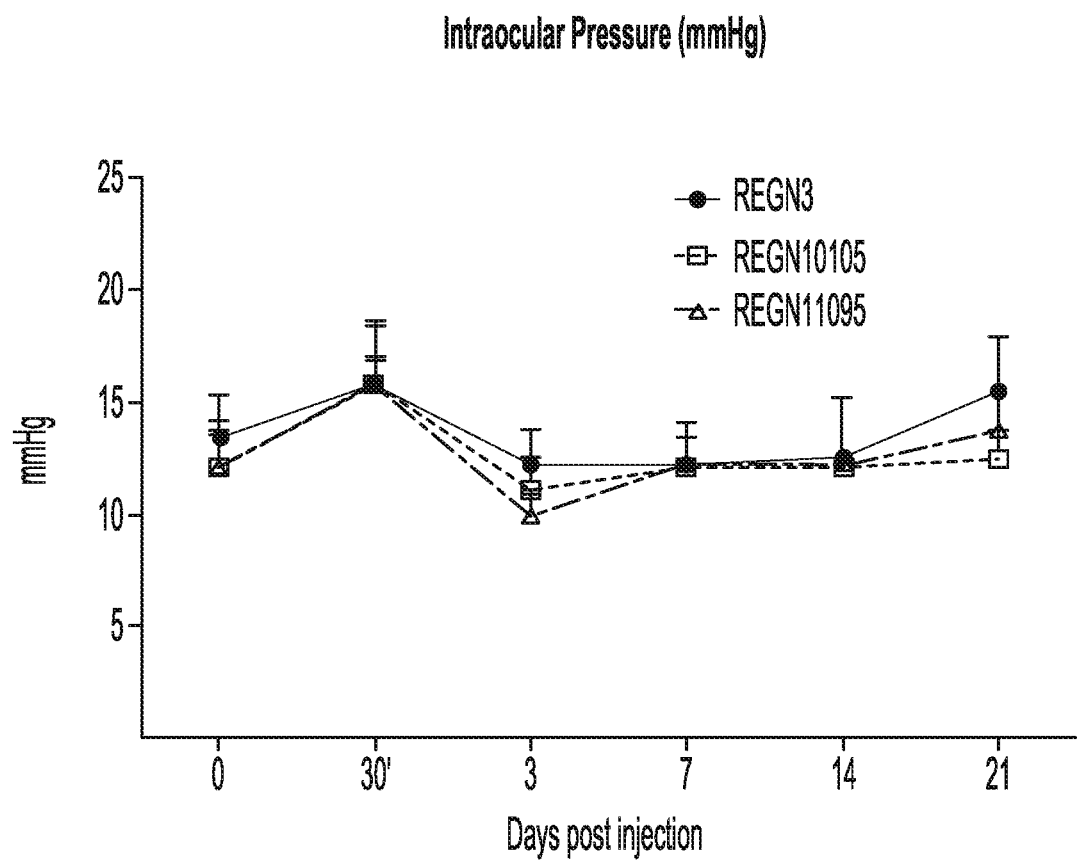
Figure 24A:
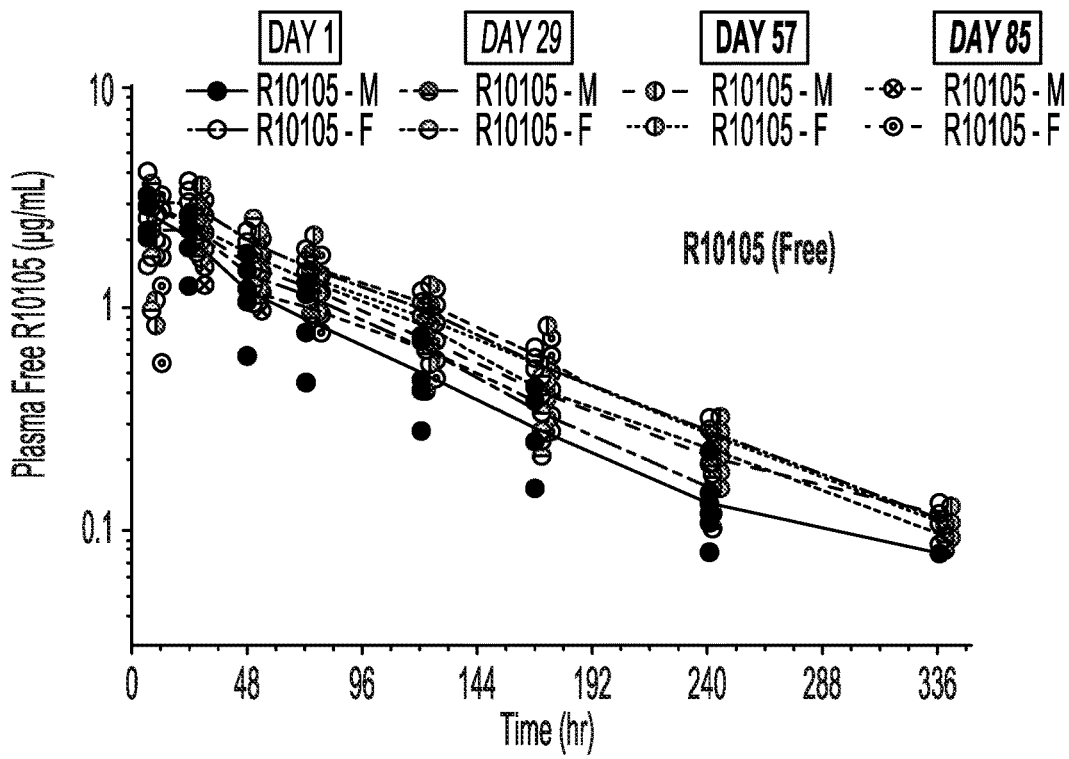
FIGS. 24 (A-D). Analyses of free and bound VEGF mini-traps in eyes of male and female non-human primates, over time, that have been dosed multiple times (on days 1, 29, 57 and 85) with REGN10105 or REGN11095. (A) free REGN10105, (B) free REGN11095, (C) bound REGN10105, (D) bound REGN11095.
Figure 24B:
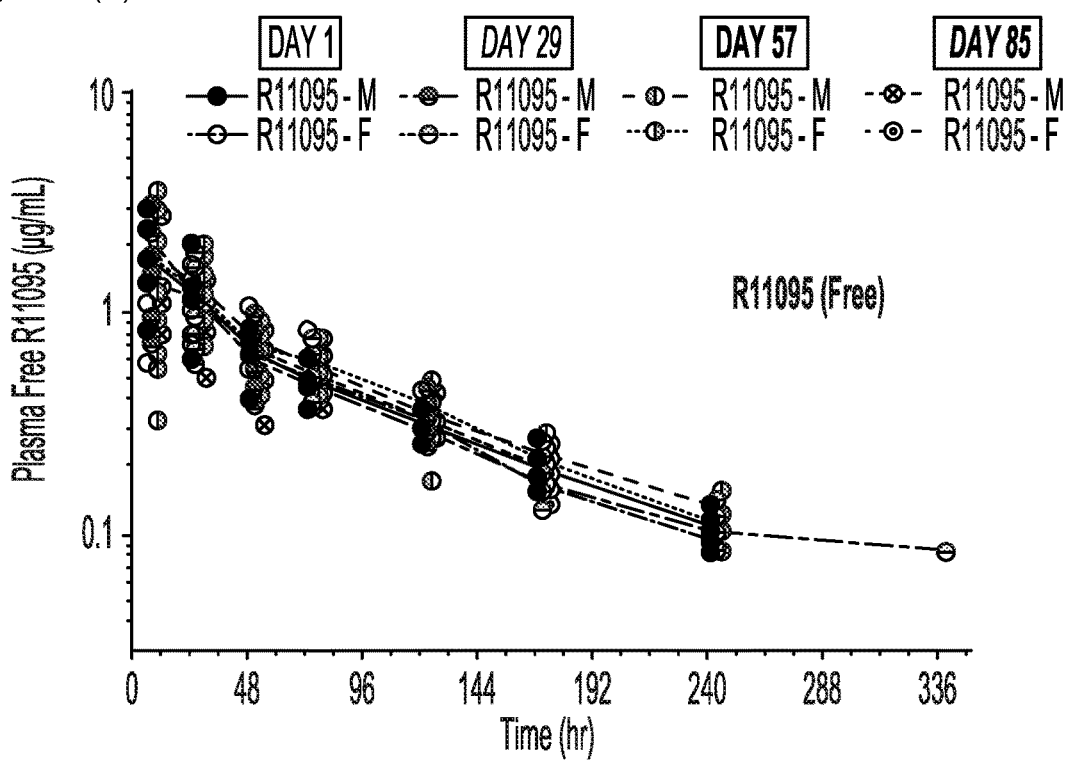
Figure 24C:
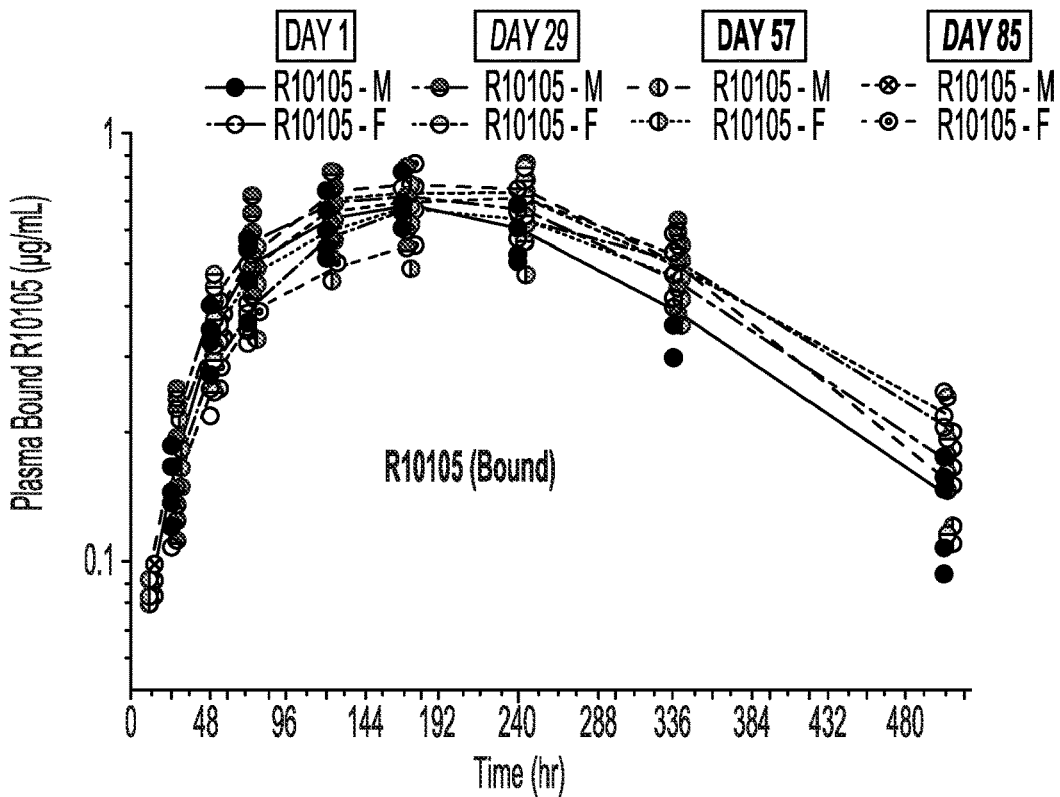
Figure 24D:
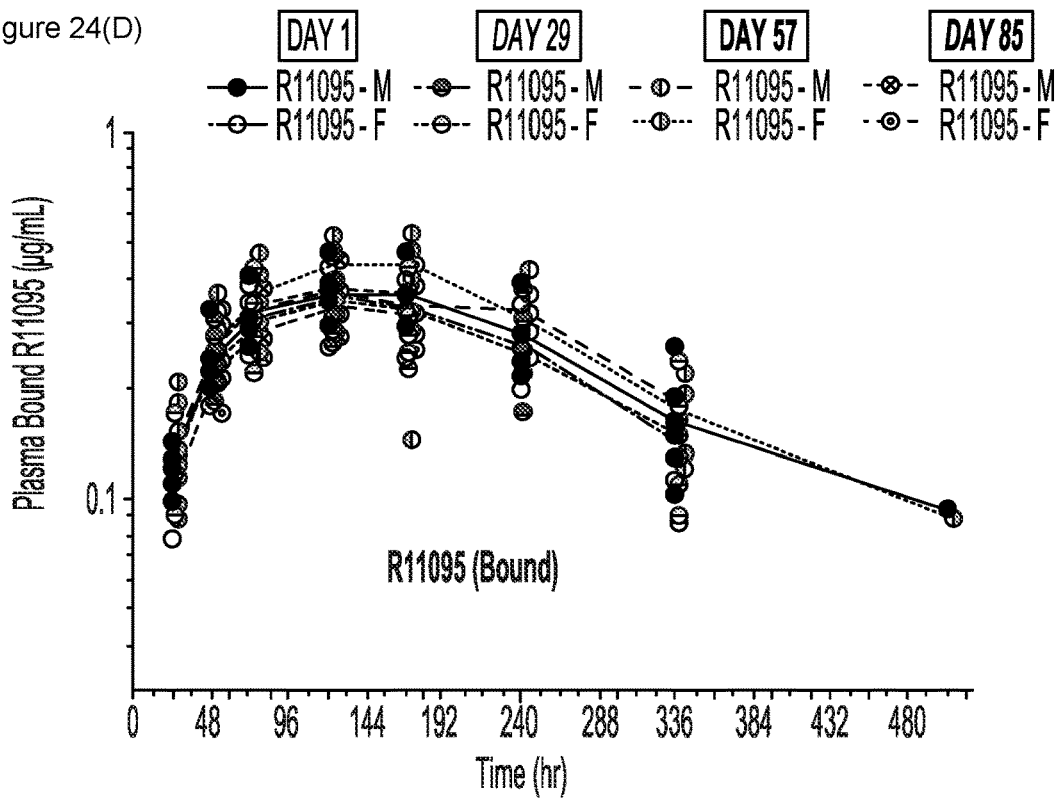

Results. The PK study of VEGF Trap (REGN3) and the VEGF mini-traps (REGN10105 and REGN11095) in NZW rabbit vitreous showed the half-lives were 5.0 (±0.4), 3.9 (±0.3), and 3.4 (±0.5) days, respectively. See FIG. 23 (A-C) There was no significant IOP change before and after IVT injection of either molecule. See FIG. 23 (D). There were no clinically notable signs observed in general ocular examination.

Example 9: Pharmacokinetic Study of VEGF Mini-Traps in Cynomolgus Monkeys

The pharmacokinetics of REGN10105 and REGN11095 in monkeys was investigated.

Concentrations of free and bound REGN10105 and REGN11095 were measured in plasma of cynomolgus monkeys (6/sex/group) following intravitreal administration. In this study, anesthetized animals received bilateral intravitreal injections of REGN10105 or REGN11095 every 4 weeks for a total of 4 doses at 5.5 mg/eye/dose. A1-cc syringe and 30-gauge needle was used for each dose administration of 50 microL/eye. Blood samples were collected after each of the 4 doses for systemic drug exposure evaluation. The assays used to measure plasma concentrations of free and bound REGN10105 and REGN11095 were enzyme-linked immunosorbent assay-based methods with a lower limit of quantitation of 0.078 µg/mL for free and bound species of each compound. See FIG. 24 (A-D).

Peak plasma concentrations of free REGN10105 were achieved by the first sampling time (6 hours) while plasma concentrations of bound REGN10105 were delayed and generally between 5 to 7 days after dosing. Plasma concentrations of free or bound REGN10105 were similar in male and female monkeys after the first dose as well as after each of the subsequent (total of 4 doses) doses of REGN10105 indicating that there were no gender differences and no systemic drug accumulation after multiple dosing. Animals dosed with REGN11095, while they shared similar plasma pharmacokinetic characteristics as REGN10105 (e.g., time to peak concentrations, lack of gender differences and no accumulation after multiple dosing), showed lower plasma concentrations and exposure than animals dosed with REGN10105.

Figure 25:
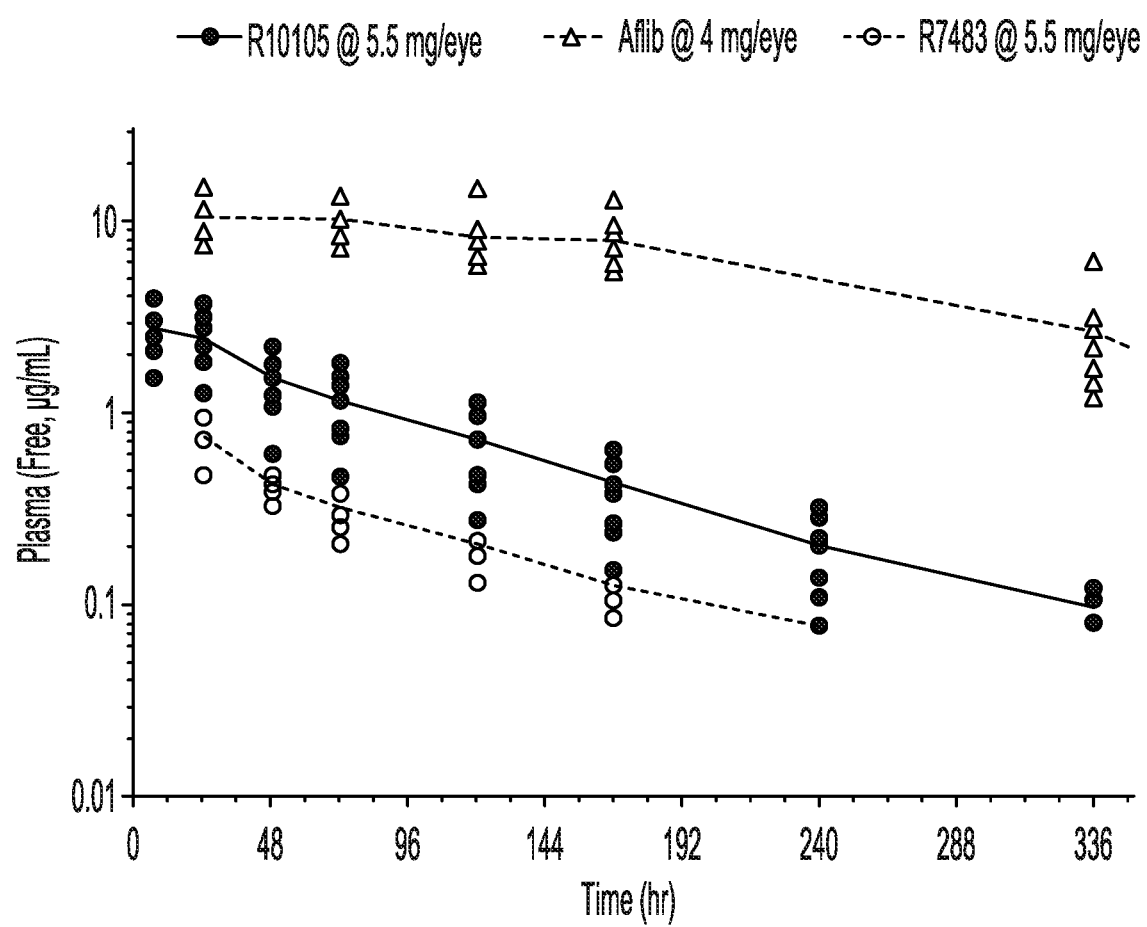
FIG. 25. Systemic (plasma) VEGF trap and mini-trap concentrations, over time, in non-human primates dosed intravitreally with REGN7483 (5.5 mg/eye), REGN10105 (5.5 mg/eye) or aflibercept (4 mg/eye).

A comparison of free REGN10105 plasma concentrations, after a single dose (the first dose of the multiple dose study), with plasma concentration profiles from REGN7483 and REGN3 shows that REGN7483 has the lower plasma concentrations (systemic exposure), followed by REGN10105, than that of REGN3 when given as intravitreal injections at similar dosages (5.5 mg/eye of either REGN10105 or REGN7483 or 4 mg/eye of REGN3). This indicates that both REGN7483 and REGN10105 have lower systemic exposure after intravitreal injections to each eye than REGN3. See FIG. 25.

Example 10: N-Linked Glycan Analysis of VEGF Mini-Trap

The glycan profile of REGN10103 and REGN10105, in particular the levels of fucosylation, galactosylation, sialylation, high mannose and bisecting glycation, was determined in this example.

N-linked glycans were released from the protein by PNGase-F in 50 mM HEPES buffer (pH 7.9) containing 0.1% Waters RapiGest and 4.2 mM TCEP at 45° C. for 25 minutes. The released glycans were labeled with RapiFluor-MS fluorescence dye at 45° C. for 30 minutes. The protein was precipitated by adding 25% DMF and 53% [v/v] acetonitrile and pelletized to the bottom of the tube through centrifugation at 16,000×g for 5 minutes. The supernatant containing the labeled glycans was collected and analyzed on an UPLC using hydrophilic interaction liquid chromatography (Waters BEH Amide column) with post-column fluorescence detection. After binding to the column, the labeled glycans were separated using a binary mobile phase gradient comprised of aqueous 50 mM ammonium formate (pH 4.4) as mobile phase A and acetonitrile as mobile phase B. The separated glycans were detected using a fluorescence detector with an excitation wavelength of 265 nm and an emission wavelength of 425 nm. Using the relative area percentages of the N-glycan peaks in the resultant chromatograms, the N-glycan distribution was reported as the total percentage of N-glycans (1) containing a core fucose residue, (2) containing at least one sialic acid residue, (3) identified as Mannose-5; (4) containing at least one galactose residue, and (5) bisecting N-glycans.

Figure 26A:
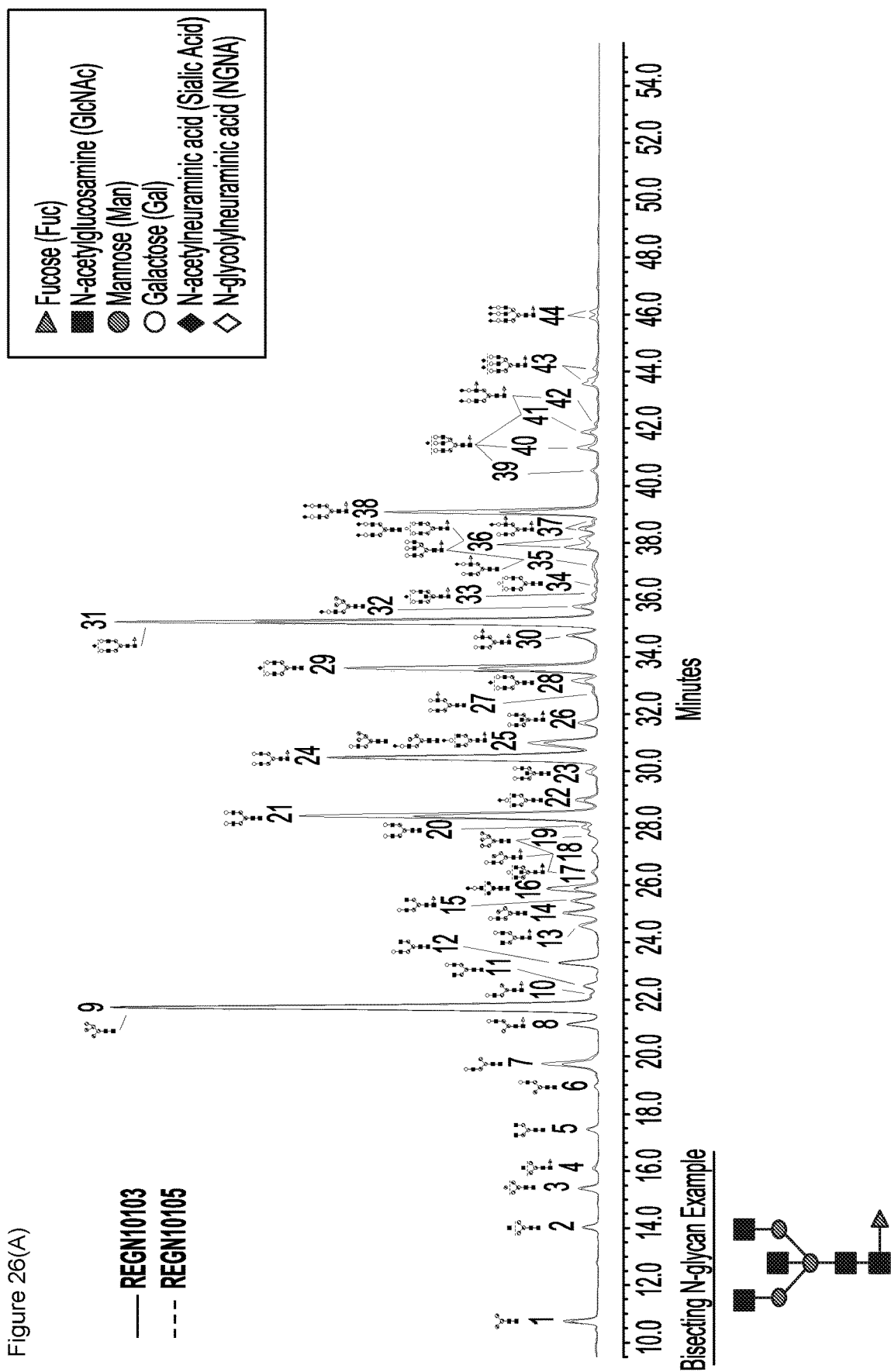
FIGS. 26 (A-B). HILIC-FLR Chromatogram of N-linked Glycans from REGN10103 and REGN10105 (A) overlaid and (B) separated. REGN10103 or REGN10105 with any
Figure 26B:
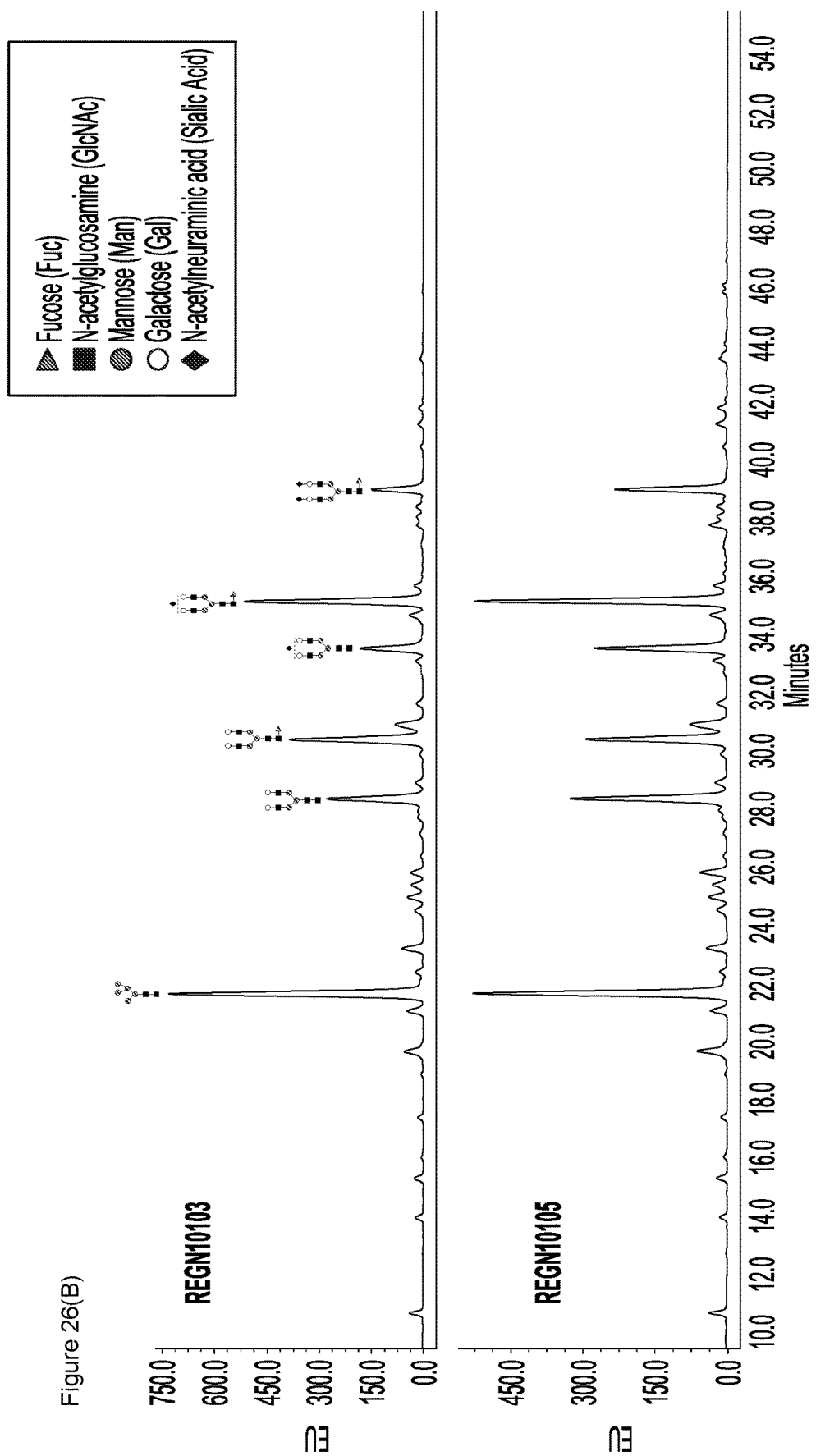

The overlaid HILIC-FLR (hydrophilic interaction chromatography-fluorescence) chromatograms of N-linked glycans from REGN10103 and REGN10105 are set forth in FIG. 26(A) and the separate chromatograms are set forth in FIG. 26(B) and summarized in Table 10-1 herein.

TABLE 10-1

Summary of Glycan Quantification

| Glycosylation | REGN10103 | REGN10105 |
|---|---|---|
| % Fucosylation | 43.3% | 44.8% |
| % Galactosylation | 64.4% | 71.6% |
| % Sialylation | 20.0% | 26.5% |
| % High Mannose | 25.2% | 18.6% |
| % Bisecting | 1.6% | 1.9% |

There was an elevated level of high-mannose species (for example, Man5) in REGN10103 relative to REGN10105. The relative abundance of galactosylation and sialylation were lower in REGN10103 than in REGN10105 possibly due to the elevated high-mannose in REGN10103.

Example 11: REGN10105 Viscosity and Stability Study

Stability (stress stability and photostability) and viscosity studies of REGN10105 was performed in this example.

REGN10105 (IgG2, 2 Cys, FabRICATOR cleaved VEGF mini-trap) was developed and found to eliminate the risk of anti-hinge antibodies associated with Fc-cleaved IgG1 molecule, REGN7483. The viscosity, thermal stability, and photostability of REGN10105 was evaluated in a composition including histidine.

The viscosity assessment was performed for REGN10105 at concentrations ranging between 38-132 mg/mL. A concentration versus viscosity graph was plotted and the results were compared with REGN7483. REGN10105 showed lower viscosity profile as compared to REGN7483 at equimolar concentrations (viscosity=5.8 cP for REGN10105 (at 90 mg/ml) versus 6.9 cP for REGN7483 (at 90 mg/ml)). The viscosity of about 12 cP was observed at concentration of 120 mg/mL REGN10105. The viscosity increased exponentially at concentrations above 120 mg/mL.

Thermal stability of REGN10105 was evaluated at 90 mg/mL and 120 mg/mL in Type I, borosilicate glass vials at a fill volume of 0.4 mL. Thermal stress stability was tested at 37° C. for 4 weeks and storage stability was assessed at 5° C. up to 3 months. The data generated was compared with the results from the stability testing for 90 mg/mL REGN7483$^F$. REGN10105 showed lower aggregation rates under thermal stress (3.74% HMW/week) as compared to REGN7483 (5.45% HMW/week) at 90 mg/mL. The storage stability for REGN10105 was comparable to REGN7483 at similar concentrations. In addition, REGN10105 formulation did not show any obvious change in aggregation levels on agitation (1000 rpm up to 15 min) and freeze thaw (2×).

The photostability of 10 mg/mL REGN10105 was evaluated in the photochamber (Bahnson ES2000 CL-LT Photo-Stability Chamber) after exposure to ambient (10 W/m$^2$ for 0.6 h and cool-white light (CWL) at 8 Klux for 18 h (6 W*h/m$^2$ and 144 klux*h)) and 0.5×ICH (10 W/m$^2$ for 10 h and 8 Klux for 75 h (100 W*h/m$^2$ and 600 Klux*h)). REGN10105 showed slightly better photostability than REGN7483. Overall, REGN10105 showed higher thermal stability and lower viscosity as compared to REGN7483.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants to relate to each and every individual publication, database entry (e.g., Genbank sequences or GeneID entries), patent application, or patent, each of which is clearly identified in even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

We claim:

1. A vascular endothelial growth factor (VEGF) mini-trap which is a homodimer comprising two polypeptides wherein the amino acid sequence of each polypeptide consists of:

(SEQ ID NO: 33)
SDTGRPFVEMYSEIPEIIHMTEGRELVIPCRVTSPNITVTLKKFPLDTL
IPDGKRIIWDSRKGFIISNATYKEIGLLTCEATVNGHLYKTNYLTHRQT
NTIIDVVLSPSHGIELSVGEKLVLNCTARTELNVGIDFNWEYPSSKHQH
KKLVNRDLKTQSGSEMKKFLSTLTIDGVTRSDQGLYTCAASSGLMTKKN
STFVRVHEKVECPPCPAPPVA;
or (SEQ ID NO: 116)
SDTGRPFVEMYSEIPEIIHMTEGRELVIPCRVTSPNITVTLKKFPLDTL
IPDGKRIIWDSRKGFIISNATYKEIGLLTCEATVNGHLYKTNYLTHRQT
NTIIDVVLSPSHGIELSVGEKLVLNCTARTELNVGIDFNWEYPSSKHQH
KKLVNRDLKTQSGSEMKKFLSTLTIDGVTRSDQGLYTCAASSGLMTKKN
STFVRVHEKVECPPCPAPPV.

2. The VEGF mini-trap of claim 1 which is glycosylated.

3. The VEGF mini-trap of claim 1 wherein
said VEGF mini-trap comprises N-linked glycans;
said VEGF mini-trap comprises O-linked glycans;
said VEGF mini-trap is sialylated, galactosylated and/or fucosylated at one or more residues;
said VEGF mini-trap comprises an N-linked mannose-5 glycan (Man5) and/or a bisecting N-glycan at one or more residues; and/or
said VEGF mini-trap comprises Chinese hamster ovary (CHO) cell glycosylation.

4. The VEGF mini-trap of claim 1 characterized by any one or more of the following:
one or more histidines are oxidized to 2-oxo-histidine,
one or more tryptophans are deoxidated;
one or more asparagines thereof are glycosylated;
one or more serines or threonines are O-glycosylated;
one or more asparagines are deamidated;
one or more Aspartate-Glycine motifs are converted to iso-aspartate-glycine and/or asparagine-glycine;
one or more methionines are oxidized;
one or more tryptophans are converted to N-formylkynurenin;
one or more arginines are converted to Arg 3-deoxyglucosone;
there are one or more non-glycosylated glycosites;
is xylosylated;
is glycated at a lysine;
comprises a cystine with a free-thiol group;
comprises an intrachain disulfide bridge;
comprises disulfide bridges in parallel or crossed orientation; and/or
comprises a lysine or arginine which is carboxymethylated.

5. A composition comprising a heterogeneous mixture of glycosylated variants of the VEGF mini-trap of claim 1.

6. The composition of claim 5 wherein about 20-27% of the VEGF mini-traps are sialylated, about 64-72% of the VEGF mini-traps are galactosylated, about 43-45% of the VEGF mini-traps are fucosylated, about 19-25% of the VEGF mini-traps are Man-5 glycosylated, and/or about 1-2% modified with bisecting N-glycan.

7. A composition comprising a VEGF mini-trap of claim 1, further comprising immunoglobulin-degrading enzyme from *Streptococcus pyogenes* (IdeS) protease or a variant thereof.

8. A complex comprising the VEGF mini-trap of claim 1 bound to VEGF or a homodimer thereof.

9. The complex of claim 8:
wherein VEGF is human VEGF;
wherein VEGF is human $VEGF_{165}$;
wherein VEGF is human $VEGF_{121}$;
which includes an anti-VEGF antibody or Fab fragment thereof;
which includes human VEGF homodimer and an anti-VEGF Fab fragment wherein the stoichiometric ratio of VEGF mini-trap homodimer:human VEGF:Fab is 1:1:2;
and/or
wherein the stoichiometric ratio of VEGF mini-trap homodimer:VEGF homodimer is 1:1.

10. A pharmaceutical formulation comprising the VEGF mini-trap of claim 1 and a pharmaceutically effective carrier.

* * * * *